US012325881B2

(12) United States Patent
Lee-Lim et al.

(10) Patent No.: US 12,325,881 B2
(45) Date of Patent: Jun. 10, 2025

(54) METHOD OF DETERMINING AND TREATING BREAST CANCER

(71) Applicants: AGENCY FOR SCIENCE, TECHNOLOGY AND RESEARCH, Singapore (SG); Singapore Health Services Pte Ltd, Singapore (SG); National University Hospital (Singapore) Pte Ltd, Singapore (SG); Tan Tock Seng Hospital Pte Ltd (TTSH), Singapore (SG); MiRXES Lab Pte. Ltd., Singapore (SG)

(72) Inventors: Siew Gek Lee-Lim, Singapore (SG); Ruiyang Zou, Singapore (SG); Lihan Zhou, Singapore (SG); He Cheng, Singapore (SG); Bo Anders Mikael Hartman, Singapore (SG); Heng-Phon Too, Singapore (SG)

(73) Assignees: AGENCY FOR SCIENCE, TECHNOLOGY AND RESEARCH, Singapore (SG); Singapore Health Services Pte Ltd, Singapore (SG); National University Hospital (Singapore) Pte Ltd, Singapore (SG); Tan Tock Seng Hospital Pte Ltd, Singapore (SG); Mirxes Lab Pte Ltd, Singapore (SG)

( * ) Notice: Subject to any disclaimer, the term of this patent is extended or adjusted under 35 U.S.C. 154(b) by 0 days.

(21) Appl. No.: 17/713,143

(22) Filed: Apr. 4, 2022

(65) Prior Publication Data
US 2023/0313308 A1    Oct. 5, 2023

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2014/0200261 A1* 7/2014 Hoge ..................... A61P 35/00
435/320.1

OTHER PUBLICATIONS

Enard et al. (Science 2002 vol. 296 p. 340) (Year: 2002).*
Cobb et al (Crit Care Med 2002 vol. 30 p. 2711) (Year: 2002).*
Loke et al., "The Future of Blood-based Biomarkers for the Early Detection of Breast Cancer", European Journal of Cancer, vol. 92, 2018, pp. 54-68.
An et al., "Serum MicroRNA as Potential Biomarker to Detect Breast Atypical Hyperplasia and Early-stage Breast Cancer", Future Oncol., vol. 14, No. 30, 2018, pp. 3145-3161.
Zou et al., "Identification and Validation of a Serum MicroRNA Panel for Detection of Early-stage Breast Cancer", Journal of Clinical Oncology, vol. 37, Issue 15, 2019, 3 pages.
Rezaei et al., "Involvement of the Dysregulation of miR-23b-3p, miR-195-5P, miR656-5p, and miR-340-5P in Trastuzumab Resistance of HER2-Postive Breast Cancer Cells and System Biology Approach to Predict Their Targets Involved in Resistance", DNA and Cell Biology, vol. 38, No. 2, 2019, pp. 184-192.
Bray et al., "Global Cancer Statistics 2018: GLOBOCAN Estimates of Incidence and Mortality Worldwide for 36 Cancers in 185 Countries", CA Cancer J. Clin, vol. 68, 2018, pp. 394-424.
Zhang et al., "A Circulating miRNA Signature as a Diagnostic Biomarker for Non-invasive Early Detection of Breast Cancer", Breast Cancer Res Treat, vol. 154, 2015, pp. 423-434.
Chan et al., "Identification of Circulating MicroRNA Signatures for Breast Cancer Detection", Clin Cancer Res, vol. 19, No. 16, Aug. 15, 2013, pp. 4477-4487.
Mar-Aguilar et al., "Serum Circulating MicroRNA Profiling for Identification of Potential Breast Cancer Biomarkers", Disease Markers, vol. 34, 2013, pp. 163-169.
Frères et al., "Circulating MicroRNA-based Screening Tool for Breast Cancer", Oncotarget, vol. 7, No. 5, Dec. 29, 2015, pp. 5416-5428.
Shin et al., "Circulating Cell-free MiRNAs as Biomarker for Triple-negative Breast Cancer", British Journal of Cancer, vol. 112, 2015, pp. 1751-1759.
Cuk et al., "Plasma MicroRNA Panel for Minimally Invasive Detection of Breast Cancer", PLoS One, vol. 8, Issue 10, Oct. 2013, 10 pages.
Thakur et al., "Identification of Specific MiRNA Signature in Paired Sera and Tissue Samples of Indian Women With Triple Negative Breast Cancer", PLoS One, vol. 11, Issue 7, Jul. 12, 2016, 21 pages.
Hannafon et al., "Plasma Exosome MicroRNAs are Indicative of Breast Cancer", Breast Cancer Research, vol. 18, No. 90, 2016, 14 pages.
Zhang et al., "Identification of MicroRNA Biomarkers in the Blood of Breast Cancer Patients Based on MicroRNA Profiling", Gene, vol. 619, 2017, pp. 10-20.
Drukteinis et al., "Beyond Mammography: New Frontiers in Breast Cancer Screening", Am J Med., vol. 126, No. 6, Jun. 2013, pp. 472-479.
Shimomura et al., "Novel Combination of Serum MicroRNA for Detecting Breast Cancer in the Early Stage", Cancer Sci., vol. 107, No. 3, Mar. 2016, pp. 326-334.
Loke et al., "A Circulating MiRNA Signature for Stratification of Breast Lesions Among Women With Abnormal Screening Mammograms", Cancers, vol. 11, 2019, 14 pages.
Gao et al., "Clinical Significance of Serum MiR-21 in Breast Cancer Compared With CA153 and CEA", Chinese Journal of Cancer Research, vol. 25, No. 6, 2013, pp. 743-748.
Schwarzenbach et al., "Diagnostic Potential of PTEN-targeting MiR-214 in the Blood of Breast Cancer Patients", Breast Cancer Res Treat, vol. 134, 2012, pp. 933-941.

(Continued)

*Primary Examiner* — Katherine D Salmon
(74) *Attorney, Agent, or Firm* — MARSHALL, GERSTEIN & BORUN LLP

(57) ABSTRACT

This technology relates to a method of treating breast cancer in a subject and a method of determining whether a breast lesion in a subject is malignant or benign using miRNA panels.

11 Claims, 5 Drawing Sheets

(56) References Cited

OTHER PUBLICATIONS

Benjamini et al., "Controlling the False Discovery Rate: a Practical and Powerful Approach to Multiple Testing", J. R. Statist. Soc. B, vol. 57, No. 1, 1995, pp. 289-300.
Benjamini et al., "The Control of the False Discovery Rate in Multiple Testing Under Dependency", The Annals of Statistics, vol. 29, No. 4, 2001, pp. 1165-1188.
Xiong et al., "Biomarker Identification by Feature Wrappers", Genome Research, vol. 11, 2001, pp. 1878-1887.
Bewick et al., "Statistics Review 14: Logistic Regression", Critical Care, vol. 9, No. 1, Feb. 2005, pp. 112-118.
Li et al., "A Serum MicroRNA Signature Predicts Trastuzumab Benefit in HER2-positive Metastatic Breast Cancer Patients", Nature Communications, vol. 9, 2018, 13 pages.
Ouyang et al., "MicroRNA Profiling Implies New Markers of Chemoresistance of Triple-negative Breast Cancer", PLoS One, vol. 9, Issue 5, May 2014, 8 pages.
Ong et al., "National Expenditure for False-positive Mammograms and Breast Cancer Overdiagnoses Estimated at $4 Billion a Year", Health Affairs, vol. 34, No. 4, Apr. 2015, pp. 576-583.
Liu et al., "MiR-451a Inhibited Cell Proliferation and Enhanced Tamoxifen Sensitive in Breast Cancer via Macrophage Migration Inhibitory Factor", BioMed Research International, vol. 2015, Article ID 207684, 12 pages.
Luo et al., "MicroRNA-195-5p is a Potential Diagnostic and Therapeutic Target for Breast Cancer", Oncology Reports, vol. 31, 2014, pp. 1096-1102.
Mishra et al., "Circulating MiRNAs Revealed as Surrogate Molecular Signatures for the Early Detection of Breast Cancer", Cancer Letters, vol. 369, 2015, pp. 67-75.
Paszek et al., "Dysregulation of MicroRNAs in Triple-negative Breast Cancer", Ginekologia Polska, Vo., 88, No. 10, 2017, pp. 530-536.
Kahraman et al., "MicroRNA in Diagnosis and Therapy Monitoring of Early-stage Triple-Negative Breast Cancer", Scientific Reports, vol. 8, 2018, 12 pages.
Taylor et al., "The Ultimate qPCR Experiment: Producing Publication Quality, Reproducible Data the First Time", Trends in Biotechnology, vol. 37, No. 7, Jul. 2019, pp. 761-774.
Sung et al., "Global Cancer Statistics 2020: GLOBOCAN Estimates of Incidence and Mortality Worldwide for 36 Cancers in 185 Countries", CA Cancer J Clin, vol. 71, 2021, pp. 209-249.
Li et al., "Non-invasive Biomarkers for Early Detection of Breast Cancer", Cancers, vol. 12, 2020, 28 pages.
Lianidou et al., "Liquid Biopsies", Genes Chromosomes Cancer, vol. 58, 2019, pp. 219-232.
Guo et al., "Ultrasound Imaging Technologies for Breast Cancer Detection and Management—A Review", Ultrasound Med Biol. vol. 44, No. 1, Jan. 2018, pp. 37-70.
Fang et al., "Plasma MicroRNA Pair Panels as Novel Biomarkers for Detection of Early Stage Breast Cancer", Frontiers in Physiology, vol. 9, Article 1879, Jan. 2019, 12 pages.
Mitchell et al., "Circulating MicroRNAs as Stable Blood-based Markers for Cancer Detection", PNAS, vol. 105, No. 30, Jul. 29, 2008, pp. 10513-10518.
Schwarzenbach et al., "Clinical Relevance of Circulating Cell-free MicroRNAs in Cancer", Nature Reviews, Clinical Oncology, vol. 11, Mar. 2014, pp. 145-156.
Hayes et al., "MicroRNAs in Cancer: Biomarkers, Functions and Therapy", Trends in Molecular Medicine, vol. 20, No. 8, Aug. 2014, pp. 460-469.
He et al., "Current State of Circulating MicroRNAs as Cancer Biomarkers", Clinical Chemistry, vol. 61, No. 9, 2015, pp. 1138-1155.
Zou et al., "Development of a microRNA Panel for Classification of Abnormal Mammograms for Breast Cancer", Cancers, 13, 2130 Apr. 28, 2021, 12 pages.

\* cited by examiner

|  | P-value | FDR-adjusted P-value | AUC | Log2 (Fold Change) |
|---|---|---|---|---|
| hsa-miR-195-5p | 0.00006 | 0.011 | 0.637 | 0.411 |
| hsa-miR-451a | 0.0004 | 0.030 | 0.629 | 0.393 |
| hsa-miR-125b-5p | 0.0005 | 0.030 | 0.642 | 0.455 |
| hsa-miR-660-5p | 0.0008 | 0.034 | 0.629 | 0.259 |
| hsa-miR-25-3p | 0.0010 | 0.034 | 0.619 | 0.281 |
| hsa-miR-143-3p | 0.0013 | 0.034 | 0.607 | 0.353 |
| hsa-miR-363-3p | 0.0014 | 0.034 | 0.617 | 0.279 |
| hsa-miR-338-3p | 0.0015 | 0.034 | 0.638 | -0.328 |

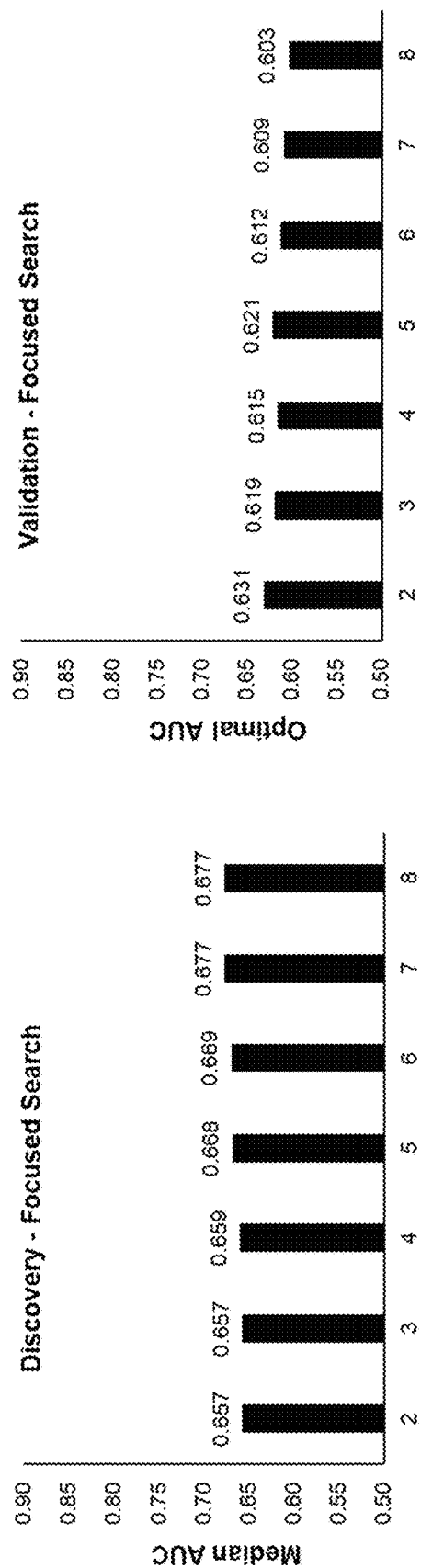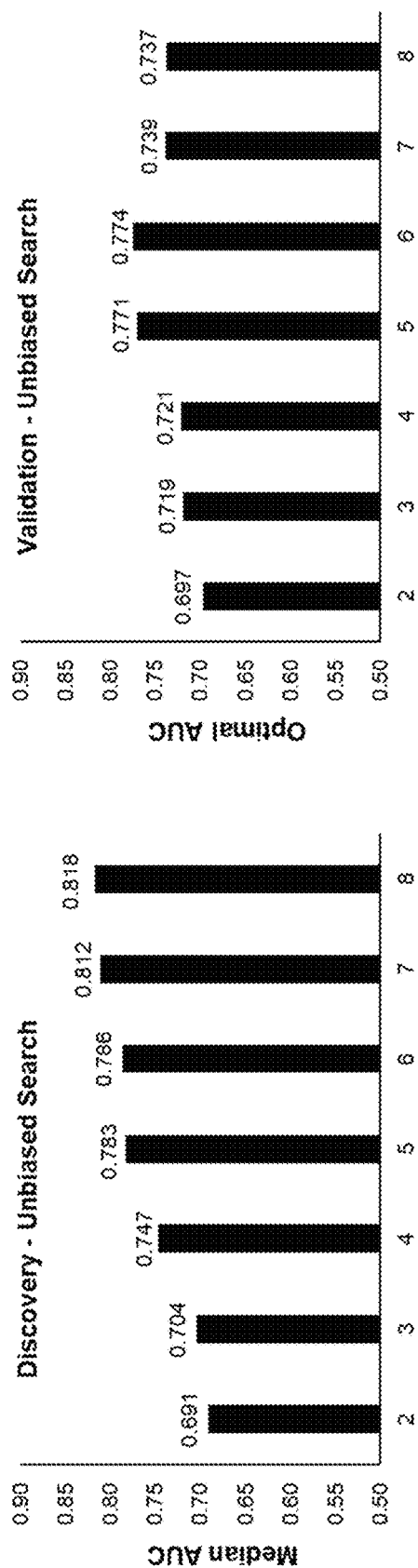
Figure 2A · Figure 2B · Figure 2C · Figure 2D

METHOD OF DETERMINING AND TREATING BREAST CANCER

FIELD OF THE INVENTION

The present invention relates generally to the field of molecular biology. In particular, the present invention relates to the use of biomarkers for the detection of cancer.

BACKGROUND

Breast cancer is the most commonly diagnosed cancer and the leading cause of cancer mortality among women worldwide. The gold standard for breast cancer screening is mammography. However, this modality yields significant false-positive results that require additional diagnostic imaging procedures and tissue biopsies. In a large study of 702,154 cases in the United States, 171,829 had abnormal screening mammogram results with only <2% (2,599/171,829) found to be true positives. As a result, a large majority of these women with abnormal screening mammograms were subjected to invasive and expensive diagnostic procedures that could have been avoided. Furthermore, mammography has about 22% of false negative rate in women under 50, and sometimes cannot accurately distinguish between benign and malignant tumours, causing delay of more than two months for timely treatment of the patients. Thus, based on the issues identified above, there is a need for minimally invasive methods of detection of breast cancer in subjects, from healthy individuals or subjects with benign breast lesions.

SUMMARY OF INVENTION

In one aspect, the present disclosure refers to a method of treating breast cancer, the method comprising: obtaining a sample from a subject thought to be suffering from or at the risk of developing breast cancer; measuring the expression level of at least two or more miRNAs selected from the group consisting of miR-451a, miR-195-5p, miR-126-5p, miR-423-3p, miR-192-5p, miR-17-5p, miR-125b-5p, miR-660-5p, miR-25-3p, miR-143-3p, miR-363-3p and miR-338-3p in the sample obtained from the subject; wherein differential or unchanged expression level of said miRNA in the sample, as compared to a control, determines the subject is suffering from, or is at risk of developing breast cancer, treating the subject diagnosed with having breast cancer with an anti-breast cancer compound.

In one example, the method as disclosed herein comprises measuring at least 3, at least 4, at least 5, at least 6, at least 7, at least 8, at least 9, at least 10, at least 11, or 12 miRNAs. In another example, the two or more miRNAs comprise or consist of miR-451a, miR-195-5p, miR-125b-5p, miR-660-5p, miR-25-3p, miR-143-3p, miR-363-3p, and miR-338-3p for the method as disclosed herein. In another example of the method as disclosed herein, the two or more miRNAs comprise or consist of miR-451a, miR-195-5p, miR-126-5p, miR-423-3p, miR-192-5p, and miR-17-5p. In another example of the method disclosed herein, the following miRNAs, if present, are upregulated: miR-451a, miR-195-5p, miR-125b-5p, miR-126-5p, miR-660-5p, miR-25-3p, miR-143-3p, and miR-363-3p. In a further example of the method disclosed herein, if present, miR-338-3p is downregulated. In yet another example, if present, the following miRNAs are unchanged: miR-423-3p, miR-192-5p, and miR-17-5p.

In another aspect, the present disclosure refers to a method for determining whether a breast lesion in a subject is malignant or benign, the method comprising: measuring the expression level of at least two or more miRNA selected from the group consisting of miR-451a, miR-195-5p, miR-126-5p, miR-423-3p, miR-192-5p, miR-17-5p, miR-125b-5p, miR-660-5p, miR-25-3p, miR-143-3p, miR-363-3p and miR-338-3p in a sample obtained from the subject, wherein differential expression or unchanged miRNA expression level of said miRNAs in the sample, as compared to a control, determines the lesion is benign or malignant.

In one example, the method as disclosed herein comprises measuring at least 3, at least 4, at least 5, at least 6, at least 7, at least 8, at least 9, at least 10, at least 11, or 12 miRNAs. In another example of the method as disclosed herein, the at least two or more miRNAs comprise or consist of miR-451a, miR-195-5p, miR-125b-5p, miR-660-5p, miR-25-3p, miR-143-3p, miR-363-3p, and miR-338-3p. In another example of the method as disclosed herein, the at least two or more miRNAs comprise or consist of miR-451a, miR-195-5p, miR-126-5p, miR-423-3p, miR-192-5p, and miR-17-5p. In another example of the method as disclosed herein, if present, the following miRNA are upregulated: miR-451a, miR-195-5p, miR-125b-5p, miR-126-5p, miR-660-5p, miR-25-3p, miR-143-3p, and miR-363-3p. In another example of the method as disclosed herein, if present, miR-338-3p is downregulated. In another example of the method as disclosed herein, if present, the following miRNA are unchanged: miR-423-3p, miR-192-5p, and miR-17-5p. In another example, the control is a cancer-free subject. In another example, the control is a subject with benign breast lesions. In another example, the control is a subject with normal mammogram results. In another example of the method as disclosed herein, the expression level of the miRNA is any one of concentration, log(concentration), Ct value, Ct/Cq value, or two to the power of Ct/Cq value. In another example, for the method as disclosed herein, the expression level of the miRNA is determined by Real-Time Quantitative Reverse Transcription Polymerase Chain Reaction (qRT-PCR). In yet another example, for the method as disclosed herein, the sample is a tissue sample or bodily fluid sample. In a further example, the bodily fluid is selected from the group consisting of cellular and non-cellular components of a liquid biopsy, amniotic fluid, bronchial lavage, cerebrospinal fluid, interstitial fluid, peritoneal fluids, pleural fluid, saliva, seminal fluid, urine, tears, peripheral blood, whole blood, plasma, and serum. In another example of the method as disclosed herein, the subject has had an abnormal mammogram result. In yet another example of the method as disclosed herein, the method includes a step of obtaining a predictive score based on the miRNA selected a mathematical model selected from linear model, logistic regression, support vector machine algorithm, logistic regression algorithm, multinomial logistic regression algorithm, Fisher's linear discriminant algorithm, quadratic classifier algorithm, perceptron algorithm, k-nearest neighbours algorithm, artificial neural network algorithm, random forests algorithm, decision tree algorithm, naive Bayes algorithm, adaptive Bayes network algorithm, and ensemble learning method combining multiple learning algorithms.

In yet another aspect, the present disclosure refers to a kit comprising a combination of primers suitable for detecting the two or more miRNA as defined in the method as disclosed herein.

BRIEF DESCRIPTION OF THE DRAWINGS

The invention will be better understood with reference to the detailed description when considered in conjunction with the non-limiting examples and the accompanying drawings, in which:

FIG. 1 provides an overview of the biomarker identification.

FIG. 2 describes the building of the biomarker panel disclosed herein. FIG. 2A shows median Area Under the Curve (AUC) values for multi-miRNA biomarker panels identified through a focused search and an unbiased search in the discovery cohort as shown in FIG. 2C. FIG. 2B shows Area Under the Curve (AUC) values for a multi-miRNA biomarker panel from the focused search. FIG. 2D shows the Area Under the Curve values (AUC) obtained from an unbiased search validated in the validation cohort. The focused search refers to a search among the 8 top-ranked differentially regulated miRNAs only (shown in FIG. 1A) while the unbiased search expands the search to all 324 miRNAs analysed.

FIG. 3 shows the validation of a biomarker panel as disclosed herein.

DEFINITIONS

Figure 1A:
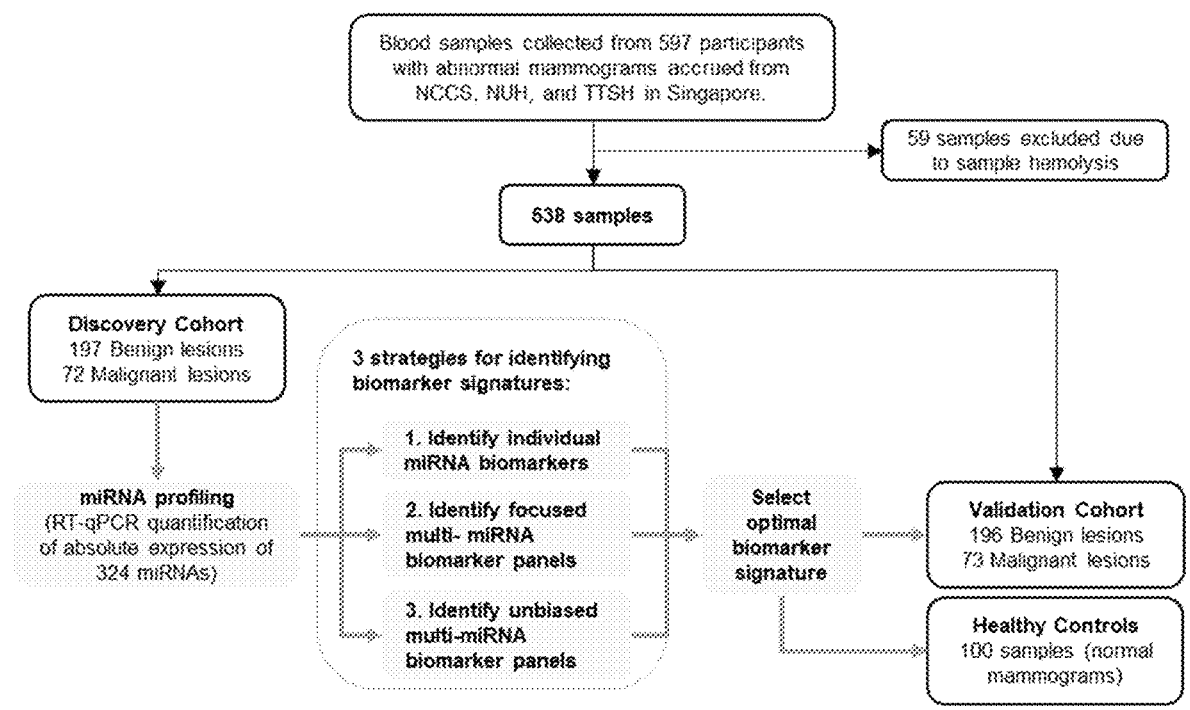
FIG. 1A shows a schematic representation of the study design. NCCS, National Cancer Centre Singapore; NUH, National University Hospital; TTSH, Tan Tock Seng Hospital.

As used herein, the term "miRNA" refers to microRNA, small non-coding RNA molecules, which in some examples contain about 19-25 nucleotides (nt), and are found in plants, animals and some viruses. miRNAs are known to have functions in RNA silencing and post-transcriptional regulation of gene expression. These highly conserved RNAs regulate the expression of genes by binding to the 3'-untranslated regions (3'-UTR) of specific mRNAs. For example, each miRNA is thought to regulate multiple genes, and since hundreds of miRNA genes are predicted to be present in higher eukaryotes. miRNAs tend to be transcribed from several different loci in the genome. These genes encode for long RNAs with a hairpin structure that when processed by a series of RNaseIII enzymes (including Drosha and Dicer) form a miRNA duplex of usually ~22 nt long with 2 nt overhangs on the 3'end.

As used herein, the term "regulation" refers to the process by which a cell increases or decreases the quantity of a cellular component, such as RNA or protein, in response to an external variable. An increase of a cellular component is called upregulation, while a decrease of a cellular component is called downregulation. The terms "deregulated" or "dysregulated", as used herein, mean either up- or down-regulated. An example of downregulation is the cellular decrease in the number of receptors to a molecule, such as a hormone or neurotransmitter, which reduces the cell's sensitivity to the molecule. This phenomenon is also an example of a locally acting negative feedback mechanism. An example of upregulation is the increased number of cytochrome P450 enzymes in liver cells when, for example, xenobiotic molecules, such as dioxin, are administered, thereby resulting in greater degradation of these molecules. Upregulation and downregulation can also happen as a response to toxins or hormones. An example of upregulation, for example in pregnancy, is hormones that cause cells in the uterus to become more sensitive to oxytocin.

As used herein, the term "differential expression" refers to the measurement of a cellular component in comparison to a control or another sample, and thereby determining the difference in, for example, concentration, presence or intensity of said cellular component. The result of such a comparison can be given in the absolute, that is a component is present in the samples and not in the control, or in the relative, that is the expression or concentration of component is increased or decreased compared to the control. The terms "increased" and "decreased" in this case can be interchanged with the terms "upregulated" and "downregulated" which are also used in the present disclosure.

As used herein, the term "control" refers to a sample used in experiments to denote a reference point. For example, controls can be used in the development and validation of the markers that are later used to confirm whether a subject has a specific disease or not. In the present context, a control can be used as a reference point in order to indicate whether or not a subject has malignant breast lesions, by comparing to the subject to be tested with the control. Thus, in one example, a control can be a healthy subject, that is to say, a healthy subject is a subject which is free of disease. In some examples, a control can be a cancer-free subject. In some other examples, a control can be a subject with benign breast lesion. It is of note that the terms "non-diseased" and "cancer-free" can be used interchangeably in the context of the present invention.

As used herein, the term "HER" or "Her2" refers to the human epidermal growth factor 2, a member of the human epidermal growth factor receptor (HER/EGFR/ERBB) family involved in normal cell growth. It is found on some types of cancer cells, including breast and ovarian. Cancer cells removed from the body may be tested for the presence of HER2/neu to help decide the best type of treatment. HER2/neu is a type of receptor tyrosine kinase. Also called c-erbB-2, human EGF receptor 2, and human epidermal growth factor receptor 2.

As used herein, the term "Luminal A" or "LA" refers to a sub-classification of breast cancers according to a multitude of genetic markers. A breast cancer can be determined to be luminal A or luminal B, in addition to being estrogen receptor (ER) positive, progesterone receptor (PR) positive and/or hormone receptor (HR) negative, among others. Clinical definition of a luminal A cancer is a cancer that is ER positive and PR positive, but negative for HER2. Luminal A breast cancers are likely to benefit from hormone therapy and may also benefit from chemotherapy. A luminal B cancer is a cancer that is ER positive, PR negative and HER2 positive. Luminal B breast cancers are likely to benefit from chemotherapy and may benefit from hormone therapy and treatment targeted to HER2.

As used herein, the term "triple negative" or "TN" refers to a breast cancer, which had been tested and found to lack (or be negative) for hormone epidermal growth factor receptor 2 (HER-2), estrogen receptors (ER), and progesterone receptors (PR). Triple negative cancers are also known to be called "basal-like" cancers Since the tumour cells in triple negative breast cancers lack the necessary receptors, common treatments, for example hormone therapy and drugs that target estrogen, progesterone, and HER-2, are ineffective. Using chemotherapy to treat triple negative breast cancer is still an effective option. In fact, triple negative breast cancer may respond even better to chemotherapy in the earlier stages than many other forms of cancer.

As used herein, the term "(statistical) classification" refers to the problem of identifying to which of a set of categories (sub-populations) a new observation belongs, on the basis of a training set of data containing observations (or instances) whose category membership is known. An example is assigning a diagnosis to a given subject as described by observed characteristics of the subject (gender, blood pressure, presence or absence of certain symptoms, etc.). In the terminology of machine learning, classification is considered an instance of supervised learning, i.e., learning where a training set of correctly identified observations is available. The corresponding unsupervised procedure is known as clustering and involves grouping data into categories based on some measure of inherent similarity or distance. Often, the individual observations are analysed into a set of quantifiable properties, known variously as explanatory variables or features. These properties may variously be categorical (e.g., "A", "B", "AB" or "O", for blood type), ordinal (e.g., "large", "medium" or "small"), integer-valued (e.g., the number of occurrences of a part word in an email) or real-valued (e.g., a measurement of blood pressure). Other classifiers work by comparing observations to previous observations by means of a similarity or distance function. An algorithm that implements classification, especially in a concrete implementation, is known as a classifier. The term "classifier" sometimes also refers to the mathematical function, implemented by a classification algorithm, which maps input data to a category.

As used herein, the term "pre-trained" or "supervised (machine) learning" refers to a machine learning task of inferring a function from labelled training data. The training data can consist of a set of training examples. In supervised learning, each example is a pair consisting of an input object (typically a vector) and a desired output value (also called the supervisory signal). A supervised learning algorithm, that is the algorithm to be trained, analyses the training data and produces an inferred function, which can be used for mapping new examples. An optimal scenario will allow for the algorithm to correctly determine the class labels for unseen instances. This requires the learning algorithm to generalize from the training data to unseen situations in a "reasonable" way.

As used herein, the term "score" and/or "prediction score" refers to an integer or number, that can be determined mathematically, for example by using computational models a known in the art, which can include but are not limited to, SMV, as an example, and that is calculated using any one of a multitude of mathematical equations and/or algorithms known in the art for the purpose of statistical classification. Such a score is used to enumerate one outcome on a spectrum of possible outcomes. The relevance and statistical significance of such a score depends on the size and the quality of the underlying data set used to establish the results spectrum. For example, a blind sample may be input into an algorithm, which in turn calculates a score based on the information provided by the analysis of the blind sample. This results in the generation of a score for said blind sample. Based on this score, a decision can be made, for example, how likely the subject, from which the blind sample was obtained, has cancer or not. The ends of the spectrum may be defined logically based on the data provided, or arbitrarily according to the requirement of the experimenter. In both cases the spectrum needs to be defined before a blind sample is tested. As a result, the score generated by such a blind sample, for example the number "45" may indicate that the corresponding subject has cancer, based on a spectrum defined as a scale from 1 to 50, with "1" being defined as being cancer-free and "50" being defined as having cancer.

As used herein, the term "breast lesion" refers to an area of abnormal tissue in the breast and may also be referred to as a nodule. A breast lesion can be either benign or malignant.

As used herein, the term "benign breast lesion" refers to conditions marked by histopathological changes in breast tissue, whereby the breast tissue does not invade or metastasise. It is accepted in the art that benign breast lesions are treated using surgical excision, whereby surgery is considered to be curative. A "benign breast lesion" can include, but is not limited to, breast cysts, inflammatory lesions, mastitis, abscess formation, granulomas, mammary duct ectasia (plasma cell mastitis, comedomastitis), subareolar abscess, lipomas, fat necrosis, fibrocystic change, ductal epithelial hyperplasia (proliferative breast disease), atypical ductal hyperplasia, juvenile papillomatosis, fibroadenoma, adenosis tumour and sclerosing adenosis, nodular pseudoangiomatous stromal hyperplasia, adenoma of the nipple, adenomyoepithelioma, pleomorphic adenoma, benign lesions during pregnancy and postpartum, granular cell tumour of the breast, and localized amyloid tumour of the breast.

As used herein, the term "malignant breast lesion" refers to changes in breast tissue which result in said breast tissue having the capability of uncontrolled division and replication. Some malignant lesions can develop the ability to invade and spear to nearby tissue and/or other regions of the host. In some examples, such metastasis can be seen to involve the vascular or lymphatic system. As used herein, the term "malignant breast lesion" is synonymous with the term "breast cancer". Common types of malignant breast lesions can include, but are not limited to, ductal carcinoma, medullary carcinoma, intraductal carcinoma, mucinous (colloid) carcinoma, tubular (well-differentiated) carcinoma, adenoid cystic carcinoma, papillary carcinoma, intracystic carcinoma, micropapillary carcinoma, secretory carcinoma, apocrine carcinoma, lobular carcinoma, inflammatory carcinoma, Paget's disease, metaplastic carcinoma, squamous cell carcinoma of the breast, radiation- and chemotherapy-induced changes of the breast, phyllodes tumour and sarcomas of the breast.

As used herein the term "treatment", refers to any and all uses which remedy a disease state or symptoms, prevent the establishment of disease, or otherwise prevent, hinder, retard, or reverse the progression of disease or other undesirable symptoms in any way whatsoever. Treatments can be used separately or in combination with other treatment modalities. Such treatments can be, but not limited to, chemotherapy, hormone therapy, immunotherapy, radiation therapy, stem cell transplant, surgery, and targeted therapy.

As used herein, the term "anti-breast cancer compound" can include, but is not limited to, raloxifene hydrochloride, tamoxifen citrate, abemaciclib, paclitaxel, ado-trastuzumab emtansine, alpelisib, anastrozole, pamidronate disodium, exemestane, atezolizumab, capecitabine, cyclophosphamide, docetaxel, doxorubicin hydrochloride, epirubicin hydrochloride, fam-trastuzumab deruxtecan-nxki, everolimus, fluorouracil, toremifene, letrozole, fulvestrant, gemcitabine hydrochloride, goserelin acetate, eribulin mesylate, trastuzumab, hyaluronidase-oysk, herceptin trastuzumab, palbociclib, ixabepilone, pembrolizumab, ribociclib, lapatinib ditosylate, olaparib, margetuximab-cmkb, megestrol acetate, methotrexate sodium, neratinib maleate, pertuzumab, hyaluronidase-zzxf, sacituzumab govitecan-hziy, talazoparib tosylate, thiotepa, tucatinib and vinblastine sulfate.

DETAILED DESCRIPTION OF THE PRESENT INVENTION

Despite being the standard for breast cancer screening, mammography has high occurrences of false positive results and is ineffective in distinguishing between benign breast lesion from breast cancer. This illustrates a need for statistically reliable and minimally invasive screening method for early breast cancer treatment and management. Liquid biopsies have enabled cancer diagnostics, therapeutics and monitoring by providing a minimally invasive clinical modality, and thereby enabling real-time personalized molecular profiling.

As disclosed herein, methods using or based on miRNA expression levels are described to determine whether a subject is suffering from, or is at risk of developing breast cancer. In one example, methods using miRNA expression levels and/or prediction scores are described to determine whether a subject is suffering from, or is at risk of developing malignant breast lesion, compared to a control. Also disclosed herein are methods using miRNA panels to determine whether a subject is suffering from, or is at risk of developing breast cancer, compared to a control. In further examples, methods using miRNA panels are described to determine whether a subject is suffering from, or is at risk of developing malignant breast lesion, compared to a control.

In another example, the present disclosure describes a method for determining whether a subject is suffering from breast cancer, the method comprising measuring the expression level of at least two or more miRNA selected from the group disclosed herein, wherein differential expression of miRNA expression in the sample, as compared to a control, determines the subject to have breast cancer. Also disclosed herein is a method for determining whether a subject is suffering from benign or malignant breast lesion, the method comprising measuring the expression level of at least two or more miRNA selected from the group as disclosed herein in a sample obtained from the subject, wherein differential expression of miRNA expression in the sample, as compared to a control, determines the subject to have breast cancer.

In some examples, the present disclosure refers to a method for determining whether a breast lesion in a subject is malignant or benign, the method comprising: measuring the expression level of at least one or more miRNA as disclosed herein in a sample obtained from the subject, wherein differential expression or unchanged miRNA expression level of said miRNAs in the sample, as compared to a control, determines the lesion is benign or malignant.

It has been found that the methods disclosed herein can be performed with at least two miRNAs as disclosed herein. This has been shown, for example, in Table 1 and 2, wherein it is shown that the claimed method had been exemplarily performed using two, three, four, five or six miRNA. Thus, in one example, the present disclosure describes a method for determining whether a subject is suffering from breast cancer, the method comprising measuring the expression level of at least two or more miRNA selected from the groups disclosed herein.

TABLE 1

Exemplary mean AUCs of the multivariate panels comprising combinations of 2 to 6 miRNA where one of the miRNAs were fixed and combined with 1 to 5 additional miRNAs selected from miR-451a, miR-195-5p, miR-126-5p, miR-423-3p, miR-192-5p, and miR-17-5p.

| | | mean AUC of panel with the selected miRNA | | | |
|---|---|---|---|---|---|
| No. | Fixed miRNA | 2 miRNA | 3 miRNA | 4 miRNA | 5 miRNA |
| 1 | hsa-miR-195-5p | 0.677 | 0.693 | 0.717 | 0.745 |
| 2 | hsa-miR-17-5p | 0.626 | 0.674 | 0.712 | 0.748 |
| 3 | hsa-miR-192-5p | 0.611 | 0.659 | 0.700 | 0.740 |
| 4 | hsa-miR-451a | 0.662 | 0.694 | 0.727 | 0.754 |
| 5 | hsa-miR-423-3p | 0.631 | 0.669 | 0.699 | 0.737 |
| 6 | hsa-miR-126-5p | 0.633 | 0.668 | 0.704 | 0.739 |

TABLE 2

Exemplary median AUCs of the multivariate panels comprising combinations of 2 to 6 miRNA where one of the miRNAs were fixed and combined with 1 to 5 additional miRNAs selected from miR-451a, miR-195-5p, miR-126-5p, miR-423-3p, miR-192-5p, and miR-17-5p.

| | | median AUC of panel with the selected miRNA | | | |
|---|---|---|---|---|---|
| No. | Fixed miRNA | 2 miRNA | 3 miRNA | 4 miRNA | 5 miRNA |
| 1 | hsa-miR-195-5p | 0.679 | 0.686 | 0.711 | 0.765 |
| 2 | hsa-miR-17-5p | 0.609 | 0.678 | 0.711 | 0.765 |
| 3 | hsa-miR-192-5p | 0.606 | 0.669 | 0.689 | 0.738 |
| 4 | hsa-miR-451a | 0.661 | 0.684 | 0.730 | 0.765 |
| 5 | hsa-miR-423-3p | 0.645 | 0.681 | 0.689 | 0.738 |
| 6 | hsa-miR-126-5p | 0.641 | 0.672 | 0.700 | 0.738 |

The described methods can be performed with the expressional levels of selected miRNAs identified herein in the multi-centre two-cohort study as described in the experimental section. The miRNAs identified can be found in, for example, FIG. 1C and Table 3.

TABLE 3

| Exemplary 6-miRNA biomarker panel | | | |
|---|---|---|---|
| six-miRNA panel | Coefficient | P-value | Log2(Fold change) |
| hsa-miR-451a | 1.84 | 0.0004 | 0.39 |
| hsa-miR-195-5p | 0.94 | 0.0001 | 0.41 |
| hsa-miR-126-5p | 0.45 | 0.01 | 0.17 |
| hsa-miR-423-3p | 0.13 | 0.40 | −0.09 |
| hsa-miR-192-5p | −0.49 | 0.57 | −0.07 |
| hsa-miR-17-5p | −2.36 | 0.10 | 0.10 |

In some examples, the methods disclosed herein comprise measuring at least 3, at least 4, at least 5, at least 6, at least 7, at least 8, at least 9, at least 10, at least 11, or 12 miRNAs.

In one example, the at least two miRNAs are, but are not limited to, the following combinations: miR-451a, miR-195-5p; miR-451a, miR-126-5p; miR-451a, miR-423-3p; miR-451a, miR-192-5p; miR-451a, miR-17-5p; miR-451a, miR- 125b-5p; miR-451a, miR-660-5p; miR-451a, miR-25-3p; miR-451a, miR-143-3p; miR-451a, miR-363-3p; miR-451a, miR-338-3p; miR-195-5p, miR-126-5p; miR-195-5p, miR-423-3p; miR-195-5p, miR-192-5p; miR-195-5p, miR-17-5p; miR-195-5p, miR-125b-5p; miR-195-5p, miR-660-5p; miR-195-5p, miR-25-3p; miR-195-5p, miR-143-3p; miR-195-5p, miR-363-3p; miR-195-5p, miR-338-3p; miR-126-5p, miR-423-3p; miR-126-5p, miR-192-5p; miR-126-5p, miR-17-5p; miR-126-5p, miR-125b-5p; miR-126-5p, miR-660-5p; miR-126-5p, miR-25-3p; miR-126-5p, miR-143-3p; miR-126-5p, miR-363-3p; miR-126-5p, miR-338-3p; miR-423-3p, miR-192-5p; miR-423-3p, miR-17-5p; miR-423-3p, miR-125b-5p; miR-423-3p, miR-660-5p; miR-423-3p, miR-25-3p; miR-423-3p, miR-143-3p; miR-423-3p, miR-363-3p; miR-423-3p, miR-338-3p; miR-192-5p, miR-17-5p; miR-192-5p, miR-125b-5p; miR-192-5p, miR-660-5p; miR-192-5p, miR-25-3p; miR-192-5p, miR-143-3p; miR-192-5p, miR-363-3p; miR-192-5p, miR-338-3p; miR-17-5p, miR-125b-5p; miR-17-5p, miR-660-5p; miR-17-5p, miR-25-3p; miR-17-5p, miR-143-3p; miR-17-5p, miR-363-3p; miR-17-5p, miR-338-3p; miR-125b-5p, miR-660-5p; miR-125b-5p, miR-25-3p; miR-125b-5p, miR-143-3p; miR-125b-5p, miR-363-3p; miR-125b-5p, miR-338-3p; miR-660-5p, miR-25-3p; miR-660-5p, miR-143-3p; miR-660-5p, miR-363-3p; miR-660-5p, miR-338-3p; miR-25-3p, miR-143-3p; miR-25-3p, miR-363-3p; miR-25-3p, miR-338-3p; miR-143-3p, miR-363-3p; miR-143-3p, miR-338-3p; or miR-363-3p, miR-338-3p.

In one example, the at least three miRNAs are, but are not limited to, the following combinations: miR-451a, miR-195-5p, miR-126-5p; miR-451a, miR-195-5p, miR-423-3p; miR-451a, miR-195-5p, miR-192-5p; miR-451a, miR-195-5p, miR-17-5p; miR-451a, miR-195-5p, miR-125b-5p; miR-451a, miR-195-5p, miR-660-5p; miR-451a, miR-195-5p, miR-25-3p; miR-451a, miR-195-5p, miR-143-3p; miR-451a, miR-195-5p, miR-363-3p; miR-451a, miR-195-5p, miR-338-3p; miR-451a, miR-126-5p, miR-423-3p; miR-451a, miR-126-5p, miR-192-5p; miR-451a, miR-126-5p, miR-17-5p; miR-451a, miR-126-5p, miR-125b-5p; miR-451a, miR-126-5p, miR-660-5p; miR-451a, miR-126-5p, miR-25-3p; miR-451a, miR-126-5p, miR-143-3p; miR-451a, miR-126-5p, miR-363-3p; miR-451a, miR-126-5p, miR-338-3p; miR-451a, miR-423-3p, miR-192-5p; miR-451a, miR-423-3p, miR-17-5p; miR-451a, miR-423-3p, miR-125b-5p; miR-451a, miR-423-3p, miR-660-5p; miR-451a, miR-423-3p, miR-25-3p; miR-451a, miR-423-3p, miR-143-3p; miR-451a, miR-423-3p, miR-363-3p; miR-451a, miR-423-3p, miR-338-3p; miR-451a, miR-192-5p, miR-17-5p; miR-451a, miR-192-5p, miR-125b-5p; miR-451a, miR-192-5p, miR-660-5p; miR-451a, miR-192-5p, miR-25-3p; miR-451a, miR-192-5p, miR-143-3p; miR-451a, miR-192-5p, miR-363-3p; miR-451a, miR-192-5p, miR-338-3p; miR-451a, miR-17-5p, miR-125b-5p; miR-451a, miR-17-5p, miR-660-5p; miR-451a, miR-17-5p, miR-25-3p; miR-451a, miR-17-5p, miR-143-3p; miR-451a, miR-17-5p, miR-363-3p; miR-451a, miR-17-5p, miR-338-3p; miR-451a, miR-125b-5p, miR-660-5p; miR-451a, miR-125b-5p, miR-25-3p; miR-451a, miR-125b-5p, miR-143-3p; miR-451a, miR-125b-5p, miR-363-3p; miR-451a, miR-125b-5p, miR-338-3p; miR-451a, miR-660-5p, miR-25-3p; miR-451a, miR-660-5p, miR-143-3p; miR-451a, miR-660-5p, miR-363-3p; miR-451a, miR-660-5p, miR-338-3p; miR-451a, miR-25-3p, miR-143-3p; miR-451a, miR-25-3p, miR-363-3p; miR-451a, miR-25-3p, miR-338-3p; miR-451a, miR-143-3p, miR-363-3p; miR-451a, miR-143-3p, miR-338-3p; miR-451a, miR-363-3p, miR-338-3p; miR-195-5p, miR-126-5p, miR-423-3p; miR-195-5p, miR-126-5p, miR-192-5p; miR-195-5p, miR-126-5p, miR-17-5p; miR-195-5p, miR-126-5p, miR-125b-5p; miR-195-5p, miR-126-5p, miR-660-5p; miR-195-5p, miR-126-5p, miR-25-3p; miR-195-5p, miR-126-5p, miR-143-3p; miR-195-5p, miR-126-5p, miR-363-3p; miR-195-5p, miR-126-5p, miR-338-3p; miR-195-5p, miR-423-3p, miR-192-5p; miR-195-5p, miR-423-3p, miR-17-5p; miR-195-5p, miR-423-3p, miR-125b-5p; miR-195-5p, miR-423-3p, miR-660-5p; miR-195-5p, miR-423-3p, miR-25-3p; miR-195-5p, miR-423-3p, miR-143-3p; miR-195-5p, miR-423-3p, miR-363-3p; miR-195-5p, miR-423-3p, miR-338-3p; miR-195-5p, miR-192-5p, miR-17-5p; miR-195-5p, miR-192-5p, miR-125b-5p; miR-195-5p, miR-192-5p, miR-660-5p; miR-195-5p, miR-192-5p, miR-25-3p; miR-195-5p, miR-192-5p, miR-143-3p; miR-195-5p, miR-192-5p, miR-363-3p; miR-195-5p, miR-192-5p, miR-338-3p; miR-195-5p, miR-17-5p, miR-125b-5p; miR-195-5p, miR-17-5p, miR-660-5p; miR-195-5p, miR-17-5p, miR-25-3p; miR-195-5p, miR-17-5p, miR-143-3p; miR-195-5p, miR-17-5p, miR-363-3p; miR-195-5p, miR-17-5p, miR-338-3p; miR-195-5p, miR-125b-5p, miR-660-5p; miR-195-5p, miR-125b-5p, miR-25-3p; miR-195-5p, miR-125b-5p, miR-143-3p; miR-195-5p, miR-125b-5p, miR-363-3p; miR-195-5p, miR-125b-5p, miR-338-3p; miR-195-5p, miR-660-5p, miR-25-3p; miR-195-5p, miR-660-5p, miR-143-3p; miR-195-5p, miR-660-5p, miR-363-3p; miR-195-5p, miR-660-5p, miR-338-3p; miR-195-5p, miR-25-3p, miR-143-3p; miR-195-5p, miR-25-3p, miR-363-3p; miR-195-5p, miR-25-3p, miR-338-3p; miR-195-5p, miR-143-3p, miR-363-3p; miR-195-5p, miR-143-3p, miR-338-3p; miR-195-5p, miR-363-3p, miR-338-3p; miR-126-5p, miR-423-3p, miR-192-5p; miR-126-5p, miR-423-3p, miR-17-5p; miR-126-5p, miR-423-3p, miR-125b-5p; miR-126-5p, miR-423-3p, miR-660-5p; miR-126-5p, miR-423-3p, miR-25-3p; miR-126-5p, miR-423-3p, miR-143-3p; miR-126-5p, miR-423-3p, miR-363-3p; miR-126-5p, miR-423-3p, miR-338-3p; miR-126-5p, miR-192-5p, miR-17-5p; miR-126-5p, miR-192-5p, miR-125b-5p; miR-126-5p, miR-192-5p, miR-660-5p; miR-126-5p, miR-192-5p, miR-25-3p; miR-126-5p, miR-192-5p, miR-143-3p; miR-126-5p, miR-192-5p, miR-363-3p; miR-126-5p, miR-192-5p, miR-338-3p; miR-126-5p, miR-17-5p, miR-125b-5p; miR-126-5p, miR-17-5p, miR-660-5p; miR-126-5p, miR-17-5p, miR-25-3p; miR-126-5p, miR-17-5p, miR-143-3p; miR-126-5p, miR-17-5p, miR-363-3p; miR-126-5p, miR-17-5p, miR-338-3p; miR-126-5p, miR-125b-5p, miR-660-5p; miR-126-5p, miR-125b-5p, miR-25-3p; miR-126-5p, miR-125b-5p, miR-143-3p; miR-126-5p, miR-125b-5p, miR-363-3p; miR-126-5p, miR-125b-5p, miR-338-3p; miR-126-5p, miR-660-5p, miR-25-3p; miR-126-5p, miR-660-5p, miR-143-3p; miR-126-5p, miR-660-5p, miR-363-3p; miR-126-5p, miR-660-5p, miR-338-3p; miR-126-5p, miR-25-3p, miR-143-3p; miR-126-5p, miR-25-3p, miR-363-3p; miR-126-5p, miR-25-3p, miR-338-3p; miR-126-5p, miR-143-3p, miR-363-3p; miR-126-5p, miR-143-3p, miR-338-3p; miR-126-5p, miR-363-3p, miR-338-3p; miR-423-3p, miR-192-5p, miR-17-5p; miR-423-3p, miR-192-5p, miR-125b-5p; miR-423-3p, miR-192-5p, miR-660-5p; miR-423-3p, miR-192-5p, miR-25-3p; miR-423-3p, miR-192-5p, miR-143-3p; miR-423-3p, miR-192-5p, miR-363-3p; miR-423-3p, miR-192-5p, miR-338-3p; miR-423-3p, miR-17-5p, miR-125b-5p; miR-423-3p, miR-17-5p, miR-660-5p; miR-423-3p, miR-17-5p, miR-25-3p; miR-423-3p, miR-17-5p, miR-143-3p; miR-423-3p, miR-17-5p, miR-363-3p; miR-423-3p, miR-17-5p, miR-338-3p; miR-423-3p, miR-125b-5p, miR-660-5p; miR-423-3p, miR-125b-5p, miR-25-3p; miR-423-3p, miR-125b-5p, miR-143-3p; miR-423-3p, miR-125b-5p, miR-363-3p; miR-423-3p, miR-125b-5p, miR-338-3p; miR-423-3p, miR-660-

5p, miR-25-3p; miR-423-3p, miR-660-5p, miR-143-3p; miR-423-3p, miR-660-5p, miR-363-3p; miR-423-3p, miR-660-5p, miR-338-3p; miR-423-3p, miR-25-3p, miR-143-3p; miR-423-3p, miR-25-3p, miR-363-3p; miR-423-3p, miR-25-3p, miR-338-3p; miR-423-3p, miR-143-3p, miR-363-3p; miR-423-3p, miR-143-3p, miR-338-3p; miR-423-3p, miR-363-3p, miR-338-3p; miR-192-5p, miR-17-5p, miR-125b-5p; miR-192-5p, miR-17-5p, miR-660-5p; miR-192-5p, miR-17-5p, miR-25-3p; miR-192-5p, miR-17-5p, miR-143-3p; miR-192-5p, miR-17-5p, miR-363-3p; miR-192-5p, miR-17-5p, miR-338-3p; miR-192-5p, miR-125b-5p, miR-660-5p; miR-192-5p, miR-125b-5p, miR-25-3p; miR-192-5p, miR-125b-5p, miR-143-3p; miR-192-5p, miR-125b-5p, miR-363-3p; miR-192-5p, miR-125b-5p, miR-338-3p; miR-192-5p, miR-660-5p, miR-25-3p; miR-192-5p, miR-660-5p, miR-143-3p; miR-192-5p, miR-660-5p, miR-363-3p; miR-192-5p, miR-660-5p, miR-338-3p; miR-192-5p, miR-25-3p, miR-143-3p; miR-192-5p, miR-25-3p, miR-363-3p; miR-192-5p, miR-25-3p, miR-338-3p; miR-192-5p, miR-143-3p, miR-363-3p; miR-192-5p, miR-143-3p, miR-338-3p; miR-192-5p, miR-363-3p, miR-338-3p; miR-17-5p, miR-125b-5p, miR-660-5p; miR-17-5p, miR-125b-5p, miR-25-3p; miR-17-5p, miR-125b-5p, miR-143-3p; miR-17-5p, miR-125b-5p, miR-363-3p; miR-17-5p, miR-125b-5p, miR-338-3p; miR-17-5p, miR-660-5p, miR-25-3p; miR-17-5p, miR-660-5p, miR-143-3p; miR-17-5p, miR-660-5p, miR-363-3p; miR-17-5p, miR-660-5p, miR-338-3p; miR-17-5p, miR-25-3p, miR-143-3p; miR-17-5p, miR-25-3p, miR-363-3p; miR-17-5p, miR-25-3p, miR-338-3p; miR-17-5p, miR-143-3p, miR-363-3p; miR-17-5p, miR-143-3p, miR-338-3p; miR-17-5p, miR-363-3p, miR-338-3p; miR-125b-5p, miR-660-5p, miR-25-3p; miR-125b-5p, miR-660-5p, miR-143-3p; miR-125b-5p, miR-660-5p, miR-363-3p; miR-125b-5p, miR-660-5p, miR-338-3p; miR-125b-5p, miR-25-3p, miR-143-3p; miR-125b-5p, miR-25-3p, miR-363-3p; miR-125b-5p, miR-25-3p, miR-338-3p; miR-125b-5p, miR-143-3p, miR-363-3p; miR-125b-5p, miR-143-3p, miR-338-3p; miR-125b-5p, miR-363-3p, miR-338-3p; miR-660-5p, miR-25-3p, miR-143-3p; miR-660-5p, miR-25-3p, miR-363-3p; miR-660-5p, miR-25-3p, miR-338-3p; miR-660-5p, miR-143-3p, miR-363-3p; miR-660-5p, miR-143-3p, miR-338-3p; miR-660-5p, miR-363-3p, miR-338-3p; miR-25-3p, miR-143-3p, miR-363-3p; miR-25-3p, miR-143-3p, miR-338-3p; or miR-25-3p, miR-363-3p, miR-338-3p; miR-143-3p, miR-363-3p, miR-338-3p.

In one example, the at least four miRNAs are, but are not limited to, the following combinations: miR-451a, miR-195-5p, miR-126-5p, miR-423-3p; miR-451a, miR-195-5p, miR-126-5p, miR-192-5p; miR-451a, miR-195-5p, miR-126-5p, miR-17-5p; miR-451a, miR-195-5p, miR-126-5p, miR-125b-5p; miR-451a, miR-195-5p, miR-126-5p, miR-660-5p; miR-451a, miR-195-5p, miR-126-5p, miR-25-3p; miR-451a, miR-195-5p, miR-126-5p, miR-143-3p; miR-451a, miR-195-5p, miR-126-5p, miR-363-3p; miR-451a, miR-195-5p, miR-126-5p, miR-338-3p; miR-451a, miR-195-5p, miR-423-3p, miR-192-5p; miR-451a, miR-195-5p, miR-423-3p, miR-17-5p; miR-451a, miR-195-5p, miR-423-3p, miR-125b-5p; miR-451a, miR-195-5p, miR-423-3p, miR-660-5p; miR-451a, miR-195-5p, miR-423-3p, miR-25-3p; miR-451a, miR-195-5p, miR-423-3p, miR-143-3p; miR-451a, miR-195-5p, miR-423-3p, miR-363-3p; miR-451a, miR-195-5p, miR-423-3p, miR-338-3p; miR-451a, miR-195-5p, miR-192-5p, miR-17-5p; miR-451a, miR-195-5p, miR-192-5p, miR-125b-5p; miR-451a, miR-195-5p, miR-192-5p, miR-660-5p; miR-451a, miR-195-5p, miR-192-5p, miR-25-3p; miR-451a, miR-195-5p, miR-192-5p, miR-143-3p; miR-451a, miR-195-5p, miR-192-5p, miR-363-3p; miR-451a, miR-195-5p, miR-192-5p, miR-338-3p; miR-451a, miR-195-5p, miR-17-5p, miR-125b-5p; miR-451a, miR-195-5p, miR-17-5p, miR-660-5p; miR-451a, miR-195-5p, miR-17-5p, miR-25-3p; miR-451a, miR-195-5p, miR-17-5p, miR-143-3p; miR-451a, miR-195-5p, miR-17-5p, miR-363-3p; miR-451a, miR-195-5p, miR-17-5p, miR-338-3p; miR-451a, miR-195-5p, miR-125b-5p, miR-660-5p; miR-451a, miR-195-5p, miR-125b-5p, miR-25-3p; miR-451a, miR-195-5p, miR-125b-5p, miR-143-3p; miR-451a, miR-195-5p, miR-125b-5p, miR-363-3p; miR-451a, miR-195-5p, miR-125b-5p, miR-338-3p; miR-451a, miR-195-5p, miR-660-5p, miR-25-3p; miR-451a, miR-195-5p, miR-660-5p, miR-143-3p; miR-451a, miR-195-5p, miR-660-5p, miR-363-3p; miR-451a, miR-195-5p, miR-660-5p, miR-338-3p; miR-451a, miR-195-5p, miR-25-3p, miR-143-3p; miR-451a, miR-195-5p, miR-25-3p, miR-363-3p; miR-451a, miR-195-5p, miR-25-3p, miR-338-3p; miR-451a, miR-195-5p, miR-143-3p, miR-363-3p; miR-451a, miR-195-5p, miR-143-3p, miR-338-3p; miR-451a, miR-195-5p, miR-363-3p, miR-338-3p; miR-451a, miR-126-5p, miR-423-3p, miR-192-5p; miR-451a, miR-126-5p, miR-423-3p, miR-17-5p; miR-451a, miR-126-5p, miR-423-3p, miR-125b-5p; miR-451a, miR-126-5p, miR-423-3p, miR-660-5p; miR-451a, miR-126-5p, miR-423-3p, miR-25-3p; miR-451a, miR-126-5p, miR-423-3p, miR-143-3p; miR-451a, miR-126-5p, miR-423-3p, miR-363-3p; miR-451a, miR-126-5p, miR-423-3p, miR-338-3p; miR-451a, miR-126-5p, miR-192-5p, miR-17-5p; miR-451a, miR-126-5p, miR-192-5p, miR-125b-5p; miR-451a, miR-126-5p, miR-192-5p, miR-660-5p; miR-451a, miR-126-5p, miR-192-5p, miR-25-3p; miR-451a, miR-126-5p, miR-192-5p, miR-143-3p; miR-451a, miR-126-5p, miR-192-5p, miR-363-3p; miR-451a, miR-126-5p, miR-192-5p, miR-338-3p; miR-451a, miR-126-5p, miR-17-5p, miR-125b-5p; miR-451a, miR-126-5p, miR-17-5p, miR-660-5p; miR-451a, miR-126-5p, miR-17-5p, miR-25-3p; miR-451a, miR-126-5p, miR-17-5p, miR-143-3p; miR-451a, miR-126-5p, miR-17-5p, miR-363-3p; miR-451a, miR-126-5p, miR-17-5p, miR-338-3p; miR-451a, miR-126-5p, miR-125b-5p, miR-660-5p; miR-451a, miR-126-5p, miR-125b-5p, miR-25-3p; miR-451a, miR-126-5p, miR-125b-5p, miR-143-3p; miR-451a, miR-126-5p, miR-125b-5p, miR-363-3p; miR-451a, miR-126-5p, miR-125b-5p, miR-338-3p; miR-451a, miR-126-5p, miR-660-5p, miR-25-3p; miR-451a, miR-126-5p, miR-660-5p, miR-143-3p; miR-451a, miR-126-5p, miR-660-5p, miR-363-3p; miR-451a, miR-126-5p, miR-660-5p, miR-338-3p; miR-451a, miR-126-5p, miR-25-3p, miR-143-3p; miR-451a, miR-126-5p, miR-25-3p, miR-363-3p; miR-451a, miR-126-5p, miR-25-3p, miR-338-3p; miR-451a, miR-126-5p, miR-143-3p, miR-363-3p; miR-451a, miR-126-5p, miR-143-3p, miR-338-3p; miR-451a, miR-126-5p, miR-363-3p, miR-338-3p; miR-451a, miR-423-3p, miR-192-5p, miR-17-5p; miR-451a, miR-423-3p, miR-192-5p, miR-125b-5p; miR-451a, miR-423-3p, miR-192-5p, miR-660-5p; miR-451a, miR-423-3p, miR-192-5p, miR-25-3p; miR-451a, miR-423-3p, miR-192-5p, miR-143-3p; miR-451a, miR-423-3p, miR-192-5p, miR-363-3p; miR-451a, miR-423-3p, miR-192-5p, miR-338-3p; miR-451a, miR-423-3p, miR-17-5p, miR-125b-5p; miR-451a, miR-423-3p, miR-17-5p, miR-660-5p; miR-451a, miR-423-3p, miR-17-5p, miR-25-3p; miR-451a, miR-423-3p, miR-17-5p, miR-143-3p; miR-451a, miR-423-3p, miR-17-5p, miR-363-3p; miR-451a, miR-423-3p, miR-17-5p, miR-338-3p; miR-451a, miR-423-3p, miR-125b-5p, miR-660-5p; miR-451a, miR-423-3p, miR-125b-5p, miR-25-3p; miR-451a, miR-423-3p, miR-125b-5p, miR-143-3p; miR-451a, miR-423-3p, miR-125b-5p, miR-363-3p; miR-451a, miR-423-3p, miR-125b-5p, miR-338-3p; miR-451a, miR-423-3p, miR-660-5p, miR-25-3p; miR-451a, miR-423-3p, miR-660-5p, miR-143-3p; miR-451a, miR-423-3p, miR-660-5p, miR-363-3p; miR-451a, miR-423-3p, miR-660-5p, miR-338-3p; miR-451a, miR-423-3p, miR-25-3p, miR-143-3p; miR-451a, miR-423-3p, miR-25-3p, miR-363-3p; miR-451a, miR-423-3p, miR-25-3p, miR-338-3p; miR-451a, miR-423-3p, miR-143-3p, miR-363-3p; miR-451a, miR-423-3p, miR-143-3p, miR-338-3p; miR-451a, miR-423-3p, miR-363-3p, miR-338-3p; miR-451a, miR-192-5p, miR-17-5p, miR-125b-5p; miR-451a, miR-192-5p, miR-17-5p, miR-660-5p; miR-451a, miR-192-5p, miR-17-5p, miR-25-3p; miR-451a, miR-192-5p, miR-17-5p, miR-143-3p; miR-451a, miR-192-5p, miR-17-5p, miR-363-3p; miR-451a, miR-192-5p, miR-17-5p, miR-338-3p; miR-451a, miR-192-5p, miR-125b-5p, miR-660-5p; miR-451a, miR-192-5p, miR-125b-5p, miR-25-3p; miR-451a, miR-192-5p, miR-125b-5p, miR-143-3p; miR-451a, miR-192-5p, miR-125b-5p, miR-363-3p; miR-451a, miR-192-5p, miR-125b-5p, miR-338-3p; miR-451a, miR-192-5p, miR-660-5p, miR-25-3p; miR-451a, miR-192-5p, miR-660-5p, miR-143-3p; miR-451a, miR-192-5p, miR-660-5p, miR-363-3p; miR-451a, miR-192-5p, miR-660-5p, miR-338-3p; miR-451a, miR-192-5p, miR-25-3p, miR-143-3p; miR-451a, miR-192-5p, miR-25-3p, miR-363-3p; miR-451a, miR-192-5p, miR-25-3p, miR-338-3p; miR-451a, miR-192-5p, miR-143-3p, miR-363-3p; miR-451a, miR-192-5p, miR-143-3p, miR-338-3p; miR-451a, miR-192-5p, miR-363-3p, miR-338-3p; miR-451a, miR-17-5p, miR-125b-5p, miR-660-5p; miR-451a, miR-17-5p, miR-125b-5p, miR-25-3p; miR-451a, miR-17-5p, miR-125b-5p, miR-143-3p; miR-451a, miR-17-5p, miR-125b-5p, miR-363-3p; miR-451a, miR-17-5p, miR-125b-5p, miR-338-3p; miR-451a, miR-17-5p, miR-660-5p, miR-25-3p; miR-451a, miR-17-5p, miR-660-5p, miR-143-3p; miR-451a, miR-17-5p, miR-660-5p, miR-363-3p; miR-451a, miR-17-5p, miR-660-5p, miR-338-3p; miR-451a, miR-17-5p, miR-25-3p, miR-143-3p; miR-451a, miR-17-5p, miR-25-3p, miR-363-3p; miR-451a, miR-17-5p, miR-25-3p, miR-338-3p; miR-451a, miR-17-5p, miR-143-3p, miR-363-3p; miR-451a, miR-17-5p, miR-143-3p, miR-338-3p; miR-451a, miR-17-5p, miR-363-3p, miR-338-3p; miR-451a, miR-125b-5p, miR-660-5p, miR-25-3p; miR-451a, miR-125b-5p, miR-660-5p, miR-143-3p; miR-451a, miR-125b-5p, miR-660-5p, miR-363-3p; miR-451a, miR-125b-5p, miR-660-5p, miR-338-3p; miR-451a, miR-125b-5p, miR-25-3p, miR-143-3p; miR-451a, miR-125b-5p, miR-25-3p, miR-363-3p; miR-451a, miR-125b-5p, miR-25-3p, miR-338-3p; miR-451a, miR-125b-5p, miR-143-3p, miR-363-3p; miR-451a, miR-125b-5p, miR-143-3p, miR-338-3p; miR-451a, miR-125b-5p, miR-363-3p, miR-338-3p; miR-451a, miR-660-5p, miR-25-3p, miR-143-3p; miR-451a, miR-660-5p, miR-25-3p, miR-363-3p; miR-451a, miR-660-5p, miR-25-3p, miR-338-3p; miR-451a, miR-660-5p, miR-143-3p, miR-363-3p; miR-451a, miR-660-5p, miR-143-3p, miR-338-3p; miR-451a, miR-660-5p, miR-363-3p, miR-338-3p; miR-451a, miR-25-3p, miR-143-3p, miR-363-3p; miR-451a, miR-25-3p, miR-143-3p, miR-338-3p; miR-451a, miR-25-3p, miR-363-3p, miR-338-3p; miR-451a, miR-143-3p, miR-363-3p, miR-338-3p; miR-195-5p, miR-126-5p, miR-423-3p, miR-192-5p; miR-195-5p, miR-126-5p, miR-423-3p, miR-17-5p; miR-195-5p, miR-126-5p, miR-423-3p, miR-125b-5p; miR-195-5p, miR-126-5p, miR-423-3p, miR-660-5p; miR-195-5p, miR-126-5p, miR-423-3p, miR-25-3p; miR-195-5p, miR-126-5p, miR-423-3p, miR-143-3p; miR-195-5p, miR-126-5p, miR-423-3p, miR-363-3p; miR-195-5p, miR-126-5p, miR-423-3p, miR-338-3p; miR-195-5p, miR-126-5p, miR-192-5p, miR-17-5p; miR-195-5p, miR-126-5p, miR-192-5p, miR-125b-5p; miR-195-5p, miR-126-5p, miR-192-5p, miR-660-5p; miR-195-5p, miR-126-5p, miR-192-5p, miR-25-3p; miR-195-5p, miR-126-5p, miR-192-5p, miR-143-3p; miR-195-5p, miR-126-5p, miR-192-5p, miR-363-3p; miR-195-5p, miR-126-5p, miR-192-5p, miR-338-3p; miR-195-5p, miR-126-5p, miR-17-5p, miR-125b-5p; miR-195-5p, miR-126-5p, miR-17-5p, miR-660-5p; miR-195-5p, miR-126-5p, miR-17-5p, miR-25-3p; miR-195-5p, miR-126-5p, miR-17-5p, miR-143-3p; miR-195-5p, miR-126-5p, miR-17-5p, miR-363-3p; miR-195-5p, miR-126-5p, miR-17-5p, miR-338-3p; miR-195-5p, miR-126-5p, miR-125b-5p, miR-660-5p; miR-195-5p, miR-126-5p, miR-125b-5p, miR-25-3p; miR-195-5p, miR-126-5p, miR-125b-5p, miR-143-3p; miR-195-5p, miR-126-5p, miR-125b-5p, miR-363-3p; miR-195-5p, miR-126-5p, miR-125b-5p, miR-338-3p; miR-195-5p, miR-126-5p, miR-660-5p, miR-25-3p; miR-195-5p, miR-126-5p, miR-660-5p, miR-143-3p; miR-195-5p, miR-126-5p, miR-660-5p, miR-363-3p; miR-195-5p, miR-126-5p, miR-660-5p, miR-338-3p; miR-195-5p, miR-126-5p, miR-25-3p, miR-143-3p; miR-195-5p, miR-126-5p, miR-25-3p, miR-363-3p; miR-195-5p, miR-126-5p, miR-25-3p, miR-338-3p; miR-195-5p, miR-126-5p, miR-143-3p, miR-363-3p; miR-195-5p, miR-126-5p, miR-143-3p, miR-338-3p; miR-195-5p, miR-126-5p, miR-363-3p, miR-338-3p; miR-195-5p, miR-423-3p, miR-192-5p, miR-17-5p; miR-195-5p, miR-423-3p, miR-192-5p, miR-125b-5p; miR-195-5p, miR-423-3p, miR-192-5p, miR-660-5p; miR-195-5p, miR-423-3p, miR-192-5p, miR-25-3p; miR-195-5p, miR-423-3p, miR-192-5p, miR-143-3p; miR-195-5p, miR-423-3p, miR-192-5p, miR-363-3p; miR-195-5p, miR-423-3p, miR-192-5p, miR-338-3p; miR-195-5p, miR-423-3p, miR-17-5p, miR-125b-5p; miR-195-5p, miR-423-3p, miR-17-5p, miR-660-5p; miR-195-5p, miR-423-3p, miR-17-5p, miR-25-3p; miR-195-5p, miR-423-3p, miR-17-5p, miR-143-3p; miR-195-5p, miR-423-3p, miR-17-5p, miR-363-3p; miR-195-5p, miR-423-3p, miR-17-5p, miR-338-3p; miR-195-5p, miR-423-3p, miR-125b-5p, miR-660-5p; miR-195-5p, miR-423-3p, miR-125b-5p, miR-25-3p; miR-195-5p, miR-423-3p, miR-125b-5p, miR-143-3p; miR-195-5p, miR-423-3p, miR-125b-5p, miR-363-3p; miR-195-5p, miR-423-3p, miR-125b-5p, miR-338-3p; miR-195-5p, miR-423-3p, miR-660-5p, miR-25-3p; miR-195-5p, miR-423-3p, miR-660-5p, miR-143-3p; miR-195-5p, miR-423-3p, miR-660-5p, miR-363-3p; miR-195-5p, miR-423-3p, miR-660-5p, miR-338-3p; miR-195-5p, miR-423-3p, miR-25-3p, miR-143-3p; miR-195-5p, miR-423-3p, miR-25-3p, miR-363-3p; miR-195-5p, miR-423-3p, miR-25-3p, miR-338-3p; miR-195-5p, miR-423-3p, miR-143-3p, miR-363-3p; miR-195-5p, miR-423-3p, miR-143-3p, miR-338-3p; miR-195-5p, miR-423-3p, miR-363-3p, miR-338-3p; miR-195-5p, miR-192-5p, miR-17-5p, miR-125b-5p; miR-195-5p, miR-192-5p, miR-17-5p, miR-660-5p; miR-195-5p, miR-192-5p, miR-17-5p, miR-25-3p; miR-195-5p, miR-192-5p, miR-17-5p, miR-143-3p; miR-195-5p, miR-192-5p, miR-17-5p, miR-363-3p; miR-195-5p, miR-192-5p, miR-17-5p, miR-338-3p; miR-195-5p, miR-192-5p, miR-125b-5p, miR-660-5p; miR-195-5p, miR-192-5p, miR-125b-5p, miR-25-3p; miR-195-5p, miR-192-5p, miR-125b-5p, miR-143-3p; miR-195-5p, miR-192-5p, miR-125b-5p, miR-363-3p; miR-195-5p, miR-192-5p, miR-125b-5p, miR-338-3p; miR-195-5p, miR-192-5p, miR-660-5p, miR-25-3p; miR-195-5p, miR-192-5p, miR-660-5p, miR-143-3p; miR-195-5p, miR-192-5p, miR-660-5p, miR-363-3p; miR-195-5p, miR-192-5p, miR-660-5p, miR-338-3p; miR-195-5p, miR-192-5p, miR-25-3p, miR-143-3p; miR-195-5p, miR-192-5p, miR-25-3p, miR-363-3p; miR-195-5p, miR-192-5p, miR-25-3p, miR-338-3p; miR-195-5p, miR-192-5p, miR-143-3p, miR-363-

3p; miR-195-5p, miR-192-5p, miR-143-3p, miR-338-3p; miR-195-5p, miR-192-5p, miR-363-3p, miR-338-3p; miR-195-5p, miR-17-5p, miR-125b-5p, miR-660-5p; miR-195-5p, miR-17-5p, miR-125b-5p, miR-25-3p; miR-195-5p, miR-17-5p, miR-125b-5p, miR-143-3p; miR-195-5p, miR-17-5p, miR-125b-5p, miR-363-3p; miR-195-5p, miR-17-5p, miR-125b-5p, miR-338-3p; miR-195-5p, miR-17-5p, miR-660-5p, miR-25-3p; miR-195-5p, miR-17-5p, miR-660-5p, miR-143-3p; miR-195-5p, miR-17-5p, miR-660-5p, miR-363-3p; miR-195-5p, miR-17-5p, miR-660-5p, miR-338-3p; miR-195-5p, miR-17-5p, miR-25-3p, miR-143-3p; miR-195-5p, miR-17-5p, miR-25-3p, miR-363-3p; miR-195-5p, miR-17-5p, miR-25-3p, miR-338-3p; miR-195-5p, miR-17-5p, miR-143-3p, miR-363-3p; miR-195-5p, miR-17-5p, miR-143-3p, miR-338-3p; miR-195-5p, miR-17-5p, miR-363-3p, miR-338-3p; miR-195-5p, miR-125b-5p, miR-660-5p, miR-25-3p; miR-195-5p, miR-125b-5p, miR-660-5p, miR-143-3p; miR-195-5p, miR-125b-5p, miR-660-5p, miR-363-3p; miR-195-5p, miR-125b-5p, miR-660-5p, miR-338-3p; miR-195-5p, miR-125b-5p, miR-25-3p, miR-143-3p; miR-195-5p, miR-125b-5p, miR-25-3p, miR-363-3p; miR-195-5p, miR-125b-5p, miR-25-3p, miR-338-3p; miR-195-5p, miR-125b-5p, miR-143-3p, miR-363-3p; miR-195-5p, miR-125b-5p, miR-143-3p, miR-338-3p; miR-195-5p, miR-125b-5p, miR-363-3p, miR-338-3p; miR-195-5p, miR-660-5p, miR-25-3p, miR-143-3p; miR-195-5p, miR-660-5p, miR-25-3p, miR-363-3p; miR-195-5p, miR-660-5p, miR-25-3p, miR-338-3p; miR-195-5p, miR-660-5p, miR-143-3p, miR-363-3p; miR-195-5p, miR-660-5p, miR-143-3p, miR-338-3p; miR-195-5p, miR-660-5p, miR-363-3p, miR-338-3p; miR-195-5p, miR-25-3p, miR-143-3p, miR-363-3p; miR-195-5p, miR-25-3p, miR-143-3p, miR-338-3p; miR-195-5p, miR-25-3p, miR-363-3p, miR-338-3p; miR-195-5p, miR-143-3p, miR-363-3p, miR-338-3p; miR-126-5p, miR-423-3p, miR-192-5p, miR-17-5p; miR-126-5p, miR-423-3p, miR-192-5p, miR-125b-5p; miR-126-5p, miR-423-3p, miR-192-5p, miR-660-5p; miR-126-5p, miR-423-3p, miR-192-5p, miR-25-3p; miR-126-5p, miR-423-3p, miR-192-5p, miR-143-3p; miR-126-5p, miR-423-3p, miR-192-5p, miR-363-3p; miR-126-5p, miR-423-3p, miR-192-5p, miR-338-3p; miR-126-5p, miR-423-3p, miR-17-5p, miR-125b-5p; miR-126-5p, miR-423-3p, miR-17-5p, miR-660-5p; miR-126-5p, miR-423-3p, miR-17-5p, miR-25-3p; miR-126-5p, miR-423-3p, miR-17-5p, miR-143-3p; miR-126-5p, miR-423-3p, miR-17-5p, miR-363-3p; miR-126-5p, miR-423-3p, miR-17-5p, miR-338-3p; miR-126-5p, miR-423-3p, miR-125b-5p, miR-660-5p; miR-126-5p, miR-423-3p, miR-125b-5p, miR-25-3p; miR-126-5p, miR-423-3p, miR-125b-5p, miR-143-3p; miR-126-5p, miR-423-3p, miR-125b-5p, miR-363-3p; miR-126-5p, miR-423-3p, miR-125b-5p, miR-338-3p; miR-126-5p, miR-423-3p, miR-660-5p, miR-25-3p; miR-126-5p, miR-423-3p, miR-660-5p, miR-143-3p; miR-126-5p, miR-423-3p, miR-660-5p, miR-363-3p; miR-126-5p, miR-423-3p, miR-660-5p, miR-338-3p; miR-126-5p, miR-423-3p, miR-25-3p, miR-143-3p; miR-126-5p, miR-423-3p, miR-25-3p, miR-363-3p; miR-126-5p, miR-423-3p, miR-25-3p, miR-338-3p; miR-126-5p, miR-423-3p, miR-143-3p, miR-363-3p; miR-126-5p, miR-423-3p, miR-143-3p, miR-338-3p; miR-126-5p, miR-423-3p, miR-363-3p, miR-338-3p; miR-126-5p, miR-192-5p, miR-17-5p, miR-125b-5p; miR-126-5p, miR-192-5p, miR-17-5p, miR-660-5p; miR-126-5p, miR-192-5p, miR-17-5p, miR-25-3p; miR-126-5p, miR-192-5p, miR-17-5p, miR-143-3p; miR-126-5p, miR-192-5p, miR-17-5p, miR-363-3p; miR-126-5p, miR-192-5p, miR-17-5p, miR-338-3p; miR-126-5p, miR-192-5p, miR-125b-5p, miR-660-5p; miR-126-5p, miR-192-5p, miR-125b-

5p, miR-143-3p; miR-126-5p, miR-192-5p, miR-125b-5p, miR-363-3p; miR-126-5p, miR-192-5p, miR-125b-5p, miR-338-3p; miR-126-5p, miR-192-5p, miR-660-5p, miR-25-3p; miR-126-5p, miR-192-5p, miR-660-5p, miR-143-3p; miR-126-5p, miR-192-5p, miR-660-5p, miR-363-3p; miR-126-5p, miR-192-5p, miR-660-5p, miR-338-3p; miR-126-5p, miR-192-5p, miR-25-3p, miR-143-3p; miR-126-5p, miR-192-5p, miR-25-3p, miR-363-3p; miR-126-5p, miR-192-5p, miR-25-3p, miR-338-3p; miR-126-5p, miR-192-5p, miR-143-3p, miR-363-3p; miR-126-5p, miR-192-5p, miR-143-3p, miR-338-3p; miR-126-5p, miR-192-5p, miR-363-3p, miR-338-3p; miR-126-5p, miR-17-5p, miR-125b-5p, miR-660-5p; miR-126-5p, miR-17-5p, miR-125b-5p, miR-25-3p; miR-126-5p, miR-17-5p, miR-125b-5p, miR-143-3p; miR-126-5p, miR-17-5p, miR-125b-5p, miR-363-3p; miR-126-5p, miR-17-5p, miR-125b-5p, miR-338-3p; miR-126-5p, miR-17-5p, miR-660-5p, miR-25-3p; miR-126-5p, miR-17-5p, miR-660-5p, miR-143-3p; miR-126-5p, miR-17-5p, miR-660-5p, miR-363-3p; miR-126-5p, miR-17-5p, miR-660-5p, miR-338-3p; miR-126-5p, miR-17-5p, miR-25-3p, miR-143-3p; miR-126-5p, miR-17-5p, miR-25-3p, miR-363-3p; miR-126-5p, miR-17-5p, miR-25-3p, miR-338-3p; miR-126-5p, miR-17-5p, miR-143-3p, miR-363-3p; miR-126-5p, miR-17-5p, miR-143-3p, miR-338-3p; miR-126-5p, miR-17-5p, miR-363-3p, miR-338-3p; miR-126-5p, miR-125b-5p, miR-660-5p, miR-25-3p; miR-126-5p, miR-125b-5p, miR-660-5p, miR-143-3p; miR-126-5p, miR-125b-5p, miR-660-5p, miR-363-3p; miR-126-5p, miR-125b-5p, miR-660-5p, miR-338-3p; miR-126-5p, miR-125b-5p, miR-25-3p, miR-143-3p; miR-126-5p, miR-125b-5p, miR-25-3p, miR-363-3p; miR-126-5p, miR-125b-5p, miR-25-3p, miR-338-3p; miR-126-5p, miR-125b-5p, miR-143-3p, miR-363-3p; miR-126-5p, miR-125b-5p, miR-143-3p, miR-338-3p; miR-126-5p, miR-125b-5p, miR-363-3p, miR-338-3p; miR-126-5p, miR-660-5p, miR-25-3p, miR-143-3p; miR-126-5p, miR-660-5p, miR-25-3p, miR-363-3p; miR-126-5p, miR-660-5p, miR-25-3p, miR-338-3p; miR-126-5p, miR-660-5p, miR-143-3p, miR-363-3p; miR-126-5p, miR-660-5p, miR-143-3p, miR-338-3p; miR-126-5p, miR-660-5p, miR-363-3p, miR-338-3p; miR-126-5p, miR-25-3p, miR-143-3p, miR-363-3p; miR-126-5p, miR-25-3p, miR-143-3p, miR-338-3p; miR-126-5p, miR-25-3p, miR-363-3p, miR-338-3p; miR-126-5p, miR-143-3p, miR-363-3p, miR-338-3p; miR-423-3p, miR-192-5p, miR-17-5p, miR-125b-5p; miR-423-3p, miR-192-5p, miR-17-5p, miR-660-5p; miR-423-3p, miR-192-5p, miR-17-5p, miR-25-3p; miR-423-3p, miR-192-5p, miR-17-5p, miR-143-3p; miR-423-3p, miR-192-5p, miR-17-5p, miR-363-3p; miR-423-3p, miR-192-5p, miR-17-5p, miR-338-3p; miR-423-3p, miR-192-5p, miR-125b-5p, miR-660-5p; miR-423-3p, miR-192-5p, miR-125b-5p, miR-25-3p; miR-423-3p, miR-192-5p, miR-125b-5p, miR-143-3p; miR-423-3p, miR-192-5p, miR-125b-5p, miR-363-3p; miR-423-3p, miR-192-5p, miR-125b-5p, miR-338-3p; miR-423-3p, miR-192-5p, miR-660-5p, miR-25-3p; miR-423-3p, miR-192-5p, miR-660-5p, miR-143-3p; miR-423-3p, miR-192-5p, miR-660-5p, miR-363-3p; miR-423-3p, miR-192-5p, miR-660-5p, miR-338-3p; miR-423-3p, miR-192-5p, miR-25-3p, miR-143-3p; miR-423-3p, miR-192-5p, miR-25-3p, miR-363-3p; miR-423-3p, miR-192-5p, miR-25-3p, miR-338-3p; miR-423-3p, miR-192-5p, miR-143-3p, miR-363-3p; miR-423-3p, miR-192-5p, miR-143-3p, miR-338-3p; miR-423-3p, miR-192-5p, miR-363-3p, miR-338-3p; miR-423-3p, miR-17-5p, miR-125b-5p, miR-660-5p; miR-423-3p, miR-17-5p, miR-125b-5p, miR-25-3p; miR-423-3p, miR-17-5p, miR-125b-5p, miR-143-3p; miR-423-3p, miR-17-5p, miR-125b-5p, miR-363-3p; miR-423-3p, miR-17-5p, miR-125b-5p, miR-338-3p; miR-423-3p, miR- 17-5p, miR-660-5p, miR-25-3p; miR-423-3p, miR-17-5p, miR-660-5p, miR-143-3p; miR-423-3p, miR-17-5p, miR-660-5p, miR-363-3p; miR-423-3p, miR-17-5p, miR-660-5p, miR-338-3p; miR-423-3p, miR-17-5p, miR-25-3p, miR-143-3p; miR-423-3p, miR-17-5p, miR-25-3p, miR-363-3p; miR-423-3p, miR-17-5p, miR-25-3p, miR-338-3p; miR-423-3p, miR-17-5p, miR-143-3p, miR-363-3p; miR-423-3p, miR-17-5p, miR-143-3p, miR-338-3p; miR-423-3p, miR-17-5p, miR-363-3p, miR-338-3p; miR-423-3p, miR-125b-5p, miR-660-5p, miR-25-3p; miR-423-3p, miR-125b-5p, miR-660-5p, miR-143-3p; miR-423-3p, miR-125b-5p, miR-660-5p, miR-363-3p; miR-423-3p, miR-125b-5p, miR-660-5p, miR-338-3p; miR-423-3p, miR-125b-5p, miR-25-3p, miR-143-3p; miR-423-3p, miR-125b-5p, miR-25-3p, miR-363-3p; miR-423-3p, miR-125b-5p, miR-25-3p, miR-338-3p; miR-423-3p, miR-125b-5p, miR-143-3p, miR-363-3p; miR-423-3p, miR-125b-5p, miR-143-3p, miR-338-3p; miR-423-3p, miR-125b-5p, miR-363-3p, miR-338-3p; miR-423-3p, miR-660-5p, miR-25-3p, miR-143-3p; miR-423-3p, miR-660-5p, miR-25-3p, miR-363-3p; miR-423-3p, miR-660-5p, miR-25-3p, miR-338-3p; miR-423-3p, miR-660-5p, miR-143-3p, miR-363-3p; miR-423-3p, miR-660-5p, miR-143-3p, miR-338-3p; miR-423-3p, miR-660-5p, miR-363-3p, miR-338-3p; miR-423-3p, miR-25-3p, miR-143-3p, miR-363-3p; miR-423-3p, miR-25-3p, miR-143-3p, miR-338-3p; miR-423-3p, miR-25-3p, miR-363-3p, miR-338-3p; miR-423-3p, miR-143-3p, miR-363-3p, miR-338-3p; miR-192-5p, miR-17-5p, miR-125b-5p, miR-660-5p; miR-192-5p, miR-17-5p, miR-125b-5p, miR-25-3p; miR-192-5p, miR-17-5p, miR-125b-5p, miR-143-3p; miR-192-5p, miR-17-5p, miR-125b-5p, miR-363-3p; miR-192-5p, miR-17-5p, miR-125b-5p, miR-338-3p; miR-192-5p, miR-17-5p, miR-660-5p, miR-25-3p; miR-192-5p, miR-17-5p, miR-660-5p, miR-143-3p; miR-192-5p, miR-17-5p, miR-660-5p, miR-363-3p; miR-192-5p, miR-17-5p, miR-660-5p, miR-338-3p; miR-192-5p, miR-17-5p, miR-25-3p, miR-143-3p; miR-192-5p, miR-17-5p, miR-25-3p, miR-363-3p; miR-192-5p, miR-17-5p, miR-25-3p, miR-338-3p; miR-192-5p, miR-17-5p, miR-143-3p, miR-363-3p; miR-192-5p, miR-17-5p, miR-143-3p, miR-338-3p; miR-192-5p, miR-17-5p, miR-363-3p, miR-338-3p; miR-192-5p, miR-125b-5p, miR-660-5p, miR-25-3p; miR-192-5p, miR-125b-5p, miR-660-5p, miR-143-3p; miR-192-5p, miR-125b-5p, miR-660-5p, miR-363-3p; miR-192-5p, miR-125b-5p, miR-660-5p, miR-338-3p; miR-192-5p, miR-125b-5p, miR-25-3p, miR-143-3p; miR-192-5p, miR-125b-5p, miR-25-3p, miR-363-3p; miR-192-5p, miR-125b-5p, miR-25-3p, miR-338-3p; miR-192-5p, miR-125b-5p, miR-143-3p, miR-363-3p; miR-192-5p, miR-125b-5p, miR-143-3p, miR-338-3p; miR-192-5p, miR-125b-5p, miR-363-3p, miR-338-3p; miR-192-5p, miR-660-5p, miR-25-3p, miR-143-3p; miR-192-5p, miR-660-5p, miR-25-3p, miR-363-3p; miR-192-5p, miR-660-5p, miR-25-3p, miR-338-3p; miR-192-5p, miR-660-5p, miR-143-3p, miR-363-3p; miR-192-5p, miR-660-5p, miR-143-3p, miR-338-3p; miR-192-5p, miR-660-5p, miR-363-3p, miR-338-3p; miR-192-5p, miR-25-3p, miR-143-3p, miR-363-3p; miR-192-5p, miR-25-3p, miR-143-3p, miR-338-3p; miR-192-5p, miR-25-3p, miR-363-3p, miR-338-3p; miR-192-5p, miR-143-3p, miR-363-3p, miR-338-3p; miR-17-5p, miR-125b-5p, miR-660-5p, miR-25-3p; miR-17-5p, miR-125b-5p, miR-660-5p, miR-143-3p; miR-17-5p, miR-125b-5p, miR-660-5p, miR-363-3p; miR-17-5p, miR-125b-5p, miR-660-5p, miR-338-3p; miR-17-5p, miR-125b-5p, miR-25-3p, miR-143-3p; miR-17-5p, miR-125b-5p, miR-25-3p, miR-363-3p; miR-17-5p, miR-125b-5p, miR-25-3p, miR-338-3p; miR-17-5p, miR-125b-5p, miR-143-3p, miR-363-3p; miR-17-5p, miR-125b-5p, miR-143-3p, miR-338-3p; miR-17-5p, miR-125b-5p, miR-363-3p, miR-338-3p; miR-17-5p, miR-660-5p, miR-25-3p, miR-143-3p; miR-17-5p, miR-660-5p, miR-25-3p, miR-363-3p; miR-17-5p, miR-660-5p, miR-25-3p, miR-338-3p; miR-17-5p, miR-660-5p, miR-143-3p, miR-363-3p; miR-17-5p, miR-660-5p, miR-143-3p, miR-338-3p; miR-17-5p, miR-660-5p, miR-363-3p, miR-338-3p; miR-17-5p, miR-25-3p, miR-143-3p, miR-363-3p; miR-17-5p, miR-25-3p, miR-143-3p, miR-338-3p; miR-17-5p, miR-25-3p, miR-363-3p, miR-338-3p; miR-17-5p, miR-143-3p, miR-363-3p, miR-338-3p; miR-125b-5p, miR-660-5p, miR-25-3p, miR-143-3p; miR-125b-5p, miR-660-5p, miR-25-3p, miR-363-3p; miR-125b-5p, miR-660-5p, miR-25-3p, miR-338-3p; miR-125b-5p, miR-660-5p, miR-143-3p, miR-363-3p; miR-125b-5p, miR-660-5p, miR-143-3p, miR-338-3p; miR-125b-5p, miR-660-5p, miR-363-3p, miR-338-3p; miR-125b-5p, miR-25-3p, miR-143-3p, miR-363-3p; miR-125b-5p, miR-25-3p, miR-143-3p, miR-338-3p; miR-125b-5p, miR-25-3p, miR-363-3p, miR-338-3p; miR-125b-5p, miR-143-3p, miR-363-3p, miR-338-3p; miR-660-5p, miR-25-3p, miR-143-3p, miR-363-3p; miR-660-5p, miR-25-3p, miR-143-3p, miR-338-3p; miR-660-5p, miR-25-3p, miR-363-3p, miR-338-3p; or miR-660-5p, miR-143-3p, miR-363-3p, miR-338-3p; miR-25-3p, miR-143-3p, miR-363-3p, miR-338-3p.

In one example, the at least five miRNAs are, but are not limited to, the following combinations: miR-451a, miR-195-5p, miR-126-5p, miR-423-3p, miR-192-5p; miR-451a, miR-195-5p, miR-126-5p, miR-423-3p, miR-17-5p; miR-451a, miR-195-5p, miR-126-5p, miR-423-3p, miR-125b-5p; miR-451a, miR-195-5p, miR-126-5p, miR-423-3p, miR-660-5p; miR-451a, miR-195-5p, miR-126-5p, miR-423-3p, miR-25-3p; miR-451a, miR-195-5p, miR-126-5p, miR-423-3p, miR-143-3p; miR-451a, miR-195-5p, miR-126-5p, miR-423-3p, miR-363-3p; miR-451a, miR-195-5p, miR-126-5p, miR-423-3p, miR-338-3p; miR-451a, miR-195-5p, miR-126-5p, miR-192-5p, miR-17-5p; miR-451a, miR-195-5p, miR-126-5p, miR-192-5p, miR-125b-5p; miR-451a, miR-195-5p, miR-126-5p, miR-192-5p, miR-660-5p; miR-451a, miR-195-5p, miR-126-5p, miR-192-5p, miR-25-3p; miR-451a, miR-195-5p, miR-126-5p, miR-192-5p, miR-143-3p; miR-451a, miR-195-5p, miR-126-5p, miR-192-5p, miR-363-3p; miR-451a, miR-195-5p, miR-126-5p, miR-192-5p, miR-338-3p; miR-451a, miR-195-5p, miR-126-5p, miR-17-5p, miR-125b-5p; miR-451a, miR-195-5p, miR-126-5p, miR-17-5p, miR-660-5p; miR-451a, miR-195-5p, miR-126-5p, miR-17-5p, miR-25-3p; miR-451a, miR-195-5p, miR-126-5p, miR-17-5p, miR-143-3p; miR-451a, miR-195-5p, miR-126-5p, miR-17-5p, miR-363-3p; miR-451a, miR-195-5p, miR-126-5p, miR-17-5p, miR-338-3p; miR-451a, miR-195-5p, miR-126-5p, miR-125b-5p, miR-660-5p; miR-451a, miR-195-5p, miR-126-5p, miR-125b-5p, miR-25-3p; miR-451a, miR-195-5p, miR-126-5p, miR-125b-5p, miR-143-3p; miR-451a, miR-195-5p, miR-126-5p, miR-125b-5p, miR-363-3p; miR-451a, miR-195-5p, miR-126-5p, miR-125b-5p, miR-338-3p; miR-451a, miR-195-5p, miR-126-5p, miR-660-5p, miR-25-3p; miR-451a, miR-195-5p, miR-126-5p, miR-660-5p, miR-143-3p; miR-451a, miR-195-5p, miR-126-5p, miR-660-5p, miR-363-3p; miR-451a, miR-195-5p, miR-126-5p, miR-660-5p, miR-338-3p; miR-451a, miR-195-5p, miR-126-5p, miR-25-3p, miR-143-3p; miR-451a, miR-195-5p, miR-126-5p, miR-25-3p, miR-363-3p; miR-451a, miR-195-5p, miR-126-5p, miR-25-3p, miR-338-3p; miR-451a, miR-195-5p, miR-126-5p, miR-143-3p, miR-363-3p; miR-451a, miR-195-5p, miR-126-5p, miR-143-3p, miR-338-3p; miR-451a, miR-195-5p, miR-126-5p, miR-363-3p, miR-338-3p; miR-451a, miR-195-5p, miR-423-3p, miR-192-5p, miR-17-5p; miR-451a, miR-195-5p, miR-423-

3p, miR-192-5p, miR-125b-5p; miR-451a, miR-195-5p, miR-423-3p, miR-192-5p, miR-660-5p; miR-451a, miR-195-5p, miR-423-3p, miR-192-5p, miR-25-3p; miR-451a, miR-195-5p, miR-423-3p, miR-192-5p, miR-143-3p; miR-451a, miR-195-5p, miR-423-3p, miR-192-5p, miR-363-3p; miR-451a, miR-195-5p, miR-423-3p, miR-192-5p, miR-338-3p; miR-451a, miR-195-5p, miR-423-3p, miR-17-5p, miR-125b-5p; miR-451a, miR-195-5p, miR-423-3p, miR-17-5p, miR-660-5p; miR-451a, miR-195-5p, miR-423-3p, miR-17-5p, miR-25-3p; miR-451a, miR-195-5p, miR-423-3p, miR-17-5p, miR-143-3p; miR-451a, miR-195-5p, miR-423-3p, miR-17-5p, miR-363-3p; miR-451a, miR-195-5p, miR-423-3p, miR-17-5p, miR-338-3p; miR-451a, miR-195-5p, miR-423-3p, miR-125b-5p, miR-660-5p; miR-451a, miR-195-5p, miR-423-3p, miR-125b-5p, miR-25-3p; miR-451a, miR-195-5p, miR-423-3p, miR-125b-5p, miR-143-3p; miR-451a, miR-195-5p, miR-423-3p, miR-125b-5p, miR-363-3p; miR-451a, miR-195-5p, miR-423-3p, miR-125b-5p, miR-338-3p; miR-451a, miR-195-5p, miR-423-3p, miR-660-5p, miR-25-3p; miR-451a, miR-195-5p, miR-423-3p, miR-660-5p, miR-143-3p; miR-451a, miR-195-5p, miR-423-3p, miR-660-5p, miR-363-3p; miR-451a, miR-195-5p, miR-423-3p, miR-660-5p, miR-338-3p; miR-451a, miR-195-5p, miR-423-3p, miR-25-3p, miR-143-3p; miR-451a, miR-195-5p, miR-423-3p, miR-25-3p, miR-363-3p; miR-451a, miR-195-5p, miR-423-3p, miR-25-3p, miR-338-3p; miR-451a, miR-195-5p, miR-423-3p, miR-143-3p, miR-363-3p; miR-451a, miR-195-5p, miR-423-3p, miR-143-3p, miR-338-3p; miR-451a, miR-195-5p, miR-423-3p, miR-363-3p, miR-338-3p; miR-451a, miR-195-5p, miR-192-5p, miR-17-5p, miR-125b-5p; miR-451a, miR-195-5p, miR-192-5p, miR-17-5p, miR-660-5p; miR-451a, miR-195-5p, miR-192-5p, miR-17-5p, miR-25-3p; miR-451a, miR-195-5p, miR-192-5p, miR-17-5p, miR-143-3p; miR-451a, miR-195-5p, miR-192-5p, miR-17-5p, miR-363-3p; miR-451a, miR-195-5p, miR-192-5p, miR-17-5p, miR-338-3p; miR-451a, miR-195-5p, miR-192-5p, miR-125b-5p, miR-660-5p; miR-451a, miR-195-5p, miR-192-5p, miR-125b-5p, miR-25-3p; miR-451a, miR-195-5p, miR-192-5p, miR-125b-5p, miR-143-3p; miR-451a, miR-195-5p, miR-192-5p, miR-125b-5p, miR-363-3p; miR-451a, miR-195-5p, miR-192-5p, miR-125b-5p, miR-338-3p; miR-451a, miR-195-5p, miR-192-5p, miR-660-5p, miR-25-3p; miR-451a, miR-195-5p, miR-192-5p, miR-660-5p, miR-143-3p; miR-451a, miR-195-5p, miR-192-5p, miR-660-5p, miR-363-3p; miR-451a, miR-195-5p, miR-192-5p, miR-660-5p, miR-338-3p; miR-451a, miR-195-5p, miR-192-5p, miR-25-3p, miR-143-3p; miR-451a, miR-195-5p, miR-192-5p, miR-25-3p, miR-363-3p; miR-451a, miR-195-5p, miR-192-5p, miR-25-3p, miR-338-3p; miR-451a, miR-195-5p, miR-192-5p, miR-143-3p, miR-363-3p; miR-451a, miR-195-5p, miR-192-5p, miR-143-3p, miR-338-3p; miR-451a, miR-195-5p, miR-192-5p, miR-363-3p, miR-338-3p; miR-451a, miR-195-5p, miR-17-5p, miR-125b-5p, miR-660-5p; miR-451a, miR-195-5p, miR-17-5p, miR-125b-5p, miR-25-3p; miR-451a, miR-195-5p, miR-17-5p, miR-125b-5p, miR-143-3p; miR-451a, miR-195-5p, miR-17-5p, miR-125b-5p, miR-363-3p; miR-451a, miR-195-5p, miR-17-5p, miR-125b-5p, miR-338-3p; miR-451a, miR-195-5p, miR-17-5p, miR-660-5p, miR-25-3p; miR-451a, miR-195-5p, miR-17-5p, miR-660-5p, miR-143-3p; miR-451a, miR-195-5p, miR-17-5p, miR-660-5p, miR-363-3p; miR-451a, miR-195-5p, miR-17-5p, miR-660-5p, miR-338-3p; miR-451a, miR-195-5p, miR-17-5p, miR-25-3p, miR-143-3p; miR-451a, miR-195-5p, miR-17-5p, miR-25-3p, miR-363-3p; miR-451a, miR-195-5p, miR-17-5p, miR-25-3p, miR-338-3p; miR-451a, miR-195-5p, miR-17-5p, miR-143-3p, miR-363-3p; miR-451a, miR-195-5p, miR-17-5p, miR-143-3p, miR-338-3p; miR-451a, miR-195-5p, miR-17-5p, miR-363-3p, miR-338-3p; miR-451a, miR-195-5p, miR-125b-5p, miR-660-5p, miR-25-3p; miR-451a, miR-195-5p, miR-125b-5p, miR-660-5p, miR-143-3p; miR-451a, miR-195-5p, miR-125b-5p, miR-660-5p, miR-363-3p; miR-451a, miR-195-5p, miR-125b-5p, miR-660-5p, miR-338-3p; miR-451a, miR-195-5p, miR-125b-5p, miR-25-3p, miR-143-3p; miR-451a, miR-195-5p, miR-125b-5p, miR-25-3p, miR-363-3p; miR-451a, miR-195-5p, miR-125b-5p, miR-25-3p, miR-338-3p; miR-451a, miR-195-5p, miR-125b-5p, miR-143-3p, miR-363-3p; miR-451a, miR-195-5p, miR-125b-5p, miR-143-3p, miR-338-3p; miR-451a, miR-195-5p, miR-125b-5p, miR-363-3p, miR-338-3p; miR-451a, miR-195-5p, miR-660-5p, miR-25-3p, miR-143-3p; miR-451a, miR-195-5p, miR-660-5p, miR-25-3p, miR-363-3p; miR-451a, miR-195-5p, miR-660-5p, miR-25-3p, miR-338-3p; miR-451a, miR-195-5p, miR-660-5p, miR-143-3p, miR-363-3p; miR-451a, miR-195-5p, miR-660-5p, miR-143-3p, miR-338-3p; miR-451a, miR-195-5p, miR-660-5p, miR-363-3p, miR-338-3p; miR-451a, miR-195-5p, miR-25-3p, miR-143-3p, miR-363-3p; miR-451a, miR-195-5p, miR-25-3p, miR-143-3p, miR-338-3p; miR-451a, miR-195-5p, miR-25-3p, miR-363-3p, miR-338-3p; miR-451a, miR-195-5p, miR-143-3p, miR-363-3p, miR-338-3p; miR-451a, miR-126-5p, miR-423-3p, miR-192-5p, miR-17-5p; miR-451a, miR-126-5p, miR-423-3p, miR-192-5p, miR-125b-5p; miR-451a, miR-126-5p, miR-423-3p, miR-192-5p, miR-660-5p; miR-451a, miR-126-5p, miR-423-3p, miR-192-5p, miR-25-3p; miR-451a, miR-126-5p, miR-423-3p, miR-192-5p, miR-143-3p; miR-451a, miR-126-5p, miR-423-3p, miR-192-5p, miR-363-3p; miR-451a, miR-126-5p, miR-423-3p, miR-192-5p, miR-338-3p; miR-451a, miR-126-5p, miR-423-3p, miR-17-5p, miR-125b-5p; miR-451a, miR-126-5p, miR-423-3p, miR-17-5p, miR-660-5p; miR-451a, miR-126-5p, miR-423-3p, miR-17-5p, miR-25-3p; miR-451a, miR-126-5p, miR-423-3p, miR-17-5p, miR-143-3p; miR-451a, miR-126-5p, miR-423-3p, miR-17-5p, miR-363-3p; miR-451a, miR-126-5p, miR-423-3p, miR-17-5p, miR-338-3p; miR-451a, miR-126-5p, miR-423-3p, miR-125b-5p, miR-660-5p; miR-451a, miR-126-5p, miR-423-3p, miR-125b-5p, miR-25-3p; miR-451a, miR-126-5p, miR-423-3p, miR-125b-5p, miR-143-3p; miR-451a, miR-126-5p, miR-423-3p, miR-125b-5p, miR-363-3p; miR-451a, miR-126-5p, miR-423-3p, miR-125b-5p, miR-338-3p; miR-451a, miR-126-5p, miR-423-3p, miR-660-5p, miR-25-3p; miR-451a, miR-126-5p, miR-423-3p, miR-660-5p, miR-143-3p; miR-451a, miR-126-5p, miR-423-3p, miR-660-5p, miR-363-3p; miR-451a, miR-126-5p, miR-423-3p, miR-660-5p, miR-338-3p; miR-451a, miR-126-5p, miR-423-3p, miR-25-3p, miR-143-3p; miR-451a, miR-126-5p, miR-423-3p, miR-25-3p, miR-363-3p; miR-451a, miR-126-5p, miR-423-3p, miR-25-3p, miR-338-3p; miR-451a, miR-126-5p, miR-423-3p, miR-143-3p, miR-363-3p; miR-451a, miR-126-5p, miR-423-3p, miR-143-3p, miR-338-3p; miR-451a, miR-126-5p, miR-423-3p, miR-363-3p, miR-338-3p; miR-451a, miR-126-5p, miR-192-5p, miR-17-5p, miR-125b-5p; miR-451a, miR-126-5p, miR-192-5p, miR-17-5p, miR-660-5p; miR-451a, miR-126-5p, miR-192-5p, miR-17-5p, miR-25-3p; miR-451a, miR-126-5p, miR-192-5p, miR-17-5p, miR-143-3p; miR-451a, miR-126-5p, miR-192-5p, miR-17-5p, miR-363-3p; miR-451a, miR-126-5p, miR-192-5p, miR-17-5p, miR-338-3p; miR-451a, miR-126-5p, miR-192-5p, miR-125b-5p, miR-660-5p; miR-451a, miR-126-5p, miR-192-5p, miR-125b-5p, miR-25-3p; miR-451a, miR-126-5p, miR-192-5p, miR-125b-5p, miR-143-3p; miR-451a, miR-126-5p, miR-192-5p, miR-125b-5p, miR-363-3p; miR-451a, miR-126-5p, miR-192-5p, miR-125b-5p, miR-338-3p; miR-451a, miR-126-5p, miR-192-5p, miR-660-5p, miR-25-3p; miR-451a, miR-126-5p, miR-192-5p, miR-660-5p, miR-143-3p; miR-451a, miR-126-5p, miR-192-5p, miR-660-5p, miR-363-3p; miR-451a, miR-126-5p, miR-192-5p, miR-660-5p, miR-338-3p; miR-451a, miR-126-5p, miR-192-5p, miR-25-3p, miR-143-3p; miR-451a, miR-126-5p, miR-192-5p, miR-25-3p, miR-363-3p; miR-451a, miR-126-5p, miR-192-5p, miR-25-3p, miR-338-3p; miR-451a, miR-126-5p, miR-192-5p, miR-143-3p, miR-363-3p; miR-451a, miR-126-5p, miR-192-5p, miR-143-3p, miR-338-3p; miR-451a, miR-126-5p, miR-192-5p, miR-363-3p, miR-338-3p; miR-451a, miR-126-5p, miR-17-5p, miR-125b-5p, miR-660-5p; miR-451a, miR-126-5p, miR-17-5p, miR-125b-5p, miR-25-3p; miR-451a, miR-126-5p, miR-17-5p, miR-125b-5p, miR-143-3p; miR-451a, miR-126-5p, miR-17-5p, miR-125b-5p, miR-363-3p; miR-451a, miR-126-5p, miR-17-5p, miR-125b-5p, miR-338-3p; miR-451a, miR-126-5p, miR-17-5p, miR-660-5p, miR-25-3p; miR-451a, miR-126-5p, miR-17-5p, miR-660-5p, miR-143-3p; miR-451a, miR-126-5p, miR-17-5p, miR-660-5p, miR-363-3p; miR-451a, miR-126-5p, miR-17-5p, miR-660-5p, miR-338-3p; miR-451a, miR-126-5p, miR-17-5p, miR-25-3p, miR-143-3p; miR-451a, miR-126-5p, miR-17-5p, miR-25-3p, miR-363-3p; miR-451a, miR-126-5p, miR-17-5p, miR-25-3p, miR-338-3p; miR-451a, miR-126-5p, miR-17-5p, miR-143-3p, miR-363-3p; miR-451a, miR-126-5p, miR-17-5p, miR-143-3p, miR-338-3p; miR-451a, miR-126-5p, miR-17-5p, miR-363-3p, miR-338-3p; miR-451a, miR-126-5p, miR-125b-5p, miR-660-5p, miR-25-3p; miR-451a, miR-126-5p, miR-125b-5p, miR-660-5p, miR-143-3p; miR-451a, miR-126-5p, miR-125b-5p, miR-660-5p, miR-363-3p; miR-451a, miR-126-5p, miR-125b-5p, miR-660-5p, miR-338-3p; miR-451a, miR-126-5p, miR-125b-5p, miR-25-3p, miR-143-3p; miR-451a, miR-126-5p, miR-125b-5p, miR-25-3p, miR-363-3p; miR-451a, miR-126-5p, miR-125b-5p, miR-25-3p, miR-338-3p; miR-451a, miR-126-5p, miR-125b-5p, miR-143-3p, miR-363-3p; miR-451a, miR-126-5p, miR-125b-5p, miR-143-3p, miR-338-3p; miR-451a, miR-126-5p, miR-125b-5p, miR-363-3p, miR-338-3p; miR-451a, miR-126-5p, miR-660-5p, miR-25-3p, miR-143-3p; miR-451a, miR-126-5p, miR-660-5p, miR-25-3p, miR-363-3p; miR-451a, miR-126-5p, miR-660-5p, miR-25-3p, miR-338-3p; miR-451a, miR-126-5p, miR-660-5p, miR-143-3p, miR-363-3p; miR-451a, miR-126-5p, miR-660-5p, miR-143-3p, miR-338-3p; miR-451a, miR-126-5p, miR-660-5p, miR-363-3p, miR-338-3p; miR-451a, miR-126-5p, miR-25-3p, miR-143-3p, miR-363-3p; miR-451a, miR-126-5p, miR-25-3p, miR-143-3p, miR-338-3p; miR-451a, miR-126-5p, miR-25-3p, miR-363-3p, miR-338-3p; miR-451a, miR-126-5p, miR-143-3p, miR-363-3p, miR-338-3p; miR-451a, miR-423-3p, miR-192-5p, miR-17-5p, miR-125b-5p; miR-451a, miR-423-3p, miR-192-5p, miR-17-5p, miR-660-5p; miR-451a, miR-423-3p, miR-192-5p, miR-17-5p, miR-25-3p; miR-451a, miR-423-3p, miR-192-5p, miR-17-5p, miR-143-3p; miR-451a, miR-423-3p, miR-192-5p, miR-17-5p, miR-363-3p; miR-451a, miR-423-3p, miR-192-5p, miR-17-5p, miR-338-3p; miR-451a, miR-423-3p, miR-192-5p, miR-125b-5p, miR-660-5p; miR-451a, miR-423-3p, miR-192-5p, miR-125b-5p, miR-25-3p; miR-451a, miR-423-3p, miR-192-5p, miR-125b-5p, miR-143-3p; miR-451a, miR-423-3p, miR-192-5p, miR-125b-5p, miR-363-3p; miR-451a, miR-423-3p, miR-192-5p, miR-125b-5p, miR-338-3p; miR-451a, miR-423-3p, miR-192-5p, miR-660-5p, miR-25-3p; miR-451a, miR-423-3p, miR-192-5p, miR-660-5p, miR-143-3p; miR-451a, miR-423-3p, miR-192-5p, miR-660-5p, miR-363-3p; miR-451a, miR-423-3p, miR-192-5p, miR-660-5p, miR-338-3p; miR-451a, miR-423-3p, miR-192-5p, miR-25-3p, miR-143-3p; miR-451a, miR-423-3p, miR-192-5p, miR-25-3p, miR-363-3p; miR-451a, miR-423-3p, miR-192-5p, miR-25-3p, miR-338-3p; miR-451a, miR-423-3p, miR-192-5p, miR-143-3p, miR-363-3p; miR-451a, miR-423-3p, miR-192-5p, miR-143-3p, miR-338-3p; miR-451a, miR-423-3p, miR-192-5p, miR-363-3p, miR-338-3p; miR-451a, miR-423-3p, miR-17-5p, miR-125b-5p, miR-660-5p; miR-451a, miR-423-3p, miR-17-5p, miR-125b-5p, miR-25-3p; miR-451a, miR-423-3p, miR-17-5p, miR-125b-5p, miR-143-3p; miR-451a, miR-423-3p, miR-17-5p, miR-125b-5p, miR-363-3p; miR-451a, miR-423-3p, miR-17-5p, miR-125b-5p, miR-338-3p; miR-451a, miR-423-3p, miR-17-5p, miR-660-5p, miR-25-3p; miR-451a, miR-423-3p, miR-17-5p, miR-660-5p, miR-143-3p; miR-451a, miR-423-3p, miR-17-5p, miR-660-5p, miR-363-3p; miR-451a, miR-423-3p, miR-17-5p, miR-660-5p, miR-338-3p; miR-451a, miR-423-3p, miR-17-5p, miR-25-3p, miR-143-3p; miR-451a, miR-423-3p, miR-17-5p, miR-25-3p, miR-363-3p; miR-451a, miR-423-3p, miR-17-5p, miR-25-3p, miR-338-3p; miR-451a, miR-423-3p, miR-17-5p, miR-143-3p, miR-363-3p; miR-451a, miR-423-3p, miR-17-5p, miR-143-3p, miR-338-3p; miR-451a, miR-423-3p, miR-17-5p, miR-363-3p, miR-338-3p; miR-451a, miR-423-3p, miR-125b-5p, miR-660-5p, miR-25-3p; miR-451a, miR-423-3p, miR-125b-5p, miR-660-5p, miR-143-3p; miR-451a, miR-423-3p, miR-125b-5p, miR-660-5p, miR-363-3p; miR-451a, miR-423-3p, miR-125b-5p, miR-660-5p, miR-338-3p; miR-451a, miR-423-3p, miR-125b-5p, miR-25-3p, miR-143-3p; miR-451a, miR-423-3p, miR-125b-5p, miR-25-3p, miR-363-3p; miR-451a, miR-423-3p, miR-125b-5p, miR-25-3p, miR-338-3p; miR-451a, miR-423-3p, miR-125b-5p, miR-143-3p, miR-363-3p; miR-451a, miR-423-3p, miR-125b-5p, miR-143-3p, miR-338-3p; miR-451a, miR-423-3p, miR-125b-5p, miR-363-3p, miR-338-3p; miR-451a, miR-423-3p, miR-660-5p, miR-25-3p, miR-143-3p; miR-451a, miR-423-3p, miR-660-5p, miR-25-3p, miR-363-3p; miR-451a, miR-423-3p, miR-660-5p, miR-25-3p, miR-338-3p; miR-451a, miR-423-3p, miR-660-5p, miR-143-3p, miR-363-3p; miR-451a, miR-423-3p, miR-660-5p, miR-143-3p, miR-338-3p; miR-451a, miR-423-3p, miR-660-5p, miR-363-3p, miR-338-3p; miR-451a, miR-423-3p, miR-25-3p, miR-143-3p, miR-363-3p; miR-451a, miR-423-3p, miR-25-3p, miR-143-3p, miR-338-3p; miR-451a, miR-423-3p, miR-25-3p, miR-363-3p, miR-338-3p; miR-451a, miR-423-3p, miR-143-3p, miR-363-3p, miR-338-3p; miR-451a, miR-192-5p, miR-17-5p, miR-125b-5p, miR-660-5p; miR-451a, miR-192-5p, miR-17-5p, miR-125b-5p, miR-25-3p; miR-451a, miR-192-5p, miR-17-5p, miR-125b-5p, miR-143-3p; miR-451a, miR-192-5p, miR-17-5p, miR-125b-5p, miR-363-3p; miR-451a, miR-192-5p, miR-17-5p, miR-125b-5p, miR-338-3p; miR-451a, miR-192-5p, miR-17-5p, miR-660-5p, miR-25-3p; miR-451a, miR-192-5p, miR-17-5p, miR-660-5p, miR-143-3p; miR-451a, miR-192-5p, miR-17-5p, miR-660-5p, miR-363-3p; miR-451a, miR-192-5p, miR-17-5p, miR-660-5p, miR-338-3p; miR-451a, miR-192-5p, miR-17-5p, miR-25-3p, miR-143-3p; miR-451a, miR-192-5p, miR-17-5p, miR-25-3p, miR-363-3p; miR-451a, miR-192-5p, miR-17-5p, miR-25-3p, miR-338-3p; miR-451a, miR-192-5p, miR-17-5p, miR-143-3p, miR-363-3p; miR-451a, miR-192-5p, miR-17-5p, miR-143-3p, miR-338-3p; miR-451a, miR-192-5p, miR-17-5p, miR-363-3p, miR-338-3p; miR-451a, miR-192-5p, miR-125b-5p, miR-660-5p, miR-25-3p; miR-451a, miR-192-5p, miR-125b-5p, miR-660-5p, miR-143-3p; miR-451a, miR-192-5p, miR-125b-5p, miR-660-5p, miR-363-3p; miR-451a, miR-192-5p, miR-125b-5p, miR-660-5p, miR-338-3p; miR-451a, miR-192-5p, miR-125b-5p, miR-25-3p, miR-143-3p; miR-451a, miR-192-5p, miR-125b-5p, miR-25-3p, miR-363-3p; miR-451a, miR-192-5p, miR-125b-5p, miR-25-3p, miR-338-3p; miR-451a, miR-192-5p, miR-125b-5p, miR-143-3p, miR-363-3p; miR-451a, miR-192-5p, miR-125b-5p, miR-143-3p, miR-338-3p; miR-451a, miR-192-5p, miR-125b-5p, miR-363-3p, miR-338-3p; miR-451a, miR-192-5p, miR-660-5p, miR-25-3p, miR-143-3p; miR-451a, miR-192-5p, miR-660-5p, miR-25-3p, miR-363-3p; miR-451a, miR-192-5p, miR-660-5p, miR-25-3p, miR-338-3p; miR-451a, miR-192-5p, miR-660-5p, miR-143-3p, miR-363-3p; miR-451a, miR-192-5p, miR-660-5p, miR-143-3p, miR-338-3p; miR-451a, miR-192-5p, miR-660-5p, miR-363-3p, miR-338-3p; miR-451a, miR-192-5p, miR-25-3p, miR-143-3p, miR-363-3p; miR-451a, miR-192-5p, miR-25-3p, miR-143-3p, miR-338-3p; miR-451a, miR-192-5p, miR-25-3p, miR-363-3p, miR-338-3p; miR-451a, miR-192-5p, miR-143-3p, miR-363-3p, miR-338-3p; miR-451a, miR-17-5p, miR-125b-5p, miR-660-5p, miR-25-3p; miR-451a, miR-17-5p, miR-125b-5p, miR-660-5p, miR-143-3p; miR-451a, miR-17-5p, miR-125b-5p, miR-660-5p, miR-363-3p; miR-451a, miR-17-5p, miR-125b-5p, miR-660-5p, miR-338-3p; miR-451a, miR-17-5p, miR-125b-5p, miR-25-3p, miR-143-3p; miR-451a, miR-17-5p, miR-125b-5p, miR-25-3p, miR-363-3p; miR-451a, miR-17-5p, miR-125b-5p, miR-25-3p, miR-338-3p; miR-451a, miR-17-5p, miR-125b-5p, miR-143-3p, miR-363-3p; miR-451a, miR-17-5p, miR-125b-5p, miR-143-3p, miR-338-3p; miR-451a, miR-17-5p, miR-125b-5p, miR-363-3p, miR-338-3p; miR-451a, miR-17-5p, miR-660-5p, miR-25-3p, miR-143-3p; miR-451a, miR-17-5p, miR-660-5p, miR-25-3p, miR-363-3p; miR-451a, miR-17-5p, miR-660-5p, miR-25-3p, miR-338-3p; miR-451a, miR-17-5p, miR-660-5p, miR-143-3p, miR-363-3p; miR-451a, miR-17-5p, miR-660-5p, miR-143-3p, miR-338-3p; miR-451a, miR-17-5p, miR-660-5p, miR-363-3p, miR-338-3p; miR-451a, miR-17-5p, miR-25-3p, miR-143-3p, miR-363-3p; miR-451a, miR-17-5p, miR-25-3p, miR-143-3p, miR-338-3p; miR-451a, miR-17-5p, miR-25-3p, miR-363-3p, miR-338-3p; miR-451a, miR-17-5p, miR-143-3p, miR-363-3p, miR-338-3p; miR-451a, miR-125b-5p, miR-660-5p, miR-25-3p, miR-143-3p; miR-451a, miR-125b-5p, miR-660-5p, miR-25-3p, miR-363-3p; miR-451a, miR-125b-5p, miR-660-5p, miR-25-3p, miR-338-3p; miR-451a, miR-125b-5p, miR-660-5p, miR-143-3p, miR-363-3p; miR-451a, miR-125b-5p, miR-660-5p, miR-143-3p, miR-338-3p; miR-451a, miR-125b-5p, miR-660-5p, miR-363-3p, miR-338-3p; miR-451a, miR-125b-5p, miR-25-3p, miR-143-3p, miR-363-3p; miR-451a, miR-125b-5p, miR-25-3p, miR-143-3p, miR-338-3p; miR-451a, miR-125b-5p, miR-25-3p, miR-363-3p, miR-338-3p; miR-451a, miR-125b-5p, miR-143-3p, miR-363-3p, miR-338-3p; miR-451a, miR-660-5p, miR-25-3p, miR-143-3p, miR-363-3p; miR-451a, miR-660-5p, miR-25-3p, miR-143-3p, miR-338-3p; miR-451a, miR-660-5p, miR-25-3p, miR-363-3p, miR-338-3p; miR-451a, miR-660-5p, miR-143-3p, miR-363-3p, miR-338-3p; miR-451a, miR-25-3p, miR-143-3p, miR-363-3p, miR-338-3p; miR-195-5p, miR-126-5p, miR-423-3p, miR-192-5p, miR-17-5p; miR-195-5p, miR-126-5p, miR-423-3p, miR-192-5p, miR-125b-5p; miR-195-5p, miR-126-5p, miR-423-3p, miR-192-5p, miR-660-5p; miR-195-5p, miR-126-5p, miR-423-3p, miR-192-5p, miR-25-3p; miR-195-5p, miR-126-5p, miR-423-3p, miR-192-5p, miR-143-3p; miR-195-5p, miR-126-5p, miR-423-3p, miR-192-5p, miR-363-3p; miR-195-5p, miR-126-5p, miR-423-3p, miR-192-5p, miR-338-3p; miR-195-5p, miR-126-5p, miR-423-3p, miR-17-5p, miR-125b-5p; miR-195-5p, miR-126-5p, miR-423-3p, miR-17-5p, miR-660-5p; miR-195-5p, miR-126-5p, miR-423-3p, miR-17-5p, miR-25-3p; miR-195-5p, miR-126-5p, miR-423-3p, miR-17-5p, miR-143-3p; miR-195-5p, miR-126-5p, miR-423-3p, miR-17-5p, miR-363-3p; miR-195-5p, miR-126-5p, miR-423-3p, miR-17-5p, miR-338-3p; miR-195-5p, miR-126-5p, miR-423-3p, miR-125b-5p, miR-660-5p; miR-195-5p, miR-126-5p, miR-423-3p, miR-125b-5p, miR-25-3p; miR-195-5p, miR-126-5p, miR-423-3p, miR-125b-5p, miR-143-3p; miR-195-5p, miR-126-5p, miR-423-3p, miR-125b-5p, miR-363-3p; miR-195-5p, miR-126-5p, miR-423-3p, miR-125b-5p, miR-338-3p; miR-195-5p, miR-126-5p, miR-423-3p, miR-660-5p, miR-25-3p; miR-195-5p, miR-126-5p, miR-423-3p, miR-660-5p, miR-143-3p; miR-195-5p, miR-126-5p, miR-423-3p, miR-660-5p, miR-363-3p; miR-195-5p, miR-126-5p, miR-423-3p, miR-660-5p, miR-338-3p; miR-195-5p, miR-126-5p, miR-423-3p, miR-25-3p, miR-143-3p; miR-195-5p, miR-126-5p, miR-423-3p, miR-25-3p, miR-363-3p; miR-195-5p, miR-126-5p, miR-423-3p, miR-25-3p, miR-338-3p; miR-195-5p, miR-126-5p, miR-423-3p, miR-143-3p, miR-363-3p; miR-195-5p, miR-126-5p, miR-423-3p, miR-143-3p, miR-338-3p; miR-195-5p, miR-126-5p, miR-423-3p, miR-363-3p, miR-338-3p; miR-195-5p, miR-126-5p, miR-192-5p, miR-17-5p, miR-125b-5p; miR-195-5p, miR-126-5p, miR-192-5p, miR-17-5p, miR-660-5p; miR-195-5p, miR-126-5p, miR-192-5p, miR-17-5p, miR-25-3p; miR-195-5p, miR-126-5p, miR-192-5p, miR-17-5p, miR-143-3p; miR-195-5p, miR-126-5p, miR-192-5p, miR-17-5p, miR-363-3p; miR-195-5p, miR-126-5p, miR-192-5p, miR-17-5p, miR-338-3p; miR-195-5p, miR-126-5p, miR-192-5p, miR-125b-5p, miR-660-5p; miR-195-5p, miR-126-5p, miR-192-5p, miR-125b-5p, miR-25-3p; miR-195-5p, miR-126-5p, miR-192-5p, miR-125b-5p, miR-143-3p; miR-195-5p, miR-126-5p, miR-192-5p, miR-125b-5p, miR-363-3p; miR-195-5p, miR-126-5p, miR-192-5p, miR-125b-5p, miR-338-3p; miR-195-5p, miR-126-5p, miR-192-5p, miR-660-5p, miR-25-3p; miR-195-5p, miR-126-5p, miR-192-5p, miR-660-5p, miR-143-3p; miR-195-5p, miR-126-5p, miR-192-5p, miR-660-5p, miR-363-3p; miR-195-5p, miR-126-5p, miR-192-5p, miR-660-5p, miR-338-3p; miR-195-5p, miR-126-5p, miR-192-5p, miR-25-3p, miR-143-3p; miR-195-5p, miR-126-5p, miR-192-5p, miR-25-3p, miR-363-3p; miR-195-5p, miR-126-5p, miR-192-5p, miR-25-3p, miR-338-3p; miR-195-5p, miR-126-5p, miR-192-5p, miR-143-3p, miR-363-3p; miR-195-5p, miR-126-5p, miR-192-5p, miR-143-3p, miR-338-3p; miR-195-5p, miR-126-5p, miR-192-5p, miR-363-3p, miR-338-3p; miR-195-5p, miR-126-5p, miR-17-5p, miR-125b-5p, miR-660-5p; miR-195-5p, miR-126-5p, miR-17-5p, miR-125b-5p, miR-25-3p; miR-195-5p, miR-126-5p, miR-17-5p, miR-125b-5p, miR-143-3p; miR-195-5p, miR-126-5p, miR-17-5p, miR-125b-5p, miR-363-3p; miR-195-5p, miR-126-5p, miR-17-5p, miR-125b-5p, miR-338-3p; miR-195-5p, miR-126-5p, miR-17-5p, miR-660-5p, miR-25-3p; miR-195-5p, miR-126-5p, miR-17-5p, miR-660-5p, miR-143-3p; miR-195-5p, miR-126-5p, miR-17-5p, miR-660-5p, miR-363-3p; miR-195-5p, miR-126-5p, miR-17-5p, miR-660-5p, miR-338-3p; miR-195-5p, miR-126-5p, miR-17-5p, miR-25-3p, miR-143-3p; miR-195-5p, miR-126-5p, miR-17-5p, miR-25-3p, miR-363-3p; miR-195-5p, miR-126-5p, miR-17-5p, miR-25-3p, miR-338-3p; miR-195-5p, miR-126-5p, miR-17-5p, miR-143-3p, miR-363-3p; miR-195-5p, miR-126-5p, miR-17-5p, miR-143-3p, miR-338-3p; miR-195-5p, miR-126-5p, miR-17-5p, miR-363-3p, miR-338-3p; miR-195-5p, miR-126-5p, miR-125b-5p, miR-660-5p, miR-25-3p; miR-195-5p, miR-126-5p, miR-125b-5p, miR-660-5p, miR-143-3p; miR-195-5p, miR-126-5p, miR-125b-5p, miR-660-5p, miR-363-3p; miR-195-5p, miR-126-5p, miR-125b-5p, miR-660-5p, miR-338-3p; miR-195-5p, miR-126-5p, miR-125b-5p, miR-25-3p, miR-143-3p; miR-195-5p, miR-126-5p, miR-125b-5p, miR-25-3p, miR-363-

3p; miR-195-5p, miR-126-5p, miR-125b-5p, miR-25-3p, miR-338-3p; miR-195-5p, miR-126-5p, miR-125b-5p, miR-143-3p, miR-363-3p; miR-195-5p, miR-126-5p, miR-125b-5p, miR-143-3p, miR-338-3p; miR-195-5p, miR-126-5p, miR-125b-5p, miR-363-3p, miR-338-3p; miR-195-5p, miR-126-5p, miR-660-5p, miR-25-3p, miR-143-3p; miR-195-5p, miR-126-5p, miR-660-5p, miR-25-3p, miR-363-3p; miR-195-5p, miR-126-5p, miR-660-5p, miR-25-3p, miR-338-3p; miR-195-5p, miR-126-5p, miR-660-5p, miR-143-3p, miR-363-3p; miR-195-5p, miR-126-5p, miR-660-5p, miR-143-3p, miR-338-3p; miR-195-5p, miR-126-5p, miR-660-5p, miR-363-3p, miR-338-3p; miR-195-5p, miR-126-5p, miR-25-3p, miR-143-3p, miR-363-3p; miR-195-5p, miR-126-5p, miR-25-3p, miR-143-3p, miR-338-3p; miR-195-5p, miR-126-5p, miR-25-3p, miR-363-3p, miR-338-3p; miR-195-5p, miR-126-5p, miR-143-3p, miR-363-3p, miR-338-3p; miR-195-5p, miR-423-3p, miR-192-5p, miR-17-5p, miR-125b-5p; miR-195-5p, miR-423-3p, miR-192-5p, miR-17-5p, miR-660-5p; miR-195-5p, miR-423-3p, miR-192-5p, miR-17-5p, miR-25-3p; miR-195-5p, miR-423-3p, miR-192-5p, miR-17-5p, miR-143-3p; miR-195-5p, miR-423-3p, miR-192-5p, miR-17-5p, miR-363-3p; miR-195-5p, miR-423-3p, miR-192-5p, miR-17-5p, miR-338-3p; miR-195-5p, miR-423-3p, miR-192-5p, miR-125b-5p, miR-660-5p; miR-195-5p, miR-423-3p, miR-192-5p, miR-125b-5p, miR-25-3p; miR-195-5p, miR-423-3p, miR-192-5p, miR-125b-5p, miR-143-3p; miR-195-5p, miR-423-3p, miR-192-5p, miR-125b-5p, miR-363-3p; miR-195-5p, miR-423-3p, miR-192-5p, miR-125b-5p, miR-338-3p; miR-195-5p, miR-423-3p, miR-192-5p, miR-660-5p, miR-25-3p; miR-195-5p, miR-423-3p, miR-192-5p, miR-660-5p, miR-143-3p; miR-195-5p, miR-423-3p, miR-192-5p, miR-660-5p, miR-363-3p; miR-195-5p, miR-423-3p, miR-192-5p, miR-660-5p, miR-338-3p; miR-195-5p, miR-423-3p, miR-192-5p, miR-25-3p, miR-143-3p; miR-195-5p, miR-423-3p, miR-192-5p, miR-25-3p, miR-363-3p; miR-195-5p, miR-423-3p, miR-192-5p, miR-25-3p, miR-338-3p; miR-195-5p, miR-423-3p, miR-192-5p, miR-143-3p, miR-363-3p; miR-195-5p, miR-423-3p, miR-192-5p, miR-143-3p, miR-338-3p; miR-195-5p, miR-423-3p, miR-192-5p, miR-363-3p, miR-338-3p; miR-195-5p, miR-423-3p, miR-17-5p, miR-125b-5p, miR-660-5p; miR-195-5p, miR-423-3p, miR-17-5p, miR-125b-5p, miR-25-3p; miR-195-5p, miR-423-3p, miR-17-5p, miR-125b-5p, miR-143-3p; miR-195-5p, miR-423-3p, miR-17-5p, miR-125b-5p, miR-363-3p; miR-195-5p, miR-423-3p, miR-17-5p, miR-125b-5p, miR-338-3p; miR-195-5p, miR-423-3p, miR-17-5p, miR-660-5p, miR-25-3p; miR-195-5p, miR-423-3p, miR-17-5p, miR-660-5p, miR-143-3p; miR-195-5p, miR-423-3p, miR-17-5p, miR-660-5p, miR-363-3p; miR-195-5p, miR-423-3p, miR-17-5p, miR-660-5p, miR-338-3p; miR-195-5p, miR-423-3p, miR-17-5p, miR-25-3p, miR-143-3p; miR-195-5p, miR-423-3p, miR-17-5p, miR-25-3p, miR-363-3p; miR-195-5p, miR-423-3p, miR-17-5p, miR-25-3p, miR-338-3p; miR-195-5p, miR-423-3p, miR-17-5p, miR-143-3p, miR-363-3p; miR-195-5p, miR-423-3p, miR-17-5p, miR-143-3p, miR-338-3p; miR-195-5p, miR-423-3p, miR-17-5p, miR-363-3p, miR-338-3p; miR-195-5p, miR-423-3p, miR-125b-5p, miR-660-5p, miR-25-3p; miR-195-5p, miR-423-3p, miR-125b-5p, miR-660-5p, miR-143-3p; miR-195-5p, miR-423-3p, miR-125b-5p, miR-660-5p, miR-363-3p; miR-195-5p, miR-423-3p, miR-125b-5p, miR-660-5p, miR-338-3p; miR-195-5p, miR-423-3p, miR-125b-5p, miR-25-3p, miR-143-3p; miR-195-5p, miR-423-3p, miR-125b-5p, miR-25-3p, miR-363-3p; miR-195-5p, miR-423-3p, miR-125b-5p, miR-25-3p, miR-338-3p; miR-195-5p, miR-423-3p, miR-125b-5p, miR-143-3p, miR-363-3p; miR-195-5p, miR-423-3p, miR-125b-5p, miR-143-3p, miR-338-3p; miR-195-5p, miR-423-3p, miR-125b-5p, miR-363-3p, miR-338-3p; miR-195-5p, miR-423-3p, miR-660-5p, miR-25-3p, miR-143-3p; miR-195-5p, miR-423-3p, miR-660-5p, miR-25-3p, miR-363-3p; miR-195-5p, miR-423-3p, miR-660-5p, miR-25-3p, miR-338-3p; miR-195-5p, miR-423-3p, miR-660-5p, miR-143-3p, miR-338-3p; miR-195-5p, miR-423-3p, miR-660-5p, miR-363-3p, miR-338-3p; miR-195-5p, miR-423-3p, miR-25-3p, miR-143-3p, miR-363-3p; miR-195-5p, miR-423-3p, miR-25-3p, miR-143-3p, miR-338-3p; miR-195-5p, miR-423-3p, miR-25-3p, miR-363-3p, miR-338-3p; miR-195-5p, miR-423-3p, miR-143-3p, miR-363-3p, miR-338-3p; miR-195-5p, miR-192-5p, miR-17-5p, miR-125b-5p, miR-660-5p; miR-195-5p, miR-192-5p, miR-17-5p, miR-125b-5p, miR-25-3p; miR-195-5p, miR-192-5p, miR-17-5p, miR-125b-5p, miR-143-3p; miR-195-5p, miR-192-5p, miR-17-5p, miR-125b-5p, miR-363-3p; miR-195-5p, miR-192-5p, miR-17-5p, miR-125b-5p, miR-338-3p; miR-195-5p, miR-192-5p, miR-17-5p, miR-660-5p, miR-25-3p; miR-195-5p, miR-192-5p, miR-17-5p, miR-660-5p, miR-143-3p; miR-195-5p, miR-192-5p, miR-17-5p, miR-660-5p, miR-363-3p; miR-195-5p, miR-192-5p, miR-17-5p, miR-660-5p, miR-338-3p; miR-195-5p, miR-192-5p, miR-17-5p, miR-25-3p, miR-143-3p; miR-195-5p, miR-192-5p, miR-17-5p, miR-25-3p, miR-363-3p; miR-195-5p, miR-192-5p, miR-17-5p, miR-25-3p, miR-338-3p; miR-195-5p, miR-192-5p, miR-17-5p, miR-143-3p, miR-363-3p; miR-195-5p, miR-192-5p, miR-17-5p, miR-143-3p, miR-338-3p; miR-195-5p, miR-192-5p, miR-17-5p, miR-363-3p, miR-338-3p; miR-195-5p, miR-192-5p, miR-125b-5p, miR-660-5p, miR-25-3p; miR-195-5p, miR-192-5p, miR-125b-5p, miR-660-5p, miR-143-3p; miR-195-5p, miR-192-5p, miR-125b-5p, miR-660-5p, miR-363-3p; miR-195-5p, miR-192-5p, miR-125b-5p, miR-660-5p, miR-338-3p; miR-195-5p, miR-192-5p, miR-125b-5p, miR-25-3p, miR-143-3p; miR-195-5p, miR-192-5p, miR-125b-5p, miR-25-3p, miR-363-3p; miR-195-5p, miR-192-5p, miR-125b-5p, miR-25-3p, miR-338-3p; miR-195-5p, miR-192-5p, miR-125b-5p, miR-143-3p, miR-363-3p; miR-195-5p, miR-192-5p, miR-125b-5p, miR-143-3p, miR-338-3p; miR-195-5p, miR-192-5p, miR-125b-5p, miR-363-3p, miR-338-3p; miR-195-5p, miR-192-5p, miR-660-5p, miR-25-3p, miR-143-3p; miR-195-5p, miR-192-5p, miR-660-5p, miR-25-3p, miR-363-3p; miR-195-5p, miR-192-5p, miR-660-5p, miR-25-3p, miR-338-3p; miR-195-5p, miR-192-5p, miR-660-5p, miR-143-3p, miR-363-3p; miR-195-5p, miR-192-5p, miR-660-5p, miR-143-3p, miR-338-3p; miR-195-5p, miR-192-5p, miR-660-5p, miR-363-3p, miR-338-3p; miR-195-5p, miR-192-5p, miR-25-3p, miR-143-3p, miR-363-3p; miR-195-5p, miR-192-5p, miR-25-3p, miR-143-3p, miR-338-3p; miR-195-5p, miR-192-5p, miR-25-3p, miR-363-3p, miR-338-3p; miR-195-5p, miR-192-5p, miR-143-3p, miR-363-3p, miR-338-3p; miR-195-5p, miR-17-5p, miR-125b-5p, miR-660-5p, miR-25-3p; miR-195-5p, miR-17-5p, miR-125b-5p, miR-660-5p, miR-143-3p; miR-195-5p, miR-17-5p, miR-125b-5p, miR-660-5p, miR-363-3p; miR-195-5p, miR-17-5p, miR-125b-5p, miR-660-5p, miR-338-3p; miR-195-5p, miR-17-5p, miR-125b-5p, miR-25-3p, miR-143-3p; miR-195-5p, miR-17-5p, miR-125b-5p, miR-25-3p, miR-363-3p; miR-195-5p, miR-17-5p, miR-125b-5p, miR-25-3p, miR-338-3p; miR-195-5p, miR-17-5p, miR-125b-5p, miR-143-3p, miR-363-3p; miR-195-5p, miR-17-5p, miR-125b-5p, miR-143-3p, miR-338-3p; miR-195-5p, miR-17-5p, miR-125b-5p, miR-363-3p, miR-338-3p; miR-195-5p, miR-17-5p, miR-660-5p, miR-25-3p, miR-143-3p; miR-195-5p, miR-17-5p, miR-660-5p, miR-25-3p, miR-363-3p; miR-195-5p, miR-17-5p, miR-660-5p, miR-25-3p, miR-338-3p; miR-195-5p, miR-17-5p, miR-660-5p, miR-143-3p, miR-363-3p; miR-195-5p, miR-17-5p, miR-660-5p, miR-143-3p, miR-338-3p; miR-195-5p, miR-17-5p, miR-660-5p, miR-363-3p, miR-338-3p; miR-195-5p, miR-17-5p, miR-25-3p, miR-143-3p, miR-363-3p; miR-195-5p, miR-17-5p, miR-25-3p, miR-143-3p, miR-338-3p; miR-195-5p, miR-17-5p, miR-25-3p, miR-363-3p, miR-338-3p; miR-195-5p, miR-17-5p, miR-143-3p, miR-363-3p, miR-338-3p; miR-195-5p, miR-125b-5p, miR-660-5p, miR-25-3p, miR-143-3p; miR-195-5p, miR-125b-5p, miR-660-5p, miR-25-3p, miR-363-3p; miR-195-5p, miR-125b-5p, miR-660-5p, miR-25-3p, miR-338-3p; miR-195-5p, miR-125b-5p, miR-660-5p, miR-143-3p, miR-363-3p; miR-195-5p, miR-125b-5p, miR-660-5p, miR-143-3p, miR-338-3p; miR-195-5p, miR-125b-5p, miR-660-5p, miR-363-3p, miR-338-3p; miR-195-5p, miR-125b-5p, miR-25-3p, miR-143-3p, miR-363-3p; miR-195-5p, miR-125b-5p, miR-25-3p, miR-143-3p, miR-338-3p; miR-195-5p, miR-125b-5p, miR-25-3p, miR-363-3p, miR-338-3p; miR-195-5p, miR-125b-5p, miR-143-3p, miR-363-3p, miR-338-3p; miR-195-5p, miR-660-5p, miR-25-3p, miR-143-3p, miR-363-3p; miR-195-5p, miR-660-5p, miR-25-3p, miR-143-3p, miR-338-3p; miR-195-5p, miR-660-5p, miR-25-3p, miR-363-3p, miR-338-3p; miR-195-5p, miR-660-5p, miR-143-3p, miR-363-3p, miR-338-3p; miR-195-5p, miR-25-3p, miR-143-3p, miR-363-3p, miR-338-3p; miR-126-5p, miR-423-3p, miR-192-5p, miR-17-5p, miR-125b-5p; miR-126-5p, miR-423-3p, miR-192-5p, miR-17-5p, miR-660-5p; miR-126-5p, miR-423-3p, miR-192-5p, miR-17-5p, miR-25-3p; miR-126-5p, miR-423-3p, miR-192-5p, miR-17-5p, miR-143-3p; miR-126-5p, miR-423-3p, miR-192-5p, miR-17-5p, miR-363-3p; miR-126-5p, miR-423-3p, miR-192-5p, miR-17-5p, miR-338-3p; miR-126-5p, miR-423-3p, miR-192-5p, miR-125b-5p, miR-660-5p; miR-126-5p, miR-423-3p, miR-192-5p, miR-125b-5p, miR-25-3p; miR-126-5p, miR-423-3p, miR-192-5p, miR-125b-5p, miR-143-3p; miR-126-5p, miR-423-3p, miR-192-5p, miR-125b-5p, miR-363-3p; miR-126-5p, miR-423-3p, miR-192-5p, miR-125b-5p, miR-338-3p; miR-126-5p, miR-423-3p, miR-192-5p, miR-660-5p, miR-25-3p; miR-126-5p, miR-423-3p, miR-192-5p, miR-660-5p, miR-143-3p; miR-126-5p, miR-423-3p, miR-192-5p, miR-660-5p, miR-363-3p; miR-126-5p, miR-423-3p, miR-192-5p, miR-660-5p, miR-338-3p; miR-126-5p, miR-423-3p, miR-192-5p, miR-25-3p, miR-143-3p; miR-126-5p, miR-423-3p, miR-192-5p, miR-25-3p, miR-363-3p; miR-126-5p, miR-423-3p, miR-192-5p, miR-25-3p, miR-338-3p; miR-126-5p, miR-423-3p, miR-192-5p, miR-143-3p, miR-363-3p; miR-126-5p, miR-423-3p, miR-192-5p, miR-143-3p, miR-338-3p; miR-126-5p, miR-423-3p, miR-192-5p, miR-363-3p, miR-338-3p; miR-126-5p, miR-423-3p, miR-17-5p, miR-125b-5p, miR-660-5p; miR-126-5p, miR-423-3p, miR-17-5p, miR-125b-5p, miR-25-3p; miR-126-5p, miR-423-3p, miR-17-5p, miR-125b-5p, miR-143-3p; miR-126-5p, miR-423-3p, miR-17-5p, miR-125b-5p, miR-363-3p; miR-126-5p, miR-423-3p, miR-17-5p, miR-125b-5p, miR-338-3p; miR-126-5p, miR-423-3p, miR-17-5p, miR-660-5p, miR-25-3p; miR-126-5p, miR-423-3p, miR-17-5p, miR-660-5p, miR-143-3p; miR-126-5p, miR-423-3p, miR-17-5p, miR-660-5p, miR-363-3p; miR-126-5p, miR-423-3p, miR-17-5p, miR-660-5p, miR-338-3p; miR-126-5p, miR-423-3p, miR-17-5p, miR-25-3p, miR-143-3p; miR-126-5p, miR-423-3p, miR-17-5p, miR-25-3p, miR-363-3p; miR-126-5p, miR-423-3p, miR-17-5p, miR-25-3p, miR-338-3p; miR-126-5p, miR-423-3p, miR-17-5p, miR-143-3p, miR-363-3p; miR-126-5p, miR-423-3p, miR-17-5p, miR-143-3p, miR-338-3p; miR-126-5p, miR-423-3p, miR-17-5p, miR-363-3p, miR-338-3p; miR-126-5p, miR-423-3p, miR-125b-5p, miR-660-5p, miR-25-3p; miR-126-5p, miR-423-3p, miR-125b-5p, miR-660-5p, miR-143-3p; miR-126-5p, miR-423-3p, miR-125b-5p, miR-660-5p, miR-363-3p; miR-126-5p, miR-423-3p, miR-125b-5p, miR-660-5p, miR-338-3p; miR-126-5p, miR-423-3p, miR-125b-5p, miR-25-3p, miR-143-3p, miR-363-3p; miR-126-5p, miR-423-3p, miR-125b-5p, miR-25-3p, miR-338-3p; miR-126-5p, miR-423-3p, miR-125b-5p, miR-143-3p, miR-363-3p; miR-126-5p, miR-423-3p, miR-125b-5p, miR-143-3p, miR-338-3p; miR-126-5p, miR-423-3p, miR-125b-5p, miR-363-3p, miR-338-3p; miR-126-5p, miR-423-3p, miR-660-5p, miR-25-3p, miR-143-3p; miR-126-5p, miR-423-3p, miR-660-5p, miR-25-3p, miR-363-3p; miR-126-5p, miR-423-3p, miR-660-5p, miR-25-3p, miR-338-3p; miR-126-5p, miR-423-3p, miR-660-5p, miR-143-3p, miR-363-3p; miR-126-5p, miR-423-3p, miR-660-5p, miR-143-3p, miR-338-3p; miR-126-5p, miR-423-3p, miR-660-5p, miR-363-3p, miR-338-3p; miR-126-5p, miR-423-3p, miR-25-3p, miR-143-3p, miR-363-3p; miR-126-5p, miR-423-3p, miR-25-3p, miR-143-3p, miR-338-3p; miR-126-5p, miR-423-3p, miR-25-3p, miR-363-3p, miR-338-3p; miR-126-5p, miR-423-3p, miR-143-3p, miR-363-3p, miR-338-3p; miR-126-5p, miR-192-5p, miR-17-5p, miR-125b-5p, miR-660-5p; miR-126-5p, miR-192-5p, miR-17-5p, miR-125b-5p, miR-25-3p; miR-126-5p, miR-192-5p, miR-17-5p, miR-125b-5p, miR-143-3p; miR-126-5p, miR-192-5p, miR-17-5p, miR-125b-5p, miR-363-3p; miR-126-5p, miR-192-5p, miR-17-5p, miR-125b-5p, miR-338-3p; miR-126-5p, miR-192-5p, miR-17-5p, miR-660-5p, miR-25-3p; miR-126-5p, miR-192-5p, miR-17-5p, miR-660-5p, miR-143-3p; miR-126-5p, miR-192-5p, miR-17-5p, miR-660-5p, miR-363-3p; miR-126-5p, miR-192-5p, miR-17-5p, miR-660-5p, miR-338-3p; miR-126-5p, miR-192-5p, miR-17-5p, miR-25-3p, miR-143-3p; miR-126-5p, miR-192-5p, miR-17-5p, miR-25-3p, miR-363-3p; miR-126-5p, miR-192-5p, miR-17-5p, miR-25-3p, miR-338-3p; miR-126-5p, miR-192-5p, miR-17-5p, miR-143-3p, miR-363-3p; miR-126-5p, miR-192-5p, miR-17-5p, miR-143-3p, miR-338-3p; miR-126-5p, miR-192-5p, miR-17-5p, miR-363-3p, miR-338-3p; miR-126-5p, miR-192-5p, miR-125b-5p, miR-660-5p, miR-25-3p; miR-126-5p, miR-192-5p, miR-125b-5p, miR-660-5p, miR-143-3p; miR-126-5p, miR-192-5p, miR-125b-5p, miR-660-5p, miR-363-3p; miR-126-5p, miR-192-5p, miR-125b-5p, miR-660-5p, miR-338-3p; miR-126-5p, miR-192-5p, miR-125b-5p, miR-25-3p, miR-143-3p; miR-126-5p, miR-192-5p, miR-125b-5p, miR-25-3p, miR-363-3p; miR-126-5p, miR-192-5p, miR-125b-5p, miR-25-3p, miR-338-3p; miR-126-5p, miR-192-5p, miR-125b-5p, miR-143-3p, miR-363-3p; miR-126-5p, miR-192-5p, miR-125b-5p, miR-143-3p, miR-338-3p; miR-126-5p, miR-192-5p, miR-125b-5p, miR-363-3p, miR-338-3p; miR-126-5p, miR-192-5p, miR-660-5p, miR-25-3p, miR-143-3p; miR-126-5p, miR-192-5p, miR-660-5p, miR-25-3p, miR-363-3p; miR-126-5p, miR-192-5p, miR-660-5p, miR-25-3p, miR-338-3p; miR-126-5p, miR-192-5p, miR-660-5p, miR-143-3p, miR-363-3p; miR-126-5p, miR-192-5p, miR-660-5p, miR-143-3p, miR-338-3p; miR-126-5p, miR-192-5p, miR-660-5p, miR-363-3p, miR-338-3p; miR-126-5p, miR-192-5p, miR-25-3p, miR-143-3p, miR-363-3p; miR-126-5p, miR-192-5p, miR-25-3p, miR-143-3p, miR-338-3p; miR-126-5p, miR-192-5p, miR-25-3p, miR-363-3p, miR-338-3p; miR-126-5p, miR-192-5p, miR-143-3p, miR-363-3p, miR-338-3p; miR-126-5p, miR-17-5p, miR-125b-5p, miR-660-5p, miR-25-3p; miR-126-5p, miR-17-5p, miR-125b-5p, miR-660-5p, miR-143-3p; miR-126-5p, miR-17-5p, miR-125b-5p, miR-660-5p, miR-363-3p; miR-126-5p, miR-17-5p, miR-125b-5p, miR-660-5p, miR-338-3p; miR-126-5p, miR-17-5p, miR-125b-5p, miR-25-3p, miR-143-3p; miR-126-5p, miR-17-5p, miR-125b-5p, miR- 25-3p, miR-363-3p; miR-126-5p, miR-17-5p, miR-125b-5p, miR-25-3p, miR-338-3p; miR-126-5p, miR-17-5p, miR-125b-5p, miR-143-3p, miR-363-3p; miR-126-5p, miR-17-5p, miR-125b-5p, miR-143-3p, miR-338-3p; miR-126-5p, miR-17-5p, miR-125b-5p, miR-363-3p, miR-338-3p; miR-126-5p, miR-17-5p, miR-660-5p, miR-25-3p, miR-143-3p; miR-126-5p, miR-17-5p, miR-660-5p, miR-25-3p, miR-363-3p; miR-126-5p, miR-17-5p, miR-660-5p, miR-25-3p, miR-338-3p; miR-126-5p, miR-17-5p, miR-660-5p, miR-143-3p, miR-363-3p; miR-126-5p, miR-17-5p, miR-660-5p, miR-143-3p, miR-338-3p; miR-126-5p, miR-17-5p, miR-660-5p, miR-363-3p, miR-338-3p; miR-126-5p, miR-17-5p, miR-25-3p, miR-143-3p, miR-363-3p; miR-126-5p, miR-17-5p, miR-25-3p, miR-143-3p, miR-338-3p; miR-126-5p, miR-17-5p, miR-25-3p, miR-363-3p, miR-338-3p; miR-126-5p, miR-17-5p, miR-143-3p, miR-363-3p, miR-338-3p; miR-126-5p, miR-125b-5p, miR-660-5p, miR-25-3p, miR-143-3p; miR-126-5p, miR-125b-5p, miR-660-5p, miR-25-3p, miR-363-3p; miR-126-5p, miR-125b-5p, miR-660-5p, miR-25-3p, miR-338-3p; miR-126-5p, miR-125b-5p, miR-660-5p, miR-143-3p, miR-363-3p; miR-126-5p, miR-125b-5p, miR-660-5p, miR-143-3p, miR-338-3p; miR-126-5p, miR-125b-5p, miR-660-5p, miR-363-3p, miR-338-3p; miR-126-5p, miR-125b-5p, miR-25-3p, miR-143-3p, miR-363-3p; miR-126-5p, miR-125b-5p, miR-25-3p, miR-143-3p, miR-338-3p; miR-126-5p, miR-125b-5p, miR-25-3p, miR-363-3p, miR-338-3p; miR-126-5p, miR-125b-5p, miR-143-3p, miR-363-3p, miR-338-3p; miR-126-5p, miR-660-5p, miR-25-3p, miR-143-3p, miR-363-3p; miR-126-5p, miR-660-5p, miR-25-3p, miR-143-3p, miR-338-3p; miR-126-5p, miR-660-5p, miR-25-3p, miR-363-3p, miR-338-3p; miR-126-5p, miR-660-5p, miR-143-3p, miR-363-3p, miR-338-3p; miR-126-5p, miR-25-3p, miR-143-3p, miR-363-3p, miR-338-3p; miR-423-3p, miR-192-5p, miR-17-5p, miR-125b-5p, miR-660-5p; miR-423-3p, miR-192-5p, miR-17-5p, miR-125b-5p, miR-25-3p; miR-423-3p, miR-192-5p, miR-17-5p, miR-125b-5p, miR-143-3p; miR-423-3p, miR-192-5p, miR-17-5p, miR-125b-5p, miR-363-3p; miR-423-3p, miR-192-5p, miR-17-5p, miR-125b-5p, miR-338-3p; miR-423-3p, miR-192-5p, miR-17-5p, miR-660-5p, miR-25-3p; miR-423-3p, miR-192-5p, miR-17-5p, miR-660-5p, miR-143-3p; miR-423-3p, miR-192-5p, miR-17-5p, miR-660-5p, miR-363-3p; miR-423-3p, miR-192-5p, miR-17-5p, miR-660-5p, miR-338-3p; miR-423-3p, miR-192-5p, miR-17-5p, miR-25-3p, miR-143-3p; miR-423-3p, miR-192-5p, miR-17-5p, miR-25-3p, miR-363-3p; miR-423-3p, miR-192-5p, miR-17-5p, miR-25-3p, miR-338-3p; miR-423-3p, miR-192-5p, miR-17-5p, miR-143-3p, miR-363-3p; miR-423-3p, miR-192-5p, miR-17-5p, miR-143-3p, miR-338-3p; miR-423-3p, miR-192-5p, miR-17-5p, miR-363-3p, miR-338-3p; miR-423-3p, miR-192-5p, miR-125b-5p, miR-660-5p, miR-25-3p; miR-423-3p, miR-192-5p, miR-125b-5p, miR-660-5p, miR-143-3p; miR-423-3p, miR-192-5p, miR-125b-5p, miR-660-5p, miR-363-3p; miR-423-3p, miR-192-5p, miR-125b-5p, miR-660-5p, miR-338-3p; miR-423-3p, miR-192-5p, miR-125b-5p, miR-25-3p, miR-143-3p; miR-423-3p, miR-192-5p, miR-125b-5p, miR-25-3p, miR-363-3p; miR-423-3p, miR-192-5p, miR-125b-5p, miR-25-3p, miR-338-3p; miR-423-3p, miR-192-5p, miR-125b-5p, miR-143-3p, miR-363-3p; miR-423-3p, miR-192-5p, miR-125b-5p, miR-143-3p, miR-338-3p; miR-423-3p, miR-192-5p, miR-125b-5p, miR-363-3p, miR-338-3p; miR-423-3p, miR-192-5p, miR-660-5p, miR-25-3p, miR-143-3p; miR-423-3p, miR-192-5p, miR-660-5p, miR-25-3p, miR-363-3p; miR-423-3p, miR-192-5p, miR-660-5p, miR-25-3p, miR-338-3p; miR-423-3p, miR-192-5p, miR-660-5p, miR-143-3p, miR-363-3p; miR-423-3p, miR-192-5p, miR-660-5p, miR-143-3p, miR-338-3p; miR-423-3p, miR-192-5p, miR-660-5p, miR-363-3p, miR-338-3p; miR-423-3p, miR-192-5p, miR-25-3p, miR-143-3p, miR-363-3p; miR-423-3p, miR-192-5p, miR-25-3p, miR-143-3p, miR-338-3p; miR-423-3p, miR-192-5p, miR-25-3p, miR-363-3p, miR-338-3p; miR-423-3p, miR-192-5p, miR-143-3p, miR-363-3p, miR-338-3p; miR-423-3p, miR-17-5p, miR-125b-5p, miR-660-5p, miR-25-3p; miR-423-3p, miR-17-5p, miR-125b-5p, miR-660-5p, miR-143-3p; miR-423-3p, miR-17-5p, miR-125b-5p, miR-660-5p, miR-363-3p; miR-423-3p, miR-17-5p, miR-125b-5p, miR-660-5p, miR-338-3p; miR-423-3p, miR-17-5p, miR-125b-5p, miR-25-3p, miR-143-3p; miR-423-3p, miR-17-5p, miR-125b-5p, miR-25-3p, miR-363-3p; miR-423-3p, miR-17-5p, miR-125b-5p, miR-25-3p, miR-338-3p; miR-423-3p, miR-17-5p, miR-125b-5p, miR-143-3p, miR-363-3p; miR-423-3p, miR-17-5p, miR-125b-5p, miR-143-3p, miR-338-3p; miR-423-3p, miR-17-5p, miR-125b-5p, miR-363-3p, miR-338-3p; miR-423-3p, miR-17-5p, miR-660-5p, miR-25-3p, miR-143-3p; miR-423-3p, miR-17-5p, miR-660-5p, miR-25-3p, miR-363-3p; miR-423-3p, miR-17-5p, miR-660-5p, miR-25-3p, miR-338-3p; miR-423-3p, miR-17-5p, miR-660-5p, miR-143-3p, miR-363-3p; miR-423-3p, miR-17-5p, miR-660-5p, miR-143-3p, miR-338-3p; miR-423-3p, miR-17-5p, miR-660-5p, miR-363-3p, miR-338-3p; miR-423-3p, miR-17-5p, miR-25-3p, miR-143-3p, miR-363-3p; miR-423-3p, miR-17-5p, miR-25-3p, miR-143-3p, miR-338-3p; miR-423-3p, miR-17-5p, miR-25-3p, miR-363-3p, miR-338-3p; miR-423-3p, miR-17-5p, miR-143-3p, miR-363-3p, miR-338-3p; miR-423-3p, miR-125b-5p, miR-660-5p, miR-25-3p, miR-143-3p; miR-423-3p, miR-125b-5p, miR-660-5p, miR-25-3p, miR-363-3p; miR-423-3p, miR-125b-5p, miR-660-5p, miR-25-3p, miR-338-3p; miR-423-3p, miR-125b-5p, miR-660-5p, miR-143-3p, miR-363-3p; miR-423-3p, miR-125b-5p, miR-660-5p, miR-143-3p, miR-338-3p; miR-423-3p, miR-125b-5p, miR-660-5p, miR-363-3p, miR-338-3p; miR-423-3p, miR-125b-5p, miR-25-3p, miR-143-3p, miR-363-3p; miR-423-3p, miR-125b-5p, miR-25-3p, miR-143-3p, miR-338-3p; miR-423-3p, miR-125b-5p, miR-25-3p, miR-363-3p, miR-338-3p; miR-423-3p, miR-125b-5p, miR-143-3p, miR-363-3p, miR-338-3p; miR-423-3p, miR-660-5p, miR-25-3p, miR-143-3p, miR-363-3p; miR-423-3p, miR-660-5p, miR-25-3p, miR-143-3p, miR-338-3p; miR-423-3p, miR-660-5p, miR-25-3p, miR-363-3p, miR-338-3p; miR-423-3p, miR-660-5p, miR-143-3p, miR-363-3p, miR-338-3p; miR-423-3p, miR-25-3p, miR-143-3p, miR-363-3p, miR-338-3p; miR-192-5p, miR-17-5p, miR-125b-5p, miR-660-5p, miR-25-3p; miR-192-5p, miR-17-5p, miR-125b-5p, miR-660-5p, miR-143-3p; miR-192-5p, miR-17-5p, miR-125b-5p, miR-660-5p, miR-363-3p; miR-192-5p, miR-17-5p, miR-125b-5p, miR-660-5p, miR-338-3p; miR-192-5p, miR-17-5p, miR-125b-5p, miR-25-3p, miR-143-3p; miR-192-5p, miR-17-5p, miR-125b-5p, miR-25-3p, miR-363-3p; miR-192-5p, miR-17-5p, miR-125b-5p, miR-25-3p, miR-338-3p; miR-192-5p, miR-17-5p, miR-125b-5p, miR-143-3p, miR-363-3p; miR-192-5p, miR-17-5p, miR-125b-5p, miR-143-3p, miR-338-3p; miR-192-5p, miR-17-5p, miR-125b-5p, miR-363-3p, miR-338-3p; miR-192-5p, miR-17-5p, miR-660-5p, miR-25-3p, miR-143-3p; miR-192-5p, miR-17-5p, miR-660-5p, miR-25-3p, miR-363-3p; miR-192-5p, miR-17-5p, miR-660-5p, miR-25-3p, miR-338-3p; miR-192-5p, miR-17-5p, miR-660-5p, miR-143-3p, miR-363-3p; miR-192-5p, miR-17-5p, miR-660-5p, miR-143-3p, miR-338-3p; miR-192-5p, miR-17-5p, miR-660-5p, miR-363-3p, miR-338-3p; miR-192-5p, miR-17-5p, miR-25-3p, miR-143-3p, miR-363-3p; miR-192-5p, miR-17-5p, miR-25-3p, miR-143-3p, miR-338-3p; miR-192-5p, miR-17-5p, miR-25-3p, miR-363-3p, miR-338-3p; miR-192-5p, miR-17-5p, miR-143-3p, miR-363-3p, miR-338-3p; miR-192-5p, miR-125b-5p, miR-660-5p, miR-25-3p, miR-143-3p; miR-192-5p, miR-125b-5p, miR-660-5p, miR-25-3p, miR-363-3p; miR-192-5p, miR-125b-5p, miR-660-5p, miR-25-3p, miR-338-3p; miR-192-5p, miR-125b-5p, miR-660-5p, miR-143-3p, miR-363-3p; miR-192-5p, miR-125b-5p, miR-660-5p, miR-143-3p, miR-338-3p; miR-192-5p, miR-125b-5p, miR-660-5p, miR-363-3p, miR-338-3p; miR-192-5p, miR-125b-5p, miR-25-3p, miR-143-3p, miR-363-3p; miR-192-5p, miR-125b-5p, miR-25-3p, miR-143-3p, miR-338-3p; miR-192-5p, miR-125b-5p, miR-25-3p, miR-363-3p, miR-338-3p; miR-192-5p, miR-125b-5p, miR-143-3p, miR-363-3p, miR-338-3p; miR-192-5p, miR-660-5p, miR-25-3p, miR-143-3p, miR-363-3p; miR-192-5p, miR-660-5p, miR-25-3p, miR-143-3p, miR-338-3p; miR-192-5p, miR-660-5p, miR-25-3p, miR-363-3p, miR-338-3p; miR-192-5p, miR-660-5p, miR-143-3p, miR-363-3p, miR-338-3p; miR-192-5p, miR-25-3p, miR-143-3p, miR-363-3p, miR-338-3p; miR-17-5p, miR-125b-5p, miR-660-5p, miR-25-3p, miR-143-3p; miR-17-5p, miR-125b-5p, miR-660-5p, miR-25-3p, miR-363-3p; miR-17-5p, miR-125b-5p, miR-660-5p, miR-25-3p, miR-338-3p; miR-17-5p, miR-125b-5p, miR-660-5p, miR-143-3p, miR-363-3p; miR-17-5p, miR-125b-5p, miR-660-5p, miR-143-3p, miR-338-3p; miR-17-5p, miR-125b-5p, miR-660-5p, miR-363-3p, miR-338-3p; miR-17-5p, miR-125b-5p, miR-25-3p, miR-143-3p, miR-363-3p; miR-17-5p, miR-125b-5p, miR-25-3p, miR-143-3p, miR-338-3p; miR-17-5p, miR-125b-5p, miR-25-3p, miR-363-3p, miR-338-3p; miR-17-5p, miR-125b-5p, miR-143-3p, miR-363-3p, miR-338-3p; miR-17-5p, miR-660-5p, miR-25-3p, miR-143-3p, miR-363-3p; miR-17-5p, miR-660-5p, miR-25-3p, miR-143-3p, miR-338-3p; miR-17-5p, miR-660-5p, miR-25-3p, miR-363-3p, miR-338-3p; miR-17-5p, miR-660-5p, miR-143-3p, miR-363-3p, miR-338-3p; miR-17-5p, miR-25-3p, miR-143-3p, miR-363-3p, miR-338-3p; miR-125b-5p, miR-660-5p, miR-25-3p, miR-143-3p, miR-363-3p; miR-125b-5p, miR-660-5p, miR-25-3p, miR-143-3p, miR-338-3p; miR-125b-5p, miR-660-5p, miR-25-3p, miR-363-3p, miR-338-3p; miR-125b-5p, miR-660-5p, miR-143-3p, miR-363-3p, miR-338-3p; miR-125b-5p, miR-25-3p, miR-143-3p, miR-363-3p, miR-338-3p; or miR-660-5p, miR-25-3p, miR-143-3p, miR-363-3p, miR-338-3p.

In one example, the at least six miRNAs are, but are not limited to, the following combinations: miR-451a, miR-195-5p, miR-126-5p, miR-423-3p, miR-192-5p, miR-17-5p; miR-451a, miR-195-5p, miR-126-5p, miR-423-3p, miR-192-5p, miR-125b-5p; miR-451a, miR-195-5p, miR-126-5p, miR-423-3p, miR-192-5p, miR-660-5p; miR-451a, miR-195-5p, miR-126-5p, miR-423-3p, miR-192-5p, miR-25-3p; miR-451a, miR-195-5p, miR-126-5p, miR-423-3p, miR-192-5p, miR-143-3p; miR-451a, miR-195-5p, miR-126-5p, miR-423-3p, miR-192-5p, miR-363-3p; miR-451a, miR-195-5p, miR-126-5p, miR-423-3p, miR-192-5p, miR-338-3p; miR-451a, miR-195-5p, miR-126-5p, miR-423-3p, miR-17-5p, miR-125b-5p; miR-451a, miR-195-5p, miR-126-5p, miR-423-3p, miR-17-5p, miR-660-5p; miR-451a, miR-195-5p, miR-126-5p, miR-423-3p, miR-17-5p, miR-25-3p; miR-451a, miR-195-5p, miR-126-5p, miR-423-3p, miR-17-5p, miR-143-3p; miR-451a, miR-195-5p, miR-126-5p, miR-423-3p, miR-17-5p, miR-363-3p; miR-451a, miR-195-5p, miR-126-5p, miR-423-3p, miR-17-5p, miR-338-3p; miR-451a, miR-195-5p, miR-126-5p, miR-423-3p, miR-125b-5p, miR-660-5p; miR-451a, miR-195-5p, miR-126-5p, miR-423-3p, miR-125b-5p, miR-25-3p; miR-451a, miR-195-5p, miR-126-5p, miR-423-3p, miR-125b-5p, miR-143-3p; miR-451a, miR-195-5p, miR-126-5p, miR-423-3p, miR-125b-5p, miR-363-3p; miR-451a, miR-195-5p, miR-126-5p, miR-423-3p, miR-125b-5p, miR-338-3p; miR-451a, miR-195-5p, miR-126-5p, miR-423-3p, miR-660-5p, miR-25-3p; miR-451a, miR-195-5p, miR-126-5p, miR-423-3p, miR-660-5p, miR-143-3p; miR-451a, miR-195-5p, miR-126-5p, miR-423-3p, miR-660-5p, miR-363-3p; miR-451a, miR-195-5p, miR-126-5p, miR-423-3p, miR-660-5p, miR-338-3p; miR-451a, miR-195-5p, miR-126-5p, miR-423-3p, miR-25-3p, miR-143-3p; miR-451a, miR-195-5p, miR-126-5p, miR-423-3p, miR-25-3p, miR-363-3p; miR-451a, miR-195-5p, miR-126-5p, miR-423-3p, miR-25-3p, miR-338-3p; miR-451a, miR-195-5p, miR-126-5p, miR-423-3p, miR-143-3p, miR-363-3p; miR-451a, miR-195-5p, miR-126-5p, miR-423-3p, miR-143-3p, miR-338-3p; miR-451a, miR-195-5p, miR-126-5p, miR-423-3p, miR-363-3p, miR-338-3p; miR-451a, miR-195-5p, miR-126-5p, miR-192-5p, miR-17-5p, miR-125b-5p; miR-451a, miR-195-5p, miR-126-5p, miR-192-5p, miR-17-5p, miR-660-5p; miR-451a, miR-195-5p, miR-126-5p, miR-192-5p, miR-17-5p, miR-25-3p; miR-451a, miR-195-5p, miR-126-5p, miR-192-5p, miR-17-5p, miR-143-3p; miR-451a, miR-195-5p, miR-126-5p, miR-192-5p, miR-17-5p, miR-363-3p; miR-451a, miR-195-5p, miR-126-5p, miR-192-5p, miR-17-5p, miR-338-3p; miR-451a, miR-195-5p, miR-126-5p, miR-192-5p, miR-125b-5p, miR-660-5p; miR-451a, miR-195-5p, miR-126-5p, miR-192-5p, miR-125b-5p, miR-25-3p; miR-451a, miR-195-5p, miR-126-5p, miR-192-5p, miR-125b-5p, miR-143-3p; miR-451a, miR-195-5p, miR-126-5p, miR-192-5p, miR-125b-5p, miR-363-3p; miR-451a, miR-195-5p, miR-126-5p, miR-192-5p, miR-125b-5p, miR-338-3p; miR-451a, miR-195-5p, miR-126-5p, miR-192-5p, miR-660-5p, miR-25-3p; miR-451a, miR-195-5p, miR-126-5p, miR-192-5p, miR-660-5p, miR-143-3p; miR-451a, miR-195-5p, miR-126-5p, miR-192-5p, miR-660-5p, miR-363-3p; miR-451a, miR-195-5p, miR-126-5p, miR-192-5p, miR-660-5p, miR-338-3p; miR-451a, miR-195-5p, miR-126-5p, miR-192-5p, miR-25-3p, miR-143-3p; miR-451a, miR-195-5p, miR-126-5p, miR-192-5p, miR-25-3p, miR-363-3p; miR-451a, miR-195-5p, miR-126-5p, miR-192-5p, miR-25-3p, miR-338-3p; miR-451a, miR-195-5p, miR-126-5p, miR-192-5p, miR-143-3p, miR-363-3p; miR-451a, miR-195-5p, miR-126-5p, miR-192-5p, miR-143-3p, miR-338-3p; miR-451a, miR-195-5p, miR-126-5p, miR-192-5p, miR-363-3p, miR-338-3p; miR-451a, miR-195-5p, miR-126-5p, miR-17-5p, miR-125b-5p, miR-660-5p; miR-451a, miR-195-5p, miR-126-5p, miR-17-5p, miR-125b-5p, miR-25-3p; miR-451a, miR-195-5p, miR-126-5p, miR-17-5p, miR-125b-5p, miR-143-3p; miR-451a, miR-195-5p, miR-126-5p, miR-17-5p, miR-125b-5p, miR-363-3p; miR-451a, miR-195-5p, miR-126-5p, miR-17-5p, miR-125b-5p, miR-338-3p; miR-451a, miR-195-5p, miR-126-5p, miR-17-5p, miR-660-5p, miR-25-3p; miR-451a, miR-195-5p, miR-126-5p, miR-17-5p, miR-660-5p, miR-143-3p; miR-451a, miR-195-5p, miR-126-5p, miR-17-5p, miR-660-5p, miR-363-3p; miR-451a, miR-195-5p, miR-126-5p, miR-17-5p, miR-660-5p, miR-338-3p; miR-451a, miR-195-5p, miR-126-5p, miR-17-5p, miR-25-3p, miR-143-3p; miR-451a, miR-195-5p, miR-126-5p, miR-17-5p, miR-25-3p, miR-363-3p; miR-451a, miR-195-5p, miR-126-5p, miR-17-5p, miR-25-3p, miR-338-3p; miR-451a, miR-195-5p, miR-126-5p, miR-17-5p, miR-143-3p, miR-363-3p; miR-451a, miR-195-5p, miR-126-5p, miR-17-5p, miR-143-3p, miR-338-3p; miR-451a, miR-195-5p, miR-126-5p, miR-17-5p, miR-363-3p, miR-338-3p; miR-451a, miR-195-5p, miR-126-5p, miR-125b-5p, miR-660-5p, miR-25-3p; miR-451a, miR-195-5p, miR-126-5p, miR-125b-5p, miR-660-5p, miR-143-3p; miR-451a, miR-195-5p, miR-126-5p, miR-125b-5p, miR-660-5p, miR-363-3p; miR-451a, miR-195-5p, miR-126-5p, miR-125b-5p, miR-660-

5p, miR-338-3p; miR-451a, miR-195-5p, miR-126-5p, miR-125b-5p, miR-25-3p, miR-143-3p; miR-451a, miR-195-5p, miR-126-5p, miR-125b-5p, miR-25-3p, miR-363-3p; miR-451a, miR-195-5p, miR-126-5p, miR-125b-5p, miR-25-3p, miR-338-3p; miR-451a, miR-195-5p, miR-126-5p, miR-125b-5p, miR-143-3p, miR-363-3p; miR-451a, miR-195-5p, miR-126-5p, miR-125b-5p, miR-143-3p, miR-338-3p; miR-451a, miR-195-5p, miR-126-5p, miR-125b-5p, miR-363-3p, miR-338-3p; miR-451a, miR-195-5p, miR-126-5p, miR-660-5p, miR-25-3p, miR-143-3p; miR-451a, miR-195-5p, miR-126-5p, miR-660-5p, miR-25-3p, miR-363-3p; miR-451a, miR-195-5p, miR-126-5p, miR-660-5p, miR-25-3p, miR-338-3p; miR-451a, miR-195-5p, miR-126-5p, miR-660-5p, miR-143-3p, miR-363-3p; miR-451a, miR-195-5p, miR-126-5p, miR-660-5p, miR-143-3p, miR-338-3p; miR-451a, miR-195-5p, miR-126-5p, miR-660-5p, miR-363-3p, miR-338-3p; miR-451a, miR-195-5p, miR-126-5p, miR-25-3p, miR-143-3p, miR-363-3p; miR-451a, miR-195-5p, miR-126-5p, miR-25-3p, miR-143-3p, miR-338-3p; miR-451a, miR-195-5p, miR-126-5p, miR-25-3p, miR-363-3p, miR-338-3p; miR-451a, miR-195-5p, miR-126-5p, miR-143-3p, miR-363-3p, miR-338-3p; miR-451a, miR-195-5p, miR-423-3p, miR-192-5p, miR-17-5p, miR-125b-5p; miR-451a, miR-195-5p, miR-423-3p, miR-192-5p, miR-17-5p, miR-660-5p; miR-451a, miR-195-5p, miR-423-3p, miR-192-5p, miR-17-5p, miR-25-3p; miR-451a, miR-195-5p, miR-423-3p, miR-192-5p, miR-17-5p, miR-143-3p; miR-451a, miR-195-5p, miR-423-3p, miR-192-5p, miR-17-5p, miR-363-3p; miR-451a, miR-195-5p, miR-423-3p, miR-192-5p, miR-17-5p, miR-338-3p; miR-451a, miR-195-5p, miR-423-3p, miR-192-5p, miR-125b-5p, miR-660-5p; miR-451a, miR-195-5p, miR-423-3p, miR-192-5p, miR-125b-5p, miR-25-3p; miR-451a, miR-195-5p, miR-423-3p, miR-192-5p, miR-125b-5p, miR-143-3p; miR-451a, miR-195-5p, miR-423-3p, miR-192-5p, miR-125b-5p, miR-363-3p; miR-451a, miR-195-5p, miR-423-3p, miR-192-5p, miR-125b-5p, miR-338-3p; miR-451a, miR-195-5p, miR-423-3p, miR-192-5p, miR-660-5p, miR-25-3p; miR-451a, miR-195-5p, miR-423-3p, miR-192-5p, miR-660-5p, miR-143-3p; miR-451a, miR-195-5p, miR-423-3p, miR-192-5p, miR-660-5p, miR-363-3p; miR-451a, miR-195-5p, miR-423-3p, miR-192-5p, miR-660-5p, miR-338-3p; miR-451a, miR-195-5p, miR-423-3p, miR-192-5p, miR-25-3p, miR-143-3p; miR-451a, miR-195-5p, miR-423-3p, miR-192-5p, miR-25-3p, miR-363-3p; miR-451a, miR-195-5p, miR-423-3p, miR-192-5p, miR-25-3p, miR-338-3p; miR-451a, miR-195-5p, miR-423-3p, miR-192-5p, miR-143-3p, miR-363-3p; miR-451a, miR-195-5p, miR-423-3p, miR-192-5p, miR-143-3p, miR-338-3p; miR-451a, miR-195-5p, miR-423-3p, miR-192-5p, miR-363-3p, miR-338-3p; miR-451a, miR-195-5p, miR-423-3p, miR-17-5p, miR-125b-5p, miR-660-5p; miR-451a, miR-195-5p, miR-423-3p, miR-17-5p, miR-125b-5p, miR-25-3p; miR-451a, miR-195-5p, miR-423-3p, miR-17-5p, miR-125b-5p, miR-143-3p; miR-451a, miR-195-5p, miR-423-3p, miR-17-5p, miR-125b-5p, miR-363-3p; miR-451a, miR-195-5p, miR-423-3p, miR-17-5p, miR-125b-5p, miR-338-3p; miR-451a, miR-195-5p, miR-423-3p, miR-17-5p, miR-660-5p, miR-25-3p; miR-451a, miR-195-5p, miR-423-3p, miR-17-5p, miR-660-5p, miR-143-3p; miR-451a, miR-195-5p, miR-423-3p, miR-17-5p, miR-660-5p, miR-363-3p; miR-451a, miR-195-5p, miR-423-3p, miR-17-5p, miR-660-5p, miR-338-3p; miR-451a, miR-195-5p, miR-423-3p, miR-17-5p, miR-25-3p, miR-143-3p; miR-451a, miR-195-5p, miR-423-3p, miR-17-5p, miR-25-3p, miR-363-3p; miR-451a, miR-195-5p, miR-423-3p, miR-17-5p, miR-25-3p, miR-338-3p; miR-451a, miR-195-5p, miR-423-3p, miR-17-5p, miR-143-3p, miR-363-3p; miR-451a, miR-195-5p, miR-423-3p, miR-17-5p, miR-143-3p, miR-338-3p; miR-451a, miR-195-5p, miR-423-3p, miR-125b-5p, miR-660-5p, miR-25-3p; miR-451a, miR-195-5p, miR-423-3p, miR-125b-5p, miR-660-5p, miR-143-3p; miR-451a, miR-195-5p, miR-423-3p, miR-125b-5p, miR-660-5p, miR-363-3p; miR-451a, miR-195-5p, miR-423-3p, miR-125b-5p, miR-660-5p, miR-338-3p; miR-451a, miR-195-5p, miR-423-3p, miR-125b-5p, miR-25-3p, miR-143-3p; miR-451a, miR-195-5p, miR-423-3p, miR-125b-5p, miR-25-3p, miR-363-3p; miR-451a, miR-195-5p, miR-423-3p, miR-125b-5p, miR-25-3p, miR-338-3p; miR-451a, miR-195-5p, miR-423-3p, miR-125b-5p, miR-143-3p, miR-363-3p; miR-451a, miR-195-5p, miR-423-3p, miR-125b-5p, miR-143-3p, miR-338-3p; miR-451a, miR-195-5p, miR-423-3p, miR-125b-5p, miR-363-3p, miR-338-3p; miR-451a, miR-195-5p, miR-423-3p, miR-660-5p, miR-25-3p, miR-143-3p; miR-451a, miR-195-5p, miR-423-3p, miR-660-5p, miR-25-3p, miR-363-3p; miR-451a, miR-195-5p, miR-423-3p, miR-660-5p, miR-25-3p, miR-338-3p; miR-451a, miR-195-5p, miR-423-3p, miR-660-5p, miR-143-3p, miR-363-3p; miR-451a, miR-195-5p, miR-423-3p, miR-660-5p, miR-143-3p, miR-338-3p; miR-451a, miR-195-5p, miR-423-3p, miR-660-5p, miR-363-3p, miR-338-3p; miR-451a, miR-195-5p, miR-423-3p, miR-25-3p, miR-143-3p, miR-363-3p; miR-451a, miR-195-5p, miR-423-3p, miR-25-3p, miR-143-3p, miR-338-3p; miR-451a, miR-195-5p, miR-423-3p, miR-25-3p, miR-363-3p, miR-338-3p; miR-451a, miR-195-5p, miR-423-3p, miR-143-3p, miR-363-3p, miR-338-3p; miR-451a, miR-195-5p, miR-192-5p, miR-17-5p, miR-125b-5p, miR-660-5p; miR-451a, miR-195-5p, miR-192-5p, miR-17-5p, miR-125b-5p, miR-25-3p; miR-451a, miR-195-5p, miR-192-5p, miR-17-5p, miR-125b-5p, miR-143-3p; miR-451a, miR-195-5p, miR-192-5p, miR-17-5p, miR-125b-5p, miR-363-3p; miR-451a, miR-195-5p, miR-192-5p, miR-17-5p, miR-125b-5p, miR-338-3p; miR-451a, miR-195-5p, miR-192-5p, miR-17-5p, miR-660-5p, miR-25-3p; miR-451a, miR-195-5p, miR-192-5p, miR-17-5p, miR-660-5p, miR-143-3p; miR-451a, miR-195-5p, miR-192-5p, miR-17-5p, miR-660-5p, miR-363-3p; miR-451a, miR-195-5p, miR-192-5p, miR-17-5p, miR-660-5p, miR-338-3p; miR-451a, miR-195-5p, miR-192-5p, miR-17-5p, miR-25-3p, miR-143-3p; miR-451a, miR-195-5p, miR-192-5p, miR-17-5p, miR-25-3p, miR-363-3p; miR-451a, miR-195-5p, miR-192-5p, miR-17-5p, miR-25-3p, miR-338-3p; miR-451a, miR-195-5p, miR-192-5p, miR-17-5p, miR-143-3p, miR-363-3p; miR-451a, miR-195-5p, miR-192-5p, miR-17-5p, miR-143-3p, miR-338-3p; miR-451a, miR-195-5p, miR-192-5p, miR-17-5p, miR-363-3p, miR-338-3p; miR-451a, miR-195-5p, miR-192-5p, miR-125b-5p, miR-660-5p, miR-25-3p; miR-451a, miR-195-5p, miR-192-5p, miR-125b-5p, miR-660-5p, miR-143-3p; miR-451a, miR-195-5p, miR-192-5p, miR-125b-5p, miR-660-5p, miR-363-3p; miR-451a, miR-195-5p, miR-192-5p, miR-125b-5p, miR-660-5p, miR-338-3p; miR-451a, miR-195-5p, miR-192-5p, miR-125b-5p, miR-25-3p, miR-143-3p; miR-451a, miR-195-5p, miR-192-5p, miR-125b-5p, miR-25-3p, miR-363-3p; miR-451a, miR-195-5p, miR-192-5p, miR-125b-5p, miR-25-3p, miR-338-3p; miR-451a, miR-195-5p, miR-192-5p, miR-125b-5p, miR-143-3p, miR-363-3p; miR-451a, miR-195-5p, miR-192-5p, miR-125b-5p, miR-143-3p, miR-338-3p; miR-451a, miR-195-5p, miR-192-5p, miR-125b-5p, miR-363-3p, miR-338-3p; miR-451a, miR-195-5p, miR-192-5p, miR-660-5p, miR-25-3p, miR-143-3p; miR-451a, miR-195-5p, miR-192-5p, miR-660-5p, miR-25-3p, miR-363-3p; miR-451a, miR-195-5p, miR-192-5p, miR-660-5p, miR-25-3p, miR-338-3p; miR-451a, miR-195-5p, miR-192-5p, miR-660-5p, miR-143-3p, miR-363-3p; miR-451a, miR-195-5p, miR-192-5p, miR-660-5p, miR-143-3p, miR-338-3p; miR-451a, miR-195-5p, miR-192-5p, miR-660-5p, miR-363-3p, miR-338-3p; miR-451a, miR-195-5p, miR-192-5p, miR-25-3p, miR-143-3p, miR-363-3p; miR-451a, miR-195-5p, miR-192-5p, miR-25-3p, miR-143-3p, miR-338-3p; miR-451a, miR-195-5p, miR-192-5p, miR-25-3p, miR-363-3p, miR-338-3p; miR-451a, miR-195-5p, miR-192-5p, miR-143-3p, miR-363-3p, miR-338-3p; miR-451a, miR-195-5p, miR-17-5p, miR-125b-5p, miR-660-5p, miR-25-3p; miR-451a, miR-195-5p, miR-17-5p, miR-125b-5p, miR-660-5p, miR-143-3p; miR-451a, miR-195-5p, miR-17-5p, miR-125b-5p, miR-660-5p, miR-363-3p; miR-451a, miR-195-5p, miR-17-5p, miR-125b-5p, miR-660-5p, miR-338-3p; miR-451a, miR-195-5p, miR-17-5p, miR-125b-5p, miR-25-3p, miR-143-3p; miR-451a, miR-195-5p, miR-17-5p, miR-125b-5p, miR-25-3p, miR-363-3p; miR-451a, miR-195-5p, miR-17-5p, miR-125b-5p, miR-25-3p, miR-338-3p; miR-451a, miR-195-5p, miR-17-5p, miR-125b-5p, miR-143-3p, miR-363-3p; miR-451a, miR-195-5p, miR-17-5p, miR-125b-5p, miR-143-3p, miR-338-3p; miR-451a, miR-195-5p, miR-17-5p, miR-125b-5p, miR-363-3p, miR-338-3p; miR-451a, miR-195-5p, miR-17-5p, miR-660-5p, miR-25-3p, miR-143-3p; miR-451a, miR-195-5p, miR-17-5p, miR-660-5p, miR-25-3p, miR-363-3p; miR-451a, miR-195-5p, miR-17-5p, miR-660-5p, miR-25-3p, miR-338-3p; miR-451a, miR-195-5p, miR-17-5p, miR-660-5p, miR-143-3p, miR-363-3p; miR-451a, miR-195-5p, miR-17-5p, miR-660-5p, miR-143-3p, miR-338-3p; miR-451a, miR-195-5p, miR-17-5p, miR-660-5p, miR-363-3p, miR-338-3p; miR-451a, miR-195-5p, miR-17-5p, miR-25-3p, miR-143-3p, miR-363-3p; miR-451a, miR-195-5p, miR-17-5p, miR-25-3p, miR-143-3p, miR-338-3p; miR-451a, miR-195-5p, miR-17-5p, miR-25-3p, miR-363-3p, miR-338-3p; miR-451a, miR-195-5p, miR-17-5p, miR-143-3p, miR-363-3p, miR-338-3p; miR-451a, miR-195-5p, miR-125b-5p, miR-660-5p, miR-25-3p, miR-143-3p; miR-451a, miR-195-5p, miR-125b-5p, miR-660-5p, miR-25-3p, miR-363-3p; miR-451a, miR-195-5p, miR-125b-5p, miR-660-5p, miR-25-3p, miR-338-3p; miR-451a, miR-195-5p, miR-125b-5p, miR-660-5p, miR-143-3p, miR-363-3p; miR-451a, miR-195-5p, miR-125b-5p, miR-660-5p, miR-143-3p, miR-338-3p; miR-451a, miR-195-5p, miR-125b-5p, miR-660-5p, miR-363-3p, miR-338-3p; miR-451a, miR-195-5p, miR-125b-5p, miR-25-3p, miR-143-3p, miR-363-3p; miR-451a, miR-195-5p, miR-125b-5p, miR-25-3p, miR-143-3p, miR-338-3p; miR-451a, miR-195-5p, miR-125b-5p, miR-25-3p, miR-363-3p, miR-338-3p; miR-451a, miR-195-5p, miR-125b-5p, miR-143-3p, miR-363-3p, miR-338-3p; miR-451a, miR-195-5p, miR-660-5p, miR-25-3p, miR-143-3p, miR-363-3p; miR-451a, miR-195-5p, miR-660-5p, miR-25-3p, miR-143-3p, miR-338-3p; miR-451a, miR-195-5p, miR-660-5p, miR-25-3p, miR-363-3p, miR-338-3p; miR-451a, miR-195-5p, miR-660-5p, miR-143-3p, miR-363-3p, miR-338-3p; miR-451a, miR-195-5p, miR-25-3p, miR-143-3p, miR-363-3p, miR-338-3p; miR-451a, miR-126-5p, miR-423-3p, miR-192-5p, miR-17-5p, miR-125b-5p; miR-451a, miR-126-5p, miR-423-3p, miR-192-5p, miR-17-5p, miR-660-5p; miR-451a, miR-126-5p, miR-423-3p, miR-192-5p, miR-17-5p, miR-25-3p; miR-451a, miR-126-5p, miR-423-3p, miR-192-5p, miR-17-5p, miR-143-3p; miR-451a, miR-126-5p, miR-423-3p, miR-192-5p, miR-17-5p, miR-363-3p; miR-451a, miR-126-5p, miR-423-3p, miR-192-5p, miR-17-5p, miR-338-3p; miR-451a, miR-126-5p, miR-423-3p, miR-192-5p, miR-125b-5p, miR-660-5p; miR-451a, miR-126-5p, miR-423-3p, miR-192-5p, miR-125b-5p, miR-25-3p; miR-451a, miR-126-5p, miR-423-3p, miR-192-5p, miR-125b-5p, miR-143-3p; miR-451a, miR-126-5p, miR-423-3p, miR-192-5p, miR-125b-5p, miR-363-3p; miR-451a, miR-126-5p, miR-423-3p, miR-192-5p, miR-125b-5p, miR-338-3p; miR-451a, miR-126-5p, miR-423-3p, miR-192-5p, miR-660-5p, miR-25-3p; miR-451a, miR-126-5p, miR-423-3p, miR-192-5p, miR-660-5p, miR-143-3p; miR-451a, miR-126-5p, miR-423-3p, miR-192-5p, miR-660-5p, miR-363-3p; miR-451a, miR-126-5p, miR-423-3p, miR-192-5p, miR-660-5p, miR-338-3p; miR-451a, miR-126-5p, miR-423-3p, miR-192-5p, miR-25-3p, miR-143-3p; miR-451a, miR-126-5p, miR-423-3p, miR-192-5p, miR-25-3p, miR-363-3p; miR-451a, miR-126-5p, miR-423-3p, miR-192-5p, miR-25-3p, miR-338-3p; miR-451a, miR-126-5p, miR-423-3p, miR-192-5p, miR-143-3p, miR-363-3p; miR-451a, miR-126-5p, miR-423-3p, miR-192-5p, miR-143-3p, miR-338-3p; miR-451a, miR-126-5p, miR-423-3p, miR-192-5p, miR-363-3p, miR-338-3p; miR-451a, miR-126-5p, miR-423-3p, miR-17-5p, miR-125b-5p, miR-660-5p; miR-451a, miR-126-5p, miR-423-3p, miR-17-5p, miR-125b-5p, miR-25-3p; miR-451a, miR-126-5p, miR-423-3p, miR-17-5p, miR-125b-5p, miR-143-3p; miR-451a, miR-126-5p, miR-423-3p, miR-17-5p, miR-125b-5p, miR-363-3p; miR-451a, miR-126-5p, miR-423-3p, miR-17-5p, miR-125b-5p, miR-338-3p; miR-451a, miR-126-5p, miR-423-3p, miR-17-5p, miR-660-5p, miR-25-3p; miR-451a, miR-126-5p, miR-423-3p, miR-17-5p, miR-660-5p, miR-143-3p; miR-451a, miR-126-5p, miR-423-3p, miR-17-5p, miR-660-5p, miR-363-3p; miR-451a, miR-126-5p, miR-423-3p, miR-17-5p, miR-660-5p, miR-338-3p; miR-451a, miR-126-5p, miR-423-3p, miR-17-5p, miR-25-3p, miR-143-3p; miR-451a, miR-126-5p, miR-423-3p, miR-17-5p, miR-25-3p, miR-363-3p; miR-451a, miR-126-5p, miR-423-3p, miR-17-5p, miR-25-3p, miR-338-3p; miR-451a, miR-126-5p, miR-423-3p, miR-17-5p, miR-143-3p, miR-363-3p; miR-451a, miR-126-5p, miR-423-3p, miR-17-5p, miR-143-3p, miR-338-3p; miR-451a, miR-126-5p, miR-423-3p, miR-17-5p, miR-363-3p, miR-338-3p; miR-451a, miR-126-5p, miR-423-3p, miR-125b-5p, miR-660-5p, miR-25-3p; miR-451a, miR-126-5p, miR-423-3p, miR-125b-5p, miR-660-5p, miR-143-3p; miR-451a, miR-126-5p, miR-423-3p, miR-125b-5p, miR-660-5p, miR-363-3p; miR-451a, miR-126-5p, miR-423-3p, miR-125b-5p, miR-660-5p, miR-338-3p; miR-451a, miR-126-5p, miR-423-3p, miR-125b-5p, miR-25-3p, miR-143-3p; miR-451a, miR-126-5p, miR-423-3p, miR-125b-5p, miR-25-3p, miR-363-3p; miR-451a, miR-126-5p, miR-423-3p, miR-125b-5p, miR-25-3p, miR-338-3p; miR-451a, miR-126-5p, miR-423-3p, miR-125b-5p, miR-143-3p, miR-363-3p; miR-451a, miR-126-5p, miR-423-3p, miR-125b-5p, miR-143-3p, miR-338-3p; miR-451a, miR-126-5p, miR-423-3p, miR-125b-5p, miR-363-3p, miR-338-3p; miR-451a, miR-126-5p, miR-423-3p, miR-660-5p, miR-25-3p, miR-143-3p; miR-451a, miR-126-5p, miR-423-3p, miR-660-5p, miR-25-3p, miR-363-3p; miR-451a, miR-126-5p, miR-423-3p, miR-660-5p, miR-25-3p, miR-338-3p; miR-451a, miR-126-5p, miR-423-3p, miR-660-5p, miR-143-3p, miR-363-3p; miR-451a, miR-126-5p, miR-423-3p, miR-660-5p, miR-143-3p, miR-338-3p; miR-451a, miR-126-5p, miR-423-3p, miR-660-5p, miR-363-3p, miR-338-3p; miR-451a, miR-126-5p, miR-423-3p, miR-25-3p, miR-143-3p, miR-363-3p; miR-451a, miR-126-5p, miR-423-3p, miR-25-3p, miR-143-3p, miR-338-3p; miR-451a, miR-126-5p, miR-423-3p, miR-25-3p, miR-363-3p, miR-338-3p; miR-451a, miR-126-5p, miR-423-3p, miR-143-3p, miR-363-3p, miR-338-3p; miR-451a, miR-126-5p, miR-192-5p, miR-17-5p, miR-125b-5p, miR-660-5p; miR-451a, miR-126-5p, miR-192-5p, miR-17-5p, miR-125b-5p, miR-25-3p; miR-451a, miR-126-5p, miR-192-5p, miR-17-5p, miR-125b-5p, miR-143-3p; miR-451a, miR-126-5p, miR-192-5p, miR-17-5p, miR-125b-5p, miR-363-3p; miR- 451a, miR-126-5p, miR-192-5p, miR-17-5p, miR-125b-5p, miR-338-3p; miR-451a, miR-126-5p, miR-192-5p, miR-17-5p, miR-660-5p, miR-25-3p; miR-451a, miR-126-5p, miR-192-5p, miR-17-5p, miR-660-5p, miR-143-3p; miR-451a, miR-126-5p, miR-192-5p, miR-17-5p, miR-660-5p, miR-363-3p; miR-451a, miR-126-5p, miR-192-5p, miR-17-5p, miR-660-5p, miR-338-3p; miR-451a, miR-126-5p, miR-192-5p, miR-17-5p, miR-25-3p, miR-143-3p; miR-451a, miR-126-5p, miR-192-5p, miR-17-5p, miR-25-3p, miR-363-3p; miR-451a, miR-126-5p, miR-192-5p, miR-17-5p, miR-25-3p, miR-338-3p; miR-451a, miR-126-5p, miR-192-5p, miR-17-5p, miR-143-3p, miR-363-3p; miR-451a, miR-126-5p, miR-192-5p, miR-17-5p, miR-143-3p, miR-338-3p; miR-451a, miR-126-5p, miR-192-5p, miR-17-5p, miR-363-3p, miR-338-3p; miR-451a, miR-126-5p, miR-192-5p, miR-125b-5p, miR-660-5p, miR-25-3p; miR-451a, miR-126-5p, miR-192-5p, miR-125b-5p, miR-660-5p, miR-143-3p; miR-451a, miR-126-5p, miR-192-5p, miR-125b-5p, miR-660-5p, miR-363-3p; miR-451a, miR-126-5p, miR-192-5p, miR-125b-5p, miR-660-5p, miR-338-3p; miR-451a, miR-126-5p, miR-192-5p, miR-125b-5p, miR-25-3p, miR-143-3p; miR-451a, miR-126-5p, miR-192-5p, miR-125b-5p, miR-25-3p, miR-363-3p; miR-451a, miR-126-5p, miR-192-5p, miR-125b-5p, miR-25-3p, miR-338-3p; miR-451a, miR-126-5p, miR-192-5p, miR-125b-5p, miR-143-3p, miR-363-3p; miR-451a, miR-126-5p, miR-192-5p, miR-125b-5p, miR-143-3p, miR-338-3p; miR-451a, miR-126-5p, miR-192-5p, miR-125b-5p, miR-363-3p, miR-338-3p; miR-451a, miR-126-5p, miR-192-5p, miR-660-5p, miR-25-3p, miR-143-3p; miR-451a, miR-126-5p, miR-192-5p, miR-660-5p, miR-25-3p, miR-363-3p; miR-451a, miR-126-5p, miR-192-5p, miR-660-5p, miR-25-3p, miR-338-3p; miR-451a, miR-126-5p, miR-192-5p, miR-660-5p, miR-143-3p, miR-363-3p; miR-451a, miR-126-5p, miR-192-5p, miR-660-5p, miR-143-3p, miR-338-3p; miR-451a, miR-126-5p, miR-192-5p, miR-660-5p, miR-363-3p, miR-338-3p; miR-451a, miR-126-5p, miR-192-5p, miR-25-3p, miR-143-3p, miR-363-3p; miR-451a, miR-126-5p, miR-192-5p, miR-25-3p, miR-143-3p, miR-338-3p; miR-451a, miR-126-5p, miR-192-5p, miR-25-3p, miR-363-3p, miR-338-3p; miR-451a, miR-126-5p, miR-192-5p, miR-143-3p, miR-363-3p, miR-338-3p; miR-451a, miR-126-5p, miR-17-5p, miR-125b-5p, miR-660-5p, miR-25-3p; miR-451a, miR-126-5p, miR-17-5p, miR-125b-5p, miR-660-5p, miR-143-3p; miR-451a, miR-126-5p, miR-17-5p, miR-125b-5p, miR-660-5p, miR-363-3p; miR-451a, miR-126-5p, miR-17-5p, miR-125b-5p, miR-660-5p, miR-338-3p; miR-451a, miR-126-5p, miR-17-5p, miR-125b-5p, miR-25-3p, miR-143-3p; miR-451a, miR-126-5p, miR-17-5p, miR-125b-5p, miR-25-3p, miR-363-3p; miR-451a, miR-126-5p, miR-17-5p, miR-125b-5p, miR-25-3p, miR-338-3p; miR-451a, miR-126-5p, miR-17-5p, miR-125b-5p, miR-143-3p, miR-363-3p; miR-451a, miR-126-5p, miR-17-5p, miR-125b-5p, miR-143-3p, miR-338-3p; miR-451a, miR-126-5p, miR-17-5p, miR-125b-5p, miR-363-3p, miR-338-3p; miR-451a, miR-126-5p, miR-17-5p, miR-660-5p, miR-25-3p, miR-143-3p; miR-451a, miR-126-5p, miR-17-5p, miR-660-5p, miR-25-3p, miR-363-3p; miR-451a, miR-126-5p, miR-17-5p, miR-660-5p, miR-25-3p, miR-338-3p; miR-451a, miR-126-5p, miR-17-5p, miR-660-5p, miR-143-3p, miR-363-3p; miR-451a, miR-126-5p, miR-17-5p, miR-660-5p, miR-143-3p, miR-338-3p; miR-451a, miR-126-5p, miR-17-5p, miR-660-5p, miR-363-3p, miR-338-3p; miR-451a, miR-126-5p, miR-17-5p, miR-25-3p, miR-143-3p, miR-363-3p; miR-451a, miR-126-5p, miR-17-5p, miR-25-3p, miR-143-3p, miR-338-3p; miR-451a, miR-126-5p, miR-17-5p, miR-25-3p, miR-363-3p, miR-338-3p; miR-451a, miR-126-5p, miR-17-5p, miR-143-3p, miR-363-3p, miR-338-3p; miR-451a, miR-126-5p, miR-125b-5p, miR-660-5p, miR-25-3p, miR-143-3p; miR-451a, miR-126-5p, miR-125b-5p, miR-660-5p, miR-25-3p, miR-363-3p; miR-451a, miR-126-5p, miR-125b-5p, miR-660-5p, miR-25-3p, miR-338-3p; miR-451a, miR-126-5p, miR-125b-5p, miR-660-5p, miR-143-3p, miR-363-3p; miR-451a, miR-126-5p, miR-125b-5p, miR-660-5p, miR-143-3p, miR-338-3p; miR-451a, miR-126-5p, miR-125b-5p, miR-660-5p, miR-363-3p, miR-338-3p; miR-451a, miR-126-5p, miR-125b-5p, miR-25-3p, miR-143-3p, miR-363-3p; miR-451a, miR-126-5p, miR-125b-5p, miR-25-3p, miR-143-3p, miR-338-3p; miR-451a, miR-126-5p, miR-125b-5p, miR-25-3p, miR-363-3p, miR-338-3p; miR-451a, miR-126-5p, miR-125b-5p, miR-143-3p, miR-363-3p, miR-338-3p; miR-451a, miR-126-5p, miR-660-5p, miR-25-3p, miR-143-3p, miR-363-3p; miR-451a, miR-126-5p, miR-660-5p, miR-25-3p, miR-143-3p, miR-338-3p; miR-451a, miR-126-5p, miR-660-5p, miR-25-3p, miR-363-3p, miR-338-3p; miR-451a, miR-126-5p, miR-660-5p, miR-143-3p, miR-363-3p, miR-338-3p; miR-451a, miR-126-5p, miR-25-3p, miR-143-3p, miR-363-3p, miR-338-3p; miR-451a, miR-423-3p, miR-192-5p, miR-17-5p, miR-125b-5p, miR-660-5p; miR-451a, miR-423-3p, miR-192-5p, miR-17-5p, miR-125b-5p, miR-25-3p; miR-451a, miR-423-3p, miR-192-5p, miR-17-5p, miR-125b-5p, miR-143-3p; miR-451a, miR-423-3p, miR-192-5p, miR-17-5p, miR-125b-5p, miR-363-3p; miR-451a, miR-423-3p, miR-192-5p, miR-17-5p, miR-125b-5p, miR-338-3p; miR-451a, miR-423-3p, miR-192-5p, miR-17-5p, miR-660-5p, miR-25-3p; miR-451a, miR-423-3p, miR-192-5p, miR-17-5p, miR-660-5p, miR-143-3p; miR-451a, miR-423-3p, miR-192-5p, miR-17-5p, miR-660-5p, miR-363-3p; miR-451a, miR-423-3p, miR-192-5p, miR-17-5p, miR-660-5p, miR-338-3p; miR-451a, miR-423-3p, miR-192-5p, miR-17-5p, miR-25-3p, miR-143-3p; miR-451a, miR-423-3p, miR-192-5p, miR-17-5p, miR-25-3p, miR-363-3p; miR-451a, miR-423-3p, miR-192-5p, miR-17-5p, miR-25-3p, miR-338-3p; miR-451a, miR-423-3p, miR-192-5p, miR-17-5p, miR-143-3p, miR-363-3p; miR-451a, miR-423-3p, miR-192-5p, miR-17-5p, miR-143-3p, miR-338-3p; miR-451a, miR-423-3p, miR-192-5p, miR-17-5p, miR-363-3p, miR-338-3p; miR-451a, miR-423-3p, miR-192-5p, miR-125b-5p, miR-660-5p, miR-25-3p; miR-451a, miR-423-3p, miR-192-5p, miR-125b-5p, miR-660-5p, miR-143-3p; miR-451a, miR-423-3p, miR-192-5p, miR-125b-5p, miR-660-5p, miR-363-3p; miR-451a, miR-423-3p, miR-192-5p, miR-125b-5p, miR-660-5p, miR-338-3p; miR-451a, miR-423-3p, miR-192-5p, miR-125b-5p, miR-25-3p, miR-143-3p; miR-451a, miR-423-3p, miR-192-5p, miR-125b-5p, miR-25-3p, miR-363-3p; miR-451a, miR-423-3p, miR-192-5p, miR-125b-5p, miR-25-3p, miR-338-3p; miR-451a, miR-423-3p, miR-192-5p, miR-125b-5p, miR-143-3p, miR-363-3p; miR-451a, miR-423-3p, miR-192-5p, miR-125b-5p, miR-143-3p, miR-338-3p; miR-451a, miR-423-3p, miR-192-5p, miR-125b-5p, miR-363-3p, miR-338-3p; miR-451a, miR-423-3p, miR-192-5p, miR-660-5p, miR-25-3p, miR-143-3p; miR-451a, miR-423-3p, miR-192-5p, miR-660-5p, miR-25-3p, miR-363-3p; miR-451a, miR-423-3p, miR-192-5p, miR-660-5p, miR-25-3p, miR-338-3p; miR-451a, miR-423-3p, miR-192-5p, miR-660-5p, miR-143-3p, miR-363-3p; miR-451a, miR-423-3p, miR-192-5p, miR-660-5p, miR-143-3p, miR-338-3p; miR-451a, miR-423-3p, miR-192-5p, miR-660-5p, miR-363-3p, miR-338-3p; miR-451a, miR-423-3p, miR-192-5p, miR-25-3p, miR-143-3p, miR-363-3p; miR-451a, miR-423-3p, miR-192-5p, miR-25-3p, miR-143-3p, miR-338-3p; miR-451a, miR-423-3p, miR-192-5p, miR-25-3p, miR-363-3p, miR-338-3p; miR-451a, miR-423-3p, miR-192-5p, miR-143-3p, miR-363-3p, miR- 338-3p; miR-451a, miR-423-3p, miR-17-5p, miR-125b-5p, miR-660-5p, miR-25-3p; miR-451a, miR-423-3p, miR-17-5p, miR-125b-5p, miR-660-5p, miR-143-3p; miR-451a, miR-423-3p, miR-17-5p, miR-125b-5p, miR-660-5p, miR-363-3p; miR-451a, miR-423-3p, miR-17-5p, miR-125b-5p, miR-660-5p, miR-338-3p; miR-451a, miR-423-3p, miR-17-5p, miR-125b-5p, miR-25-3p, miR-143-3p; miR-451a, miR-423-3p, miR-17-5p, miR-125b-5p, miR-25-3p, miR-363-3p; miR-451a, miR-423-3p, miR-17-5p, miR-125b-5p, miR-25-3p, miR-338-3p; miR-451a, miR-423-3p, miR-17-5p, miR-125b-5p, miR-143-3p, miR-363-3p; miR-451a, miR-423-3p, miR-17-5p, miR-125b-5p, miR-143-3p, miR-338-3p; miR-451a, miR-423-3p, miR-17-5p, miR-125b-5p, miR-363-3p, miR-338-3p; miR-451a, miR-423-3p, miR-17-5p, miR-660-5p, miR-25-3p, miR-143-3p; miR-451a, miR-423-3p, miR-17-5p, miR-660-5p, miR-25-3p, miR-363-3p; miR-451a, miR-423-3p, miR-17-5p, miR-660-5p, miR-25-3p, miR-338-3p; miR-451a, miR-423-3p, miR-17-5p, miR-660-5p, miR-143-3p, miR-363-3p; miR-451a, miR-423-3p, miR-17-5p, miR-660-5p, miR-143-3p, miR-338-3p; miR-451a, miR-423-3p, miR-17-5p, miR-660-5p, miR-363-3p, miR-338-3p; miR-451a, miR-423-3p, miR-17-5p, miR-25-3p, miR-143-3p, miR-363-3p; miR-451a, miR-423-3p, miR-17-5p, miR-25-3p, miR-143-3p, miR-338-3p; miR-451a, miR-423-3p, miR-17-5p, miR-25-3p, miR-363-3p, miR-338-3p; miR-451a, miR-423-3p, miR-17-5p, miR-143-3p, miR-363-3p, miR-338-3p; miR-451a, miR-423-3p, miR-125b-5p, miR-660-5p, miR-25-3p, miR-143-3p; miR-451a, miR-423-3p, miR-125b-5p, miR-660-5p, miR-25-3p, miR-363-3p; miR-451a, miR-423-3p, miR-125b-5p, miR-660-5p, miR-25-3p, miR-338-3p; miR-451a, miR-423-3p, miR-125b-5p, miR-660-5p, miR-143-3p, miR-363-3p; miR-451a, miR-423-3p, miR-125b-5p, miR-660-5p, miR-143-3p, miR-338-3p; miR-451a, miR-423-3p, miR-125b-5p, miR-660-5p, miR-363-3p, miR-338-3p; miR-451a, miR-423-3p, miR-125b-5p, miR-25-3p, miR-143-3p, miR-363-3p; miR-451a, miR-423-3p, miR-125b-5p, miR-25-3p, miR-143-3p, miR-338-3p; miR-451a, miR-423-3p, miR-125b-5p, miR-25-3p, miR-363-3p, miR-338-3p; miR-451a, miR-423-3p, miR-125b-5p, miR-143-3p, miR-363-3p, miR-338-3p; miR-451a, miR-423-3p, miR-660-5p, miR-25-3p, miR-143-3p, miR-363-3p; miR-451a, miR-423-3p, miR-660-5p, miR-25-3p, miR-143-3p, miR-338-3p; miR-451a, miR-423-3p, miR-660-5p, miR-25-3p, miR-363-3p, miR-338-3p; miR-451a, miR-423-3p, miR-660-5p, miR-143-3p, miR-363-3p, miR-338-3p; miR-451a, miR-423-3p, miR-25-3p, miR-143-3p, miR-363-3p, miR-338-3p; miR-451a, miR-192-5p, miR-17-5p, miR-125b-5p, miR-660-5p, miR-25-3p; miR-451a, miR-192-5p, miR-17-5p, miR-125b-5p, miR-660-5p, miR-143-3p; miR-451a, miR-192-5p, miR-17-5p, miR-125b-5p, miR-660-5p, miR-363-3p; miR-451a, miR-192-5p, miR-17-5p, miR-125b-5p, miR-660-5p, miR-338-3p; miR-451a, miR-192-5p, miR-17-5p, miR-125b-5p, miR-25-3p, miR-143-3p; miR-451a, miR-192-5p, miR-17-5p, miR-125b-5p, miR-25-3p, miR-363-3p; miR-451a, miR-192-5p, miR-17-5p, miR-125b-5p, miR-25-3p, miR-338-3p; miR-451a, miR-192-5p, miR-17-5p, miR-125b-5p, miR-143-3p, miR-363-3p; miR-451a, miR-192-5p, miR-17-5p, miR-125b-5p, miR-143-3p, miR-338-3p; miR-451a, miR-192-5p, miR-17-5p, miR-125b-5p, miR-363-3p, miR-338-3p; miR-451a, miR-192-5p, miR-17-5p, miR-660-5p, miR-25-3p, miR-143-3p; miR-451a, miR-192-5p, miR-17-5p, miR-660-5p, miR-25-3p, miR-363-3p; miR-451a, miR-192-5p, miR-17-5p, miR-660-5p, miR-25-3p, miR-338-3p; miR-451a, miR-192-5p, miR-17-5p, miR-660-5p, miR-143-3p, miR-363-3p; miR-451a, miR-192-5p, miR-17-5p, miR-660-5p, miR-143-3p, miR-338-3p; miR-451a, miR-192-5p, miR-17-5p, miR-660-5p, miR-363-3p, miR-338-3p; miR-451a, miR-192-5p, miR-17-5p, miR-25-3p, miR-143-3p, miR-363-3p; miR-451a, miR-192-5p, miR-17-5p, miR-25-3p, miR-143-3p, miR-338-3p; miR-451a, miR-192-5p, miR-17-5p, miR-25-3p, miR-363-3p, miR-338-3p; miR-451a, miR-192-5p, miR-17-5p, miR-143-3p, miR-363-3p, miR-338-3p; miR-451a, miR-192-5p, miR-125b-5p, miR-660-5p, miR-25-3p, miR-143-3p; miR-451a, miR-192-5p, miR-125b-5p, miR-660-5p, miR-25-3p, miR-363-3p; miR-451a, miR-192-5p, miR-125b-5p, miR-660-5p, miR-25-3p, miR-338-3p; miR-451a, miR-192-5p, miR-125b-5p, miR-660-5p, miR-143-3p, miR-363-3p; miR-451a, miR-192-5p, miR-125b-5p, miR-660-5p, miR-143-3p, miR-338-3p; miR-451a, miR-192-5p, miR-125b-5p, miR-660-5p, miR-363-3p, miR-338-3p; miR-451a, miR-192-5p, miR-125b-5p, miR-25-3p, miR-143-3p, miR-363-3p; miR-451a, miR-192-5p, miR-125b-5p, miR-25-3p, miR-143-3p, miR-338-3p; miR-451a, miR-192-5p, miR-125b-5p, miR-25-3p, miR-363-3p, miR-338-3p; miR-451a, miR-192-5p, miR-125b-5p, miR-143-3p, miR-363-3p, miR-338-3p; miR-451a, miR-192-5p, miR-660-5p, miR-25-3p, miR-143-3p, miR-363-3p; miR-451a, miR-192-5p, miR-660-5p, miR-25-3p, miR-143-3p, miR-338-3p; miR-451a, miR-192-5p, miR-660-5p, miR-25-3p, miR-363-3p, miR-338-3p; miR-451a, miR-192-5p, miR-660-5p, miR-143-3p, miR-363-3p, miR-338-3p; miR-451a, miR-192-5p, miR-25-3p, miR-143-3p, miR-363-3p, miR-338-3p; miR-451a, miR-17-5p, miR-125b-5p, miR-660-5p, miR-25-3p, miR-143-3p; miR-451a, miR-17-5p, miR-125b-5p, miR-660-5p, miR-25-3p, miR-363-3p; miR-451a, miR-17-5p, miR-125b-5p, miR-660-5p, miR-25-3p, miR-338-3p; miR-451a, miR-17-5p, miR-125b-5p, miR-660-5p, miR-143-3p, miR-363-3p; miR-451a, miR-17-5p, miR-125b-5p, miR-660-5p, miR-143-3p, miR-338-3p; miR-451a, miR-17-5p, miR-125b-5p, miR-660-5p, miR-363-3p, miR-338-3p; miR-451a, miR-17-5p, miR-125b-5p, miR-25-3p, miR-143-3p, miR-363-3p; miR-451a, miR-17-5p, miR-125b-5p, miR-25-3p, miR-143-3p, miR-338-3p; miR-451a, miR-17-5p, miR-125b-5p, miR-25-3p, miR-363-3p, miR-338-3p; miR-451a, miR-17-5p, miR-125b-5p, miR-143-3p, miR-363-3p, miR-338-3p; miR-451a, miR-17-5p, miR-660-5p, miR-25-3p, miR-143-3p, miR-363-3p; miR-451a, miR-17-5p, miR-660-5p, miR-25-3p, miR-143-3p, miR-338-3p; miR-451a, miR-17-5p, miR-660-5p, miR-25-3p, miR-363-3p, miR-338-3p; miR-451a, miR-17-5p, miR-660-5p, miR-143-3p, miR-363-3p, miR-338-3p; miR-451a, miR-17-5p, miR-25-3p, miR-143-3p, miR-363-3p, miR-338-3p; miR-451a, miR-125b-5p, miR-660-5p, miR-25-3p, miR-143-3p, miR-363-3p; miR-451a, miR-125b-5p, miR-660-5p, miR-25-3p, miR-143-3p, miR-338-3p; miR-451a, miR-125b-5p, miR-660-5p, miR-25-3p, miR-363-3p, miR-338-3p; miR-451a, miR-125b-5p, miR-660-5p, miR-143-3p, miR-363-3p, miR-338-3p; miR-451a, miR-125b-5p, miR-25-3p, miR-143-3p, miR-363-3p, miR-338-3p; miR-451a, miR-660-5p, miR-25-3p, miR-143-3p, miR-363-3p, miR-338-3p; miR-195-5p, miR-126-5p, miR-423-3p, miR-192-5p, miR-17-5p, miR-125b-5p; miR-195-5p, miR-126-5p, miR-423-3p, miR-192-5p, miR-17-5p, miR-660-5p; miR-195-5p, miR-126-5p, miR-423-3p, miR-192-5p, miR-17-5p, miR-25-3p; miR-195-5p, miR-126-5p, miR-423-3p, miR-192-5p, miR-17-5p, miR-143-3p; miR-195-5p, miR-126-5p, miR-423-3p, miR-192-5p, miR-17-5p, miR-363-3p; miR-195-5p, miR-126-5p, miR-423-3p, miR-192-5p, miR-17-5p, miR-338-3p; miR-195-5p, miR-126-5p, miR-423-3p, miR-192-5p, miR-125b-5p, miR-660-5p; miR-195-5p, miR-126-5p, miR-423-3p, miR-192-5p, miR-125b-5p, miR-25-3p; miR-195-5p, miR-126-5p, miR-423-3p, miR-192-5p, miR-125b-5p, miR-143-3p; miR-195-5p, miR-126-5p, miR-423-3p, miR-192-5p, miR-125b-5p, miR-363-

3p; miR-195-5p, miR-126-5p, miR-423-3p, miR-192-5p, miR-125b-5p, miR-338-3p; miR-195-5p, miR-126-5p, miR-423-3p, miR-192-5p, miR-660-5p, miR-25-3p; miR-195-5p, miR-126-5p, miR-423-3p, miR-192-5p, miR-660-5p, miR-143-3p; miR-195-5p, miR-126-5p, miR-423-3p, miR-192-5p, miR-660-5p, miR-363-3p; miR-195-5p, miR-126-5p, miR-423-3p, miR-192-5p, miR-660-5p, miR-338-3p; miR-195-5p, miR-126-5p, miR-423-3p, miR-192-5p, miR-25-3p, miR-143-3p; miR-195-5p, miR-126-5p, miR-423-3p, miR-192-5p, miR-25-3p, miR-363-3p; miR-195-5p, miR-126-5p, miR-423-3p, miR-192-5p, miR-25-3p, miR-338-3p; miR-195-5p, miR-126-5p, miR-423-3p, miR-192-5p, miR-143-3p, miR-363-3p; miR-195-5p, miR-126-5p, miR-423-3p, miR-192-5p, miR-143-3p, miR-338-3p; miR-195-5p, miR-126-5p, miR-423-3p, miR-192-5p, miR-363-3p, miR-338-3p; miR-195-5p, miR-126-5p, miR-423-3p, miR-17-5p, miR-125b-5p, miR-660-5p; miR-195-5p, miR-126-5p, miR-423-3p, miR-17-5p, miR-125b-5p, miR-25-3p; miR-195-5p, miR-126-5p, miR-423-3p, miR-17-5p, miR-125b-5p, miR-143-3p; miR-195-5p, miR-126-5p, miR-423-3p, miR-17-5p, miR-125b-5p, miR-363-3p; miR-195-5p, miR-126-5p, miR-423-3p, miR-17-5p, miR-125b-5p, miR-338-3p; miR-195-5p, miR-126-5p, miR-423-3p, miR-17-5p, miR-660-5p, miR-25-3p; miR-195-5p, miR-126-5p, miR-423-3p, miR-17-5p, miR-660-5p, miR-143-3p; miR-195-5p, miR-126-5p, miR-423-3p, miR-17-5p, miR-660-5p, miR-363-3p; miR-195-5p, miR-126-5p, miR-423-3p, miR-17-5p, miR-660-5p, miR-338-3p; miR-195-5p, miR-126-5p, miR-423-3p, miR-17-5p, miR-25-3p, miR-143-3p; miR-195-5p, miR-126-5p, miR-423-3p, miR-17-5p, miR-25-3p, miR-363-3p; miR-195-5p, miR-126-5p, miR-423-3p, miR-17-5p, miR-25-3p, miR-338-3p; miR-195-5p, miR-126-5p, miR-423-3p, miR-17-5p, miR-143-3p, miR-363-3p; miR-195-5p, miR-126-5p, miR-423-3p, miR-17-5p, miR-143-3p, miR-338-3p; miR-195-5p, miR-126-5p, miR-423-3p, miR-17-5p, miR-363-3p, miR-338-3p; miR-195-5p, miR-126-5p, miR-423-3p, miR-125b-5p, miR-660-5p, miR-25-3p; miR-195-5p, miR-126-5p, miR-423-3p, miR-125b-5p, miR-660-5p, miR-143-3p; miR-195-5p, miR-126-5p, miR-423-3p, miR-125b-5p, miR-660-5p, miR-363-3p; miR-195-5p, miR-126-5p, miR-423-3p, miR-125b-5p, miR-660-5p, miR-338-3p; miR-195-5p, miR-126-5p, miR-423-3p, miR-125b-5p, miR-25-3p, miR-143-3p; miR-195-5p, miR-126-5p, miR-423-3p, miR-125b-5p, miR-25-3p, miR-363-3p; miR-195-5p, miR-126-5p, miR-423-3p, miR-125b-5p, miR-25-3p, miR-338-3p; miR-195-5p, miR-126-5p, miR-423-3p, miR-125b-5p, miR-143-3p, miR-363-3p; miR-195-5p, miR-126-5p, miR-423-3p, miR-125b-5p, miR-143-3p, miR-338-3p; miR-195-5p, miR-126-5p, miR-423-3p, miR-125b-5p, miR-363-3p, miR-338-3p; miR-195-5p, miR-126-5p, miR-423-3p, miR-660-5p, miR-25-3p, miR-143-3p; miR-195-5p, miR-126-5p, miR-423-3p, miR-660-5p, miR-25-3p, miR-363-3p; miR-195-5p, miR-126-5p, miR-423-3p, miR-660-5p, miR-25-3p, miR-338-3p; miR-195-5p, miR-126-5p, miR-423-3p, miR-660-5p, miR-143-3p, miR-363-3p; miR-195-5p, miR-126-5p, miR-423-3p, miR-660-5p, miR-363-3p, miR-338-3p; miR-195-5p, miR-126-5p, miR-423-3p, miR-25-3p, miR-143-3p, miR-363-3p; miR-195-5p, miR-126-5p, miR-423-3p, miR-25-3p, miR-143-3p, miR-338-3p; miR-195-5p, miR-126-5p, miR-423-3p, miR-25-3p, miR-363-3p, miR-338-3p; miR-195-5p, miR-126-5p, miR-423-3p, miR-143-3p, miR-363-3p, miR-338-3p; miR-195-5p, miR-126-5p, miR-192-5p, miR-17-5p, miR-125b-5p, miR-660-5p; miR-195-5p, miR-126-5p, miR-192-5p, miR-17-5p, miR-125b-5p, miR-25-3p; miR-195-5p, miR-126-5p, miR-192-5p, miR-17-5p, miR-125b-5p, miR-143-3p; miR-195-5p, miR-126-5p, miR-192-5p, miR-17-5p, miR-125b-5p, miR-363-3p; miR-195-5p, miR-126-5p, miR-192-5p, miR-17-5p, miR-125b-5p, miR-338-3p; miR-195-5p, miR-126-5p, miR-192-5p, miR-17-5p, miR-660-5p, miR-25-3p; miR-195-5p, miR-126-5p, miR-192-5p, miR-17-5p, miR-660-5p, miR-143-3p; miR-195-5p, miR-126-5p, miR-192-5p, miR-17-5p, miR-660-5p, miR-363-3p; miR-195-5p, miR-126-5p, miR-192-5p, miR-17-5p, miR-660-5p, miR-338-3p; miR-195-5p, miR-126-5p, miR-192-5p, miR-17-5p, miR-25-3p, miR-143-3p; miR-195-5p, miR-126-5p, miR-192-5p, miR-17-5p, miR-25-3p, miR-363-3p; miR-195-5p, miR-126-5p, miR-192-5p, miR-17-5p, miR-25-3p, miR-338-3p; miR-195-5p, miR-126-5p, miR-192-5p, miR-17-5p, miR-143-3p, miR-363-3p; miR-195-5p, miR-126-5p, miR-192-5p, miR-17-5p, miR-143-3p, miR-338-3p; miR-195-5p, miR-126-5p, miR-192-5p, miR-17-5p, miR-363-3p, miR-338-3p; miR-195-5p, miR-126-5p, miR-192-5p, miR-125b-5p, miR-660-5p, miR-25-3p; miR-195-5p, miR-126-5p, miR-192-5p, miR-125b-5p, miR-660-5p, miR-143-3p; miR-195-5p, miR-126-5p, miR-192-5p, miR-125b-5p, miR-660-5p, miR-363-3p; miR-195-5p, miR-126-5p, miR-192-5p, miR-125b-5p, miR-660-5p, miR-338-3p; miR-195-5p, miR-126-5p, miR-192-5p, miR-125b-5p, miR-25-3p, miR-143-3p; miR-195-5p, miR-126-5p, miR-192-5p, miR-125b-5p, miR-25-3p, miR-363-3p; miR-195-5p, miR-126-5p, miR-192-5p, miR-125b-5p, miR-25-3p, miR-338-3p; miR-195-5p, miR-126-5p, miR-192-5p, miR-125b-5p, miR-143-3p, miR-363-3p; miR-195-5p, miR-126-5p, miR-192-5p, miR-125b-5p, miR-143-3p, miR-338-3p; miR-195-5p, miR-126-5p, miR-192-5p, miR-125b-5p, miR-363-3p, miR-338-3p; miR-195-5p, miR-126-5p, miR-192-5p, miR-660-5p, miR-25-3p, miR-143-3p; miR-195-5p, miR-126-5p, miR-192-5p, miR-660-5p, miR-25-3p, miR-363-3p; miR-195-5p, miR-126-5p, miR-192-5p, miR-660-5p, miR-25-3p, miR-338-3p; miR-195-5p, miR-126-5p, miR-192-5p, miR-660-5p, miR-143-3p, miR-363-3p; miR-195-5p, miR-126-5p, miR-192-5p, miR-660-5p, miR-143-3p, miR-338-3p; miR-195-5p, miR-126-5p, miR-192-5p, miR-660-5p, miR-363-3p, miR-338-3p; miR-195-5p, miR-126-5p, miR-192-5p, miR-25-3p, miR-143-3p, miR-363-3p; miR-195-5p, miR-126-5p, miR-192-5p, miR-25-3p, miR-143-3p, miR-338-3p; miR-195-5p, miR-126-5p, miR-192-5p, miR-25-3p, miR-363-3p, miR-338-3p; miR-195-5p, miR-126-5p, miR-192-5p, miR-143-3p, miR-363-3p, miR-338-3p; miR-195-5p, miR-126-5p, miR-17-5p, miR-125b-5p, miR-660-5p, miR-25-3p; miR-195-5p, miR-126-5p, miR-17-5p, miR-125b-5p, miR-660-5p, miR-143-3p; miR-195-5p, miR-126-5p, miR-17-5p, miR-125b-5p, miR-660-5p, miR-363-3p; miR-195-5p, miR-126-5p, miR-17-5p, miR-125b-5p, miR-660-5p, miR-338-3p; miR-195-5p, miR-126-5p, miR-17-5p, miR-125b-5p, miR-25-3p, miR-143-3p; miR-195-5p, miR-126-5p, miR-17-5p, miR-125b-5p, miR-25-3p, miR-363-3p; miR-195-5p, miR-126-5p, miR-17-5p, miR-125b-5p, miR-25-3p, miR-338-3p; miR-195-5p, miR-126-5p, miR-17-5p, miR-125b-5p, miR-143-3p, miR-363-3p; miR-195-5p, miR-126-5p, miR-17-5p, miR-125b-5p, miR-143-3p, miR-338-3p; miR-195-5p, miR-126-5p, miR-17-5p, miR-125b-5p, miR-363-3p, miR-338-3p; miR-195-5p, miR-126-5p, miR-17-5p, miR-660-5p, miR-25-3p, miR-143-3p; miR-195-5p, miR-126-5p, miR-17-5p, miR-660-5p, miR-25-3p, miR-363-3p; miR-195-5p, miR-126-5p, miR-17-5p, miR-660-5p, miR-25-3p, miR-338-3p; miR-195-5p, miR-126-5p, miR-17-5p, miR-660-5p, miR-143-3p, miR-363-3p; miR-195-5p, miR-126-5p, miR-17-5p, miR-660-5p, miR-143-3p, miR-338-3p; miR-195-5p, miR-126-5p, miR-17-5p, miR-660-5p, miR-363-3p, miR-338-3p; miR-195-5p, miR-126-5p, miR-17-5p, miR-25-3p, miR-143-3p, miR-363-3p; miR-195-5p, miR-126-5p, miR-17-5p, miR- 126-5p, miR-17-5p, miR-25-3p, miR-143-3p, miR-338-3p; miR-195-5p, miR-126-5p, miR-17-5p, miR-25-3p, miR-363-3p, miR-338-3p; miR-195-5p, miR-126-5p, miR-17-5p, miR-143-3p, miR-363-3p, miR-338-3p; miR-195-5p, miR-126-5p, miR-125b-5p, miR-660-5p, miR-25-3p, miR-143-3p; miR-195-5p, miR-126-5p, miR-125b-5p, miR-660-5p, miR-25-3p, miR-363-3p; miR-195-5p, miR-126-5p, miR-125b-5p, miR-660-5p, miR-25-3p, miR-338-3p; miR-195-5p, miR-126-5p, miR-125b-5p, miR-660-5p, miR-143-3p, miR-363-3p; miR-195-5p, miR-126-5p, miR-125b-5p, miR-660-5p, miR-143-3p, miR-338-3p; miR-195-5p, miR-126-5p, miR-125b-5p, miR-660-5p, miR-363-3p, miR-338-3p; miR-195-5p, miR-126-5p, miR-125b-5p, miR-25-3p, miR-143-3p, miR-363-3p; miR-195-5p, miR-126-5p, miR-125b-5p, miR-25-3p, miR-143-3p, miR-338-3p; miR-195-5p, miR-126-5p, miR-125b-5p, miR-25-3p, miR-363-3p, miR-338-3p; miR-195-5p, miR-126-5p, miR-125b-5p, miR-143-3p, miR-363-3p, miR-338-3p; miR-195-5p, miR-126-5p, miR-660-5p, miR-25-3p, miR-143-3p, miR-363-3p; miR-195-5p, miR-126-5p, miR-660-5p, miR-25-3p, miR-143-3p, miR-338-3p; miR-195-5p, miR-126-5p, miR-660-5p, miR-25-3p, miR-363-3p, miR-338-3p; miR-195-5p, miR-126-5p, miR-660-5p, miR-143-3p, miR-363-3p, miR-338-3p; miR-195-5p, miR-126-5p, miR-25-3p, miR-143-3p, miR-363-3p, miR-338-3p; miR-195-5p, miR-423-3p, miR-192-5p, miR-17-5p, miR-125b-5p, miR-660-5p; miR-195-5p, miR-423-3p, miR-192-5p, miR-17-5p, miR-125b-5p, miR-25-3p; miR-195-5p, miR-423-3p, miR-192-5p, miR-17-5p, miR-125b-5p, miR-143-3p; miR-195-5p, miR-423-3p, miR-192-5p, miR-17-5p, miR-125b-5p, miR-363-3p; miR-195-5p, miR-423-3p, miR-192-5p, miR-17-5p, miR-125b-5p, miR-338-3p; miR-195-5p, miR-423-3p, miR-192-5p, miR-17-5p, miR-660-5p, miR-25-3p; miR-195-5p, miR-423-3p, miR-192-5p, miR-17-5p, miR-660-5p, miR-143-3p; miR-195-5p, miR-423-3p, miR-192-5p, miR-17-5p, miR-660-5p, miR-363-3p; miR-195-5p, miR-423-3p, miR-192-5p, miR-17-5p, miR-660-5p, miR-338-3p; miR-195-5p, miR-423-3p, miR-192-5p, miR-17-5p, miR-25-3p, miR-143-3p; miR-195-5p, miR-423-3p, miR-192-5p, miR-17-5p, miR-25-3p, miR-363-3p; miR-195-5p, miR-423-3p, miR-192-5p, miR-17-5p, miR-25-3p, miR-338-3p; miR-195-5p, miR-423-3p, miR-192-5p, miR-17-5p, miR-143-3p, miR-363-3p; miR-195-5p, miR-423-3p, miR-192-5p, miR-17-5p, miR-143-3p, miR-338-3p; miR-195-5p, miR-423-3p, miR-192-5p, miR-17-5p, miR-363-3p, miR-338-3p; miR-195-5p, miR-423-3p, miR-192-5p, miR-125b-5p, miR-660-5p, miR-25-3p; miR-195-5p, miR-423-3p, miR-192-5p, miR-125b-5p, miR-660-5p, miR-143-3p; miR-195-5p, miR-423-3p, miR-192-5p, miR-125b-5p, miR-660-5p, miR-363-3p; miR-195-5p, miR-423-3p, miR-192-5p, miR-125b-5p, miR-660-5p, miR-338-3p; miR-195-5p, miR-423-3p, miR-192-5p, miR-125b-5p, miR-25-3p, miR-143-3p; miR-195-5p, miR-423-3p, miR-192-5p, miR-125b-5p, miR-25-3p, miR-363-3p; miR-195-5p, miR-423-3p, miR-192-5p, miR-125b-5p, miR-25-3p, miR-338-3p; miR-195-5p, miR-423-3p, miR-192-5p, miR-125b-5p, miR-143-3p, miR-363-3p; miR-195-5p, miR-423-3p, miR-192-5p, miR-125b-5p, miR-143-3p, miR-338-3p; miR-195-5p, miR-423-3p, miR-192-5p, miR-125b-5p, miR-363-3p, miR-338-3p; miR-195-5p, miR-423-3p, miR-192-5p, miR-660-5p, miR-25-3p, miR-143-3p; miR-195-5p, miR-423-3p, miR-192-5p, miR-660-5p, miR-25-3p, miR-363-3p; miR-195-5p, miR-423-3p, miR-192-5p, miR-660-5p, miR-25-3p, miR-338-3p; miR-195-5p, miR-423-3p, miR-192-5p, miR-660-5p, miR-143-3p, miR-363-3p; miR-195-5p, miR-423-3p, miR-192-5p, miR-660-5p, miR-143-3p, miR-338-3p; miR-195-5p, miR-423-3p, miR-192-5p, miR-660-5p, miR-363-3p, miR-338-3p; miR-195-5p, miR-423-3p, miR-192-5p, miR-25-3p, miR-143-3p, miR-363-3p; miR-195-5p, miR-423-3p, miR-192-5p, miR-25-3p, miR-143-3p, miR-338-3p; miR-195-5p, miR-423-3p, miR-192-5p, miR-25-3p, miR-363-3p, miR-338-3p; miR-195-5p, miR-423-3p, miR-192-5p, miR-143-3p, miR-363-3p, miR-338-3p; miR-195-5p, miR-423-3p, miR-17-5p, miR-125b-5p, miR-660-5p, miR-25-3p; miR-195-5p, miR-423-3p, miR-17-5p, miR-125b-5p, miR-660-5p, miR-143-3p; miR-195-5p, miR-423-3p, miR-17-5p, miR-125b-5p, miR-660-5p, miR-363-3p; miR-195-5p, miR-423-3p, miR-17-5p, miR-125b-5p, miR-660-5p, miR-338-3p; miR-195-5p, miR-423-3p, miR-17-5p, miR-125b-5p, miR-25-3p, miR-143-3p; miR-195-5p, miR-423-3p, miR-17-5p, miR-125b-5p, miR-25-3p, miR-363-3p; miR-195-5p, miR-423-3p, miR-17-5p, miR-125b-5p, miR-25-3p, miR-338-3p; miR-195-5p, miR-423-3p, miR-17-5p, miR-125b-5p, miR-143-3p, miR-363-3p; miR-195-5p, miR-423-3p, miR-17-5p, miR-125b-5p, miR-143-3p, miR-338-3p; miR-195-5p, miR-423-3p, miR-17-5p, miR-125b-5p, miR-363-3p, miR-338-3p; miR-195-5p, miR-423-3p, miR-17-5p, miR-660-5p, miR-25-3p, miR-143-3p; miR-195-5p, miR-423-3p, miR-17-5p, miR-660-5p, miR-25-3p, miR-363-3p; miR-195-5p, miR-423-3p, miR-17-5p, miR-660-5p, miR-25-3p, miR-338-3p; miR-195-5p, miR-423-3p, miR-17-5p, miR-660-5p, miR-143-3p, miR-363-3p; miR-195-5p, miR-423-3p, miR-17-5p, miR-660-5p, miR-143-3p, miR-338-3p; miR-195-5p, miR-423-3p, miR-17-5p, miR-660-5p, miR-363-3p, miR-338-3p; miR-195-5p, miR-423-3p, miR-17-5p, miR-25-3p, miR-143-3p, miR-363-3p; miR-195-5p, miR-423-3p, miR-17-5p, miR-25-3p, miR-143-3p, miR-338-3p; miR-195-5p, miR-423-3p, miR-17-5p, miR-25-3p, miR-363-3p, miR-338-3p; miR-195-5p, miR-423-3p, miR-17-5p, miR-143-3p, miR-363-3p, miR-338-3p; miR-195-5p, miR-423-3p, miR-125b-5p, miR-660-5p, miR-25-3p, miR-143-3p; miR-195-5p, miR-423-3p, miR-125b-5p, miR-660-5p, miR-25-3p, miR-363-3p; miR-195-5p, miR-423-3p, miR-125b-5p, miR-660-5p, miR-25-3p, miR-338-3p; miR-195-5p, miR-423-3p, miR-125b-5p, miR-660-5p, miR-143-3p, miR-363-3p; miR-195-5p, miR-423-3p, miR-125b-5p, miR-660-5p, miR-143-3p, miR-338-3p; miR-195-5p, miR-423-3p, miR-125b-5p, miR-660-5p, miR-363-3p, miR-338-3p; miR-195-5p, miR-423-3p, miR-125b-5p, miR-25-3p, miR-143-3p, miR-363-3p; miR-195-5p, miR-423-3p, miR-125b-5p, miR-25-3p, miR-143-3p, miR-338-3p; miR-195-5p, miR-423-3p, miR-125b-5p, miR-25-3p, miR-363-3p, miR-338-3p; miR-195-5p, miR-423-3p, miR-125b-5p, miR-143-3p, miR-363-3p, miR-338-3p; miR-195-5p, miR-423-3p, miR-660-5p, miR-25-3p, miR-143-3p, miR-363-3p; miR-195-5p, miR-423-3p, miR-660-5p, miR-25-3p, miR-143-3p, miR-338-3p; miR-195-5p, miR-423-3p, miR-660-5p, miR-25-3p, miR-363-3p, miR-338-3p; miR-195-5p, miR-423-3p, miR-660-5p, miR-143-3p, miR-363-3p, miR-338-3p; miR-195-5p, miR-423-3p, miR-25-3p, miR-143-3p, miR-363-3p, miR-338-3p; miR-195-5p, miR-192-5p, miR-17-5p, miR-125b-5p, miR-660-5p, miR-25-3p; miR-195-5p, miR-192-5p, miR-17-5p, miR-125b-5p, miR-660-5p, miR-143-3p; miR-195-5p, miR-192-5p, miR-17-5p, miR-125b-5p, miR-660-5p, miR-363-3p; miR-195-5p, miR-192-5p, miR-17-5p, miR-125b-5p, miR-660-5p, miR-338-3p; miR-195-5p, miR-192-5p, miR-17-5p, miR-125b-5p, miR-25-3p, miR-143-3p; miR-195-5p, miR-192-5p, miR-17-5p, miR-125b-5p, miR-25-3p, miR-363-3p; miR-195-5p, miR-192-5p, miR-17-5p, miR-125b-5p, miR-25-3p, miR-338-3p; miR-195-5p, miR-192-5p, miR-17-5p, miR-125b-5p, miR-143-3p, miR-363-3p; miR-195-5p, miR-192-5p, miR-17-5p, miR-125b-5p, miR-143-3p, miR-338-3p; miR-195-5p, miR-192-5p, miR-17-5p, miR-125b-5p, miR-363-3p, miR-338-3p; miR-195-5p, miR-192-5p, miR-17-5p, miR-660-5p, miR-25-3p, miR-143-3p; miR-195-5p, miR-192-5p, miR-17-5p, miR-660-5p, miR-25-3p, miR-363-3p; miR-195-5p, miR-192-5p, miR-17-5p, miR-660-5p, miR-25-3p, miR-338-3p; miR-195-5p, miR-192-5p, miR-17-5p, miR-660-5p, miR-143-3p, miR-363-3p; miR-195-5p, miR-192-5p, miR-17-5p, miR-660-5p, miR-143-3p, miR-338-3p; miR-195-5p, miR-192-5p, miR-17-5p, miR-660-5p, miR-363-3p, miR-338-3p; miR-195-5p, miR-192-5p, miR-17-5p, miR-25-3p, miR-143-3p, miR-363-3p; miR-195-5p, miR-192-5p, miR-17-5p, miR-25-3p, miR-143-3p, miR-338-3p; miR-195-5p, miR-192-5p, miR-17-5p, miR-25-3p, miR-363-3p, miR-338-3p; miR-195-5p, miR-192-5p, miR-17-5p, miR-143-3p, miR-363-3p, miR-338-3p; miR-195-5p, miR-192-5p, miR-125b-5p, miR-660-5p, miR-25-3p, miR-143-3p; miR-195-5p, miR-192-5p, miR-125b-5p, miR-660-5p, miR-25-3p, miR-363-3p; miR-195-5p, miR-192-5p, miR-125b-5p, miR-660-5p, miR-25-3p, miR-338-3p; miR-195-5p, miR-192-5p, miR-125b-5p, miR-660-5p, miR-143-3p, miR-363-3p; miR-195-5p, miR-192-5p, miR-125b-5p, miR-660-5p, miR-143-3p, miR-338-3p; miR-195-5p, miR-192-5p, miR-125b-5p, miR-660-5p, miR-363-3p, miR-338-3p; miR-195-5p, miR-192-5p, miR-125b-5p, miR-25-3p, miR-143-3p, miR-363-3p; miR-195-5p, miR-192-5p, miR-125b-5p, miR-25-3p, miR-143-3p, miR-338-3p; miR-195-5p, miR-192-5p, miR-125b-5p, miR-25-3p, miR-363-3p, miR-338-3p; miR-195-5p, miR-192-5p, miR-125b-5p, miR-143-3p, miR-363-3p, miR-338-3p; miR-195-5p, miR-192-5p, miR-660-5p, miR-25-3p, miR-143-3p, miR-363-3p; miR-195-5p, miR-192-5p, miR-660-5p, miR-25-3p, miR-143-3p, miR-338-3p; miR-195-5p, miR-192-5p, miR-660-5p, miR-25-3p, miR-363-3p, miR-338-3p; miR-195-5p, miR-192-5p, miR-660-5p, miR-143-3p, miR-363-3p, miR-338-3p; miR-195-5p, miR-192-5p, miR-25-3p, miR-143-3p, miR-363-3p, miR-338-3p; miR-195-5p, miR-17-5p, miR-125b-5p, miR-660-5p, miR-25-3p, miR-143-3p; miR-195-5p, miR-17-5p, miR-125b-5p, miR-660-5p, miR-25-3p, miR-363-3p; miR-195-5p, miR-17-5p, miR-125b-5p, miR-660-5p, miR-25-3p, miR-338-3p; miR-195-5p, miR-17-5p, miR-125b-5p, miR-660-5p, miR-143-3p, miR-363-3p; miR-195-5p, miR-17-5p, miR-125b-5p, miR-660-5p, miR-143-3p, miR-338-3p; miR-195-5p, miR-17-5p, miR-125b-5p, miR-660-5p, miR-363-3p, miR-338-3p; miR-195-5p, miR-17-5p, miR-125b-5p, miR-25-3p, miR-143-3p, miR-363-3p; miR-195-5p, miR-17-5p, miR-125b-5p, miR-25-3p, miR-143-3p, miR-338-3p; miR-195-5p, miR-17-5p, miR-125b-5p, miR-25-3p, miR-363-3p, miR-338-3p; miR-195-5p, miR-17-5p, miR-125b-5p, miR-143-3p, miR-363-3p, miR-338-3p; miR-195-5p, miR-17-5p, miR-660-5p, miR-25-3p, miR-143-3p, miR-363-3p; miR-195-5p, miR-17-5p, miR-660-5p, miR-25-3p, miR-143-3p, miR-338-3p; miR-195-5p, miR-17-5p, miR-660-5p, miR-25-3p, miR-363-3p, miR-338-3p; miR-195-5p, miR-17-5p, miR-660-5p, miR-143-3p, miR-363-3p, miR-338-3p; miR-195-5p, miR-17-5p, miR-25-3p, miR-143-3p, miR-363-3p, miR-338-3p; miR-195-5p, miR-125b-5p, miR-660-5p, miR-25-3p, miR-143-3p, miR-363-3p; miR-195-5p, miR-125b-5p, miR-660-5p, miR-25-3p, miR-143-3p, miR-338-3p; miR-195-5p, miR-125b-5p, miR-660-5p, miR-25-3p, miR-363-3p, miR-338-3p; miR-195-5p, miR-125b-5p, miR-660-5p, miR-143-3p, miR-363-3p, miR-338-3p; miR-195-5p, miR-125b-5p, miR-25-3p, miR-143-3p, miR-363-3p, miR-338-3p; miR-195-5p, miR-660-5p, miR-25-3p, miR-143-3p, miR-363-3p, miR-338-3p; miR-126-5p, miR-423-3p, miR-192-5p, miR-17-5p, miR-125b-5p, miR-660-5p; miR-126-5p, miR-423-3p, miR-192-5p, miR-17-5p, miR-125b-5p, miR-25-3p; miR-126-5p, miR-423-3p, miR-192-5p, miR-17-5p, miR-125b-5p, miR-143-3p; miR-126-5p, miR-423-3p, miR-192-5p, miR-17-5p, miR-125b-5p, miR-363-3p; miR-126-5p, miR-423-3p, miR-192-5p, miR-17-5p, miR-125b-5p, miR-338-3p; miR-126-5p, miR-423-3p, miR-192-5p, miR-17-5p, miR-660-5p, miR-25-3p; miR-126-5p, miR-423-3p, miR-192-5p, miR-17-5p, miR-660-5p, miR-143-3p; miR-126-5p, miR-423-3p, miR-192-5p, miR-17-5p, miR-660-5p, miR-363-3p; miR-126-5p, miR-423-3p, miR-192-5p, miR-17-5p, miR-660-5p, miR-338-3p; miR-126-5p, miR-423-3p, miR-192-5p, miR-17-5p, miR-25-3p, miR-143-3p; miR-126-5p, miR-423-3p, miR-192-5p, miR-17-5p, miR-25-3p, miR-363-3p; miR-126-5p, miR-423-3p, miR-192-5p, miR-17-5p, miR-25-3p, miR-338-3p; miR-126-5p, miR-423-3p, miR-192-5p, miR-17-5p, miR-143-3p, miR-363-3p; miR-126-5p, miR-423-3p, miR-192-5p, miR-17-5p, miR-143-3p, miR-338-3p; miR-126-5p, miR-423-3p, miR-192-5p, miR-17-5p, miR-363-3p, miR-338-3p; miR-126-5p, miR-423-3p, miR-192-5p, miR-125b-5p, miR-660-5p, miR-25-3p; miR-126-5p, miR-423-3p, miR-192-5p, miR-125b-5p, miR-660-5p, miR-143-3p; miR-126-5p, miR-423-3p, miR-192-5p, miR-125b-5p, miR-660-5p, miR-363-3p; miR-126-5p, miR-423-3p, miR-192-5p, miR-125b-5p, miR-660-5p, miR-338-3p; miR-126-5p, miR-423-3p, miR-192-5p, miR-125b-5p, miR-25-3p, miR-143-3p; miR-126-5p, miR-423-3p, miR-192-5p, miR-125b-5p, miR-25-3p, miR-363-3p; miR-126-5p, miR-423-3p, miR-192-5p, miR-125b-5p, miR-25-3p, miR-338-3p; miR-126-5p, miR-423-3p, miR-192-5p, miR-125b-5p, miR-143-3p, miR-363-3p; miR-126-5p, miR-423-3p, miR-192-5p, miR-125b-5p, miR-143-3p, miR-338-3p; miR-126-5p, miR-423-3p, miR-192-5p, miR-125b-5p, miR-363-3p, miR-338-3p; miR-126-5p, miR-423-3p, miR-192-5p, miR-660-5p, miR-25-3p, miR-143-3p; miR-126-5p, miR-423-3p, miR-192-5p, miR-660-5p, miR-25-3p, miR-363-3p; miR-126-5p, miR-423-3p, miR-192-5p, miR-660-5p, miR-25-3p, miR-338-3p; miR-126-5p, miR-423-3p, miR-192-5p, miR-660-5p, miR-143-3p, miR-363-3p; miR-126-5p, miR-423-3p, miR-192-5p, miR-660-5p, miR-143-3p, miR-338-3p; miR-126-5p, miR-423-3p, miR-192-5p, miR-660-5p, miR-363-3p, miR-338-3p; miR-126-5p, miR-423-3p, miR-192-5p, miR-25-3p, miR-143-3p, miR-363-3p; miR-126-5p, miR-423-3p, miR-192-5p, miR-25-3p, miR-143-3p, miR-338-3p; miR-126-5p, miR-423-3p, miR-192-5p, miR-25-3p, miR-363-3p, miR-338-3p; miR-126-5p, miR-423-3p, miR-192-5p, miR-143-3p, miR-363-3p, miR-338-3p; miR-126-5p, miR-423-3p, miR-17-5p, miR-125b-5p, miR-660-5p, miR-25-3p; miR-126-5p, miR-423-3p, miR-17-5p, miR-125b-5p, miR-660-5p, miR-143-3p; miR-126-5p, miR-423-3p, miR-17-5p, miR-125b-5p, miR-660-5p, miR-363-3p; miR-126-5p, miR-423-3p, miR-17-5p, miR-125b-5p, miR-660-5p, miR-338-3p; miR-126-5p, miR-423-3p, miR-17-5p, miR-125b-5p, miR-25-3p, miR-143-3p; miR-126-5p, miR-423-3p, miR-17-5p, miR-125b-5p, miR-25-3p, miR-363-3p; miR-126-5p, miR-423-3p, miR-17-5p, miR-125b-5p, miR-25-3p, miR-338-3p; miR-126-5p, miR-423-3p, miR-17-5p, miR-125b-5p, miR-143-3p, miR-363-3p; miR-126-5p, miR-423-3p, miR-17-5p, miR-125b-5p, miR-363-3p, miR-338-3p; miR-126-5p, miR-423-3p, miR-17-5p, miR-660-5p, miR-25-3p, miR-143-3p; miR-126-5p, miR-423-3p, miR-17-5p, miR-660-5p, miR-25-3p, miR-363-3p; miR-126-5p, miR-423-3p, miR-17-5p, miR-660-5p, miR-25-3p, miR-338-3p; miR-126-5p, miR-423-3p, miR-17-5p, miR-660-5p, miR-143-3p, miR-363-3p; miR-126-5p, miR-423-3p, miR-17-5p, miR-660-5p, miR-143-3p, miR-338-3p; miR-126-5p, miR-423-3p, miR-17-5p, miR-660-5p, miR-363-3p, miR-338-3p; miR-126-5p, miR-423-3p, miR-17-5p, miR-25-3p, miR-143-3p, miR-363-3p; miR-126-5p, miR-423-3p, miR-17-5p, miR-25-3p, miR-143-3p, miR-338-3p; miR-126-5p, miR-423-3p, miR-17-5p, miR-25-3p, miR-363-3p, miR-338-3p; miR-126-5p, miR-423-3p, miR-17-5p, miR-143-3p, miR-363-3p, miR-338-3p; miR-126-5p, miR-423-3p, miR-125b-5p, miR-660-5p, miR-25-3p, miR-143-3p, miR-126-5p, miR-423-3p, miR-125b-5p, miR-660-5p, miR-25-3p, miR-363-3p; miR-126-5p, miR-423-3p, miR-125b-5p, miR-660-5p, miR-25-3p, miR-338-3p; miR-126-5p, miR-423-3p, miR-125b-5p, miR-660-5p, miR-143-3p, miR-363-3p; miR-126-5p, miR-423-3p, miR-125b-5p, miR-660-5p, miR-143-3p, miR-338-3p; miR-126-5p, miR-423-3p, miR-125b-5p, miR-660-5p, miR-363-3p, miR-338-3p; miR-126-5p, miR-423-3p, miR-125b-5p, miR-25-3p, miR-143-3p, miR-363-3p; miR-126-5p, miR-423-3p, miR-125b-5p, miR-25-3p, miR-143-3p, miR-338-3p; miR-126-5p, miR-423-3p, miR-125b-5p, miR-25-3p, miR-363-3p, miR-338-3p; miR-126-5p, miR-423-3p, miR-125b-5p, miR-143-3p, miR-363-3p, miR-338-3p; miR-126-5p, miR-423-3p, miR-660-5p, miR-25-3p, miR-143-3p, miR-363-3p; miR-126-5p, miR-423-3p, miR-660-5p, miR-25-3p, miR-143-3p, miR-338-3p; miR-126-5p, miR-423-3p, miR-660-5p, miR-25-3p, miR-363-3p, miR-338-3p; miR-126-5p, miR-423-3p, miR-660-5p, miR-143-3p, miR-363-3p, miR-338-3p; miR-126-5p, miR-423-3p, miR-25-3p, miR-143-3p, miR-363-3p, miR-338-3p; miR-126-5p, miR-192-5p, miR-17-5p, miR-125b-5p, miR-660-5p, miR-25-3p; miR-126-5p, miR-192-5p, miR-17-5p, miR-125b-5p, miR-660-5p, miR-143-3p; miR-126-5p, miR-192-5p, miR-17-5p, miR-125b-5p, miR-660-5p, miR-363-3p; miR-126-5p, miR-192-5p, miR-17-5p, miR-125b-5p, miR-660-5p, miR-338-3p; miR-126-5p, miR-192-5p, miR-17-5p, miR-125b-5p, miR-25-3p, miR-143-3p; miR-126-5p, miR-192-5p, miR-17-5p, miR-125b-5p, miR-25-3p, miR-363-3p; miR-126-5p, miR-192-5p, miR-17-5p, miR-125b-5p, miR-25-3p, miR-338-3p; miR-126-5p, miR-192-5p, miR-17-5p, miR-125b-5p, miR-143-3p, miR-363-3p; miR-126-5p, miR-192-5p, miR-17-5p, miR-125b-5p, miR-143-3p, miR-338-3p; miR-126-5p, miR-192-5p, miR-17-5p, miR-125b-5p, miR-363-3p, miR-338-3p; miR-126-5p, miR-192-5p, miR-17-5p, miR-660-5p, miR-25-3p, miR-143-3p; miR-126-5p, miR-192-5p, miR-17-5p, miR-660-5p, miR-25-3p, miR-363-3p; miR-126-5p, miR-192-5p, miR-17-5p, miR-660-5p, miR-25-3p, miR-338-3p; miR-126-5p, miR-192-5p, miR-17-5p, miR-660-5p, miR-143-3p, miR-363-3p; miR-126-5p, miR-192-5p, miR-17-5p, miR-660-5p, miR-143-3p, miR-338-3p; miR-126-5p, miR-192-5p, miR-17-5p, miR-660-5p, miR-363-3p, miR-338-3p; miR-126-5p, miR-192-5p, miR-17-5p, miR-25-3p, miR-143-3p, miR-363-3p; miR-126-5p, miR-192-5p, miR-17-5p, miR-25-3p, miR-143-3p, miR-338-3p; miR-126-5p, miR-192-5p, miR-17-5p, miR-25-3p, miR-363-3p, miR-338-3p; miR-126-5p, miR-192-5p, miR-17-5p, miR-143-3p, miR-363-3p, miR-338-3p; miR-126-5p, miR-192-5p, miR-125b-5p, miR-660-5p, miR-25-3p, miR-143-3p; miR-126-5p, miR-192-5p, miR-125b-5p, miR-660-5p, miR-25-3p, miR-363-3p; miR-126-5p, miR-192-5p, miR-125b-5p, miR-660-5p, miR-25-3p, miR-338-3p; miR-126-5p, miR-192-5p, miR-125b-5p, miR-660-5p, miR-143-3p, miR-363-3p; miR-126-5p, miR-192-5p, miR-125b-5p, miR-660-5p, miR-143-3p, miR-338-3p; miR-126-5p, miR-192-5p, miR-125b-5p, miR-660-5p, miR-363-3p, miR-338-3p; miR-126-5p, miR-192-5p, miR-125b-5p, miR-25-3p, miR-143-3p, miR-363-3p; miR-126-5p, miR-192-5p, miR-125b-5p, miR-25-3p, miR-143-3p, miR-338-3p; miR-126-5p, miR-192-5p, miR-125b-5p, miR-25-3p, miR-363-3p, miR-338-3p; miR-126-5p, miR-192-5p, miR-125b-5p, miR-143-3p, miR-363-3p, miR-338-3p; miR-126-5p, miR-192-5p, miR-660-5p, miR-25-3p, miR-143-3p, miR-363-3p; miR-126-5p, miR-192-5p, miR-660-5p, miR-25-3p, miR-338-3p; miR-126-5p, miR-192-5p, miR-660-5p, miR-143-3p, miR-363-3p, miR-338-3p; miR-126-5p, miR-192-5p, miR-25-3p, miR-143-3p, miR-363-3p, miR-338-3p; miR-126-5p, miR-17-5p, miR-125b-5p, miR-660-5p, miR-25-3p, miR-143-3p; miR-126-5p, miR-17-5p, miR-125b-5p, miR-660-5p, miR-25-3p, miR-363-3p; miR-126-5p, miR-17-5p, miR-125b-5p, miR-660-5p, miR-25-3p, miR-338-3p; miR-126-5p, miR-17-5p, miR-125b-5p, miR-660-5p, miR-143-3p, miR-363-3p; miR-126-5p, miR-17-5p, miR-125b-5p, miR-660-5p, miR-143-3p, miR-338-3p; miR-126-5p, miR-17-5p, miR-125b-5p, miR-660-5p, miR-363-3p, miR-338-3p; miR-126-5p, miR-17-5p, miR-125b-5p, miR-25-3p, miR-143-3p, miR-363-3p; miR-126-5p, miR-17-5p, miR-125b-5p, miR-25-3p, miR-143-3p, miR-338-3p; miR-126-5p, miR-17-5p, miR-125b-5p, miR-25-3p, miR-363-3p, miR-338-3p; miR-126-5p, miR-17-5p, miR-125b-5p, miR-143-3p, miR-363-3p, miR-338-3p; miR-126-5p, miR-17-5p, miR-660-5p, miR-25-3p, miR-143-3p, miR-363-3p; miR-126-5p, miR-17-5p, miR-660-5p, miR-25-3p, miR-143-3p, miR-338-3p; miR-126-5p, miR-17-5p, miR-660-5p, miR-25-3p, miR-363-3p, miR-338-3p; miR-126-5p, miR-17-5p, miR-660-5p, miR-143-3p, miR-363-3p, miR-338-3p; miR-126-5p, miR-17-5p, miR-25-3p, miR-143-3p, miR-363-3p, miR-338-3p; miR-126-5p, miR-125b-5p, miR-660-5p, miR-25-3p, miR-143-3p, miR-363-3p; miR-126-5p, miR-125b-5p, miR-660-5p, miR-25-3p, miR-143-3p, miR-338-3p; miR-126-5p, miR-125b-5p, miR-660-5p, miR-25-3p, miR-363-3p, miR-338-3p; miR-126-5p, miR-125b-5p, miR-660-5p, miR-143-3p, miR-363-3p, miR-338-3p; miR-126-5p, miR-125b-5p, miR-25-3p, miR-143-3p, miR-363-3p, miR-338-3p; miR-126-5p, miR-660-5p, miR-25-3p, miR-143-3p, miR-363-3p, miR-338-3p; miR-423-3p, miR-192-5p, miR-17-5p, miR-125b-5p, miR-660-5p, miR-25-3p; miR-423-3p, miR-192-5p, miR-17-5p, miR-125b-5p, miR-660-5p, miR-143-3p; miR-423-3p, miR-192-5p, miR-17-5p, miR-125b-5p, miR-660-5p, miR-363-3p; miR-423-3p, miR-192-5p, miR-17-5p, miR-125b-5p, miR-660-5p, miR-338-3p; miR-423-3p, miR-192-5p, miR-17-5p, miR-125b-5p, miR-25-3p, miR-143-3p; miR-423-3p, miR-192-5p, miR-17-5p, miR-125b-5p, miR-25-3p, miR-363-3p; miR-423-3p, miR-192-5p, miR-17-5p, miR-125b-5p, miR-25-3p, miR-338-3p; miR-423-3p, miR-192-5p, miR-17-5p, miR-125b-5p, miR-143-3p, miR-363-3p; miR-423-3p, miR-192-5p, miR-17-5p, miR-125b-5p, miR-143-3p, miR-338-3p; miR-423-3p, miR-192-5p, miR-17-5p, miR-125b-5p, miR-363-3p, miR-338-3p; miR-423-3p, miR-192-5p, miR-17-5p, miR-660-5p, miR-25-3p, miR-143-3p; miR-423-3p, miR-192-5p, miR-17-5p, miR-660-5p, miR-25-3p, miR-363-3p; miR-423-3p, miR-192-5p, miR-17-5p, miR-660-5p, miR-25-3p, miR-338-3p; miR-423-3p, miR-192-5p, miR-17-5p, miR-660-5p, miR-143-3p, miR-363-3p; miR-423-3p, miR-192-5p, miR-17-5p, miR-660-5p, miR-143-3p, miR-338-3p; miR-423-3p, miR-192-5p, miR-17-5p, miR-660-5p, miR-363-3p, miR-338-3p; miR-423-3p, miR-192-5p, miR-17-5p, miR-25-3p, miR-143-3p, miR-363-3p; miR-423-3p, miR-192-5p, miR-17-5p, miR-25-3p, miR-143-3p, miR-338-3p; miR-423-3p, miR-192-5p, miR-17-5p, miR-25-3p, miR-363-3p, miR-338-3p; miR-423-3p, miR-192-5p, miR-17-5p, miR-143-3p, miR-363-3p, miR-338-3p; miR-423-3p, miR-192-5p, miR-125b-5p, miR-660-5p, miR-25-3p, miR-143-3p; miR-423-3p, miR-192-5p, miR-125b-5p, miR-660-5p, miR-25-3p, miR-363-3p; miR-423-3p, miR-192-5p, miR-125b-5p, miR-660-5p, miR-25-3p, miR-338-3p; miR-423-3p, miR-192-5p, miR-125b-5p, miR-660-5p, miR-143-3p, miR-363-3p, miR-338-3p; miR-423-3p, miR-192-5p, miR-125b-5p, miR-660-5p, miR-363-3p, miR-338-3p; miR-423-3p, miR-192-5p, miR-125b-5p, miR-25-3p, miR-143-3p, miR-363-3p; miR-423-3p, miR-192-5p, miR-125b-5p, miR-25-3p, miR-143-3p, miR-338-3p; miR-423-3p, miR-192-5p, miR-125b-5p, miR-25-3p, miR-363-3p, miR-338-3p; miR-423-3p, miR-192-5p, miR-125b-5p, miR-143-3p, miR-363-3p, miR-338-3p; miR-423-3p, miR-192-5p, miR-660-5p, miR-25-3p, miR-143-3p, miR-363-3p; miR-423-3p, miR-192-5p, miR-660-5p, miR-25-3p, miR-143-3p, miR-338-3p; miR-423-3p, miR-192-5p, miR-660-5p, miR-25-3p, miR-363-3p, miR-338-3p; miR-423-3p, miR-192-5p, miR-660-5p, miR-143-3p, miR-363-3p, miR-338-3p; miR-423-3p, miR-192-5p, miR-25-3p, miR-143-3p, miR-363-3p, miR-338-3p; miR-423-3p, miR-17-5p, miR-125b-5p, miR-660-5p, miR-25-3p, miR-143-3p; miR-423-3p, miR-17-5p, miR-125b-5p, miR-660-5p, miR-25-3p, miR-363-3p; miR-423-3p, miR-17-5p, miR-125b-5p, miR-660-5p, miR-25-3p, miR-338-3p; miR-423-3p, miR-17-5p, miR-125b-5p, miR-660-5p, miR-143-3p, miR-363-3p; miR-423-3p, miR-17-5p, miR-125b-5p, miR-660-5p, miR-143-3p, miR-338-3p; miR-423-3p, miR-17-5p, miR-125b-5p, miR-660-5p, miR-363-3p, miR-338-3p; miR-423-3p, miR-17-5p, miR-125b-5p, miR-25-3p, miR-143-3p, miR-363-3p; miR-423-3p, miR-17-5p, miR-125b-5p, miR-25-3p, miR-143-3p, miR-338-3p; miR-423-3p, miR-17-5p, miR-125b-5p, miR-25-3p, miR-363-3p, miR-338-3p; miR-423-3p, miR-17-5p, miR-125b-5p, miR-143-3p, miR-363-3p, miR-338-3p; miR-423-3p, miR-17-5p, miR-660-5p, miR-25-3p, miR-143-3p, miR-363-3p; miR-423-3p, miR-17-5p, miR-660-5p, miR-25-3p, miR-143-3p, miR-338-3p; miR-423-3p, miR-17-5p, miR-660-5p, miR-25-3p, miR-363-3p, miR-338-3p; miR-423-3p, miR-17-5p, miR-660-5p, miR-143-3p, miR-363-3p, miR-338-3p; miR-423-3p, miR-17-5p, miR-25-3p, miR-143-3p, miR-363-3p, miR-338-3p; miR-423-3p, miR-125b-5p, miR-660-5p, miR-25-3p, miR-143-3p, miR-363-3p; miR-423-3p, miR-125b-5p, miR-660-5p, miR-25-3p, miR-143-3p, miR-338-3p; miR-423-3p, miR-125b-5p, miR-660-5p, miR-25-3p, miR-363-3p, miR-338-3p; miR-423-3p, miR-125b-5p, miR-660-5p, miR-143-3p, miR-363-3p, miR-338-3p; miR-423-3p, miR-125b-5p, miR-25-3p, miR-143-3p, miR-363-3p, miR-338-3p; miR-423-3p, miR-660-5p, miR-25-3p, miR-143-3p, miR-363-3p, miR-338-3p; miR-192-5p, miR-17-5p, miR-125b-5p, miR-660-5p, miR-25-3p, miR-143-3p; miR-192-5p, miR-17-5p, miR-125b-5p, miR-660-5p, miR-25-3p, miR-363-3p; miR-192-5p, miR-17-5p, miR-125b-5p, miR-660-5p, miR-25-3p, miR-338-3p; miR-192-5p, miR-17-5p, miR-125b-5p, miR-660-5p, miR-143-3p, miR-363-3p; miR-192-5p, miR-17-5p, miR-125b-5p, miR-660-5p, miR-143-3p, miR-338-3p; miR-192-5p, miR-17-5p, miR-125b-5p, miR-660-5p, miR-363-3p, miR-338-3p; miR-192-5p, miR-17-5p, miR-125b-5p, miR-25-3p, miR-143-3p, miR-363-3p; miR-192-5p, miR-17-5p, miR-125b-5p, miR-25-3p, miR-143-3p, miR-338-3p; miR-192-5p, miR-17-5p, miR-125b-5p, miR-25-3p, miR-363-3p, miR-338-3p; miR-192-5p, miR-17-5p, miR-125b-5p, miR-143-3p, miR-363-3p, miR-338-3p; miR-192-5p, miR-17-5p, miR-660-5p, miR-25-3p, miR-143-3p, miR-363-3p; miR-192-5p, miR-17-5p, miR-660-5p, miR-25-3p, miR-143-3p, miR-338-3p; miR-192-5p, miR-17-5p, miR-660-5p, miR-25-3p, miR-363-3p, miR-338-3p; miR-192-5p, miR-17-5p, miR-660-5p, miR-143-3p, miR-363-3p, miR-338-3p; miR-192-5p, miR-17-5p, miR-25-3p, miR-143-3p, miR-363-3p, miR-338-3p; miR-192-5p, miR-125b-5p, miR-660-5p, miR-25-3p, miR-143-3p, miR-363-3p; miR-192-5p, miR-125b-5p, miR-660-5p, miR-25-3p, miR-143-3p, miR-338-3p; miR-192-5p, miR-125b-5p, miR-660-5p, miR-25-3p, miR-363-3p, miR-338-3p; miR-192-5p, miR-125b-5p, miR-660-5p, miR-143-3p, miR-363-3p, miR-338-3p; miR-192-5p, miR-125b-5p, miR-25-3p, miR-143-3p, miR-363-3p, miR-338-3p; miR-192-5p, miR-660-5p, miR-25-3p, miR-143-3p, miR-363-3p, miR-338-3p; miR-17-5p, miR-125b-5p, miR-660-5p, miR-25-3p, miR-143-3p, miR-363-3p; miR-17-5p, miR-125b-5p, miR-660-5p, miR-25-3p, miR-143-3p, miR-338-3p; miR-17-5p, miR-125b-5p, miR-660-5p, miR-25-3p, miR-363-3p, miR-338-3p; miR-17-5p, miR-125b-5p, miR-660-5p, miR-143-3p, miR-363-3p, miR-338-3p; miR-17-5p, miR-125b-5p, miR-25-3p, miR-143-3p, miR-363-3p, miR-338-3p; miR-17-5p, miR-660-5p, miR-25-3p, miR-143-3p, miR-363-3p, miR-338-3p; or miR-125b-5p, miR-660-5p, miR-25-3p, miR-143-3p, miR-363-3p, miR-338-3p.

In one example, the at least seven miRNAs are, but are not limited to, the following combinations: miR-451a, miR-195-5p, miR-126-5p, miR-423-3p, miR-192-5p, miR-17-5p, miR-125b-5p; miR-451a, miR-195-5p, miR-126-5p, miR-423-3p, miR-192-5p, miR-17-5p, miR-660-5p; miR-451a, miR-195-5p, miR-126-5p, miR-423-3p, miR-192-5p, miR-17-5p, miR-25-3p; miR-451a, miR-195-5p, miR-126-5p, miR-423-3p, miR-192-5p, miR-17-5p, miR-143-3p; miR-451a, miR-195-5p, miR-126-5p, miR-423-3p, miR-192-5p, miR-17-5p, miR-363-3p; miR-451a, miR-195-5p, miR-126-5p, miR-423-3p, miR-192-5p, miR-17-5p, miR-338-3p; miR-451a, miR-195-5p, miR-126-5p, miR-423-3p, miR-192-5p, miR-125b-5p, miR-660-5p; miR-451a, miR-195-5p, miR-126-5p, miR-423-3p, miR-192-5p, miR-125b-5p, miR-25-3p; miR-451a, miR-195-5p, miR-126-5p, miR-423-3p, miR-192-5p, miR-125b-5p, miR-143-3p; miR-451a, miR-195-5p, miR-126-5p, miR-423-3p, miR-192-5p, miR-125b-5p, miR-363-3p; miR-451a, miR-195-5p, miR-126-5p, miR-423-3p, miR-192-5p, miR-125b-5p, miR-338-3p; miR-451a, miR-195-5p, miR-126-5p, miR-423-3p, miR-192-5p, miR-660-5p, miR-25-3p; miR-451a, miR-195-5p, miR-126-5p, miR-423-3p, miR-192-5p, miR-660-5p, miR-143-3p; miR-451a, miR-195-5p, miR-126-5p, miR-423-3p, miR-192-5p, miR-660-5p, miR-363-3p; miR-451a, miR-195-5p, miR-126-5p, miR-423-3p, miR-192-5p, miR-660-5p, miR-338-3p; miR-451a, miR-195-5p, miR-126-5p, miR-423-3p, miR-192-5p, miR-25-3p, miR-143-3p; miR-451a, miR-195-5p, miR-126-5p, miR-423-3p, miR-192-5p, miR-25-3p, miR-363-3p; miR-451a, miR-195-5p, miR-126-5p, miR-423-3p, miR-192-5p, miR-25-3p, miR-338-3p; miR-451a, miR-195-5p, miR-126-5p, miR-423-3p, miR-192-5p, miR-143-3p, miR-363-3p; miR-451a, miR-195-5p, miR-126-5p, miR-423-3p, miR-192-5p, miR-143-3p, miR-338-3p; miR-451a, miR-195-5p, miR-126-5p, miR-423-3p, miR-192-5p, miR-363-3p, miR-338-3p; miR-451a, miR-195-5p, miR-126-5p, miR-423-3p, miR-17-5p, miR-125b-5p, miR-660-5p; miR-451a, miR-195-5p, miR-126-5p, miR-423-3p, miR-17-5p, miR-125b-5p, miR-25-3p; miR-451a, miR-195-5p, miR-126-5p, miR-423-3p, miR-17-5p, miR-125b-5p, miR-143-3p; miR-451a, miR-195-5p, miR-126-5p, miR-423-3p, miR-17-5p, miR-125b-5p, miR-363-3p; miR-451a, miR-195-5p, miR-126-5p, miR-423-3p, miR-17-5p, miR-125b-5p, miR-338-3p; miR-451a, miR-195-5p, miR-126-5p, miR-423-3p, miR-17-5p, miR-660-5p, miR-25-3p; miR-451a, miR-195-5p, miR-126-5p, miR-423-3p, miR-17-5p, miR-660-5p, miR-143-3p; miR-451a, miR-195-5p, miR-126-5p, miR-423-3p, miR-17-5p, miR-660-5p, miR-363-3p; miR-451a, miR-195-5p, miR-126-5p, miR-423-3p, miR-17-5p, miR-660-5p, miR-338-3p; miR-451a, miR-195-5p, miR-126-5p, miR-423-3p, miR-17-5p, miR-25-3p, miR-143-3p; miR-451a, miR-195-5p, miR-126-5p, miR-423-3p, miR-17-5p, miR-25-3p, miR-363-3p; miR-451a, miR-195-5p, miR-126-5p, miR-423-3p, miR-17-5p, miR-25-3p, miR-338-3p; miR-451a, miR-195-5p, miR-126-5p, miR-423-3p, miR-17-

5p, miR-143-3p, miR-363-3p; miR-451a, miR-195-5p, miR-126-5p, miR-423-3p, miR-17-5p, miR-143-3p, miR-338-3p; miR-451a, miR-195-5p, miR-126-5p, miR-423-3p, miR-17-5p, miR-363-3p, miR-338-3p; miR-451a, miR-195-5p, miR-126-5p, miR-423-3p, miR-125b-5p, miR-660-5p, miR-25-3p; miR-451a, miR-195-5p, miR-126-5p, miR-423-3p, miR-125b-5p, miR-660-5p, miR-143-3p; miR-451a, miR-195-5p, miR-126-5p, miR-423-3p, miR-125b-5p, miR-660-5p, miR-363-3p; miR-451a, miR-195-5p, miR-126-5p, miR-423-3p, miR-125b-5p, miR-660-5p, miR-338-3p; miR-451a, miR-195-5p, miR-126-5p, miR-423-3p, miR-125b-5p, miR-25-3p, miR-143-3p; miR-451a, miR-195-5p, miR-126-5p, miR-423-3p, miR-125b-5p, miR-25-3p, miR-363-3p; miR-451a, miR-195-5p, miR-126-5p, miR-423-3p, miR-125b-5p, miR-25-3p, miR-338-3p; miR-451a, miR-195-5p, miR-126-5p, miR-423-3p, miR-125b-5p, miR-143-3p, miR-363-3p; miR-451a, miR-195-5p, miR-126-5p, miR-423-3p, miR-125b-5p, miR-143-3p, miR-338-3p; miR-451a, miR-195-5p, miR-126-5p, miR-423-3p, miR-125b-5p, miR-363-3p, miR-338-3p; miR-451a, miR-195-5p, miR-126-5p, miR-423-3p, miR-660-5p, miR-25-3p, miR-143-3p; miR-451a, miR-195-5p, miR-126-5p, miR-423-3p, miR-660-5p, miR-25-3p, miR-363-3p; miR-451a, miR-195-5p, miR-126-5p, miR-423-3p, miR-660-5p, miR-25-3p, miR-338-3p; miR-451a, miR-195-5p, miR-126-5p, miR-423-3p, miR-660-5p, miR-143-3p, miR-363-3p; miR-451a, miR-195-5p, miR-126-5p, miR-423-3p, miR-660-5p, miR-143-3p, miR-338-3p; miR-451a, miR-195-5p, miR-126-5p, miR-423-3p, miR-660-5p, miR-363-3p, miR-338-3p; miR-451a, miR-195-5p, miR-126-5p, miR-423-3p, miR-25-3p, miR-143-3p, miR-363-3p; miR-451a, miR-195-5p, miR-126-5p, miR-423-3p, miR-25-3p, miR-143-3p, miR-338-3p; miR-451a, miR-195-5p, miR-126-5p, miR-423-3p, miR-25-3p, miR-363-3p, miR-338-3p; miR-451a, miR-195-5p, miR-126-5p, miR-423-3p, miR-143-3p, miR-363-3p, miR-338-3p; miR-451a, miR-195-5p, miR-126-5p, miR-192-5p, miR-17-5p, miR-125b-5p, miR-660-5p; miR-451a, miR-195-5p, miR-126-5p, miR-192-5p, miR-17-5p, miR-125b-5p, miR-25-3p; miR-451a, miR-195-5p, miR-126-5p, miR-192-5p, miR-17-5p, miR-125b-5p, miR-143-3p; miR-451a, miR-195-5p, miR-126-5p, miR-192-5p, miR-17-5p, miR-125b-5p, miR-363-3p; miR-451a, miR-195-5p, miR-126-5p, miR-192-5p, miR-17-5p, miR-125b-5p, miR-338-3p; miR-451a, miR-195-5p, miR-126-5p, miR-192-5p, miR-17-5p, miR-660-5p, miR-25-3p; miR-451a, miR-195-5p, miR-126-5p, miR-192-5p, miR-17-5p, miR-660-5p, miR-143-3p; miR-451a, miR-195-5p, miR-126-5p, miR-192-5p, miR-17-5p, miR-660-5p, miR-363-3p; miR-451a, miR-195-5p, miR-126-5p, miR-192-5p, miR-17-5p, miR-660-5p, miR-338-3p; miR-451a, miR-195-5p, miR-126-5p, miR-192-5p, miR-17-5p, miR-25-3p, miR-143-3p; miR-451a, miR-195-5p, miR-126-5p, miR-192-5p, miR-17-5p, miR-25-3p, miR-363-3p; miR-451a, miR-195-5p, miR-126-5p, miR-192-5p, miR-17-5p, miR-25-3p, miR-338-3p; miR-451a, miR-195-5p, miR-126-5p, miR-192-5p, miR-17-5p, miR-143-3p, miR-363-3p; miR-451a, miR-195-5p, miR-126-5p, miR-192-5p, miR-17-5p, miR-143-3p, miR-338-3p; miR-451a, miR-195-5p, miR-126-5p, miR-192-5p, miR-17-5p, miR-363-3p, miR-338-3p; miR-451a, miR-195-5p, miR-126-5p, miR-192-5p, miR-125b-5p, miR-660-5p, miR-25-3p; miR-451a, miR-195-5p, miR-126-5p, miR-192-5p, miR-125b-5p, miR-660-5p, miR-143-3p; miR-451a, miR-195-5p, miR-126-5p, miR-192-5p, miR-125b-5p, miR-660-5p, miR-363-3p; miR-451a, miR-195-5p, miR-126-5p, miR-192-5p, miR-125b-5p, miR-660-5p, miR-338-3p; miR-451a, miR-195-5p, miR-126-5p, miR-192-5p, miR-125b-5p, miR-25-3p, miR-143-3p; miR-451a, miR-195-5p, miR-126-5p, miR-192-5p, miR-125b-5p, miR-25-3p, miR-363-3p; miR-451a, miR-195-5p, miR-126-5p, miR-192-5p, miR-125b-5p, miR-25-3p, miR-338-3p; miR-451a, miR-195-5p, miR-126-5p, miR-192-5p, miR-125b-5p, miR-143-3p, miR-363-3p; miR-451a, miR-195-5p, miR-126-5p, miR-192-5p, miR-125b-5p, miR-143-3p, miR-338-3p; miR-451a, miR-195-5p, miR-126-5p, miR-192-5p, miR-125b-5p, miR-363-3p, miR-338-3p; miR-451a, miR-195-5p, miR-126-5p, miR-192-5p, miR-660-5p, miR-25-3p, miR-143-3p; miR-451a, miR-195-5p, miR-126-5p, miR-192-5p, miR-660-5p, miR-25-3p, miR-363-3p; miR-451a, miR-195-5p, miR-126-5p, miR-192-5p, miR-660-5p, miR-25-3p, miR-338-3p; miR-451a, miR-195-5p, miR-126-5p, miR-192-5p, miR-660-5p, miR-143-3p, miR-363-3p; miR-451a, miR-195-5p, miR-126-5p, miR-192-5p, miR-660-5p, miR-143-3p, miR-338-3p; miR-451a, miR-195-5p, miR-126-5p, miR-192-5p, miR-660-5p, miR-363-3p, miR-338-3p; miR-451a, miR-195-5p, miR-126-5p, miR-192-5p, miR-25-3p, miR-143-3p, miR-338-3p; miR-451a, miR-195-5p, miR-126-5p, miR-192-5p, miR-25-3p, miR-363-3p, miR-338-3p; miR-451a, miR-195-5p, miR-126-5p, miR-192-5p, miR-143-3p, miR-363-3p, miR-338-3p; miR-451a, miR-195-5p, miR-126-5p, miR-17-5p, miR-125b-5p, miR-660-5p, miR-25-3p; miR-451a, miR-195-5p, miR-126-5p, miR-17-5p, miR-125b-5p, miR-660-5p, miR-143-3p; miR-451a, miR-195-5p, miR-126-5p, miR-17-5p, miR-125b-5p, miR-660-5p, miR-363-3p; miR-451a, miR-195-5p, miR-126-5p, miR-17-5p, miR-125b-5p, miR-660-5p, miR-338-3p; miR-451a, miR-195-5p, miR-126-5p, miR-17-5p, miR-125b-5p, miR-25-3p, miR-143-3p; miR-451a, miR-195-5p, miR-126-5p, miR-17-5p, miR-125b-5p, miR-25-3p, miR-363-3p; miR-451a, miR-195-5p, miR-126-5p, miR-17-5p, miR-125b-5p, miR-25-3p, miR-338-3p; miR-451a, miR-195-5p, miR-126-5p, miR-17-5p, miR-125b-5p, miR-143-3p, miR-363-3p; miR-451a, miR-195-5p, miR-126-5p, miR-17-5p, miR-125b-5p, miR-143-3p, miR-338-3p; miR-451a, miR-195-5p, miR-126-5p, miR-17-5p, miR-125b-5p, miR-363-3p, miR-338-3p; miR-451a, miR-195-5p, miR-126-5p, miR-17-5p, miR-660-5p, miR-25-3p, miR-143-3p; miR-451a, miR-195-5p, miR-126-5p, miR-17-5p, miR-660-5p, miR-25-3p, miR-363-3p; miR-451a, miR-195-5p, miR-126-5p, miR-17-5p, miR-660-5p, miR-25-3p, miR-338-3p; miR-451a, miR-195-5p, miR-126-5p, miR-17-5p, miR-660-5p, miR-143-3p, miR-363-3p; miR-451a, miR-195-5p, miR-126-5p, miR-17-5p, miR-660-5p, miR-143-3p, miR-338-3p; miR-451a, miR-195-5p, miR-126-5p, miR-17-5p, miR-660-5p, miR-363-3p, miR-338-3p; miR-451a, miR-195-5p, miR-126-5p, miR-17-5p, miR-25-3p, miR-143-3p, miR-363-3p; miR-451a, miR-195-5p, miR-126-5p, miR-17-5p, miR-25-3p, miR-143-3p, miR-338-3p; miR-451a, miR-195-5p, miR-126-5p, miR-17-5p, miR-25-3p, miR-363-3p, miR-338-3p; miR-451a, miR-195-5p, miR-126-5p, miR-17-5p, miR-143-3p, miR-363-3p, miR-338-3p; miR-451a, miR-195-5p, miR-126-5p, miR-125b-5p, miR-660-5p, miR-25-3p, miR-143-3p; miR-451a, miR-195-5p, miR-126-5p, miR-125b-5p, miR-660-5p, miR-25-3p, miR-363-3p; miR-451a, miR-195-5p, miR-126-5p, miR-125b-5p, miR-660-5p, miR-25-3p, miR-338-3p; miR-451a, miR-195-5p, miR-126-5p, miR-125b-5p, miR-660-5p, miR-143-3p, miR-363-3p; miR-451a, miR-195-5p, miR-126-5p, miR-125b-5p, miR-660-5p, miR-143-3p, miR-338-3p; miR-451a, miR-195-5p, miR-126-5p, miR-125b-5p, miR-660-5p, miR-363-3p, miR-338-3p; miR-451a, miR-195-5p, miR-126-5p, miR-125b-5p, miR-25-3p, miR-143-3p, miR-363-3p; miR-451a, miR-195-5p, miR-126-5p, miR-125b-5p, miR-25-3p, miR-143-3p, miR-338-3p; miR-451a, miR-195-5p, miR-126-5p, miR-125b-5p, miR-25-3p, miR-363-3p, miR-338-3p; miR-451a, miR-195-5p, miR-126-5p, miR-125b-5p, miR-143-3p, miR-363-3p, miR-338-3p; miR-451a, miR-195-5p, miR-126-5p, miR-660-5p, miR-25-3p, miR-143-3p, miR-363-3p; miR-451a, miR-195-5p, miR-126-5p, miR-660-5p, miR-25-3p, miR-143-3p, miR-338-3p; miR-451a, miR-195-5p, miR-126-5p, miR-660-5p, miR-25-3p, miR-363-3p, miR-338-3p; miR-451a, miR-195-5p, miR-126-5p, miR-660-5p, miR-143-3p, miR-363-3p, miR-338-3p; miR-451a, miR-195-5p, miR-126-5p, miR-25-3p, miR-143-3p, miR-363-3p, miR-338-3p; miR-451a, miR-195-5p, miR-423-3p, miR-192-5p, miR-17-5p, miR-125b-5p, miR-660-5p; miR-451a, miR-195-5p, miR-423-3p, miR-192-5p, miR-17-5p, miR-125b-5p, miR-25-3p; miR-451a, miR-195-5p, miR-423-3p, miR-192-5p, miR-17-5p, miR-125b-5p, miR-143-3p; miR-451a, miR-195-5p, miR-423-3p, miR-192-5p, miR-17-5p, miR-125b-5p, miR-363-3p; miR-451a, miR-195-5p, miR-423-3p, miR-192-5p, miR-17-5p, miR-125b-5p, miR-338-3p; miR-451a, miR-195-5p, miR-423-3p, miR-192-5p, miR-17-5p, miR-660-5p, miR-25-3p; miR-451a, miR-195-5p, miR-423-3p, miR-192-5p, miR-17-5p, miR-660-5p, miR-143-3p; miR-451a, miR-195-5p, miR-423-3p, miR-192-5p, miR-17-5p, miR-660-5p, miR-363-3p; miR-451a, miR-195-5p, miR-423-3p, miR-192-5p, miR-17-5p, miR-660-5p, miR-338-3p; miR-451a, miR-195-5p, miR-423-3p, miR-192-5p, miR-17-5p, miR-25-3p, miR-143-3p; miR-451a, miR-195-5p, miR-423-3p, miR-192-5p, miR-17-5p, miR-25-3p, miR-363-3p; miR-451a, miR-195-5p, miR-423-3p, miR-192-5p, miR-17-5p, miR-25-3p, miR-338-3p; miR-451a, miR-195-5p, miR-423-3p, miR-192-5p, miR-17-5p, miR-143-3p, miR-363-3p; miR-451a, miR-195-5p, miR-423-3p, miR-192-5p, miR-17-5p, miR-143-3p, miR-338-3p; miR-451a, miR-195-5p, miR-423-3p, miR-192-5p, miR-17-5p, miR-363-3p, miR-338-3p; miR-451a, miR-195-5p, miR-423-3p, miR-192-5p, miR-125b-5p, miR-660-5p, miR-25-3p; miR-451a, miR-195-5p, miR-423-3p, miR-192-5p, miR-125b-5p, miR-660-5p, miR-143-3p; miR-451a, miR-195-5p, miR-423-3p, miR-192-5p, miR-125b-5p, miR-660-5p, miR-363-3p; miR-451a, miR-195-5p, miR-423-3p, miR-192-5p, miR-125b-5p, miR-660-5p, miR-338-3p; miR-451a, miR-195-5p, miR-423-3p, miR-192-5p, miR-125b-5p, miR-25-3p, miR-143-3p; miR-451a, miR-195-5p, miR-423-3p, miR-192-5p, miR-125b-5p, miR-25-3p, miR-363-3p; miR-451a, miR-195-5p, miR-423-3p, miR-192-5p, miR-125b-5p, miR-25-3p, miR-338-3p; miR-451a, miR-195-5p, miR-423-3p, miR-192-5p, miR-125b-5p, miR-143-3p, miR-363-3p; miR-451a, miR-195-5p, miR-423-3p, miR-192-5p, miR-125b-5p, miR-143-3p, miR-338-3p; miR-451a, miR-195-5p, miR-423-3p, miR-192-5p, miR-125b-5p, miR-363-3p, miR-338-3p; miR-451a, miR-195-5p, miR-423-3p, miR-192-5p, miR-660-5p, miR-25-3p, miR-143-3p; miR-451a, miR-195-5p, miR-423-3p, miR-192-5p, miR-660-5p, miR-25-3p, miR-363-3p; miR-451a, miR-195-5p, miR-423-3p, miR-192-5p, miR-660-5p, miR-25-3p, miR-338-3p; miR-451a, miR-195-5p, miR-423-3p, miR-192-5p, miR-660-5p, miR-143-3p, miR-363-3p; miR-451a, miR-195-5p, miR-423-3p, miR-192-5p, miR-660-5p, miR-143-3p, miR-338-3p; miR-451a, miR-195-5p, miR-423-3p, miR-192-5p, miR-660-5p, miR-363-3p, miR-338-3p; miR-451a, miR-195-5p, miR-423-3p, miR-192-5p, miR-25-3p, miR-143-3p, miR-363-3p; miR-451a, miR-195-5p, miR-423-3p, miR-192-5p, miR-25-3p, miR-143-3p, miR-338-3p; miR-451a, miR-195-5p, miR-423-3p, miR-192-5p, miR-25-3p, miR-363-3p, miR-338-3p; miR-451a, miR-195-5p, miR-423-3p, miR-192-5p, miR-143-3p, miR-363-3p, miR-338-3p; miR-451a, miR-195-5p, miR-423-3p, miR-17-5p, miR-125b-5p, miR-660-5p, miR-25-3p; miR-451a, miR-195-5p, miR-423-3p, miR-17-5p, miR-125b-5p, miR-660-5p, miR-143-3p; miR-451a, miR-195-5p, miR-423-3p, miR-17-5p, miR-125b-5p, miR-660-5p, miR-363-3p; miR-451a, miR-195-5p, miR-423-3p, miR-17-5p, miR-125b-5p, miR-660-5p, miR-338-3p; miR-451a, miR-195-5p, miR-423-3p, miR-17-5p, miR-125b-5p, miR-25-3p, miR-143-3p; miR-451a, miR-195-5p, miR-423-3p, miR-17-5p, miR-125b-5p, miR-25-3p, miR-363-3p; miR-451a, miR-195-5p, miR-423-3p, miR-17-5p, miR-125b-5p, miR-25-3p, miR-338-3p; miR-451a, miR-195-5p, miR-423-3p, miR-17-5p, miR-125b-5p, miR-143-3p, miR-363-3p; miR-451a, miR-195-5p, miR-423-3p, miR-17-5p, miR-125b-5p, miR-143-3p, miR-338-3p; miR-451a, miR-195-5p, miR-423-3p, miR-17-5p, miR-125b-5p, miR-363-3p, miR-338-3p; miR-451a, miR-195-5p, miR-423-3p, miR-17-5p, miR-660-5p, miR-25-3p, miR-143-3p; miR-451a, miR-195-5p, miR-423-3p, miR-17-5p, miR-660-5p, miR-25-3p, miR-363-3p; miR-451a, miR-195-5p, miR-423-3p, miR-17-5p, miR-660-5p, miR-25-3p, miR-338-3p; miR-451a, miR-195-5p, miR-423-3p, miR-17-5p, miR-660-5p, miR-143-3p, miR-363-3p; miR-451a, miR-195-5p, miR-423-3p, miR-17-5p, miR-660-5p, miR-143-3p, miR-338-3p; miR-451a, miR-195-5p, miR-423-3p, miR-17-5p, miR-660-5p, miR-363-3p, miR-338-3p; miR-451a, miR-195-5p, miR-423-3p, miR-17-5p, miR-25-3p, miR-143-3p, miR-363-3p; miR-451a, miR-195-5p, miR-423-3p, miR-17-5p, miR-25-3p, miR-143-3p, miR-338-3p; miR-451a, miR-195-5p, miR-423-3p, miR-17-5p, miR-25-3p, miR-363-3p, miR-338-3p; miR-451a, miR-195-5p, miR-423-3p, miR-17-5p, miR-143-3p, miR-363-3p, miR-338-3p; miR-451a, miR-195-5p, miR-423-3p, miR-125b-5p, miR-660-5p, miR-25-3p, miR-143-3p; miR-451a, miR-195-5p, miR-423-3p, miR-125b-5p, miR-660-5p, miR-25-3p, miR-363-3p; miR-451a, miR-195-5p, miR-423-3p, miR-125b-5p, miR-660-5p, miR-25-3p, miR-338-3p; miR-451a, miR-195-5p, miR-423-3p, miR-125b-5p, miR-660-5p, miR-143-3p, miR-363-3p; miR-451a, miR-195-5p, miR-423-3p, miR-125b-5p, miR-660-5p, miR-143-3p, miR-338-3p; miR-451a, miR-195-5p, miR-423-3p, miR-125b-5p, miR-660-5p, miR-363-3p, miR-338-3p; miR-451a, miR-195-5p, miR-423-3p, miR-125b-5p, miR-25-3p, miR-143-3p, miR-363-3p; miR-451a, miR-195-5p, miR-423-3p, miR-125b-5p, miR-25-3p, miR-143-3p, miR-338-3p; miR-451a, miR-195-5p, miR-423-3p, miR-125b-5p, miR-25-3p, miR-363-3p, miR-338-3p; miR-451a, miR-195-5p, miR-423-3p, miR-125b-5p, miR-143-3p, miR-363-3p, miR-338-3p; miR-451a, miR-195-5p, miR-423-3p, miR-660-5p, miR-25-3p, miR-143-3p, miR-363-3p; miR-451a, miR-195-5p, miR-423-3p, miR-660-5p, miR-25-3p, miR-143-3p, miR-338-3p; miR-451a, miR-195-5p, miR-423-3p, miR-660-5p, miR-25-3p, miR-363-3p, miR-338-3p; miR-451a, miR-195-5p, miR-423-3p, miR-660-5p, miR-143-3p, miR-363-3p, miR-338-3p; miR-451a, miR-195-5p, miR-423-3p, miR-25-3p, miR-143-3p, miR-363-3p, miR-338-3p; miR-451a, miR-195-5p, miR-192-5p, miR-17-5p, miR-125b-5p, miR-660-5p, miR-25-3p; miR-451a, miR-195-5p, miR-192-5p, miR-17-5p, miR-125b-5p, miR-660-5p, miR-143-3p; miR-451a, miR-195-5p, miR-192-5p, miR-17-5p, miR-125b-5p, miR-660-5p, miR-363-3p; miR-451a, miR-195-5p, miR-192-5p, miR-17-5p, miR-125b-5p, miR-660-5p, miR-338-3p; miR-451a, miR-195-5p, miR-192-5p, miR-17-5p, miR-125b-5p, miR-25-3p, miR-143-3p; miR-451a, miR-195-5p, miR-192-5p, miR-17-5p, miR-125b-5p, miR-25-3p, miR-363-3p; miR-451a, miR-195-5p, miR-192-5p, miR-17-5p, miR-125b-5p, miR-25-3p, miR-338-3p; miR-451a, miR-195-5p, miR-192-5p, miR-17-5p, miR-125b-5p, miR-143-3p, miR-363-3p; miR-451a, miR-195-5p, miR-192-5p, miR-17-5p, miR-125b-5p, miR-143-3p, miR-338-3p; miR-451a, miR-195-5p, miR-192-5p, miR-17-5p, miR-125b-5p, miR-363-3p, miR-338-3p; miR-451a, miR-195-5p, miR-192-5p, miR-17-5p, miR-660-5p, miR-25-3p, miR-143-3p; miR-451a, miR-195-5p, miR-192-5p, miR-17-5p, miR-660-5p, miR-25-3p, miR-363-3p; miR-451a, miR-195-5p, miR-192-5p, miR-17-5p, miR-660-5p, miR-25-3p, miR-338-3p; miR-451a, miR-195-5p, miR-192-5p, miR-17-5p, miR-660-5p, miR-143-3p, miR-363-3p; miR-451a, miR-195-5p, miR-192-5p, miR-17-5p, miR-660-5p, miR-143-3p, miR-338-3p; miR-451a, miR-195-5p, miR-192-5p, miR-17-5p, miR-660-5p, miR-363-3p, miR-338-3p; miR-451a, miR-195-5p, miR-192-5p, miR-17-5p, miR-25-3p, miR-143-3p, miR-363-3p; miR-451a, miR-195-5p, miR-192-5p, miR-17-5p, miR-25-3p, miR-143-3p, miR-338-3p; miR-451a, miR-195-5p, miR-192-5p, miR-17-5p, miR-25-3p, miR-363-3p, miR-338-3p; miR-451a, miR-195-5p, miR-192-5p, miR-17-5p, miR-143-3p, miR-363-3p, miR-338-3p; miR-451a, miR-195-5p, miR-192-5p, miR-125b-5p, miR-660-5p, miR-25-3p, miR-143-3p; miR-451a, miR-195-5p, miR-192-5p, miR-125b-5p, miR-660-5p, miR-25-3p, miR-363-3p; miR-451a, miR-195-5p, miR-192-5p, miR-125b-5p, miR-660-5p, miR-25-3p, miR-338-3p; miR-451a, miR-195-5p, miR-192-5p, miR-125b-5p, miR-660-5p, miR-143-3p, miR-363-3p; miR-451a, miR-195-5p, miR-192-5p, miR-125b-5p, miR-660-5p, miR-143-3p, miR-338-3p; miR-451a, miR-195-5p, miR-192-5p, miR-125b-5p, miR-660-5p, miR-363-3p, miR-338-3p; miR-451a, miR-195-5p, miR-192-5p, miR-125b-5p, miR-25-3p, miR-143-3p, miR-363-3p; miR-451a, miR-195-5p, miR-192-5p, miR-125b-5p, miR-25-3p, miR-143-3p, miR-338-3p; miR-451a, miR-195-5p, miR-192-5p, miR-125b-5p, miR-25-3p, miR-363-3p, miR-338-3p; miR-451a, miR-195-5p, miR-192-5p, miR-125b-5p, miR-143-3p, miR-363-3p, miR-338-3p; miR-451a, miR-195-5p, miR-192-5p, miR-660-5p, miR-25-3p, miR-143-3p, miR-363-3p; miR-451a, miR-195-5p, miR-192-5p, miR-660-5p, miR-25-3p, miR-143-3p, miR-338-3p; miR-451a, miR-195-5p, miR-192-5p, miR-660-5p, miR-25-3p, miR-363-3p, miR-338-3p; miR-451a, miR-195-5p, miR-192-5p, miR-660-5p, miR-143-3p, miR-363-3p, miR-338-3p; miR-451a, miR-195-5p, miR-192-5p, miR-25-3p, miR-143-3p, miR-363-3p, miR-338-3p; miR-451a, miR-195-5p, miR-17-5p, miR-125b-5p, miR-660-5p, miR-25-3p, miR-143-3p; miR-451a, miR-195-5p, miR-17-5p, miR-125b-5p, miR-660-5p, miR-25-3p, miR-363-3p; miR-451a, miR-195-5p, miR-17-5p, miR-125b-5p, miR-660-5p, miR-25-3p, miR-338-3p; miR-451a, miR-195-5p, miR-17-5p, miR-125b-5p, miR-660-5p, miR-143-3p, miR-363-3p; miR-451a, miR-195-5p, miR-17-5p, miR-125b-5p, miR-660-5p, miR-143-3p, miR-338-3p; miR-451a, miR-195-5p, miR-17-5p, miR-125b-5p, miR-660-5p, miR-363-3p, miR-338-3p; miR-451a, miR-195-5p, miR-17-5p, miR-125b-5p, miR-25-3p, miR-143-3p, miR-363-3p; miR-451a, miR-195-5p, miR-17-5p, miR-125b-5p, miR-25-3p, miR-143-3p, miR-338-3p; miR-451a, miR-195-5p, miR-17-5p, miR-125b-5p, miR-25-3p, miR-363-3p, miR-338-3p; miR-451a, miR-195-5p, miR-17-5p, miR-125b-5p, miR-143-3p, miR-363-3p, miR-338-3p; miR-451a, miR-195-5p, miR-17-5p, miR-660-5p, miR-25-3p, miR-143-3p, miR-363-3p; miR-451a, miR-195-5p, miR-17-5p, miR-660-5p, miR-25-3p, miR-143-3p, miR-338-3p; miR-451a, miR-195-5p, miR-17-5p, miR-660-5p, miR-25-3p, miR-363-3p, miR-338-3p; miR-451a, miR-195-5p, miR-17-5p, miR-660-5p, miR-143-3p, miR-363-3p, miR-338-3p; miR-451a, miR-195-5p, miR-17-5p, miR-25-3p, miR-143-3p, miR-363-3p, miR-338-3p; miR-451a, miR-195-5p, miR-125b-5p, miR-660-5p, miR-25-3p, miR-143-3p, miR-363-3p; miR-451a, miR-195-5p, miR-125b-5p, miR-660-5p, miR-25-3p, miR-143-3p, miR-338-3p; miR-451a, miR-195-5p, miR-125b-5p, miR-660-5p, miR-25-3p, miR-363-3p, miR-338-3p; miR-451a, miR-195-5p, miR- 125b-5p, miR-660-5p, miR-143-3p, miR-363-3p, miR-338-3p; miR-451a, miR-195-5p, miR-125b-5p, miR-25-3p, miR-143-3p, miR-363-3p, miR-338-3p; miR-451a, miR-195-5p, miR-660-5p, miR-25-3p, miR-143-3p, miR-363-3p, miR-338-3p; miR-451a, miR-126-5p, miR-423-3p, miR-192-5p, miR-17-5p, miR-125b-5p, miR-660-5p; miR-451a, miR-126-5p, miR-423-3p, miR-192-5p, miR-17-5p, miR-125b-5p, miR-25-3p; miR-451a, miR-126-5p, miR-423-3p, miR-192-5p, miR-17-5p, miR-125b-5p, miR-143-3p; miR-451a, miR-126-5p, miR-423-3p, miR-192-5p, miR-17-5p, miR-125b-5p, miR-363-3p; miR-451a, miR-126-5p, miR-423-3p, miR-192-5p, miR-17-5p, miR-125b-5p, miR-338-3p; miR-451a, miR-126-5p, miR-423-3p, miR-192-5p, miR-17-5p, miR-660-5p, miR-25-3p; miR-451a, miR-126-5p, miR-423-3p, miR-192-5p, miR-17-5p, miR-660-5p, miR-143-3p; miR-451a, miR-126-5p, miR-423-3p, miR-192-5p, miR-17-5p, miR-660-5p, miR-363-3p; miR-451a, miR-126-5p, miR-423-3p, miR-192-5p, miR-17-5p, miR-660-5p, miR-338-3p; miR-451a, miR-126-5p, miR-423-3p, miR-192-5p, miR-17-5p, miR-25-3p, miR-143-3p; miR-451a, miR-126-5p, miR-423-3p, miR-192-5p, miR-17-5p, miR-25-3p, miR-363-3p; miR-451a, miR-126-5p, miR-423-3p, miR-192-5p, miR-17-5p, miR-25-3p, miR-338-3p; miR-451a, miR-126-5p, miR-423-3p, miR-192-5p, miR-17-5p, miR-143-3p, miR-363-3p; miR-451a, miR-126-5p, miR-423-3p, miR-192-5p, miR-17-5p, miR-143-3p, miR-338-3p; miR-451a, miR-126-5p, miR-423-3p, miR-192-5p, miR-17-5p, miR-363-3p, miR-338-3p; miR-451a, miR-126-5p, miR-423-3p, miR-192-5p, miR-125b-5p, miR-660-5p, miR-25-3p; miR-451a, miR-126-5p, miR-423-3p, miR-192-5p, miR-125b-5p, miR-660-5p, miR-143-3p; miR-451a, miR-126-5p, miR-423-3p, miR-192-5p, miR-125b-5p, miR-660-5p, miR-363-3p; miR-451a, miR-126-5p, miR-423-3p, miR-192-5p, miR-125b-5p, miR-660-5p, miR-338-3p; miR-451a, miR-126-5p, miR-423-3p, miR-192-5p, miR-125b-5p, miR-25-3p, miR-143-3p; miR-451a, miR-126-5p, miR-423-3p, miR-192-5p, miR-125b-5p, miR-25-3p, miR-363-3p; miR-451a, miR-126-5p, miR-423-3p, miR-192-5p, miR-125b-5p, miR-25-3p, miR-338-3p; miR-451a, miR-126-5p, miR-423-3p, miR-192-5p, miR-125b-5p, miR-143-3p, miR-363-3p; miR-451a, miR-126-5p, miR-423-3p, miR-192-5p, miR-125b-5p, miR-143-3p, miR-338-3p; miR-451a, miR-126-5p, miR-423-3p, miR-192-5p, miR-125b-5p, miR-363-3p, miR-338-3p; miR-451a, miR-126-5p, miR-423-3p, miR-192-5p, miR-660-5p, miR-25-3p, miR-143-3p; miR-451a, miR-126-5p, miR-423-3p, miR-192-5p, miR-660-5p, miR-25-3p, miR-363-3p; miR-451a, miR-126-5p, miR-423-3p, miR-192-5p, miR-660-5p, miR-25-3p, miR-338-3p; miR-451a, miR-126-5p, miR-423-3p, miR-192-5p, miR-660-5p, miR-143-3p, miR-363-3p; miR-451a, miR-126-5p, miR-423-3p, miR-192-5p, miR-660-5p, miR-143-3p, miR-338-3p; miR-451a, miR-126-5p, miR-423-3p, miR-192-5p, miR-660-5p, miR-363-3p, miR-338-3p; miR-451a, miR-126-5p, miR-423-3p, miR-192-5p, miR-25-3p, miR-143-3p, miR-363-3p; miR-451a, miR-126-5p, miR-423-3p, miR-192-5p, miR-25-3p, miR-143-3p, miR-338-3p; miR-451a, miR-126-5p, miR-423-3p, miR-192-5p, miR-25-3p, miR-363-3p, miR-338-3p; miR-451a, miR-126-5p, miR-423-3p, miR-192-5p, miR-143-3p, miR-363-3p, miR-338-3p; miR-451a, miR-126-5p, miR-423-3p, miR-17-5p, miR-125b-5p, miR-660-5p, miR-25-3p; miR-451a, miR-126-5p, miR-423-3p, miR-17-5p, miR-125b-5p, miR-660-5p, miR-143-3p; miR-451a, miR-126-5p, miR-423-3p, miR-17-5p, miR-125b-5p, miR-660-5p, miR-363-3p; miR-451a, miR-126-5p, miR-423-3p, miR-17-5p, miR-125b-5p, miR-660-5p, miR-338-3p; miR-451a, miR-126-5p, miR-423-3p, miR-17-5p, miR-125b-5p, miR-25-3p, miR-143-3p; miR-451a, miR-126-5p, miR-423-3p, miR-17-5p, miR-125b-5p, miR-25-3p, miR-363-3p; miR-451a, miR-126-5p, miR-423-3p, miR-17-5p, miR-125b-5p, miR-25-3p, miR-338-3p; miR-451a, miR-126-5p, miR-423-3p, miR-17-5p, miR-125b-5p, miR-143-3p, miR-363-3p; miR-451a, miR-126-5p, miR-423-3p, miR-17-5p, miR-125b-5p, miR-143-3p, miR-338-3p; miR-451a, miR-126-5p, miR-423-3p, miR-17-5p, miR-125b-5p, miR-363-3p, miR-338-3p; miR-451a, miR-126-5p, miR-423-3p, miR-17-5p, miR-660-5p, miR-25-3p, miR-143-3p; miR-451a, miR-126-5p, miR-423-3p, miR-17-5p, miR-660-5p, miR-25-3p, miR-363-3p; miR-451a, miR-126-5p, miR-423-3p, miR-17-5p, miR-660-5p, miR-25-3p, miR-338-3p; miR-451a, miR-126-5p, miR-423-3p, miR-17-5p, miR-660-5p, miR-143-3p, miR-363-3p; miR-451a, miR-126-5p, miR-423-3p, miR-17-5p, miR-660-5p, miR-143-3p, miR-338-3p; miR-451a, miR-126-5p, miR-423-3p, miR-17-5p, miR-660-5p, miR-363-3p, miR-338-3p; miR-451a, miR-126-5p, miR-423-3p, miR-17-5p, miR-25-3p, miR-143-3p, miR-363-3p; miR-451a, miR-126-5p, miR-423-3p, miR-17-5p, miR-25-3p, miR-143-3p, miR-338-3p; miR-451a, miR-126-5p, miR-423-3p, miR-17-5p, miR-25-3p, miR-363-3p, miR-338-3p; miR-451a, miR-126-5p, miR-423-3p, miR-17-5p, miR-143-3p, miR-363-3p, miR-338-3p; miR-451a, miR-126-5p, miR-423-3p, miR-125b-5p, miR-660-5p, miR-25-3p, miR-143-3p; miR-451a, miR-126-5p, miR-423-3p, miR-125b-5p, miR-660-5p, miR-25-3p, miR-363-3p; miR-451a, miR-126-5p, miR-423-3p, miR-125b-5p, miR-660-5p, miR-25-3p, miR-338-3p; miR-451a, miR-126-5p, miR-423-3p, miR-125b-5p, miR-660-5p, miR-143-3p, miR-363-3p; miR-451a, miR-126-5p, miR-423-3p, miR-125b-5p, miR-660-5p, miR-143-3p, miR-338-3p; miR-451a, miR-126-5p, miR-423-3p, miR-125b-5p, miR-660-5p, miR-363-3p, miR-338-3p; miR-451a, miR-126-5p, miR-423-3p, miR-125b-5p, miR-25-3p, miR-143-3p, miR-363-3p; miR-451a, miR-126-5p, miR-423-3p, miR-125b-5p, miR-25-3p, miR-143-3p, miR-338-3p; miR-451a, miR-126-5p, miR-423-3p, miR-125b-5p, miR-25-3p, miR-363-3p, miR-338-3p; miR-451a, miR-126-5p, miR-423-3p, miR-125b-5p, miR-143-3p, miR-363-3p, miR-338-3p; miR-451a, miR-126-5p, miR-423-3p, miR-660-5p, miR-25-3p, miR-143-3p, miR-363-3p; miR-451a, miR-126-5p, miR-423-3p, miR-660-5p, miR-25-3p, miR-143-3p, miR-338-3p; miR-451a, miR-126-5p, miR-423-3p, miR-660-5p, miR-25-3p, miR-363-3p, miR-338-3p; miR-451a, miR-126-5p, miR-423-3p, miR-660-5p, miR-143-3p, miR-363-3p, miR-338-3p; miR-451a, miR-126-5p, miR-423-3p, miR-25-3p, miR-143-3p, miR-363-3p, miR-338-3p; miR-451a, miR-126-5p, miR-192-5p, miR-17-5p, miR-125b-5p, miR-660-5p, miR-25-3p; miR-451a, miR-126-5p, miR-192-5p, miR-17-5p, miR-125b-5p, miR-660-5p, miR-143-3p; miR-451a, miR-126-5p, miR-192-5p, miR-17-5p, miR-125b-5p, miR-660-5p, miR-363-3p; miR-451a, miR-126-5p, miR-192-5p, miR-17-5p, miR-125b-5p, miR-660-5p, miR-338-3p; miR-451a, miR-126-5p, miR-192-5p, miR-17-5p, miR-125b-5p, miR-25-3p, miR-143-3p; miR-451a, miR-126-5p, miR-192-5p, miR-17-5p, miR-125b-5p, miR-25-3p, miR-363-3p; miR-451a, miR-126-5p, miR-192-5p, miR-17-5p, miR-125b-5p, miR-25-3p, miR-338-3p; miR-451a, miR-126-5p, miR-192-5p, miR-17-5p, miR-125b-5p, miR-143-3p, miR-363-3p; miR-451a, miR-126-5p, miR-192-5p, miR-17-5p, miR-125b-5p, miR-143-3p, miR-338-3p; miR-451a, miR-126-5p, miR-192-5p, miR-17-5p, miR-660-5p, miR-25-3p, miR-143-3p; miR-451a, miR-126-5p, miR-192-5p, miR-17-5p, miR-660-5p, miR-25-3p, miR-363-3p, miR-338-3p; miR-451a, miR-126-5p, miR-192-5p, miR-17-5p, miR-660-5p, miR-143-3p, miR-363-3p, miR-338-3p; miR-451a, miR-126-5p, miR-192-5p, miR-17-5p, miR-25-3p, miR-143-3p, miR-363-3p, miR-338-3p; miR-451a, miR-126-5p, miR-192-5p, miR-17-5p, miR-125b-5p, miR-660-5p, miR-25-3p, miR-143-3p; miR-451a, miR-126-5p, miR-192-5p, miR-17-5p, miR-125b-5p, miR-660-5p, miR-25-3p, miR-363-3p; miR-451a, miR-126-5p, miR-192-5p, miR-17-5p, miR-125b-5p, miR-660-5p, miR-25-3p, miR-338-3p; miR-451a, miR-126-5p, miR-192-5p, miR-17-5p, miR-125b-5p, miR-660-5p, miR-143-3p, miR-363-3p; miR-451a, miR-126-5p, miR-192-5p, miR-17-5p, miR-125b-5p, miR-660-5p, miR-143-3p, miR-338-3p; miR-451a, miR-126-5p, miR-192-5p, miR-17-5p, miR-125b-5p, miR-660-5p, miR-363-3p, miR-338-3p; miR-451a, miR-126-5p, miR-192-5p, miR-17-5p, miR-125b-5p, miR-25-3p, miR-143-3p, miR-363-3p; miR-451a, miR-126-5p, miR-192-5p, miR-17-5p, miR-125b-5p, miR-25-3p, miR-143-3p, miR-338-3p; miR-451a, miR-126-5p, miR-192-5p, miR-17-5p, miR-125b-5p, miR-25-3p, miR-363-3p, miR-338-3p; miR-451a, miR-126-5p, miR-192-5p, miR-17-5p, miR-125b-5p, miR-143-3p, miR-363-3p, miR-338-3p; miR-451a, miR-126-5p, miR-192-5p, miR-17-5p, miR-660-5p, miR-25-3p, miR-143-3p, miR-363-3p; miR-451a, miR-126-5p, miR-192-5p, miR-17-5p, miR-660-5p, miR-25-3p, miR-143-3p, miR-338-3p; miR-451a, miR-126-5p, miR-192-5p, miR-17-5p, miR-660-5p, miR-25-3p, miR-363-3p, miR-338-3p; miR-451a, miR-126-5p, miR-192-5p, miR-17-5p, miR-660-5p, miR-143-3p, miR-363-3p, miR-338-3p; miR-451a, miR-126-5p, miR-192-5p, miR-17-5p, miR-25-3p, miR-143-3p, miR-363-3p, miR-338-3p; miR-451a, miR-126-5p, miR-17-5p, miR-125b-5p, miR-660-5p, miR-25-3p, miR-143-3p; miR-451a, miR-126-5p, miR-17-5p, miR-125b-5p, miR-660-5p, miR-25-3p, miR-363-3p; miR-451a, miR-126-5p, miR-17-5p, miR-125b-5p, miR-660-5p, miR-25-3p, miR-338-3p; miR-451a, miR-126-5p, miR-17-5p, miR-125b-5p, miR-660-5p, miR-143-3p, miR-363-3p; miR-451a, miR-126-5p, miR-17-5p, miR-125b-5p, miR-660-5p, miR-143-3p, miR-338-3p; miR-451a, miR-126-5p, miR-17-5p, miR-125b-5p, miR-660-5p, miR-363-3p, miR-338-3p; miR-451a, miR-126-5p, miR-17-5p, miR-125b-5p, miR-25-3p, miR-143-3p, miR-363-3p; miR-451a, miR-126-5p, miR-17-5p, miR-125b-5p, miR-25-3p, miR-143-3p, miR-338-3p; miR-451a, miR-126-5p, miR-17-5p, miR-125b-5p, miR-25-3p, miR-363-3p, miR-338-3p; miR-451a, miR-126-5p, miR-17-5p, miR-125b-5p, miR-143-3p, miR-363-3p, miR-338-3p; miR-451a, miR-126-5p, miR-17-5p, miR-660-5p, miR-25-3p, miR-143-3p, miR-363-3p; miR-451a, miR-126-5p, miR-17-5p, miR-660-5p, miR-25-3p, miR-143-3p, miR-338-3p; miR-451a, miR-126-5p, miR-17-5p, miR-660-5p, miR-25-3p, miR-363-3p, miR-338-3p; miR-451a, miR-126-5p, miR-17-5p, miR-660-5p, miR-143-3p, miR-363-3p, miR-338-3p; miR-451a, miR-126-5p, miR-17-5p, miR-25-3p, miR-143-3p, miR-363-3p, miR-338-3p; miR-451a, miR-126-5p, miR-125b-5p, miR-660-5p, miR-25-3p, miR-143-3p, miR-363-3p; miR-451a, miR-126-5p, miR-125b-5p, miR-660-5p, miR-25-3p, miR-143-3p, miR-338-3p; miR-451a, miR-126-5p, miR-125b-5p, miR-660-5p, miR-25-3p, miR-363-3p, miR-338-3p; miR-451a, miR-126-5p, miR-125b-5p, miR-660-5p, miR-143-3p, miR-363-3p, miR-338-3p; miR-451a, miR-126-5p, miR-125b-5p, miR-25-3p, miR-143-3p, miR-363-3p, miR-338-3p; miR-451a, miR-126-5p, miR-660-5p, miR-25-3p, miR-143-3p, miR-363-3p, miR-338-3p; miR-451a, miR-423-3p, miR-192-5p, miR-17-5p, miR-125b-5p, miR-660-5p, miR-25-3p; miR-451a, miR- 423-3p, miR-192-5p, miR-17-5p, miR-125b-5p, miR-660-5p, miR-143-3p; miR-451a, miR-423-3p, miR-192-5p, miR-17-5p, miR-125b-5p, miR-660-5p, miR-363-3p; miR-451a, miR-423-3p, miR-192-5p, miR-17-5p, miR-125b-5p, miR-660-5p, miR-338-3p; miR-451a, miR-423-3p, miR-192-5p, miR-17-5p, miR-125b-5p, miR-25-3p, miR-143-3p; miR-451a, miR-423-3p, miR-192-5p, miR-17-5p, miR-125b-5p, miR-25-3p, miR-363-3p; miR-451a, miR-423-3p, miR-192-5p, miR-17-5p, miR-125b-5p, miR-25-3p, miR-338-3p; miR-451a, miR-423-3p, miR-192-5p, miR-17-5p, miR-125b-5p, miR-143-3p, miR-363-3p; miR-451a, miR-423-3p, miR-192-5p, miR-17-5p, miR-125b-5p, miR-143-3p, miR-338-3p; miR-451a, miR-423-3p, miR-192-5p, miR-17-5p, miR-125b-5p, miR-363-3p, miR-338-3p; miR-451a, miR-423-3p, miR-192-5p, miR-17-5p, miR-660-5p, miR-25-3p, miR-143-3p; miR-451a, miR-423-3p, miR-192-5p, miR-17-5p, miR-660-5p, miR-25-3p, miR-363-3p; miR-451a, miR-423-3p, miR-192-5p, miR-17-5p, miR-660-5p, miR-25-3p, miR-338-3p; miR-451a, miR-423-3p, miR-192-5p, miR-17-5p, miR-660-5p, miR-143-3p, miR-363-3p; miR-451a, miR-423-3p, miR-192-5p, miR-17-5p, miR-660-5p, miR-143-3p, miR-338-3p; miR-451a, miR-423-3p, miR-192-5p, miR-17-5p, miR-660-5p, miR-363-3p, miR-338-3p; miR-451a, miR-423-3p, miR-192-5p, miR-17-5p, miR-25-3p, miR-143-3p, miR-363-3p; miR-451a, miR-423-3p, miR-192-5p, miR-17-5p, miR-25-3p, miR-143-3p, miR-338-3p; miR-451a, miR-423-3p, miR-192-5p, miR-17-5p, miR-25-3p, miR-363-3p, miR-338-3p; miR-451a, miR-423-3p, miR-192-5p, miR-17-5p, miR-143-3p, miR-363-3p, miR-338-3p; miR-451a, miR-423-3p, miR-192-5p, miR-125b-5p, miR-660-5p, miR-25-3p, miR-143-3p; miR-451a, miR-423-3p, miR-192-5p, miR-125b-5p, miR-660-5p, miR-25-3p, miR-363-3p; miR-451a, miR-423-3p, miR-192-5p, miR-125b-5p, miR-660-5p, miR-25-3p, miR-338-3p; miR-451a, miR-423-3p, miR-192-5p, miR-125b-5p, miR-660-5p, miR-143-3p, miR-363-3p; miR-451a, miR-423-3p, miR-192-5p, miR-125b-5p, miR-660-5p, miR-143-3p, miR-338-3p; miR-451a, miR-423-3p, miR-192-5p, miR-125b-5p, miR-660-5p, miR-363-3p, miR-338-3p; miR-451a, miR-423-3p, miR-192-5p, miR-125b-5p, miR-25-3p, miR-143-3p, miR-363-3p; miR-451a, miR-423-3p, miR-192-5p, miR-125b-5p, miR-25-3p, miR-143-3p, miR-338-3p; miR-451a, miR-423-3p, miR-192-5p, miR-125b-5p, miR-25-3p, miR-363-3p, miR-338-3p; miR-451a, miR-423-3p, miR-192-5p, miR-125b-5p, miR-143-3p, miR-363-3p, miR-338-3p; miR-451a, miR-423-3p, miR-192-5p, miR-660-5p, miR-25-3p, miR-143-3p, miR-363-3p; miR-451a, miR-423-3p, miR-192-5p, miR-660-5p, miR-25-3p, miR-143-3p, miR-338-3p; miR-451a, miR-423-3p, miR-192-5p, miR-660-5p, miR-25-3p, miR-363-3p, miR-338-3p; miR-451a, miR-423-3p, miR-192-5p, miR-660-5p, miR-143-3p, miR-363-3p, miR-338-3p; miR-451a, miR-423-3p, miR-192-5p, miR-25-3p, miR-143-3p, miR-363-3p, miR-338-3p; miR-451a, miR-423-3p, miR-17-5p, miR-125b-5p, miR-660-5p, miR-25-3p, miR-143-3p; miR-451a, miR-423-3p, miR-17-5p, miR-125b-5p, miR-660-5p, miR-25-3p, miR-363-3p; miR-451a, miR-423-3p, miR-17-5p, miR-125b-5p, miR-660-5p, miR-25-3p, miR-338-3p; miR-451a, miR-423-3p, miR-17-5p, miR-125b-5p, miR-660-5p, miR-143-3p, miR-363-3p; miR-451a, miR-423-3p, miR-17-5p, miR-125b-5p, miR-660-5p, miR-363-3p, miR-338-3p; miR-451a, miR-423-3p, miR-17-5p, miR-125b-5p, miR-25-3p, miR-143-3p, miR-363-3p; miR-451a, miR-423-3p, miR-17-5p, miR-125b-5p, miR-25-3p, miR-143-3p, miR-338-3p; miR-451a, miR-423-3p, miR-17-5p, miR-125b-5p, miR-25-3p, miR-363-3p, miR-338-3p; miR-451a, miR-423-3p, miR- 17-5p, miR-125b-5p, miR-143-3p, miR-363-3p, miR-338-3p; miR-451a, miR-423-3p, miR-17-5p, miR-660-5p, miR-25-3p, miR-143-3p, miR-363-3p; miR-451a, miR-423-3p, miR-17-5p, miR-660-5p, miR-25-3p, miR-143-3p, miR-338-3p; miR-451a, miR-423-3p, miR-17-5p, miR-660-5p, miR-25-3p, miR-363-3p, miR-338-3p; miR-451a, miR-423-3p, miR-17-5p, miR-660-5p, miR-143-3p, miR-363-3p, miR-338-3p; miR-451a, miR-423-3p, miR-17-5p, miR-25-3p, miR-143-3p, miR-363-3p, miR-338-3p; miR-451a, miR-423-3p, miR-125b-5p, miR-660-5p, miR-25-3p, miR-143-3p, miR-363-3p; miR-451a, miR-423-3p, miR-125b-5p, miR-660-5p, miR-25-3p, miR-143-3p, miR-338-3p; miR-451a, miR-423-3p, miR-125b-5p, miR-660-5p, miR-25-3p, miR-363-3p, miR-338-3p; miR-451a, miR-423-3p, miR-125b-5p, miR-660-5p, miR-143-3p, miR-363-3p, miR-338-3p; miR-451a, miR-423-3p, miR-125b-5p, miR-25-3p, miR-143-3p, miR-363-3p, miR-338-3p; miR-451a, miR-423-3p, miR-660-5p, miR-25-3p, miR-143-3p, miR-363-3p, miR-338-3p; miR-451a, miR-192-5p, miR-17-5p, miR-125b-5p, miR-660-5p, miR-25-3p, miR-143-3p; miR-451a, miR-192-5p, miR-17-5p, miR-125b-5p, miR-660-5p, miR-25-3p, miR-363-3p; miR-451a, miR-192-5p, miR-17-5p, miR-125b-5p, miR-660-5p, miR-25-3p, miR-338-3p; miR-451a, miR-192-5p, miR-17-5p, miR-125b-5p, miR-660-5p, miR-143-3p, miR-363-3p; miR-451a, miR-192-5p, miR-17-5p, miR-125b-5p, miR-660-5p, miR-143-3p, miR-338-3p; miR-451a, miR-192-5p, miR-17-5p, miR-125b-5p, miR-660-5p, miR-363-3p, miR-338-3p; miR-451a, miR-192-5p, miR-17-5p, miR-125b-5p, miR-25-3p, miR-143-3p, miR-363-3p; miR-451a, miR-192-5p, miR-17-5p, miR-125b-5p, miR-25-3p, miR-143-3p, miR-338-3p; miR-451a, miR-192-5p, miR-17-5p, miR-125b-5p, miR-25-3p, miR-363-3p, miR-338-3p; miR-451a, miR-192-5p, miR-17-5p, miR-125b-5p, miR-143-3p, miR-363-3p, miR-338-3p; miR-451a, miR-192-5p, miR-17-5p, miR-660-5p, miR-25-3p, miR-143-3p, miR-363-3p; miR-451a, miR-192-5p, miR-17-5p, miR-660-5p, miR-25-3p, miR-143-3p, miR-338-3p; miR-451a, miR-192-5p, miR-17-5p, miR-660-5p, miR-25-3p, miR-363-3p, miR-338-3p; miR-451a, miR-192-5p, miR-17-5p, miR-660-5p, miR-143-3p, miR-363-3p, miR-338-3p; miR-451a, miR-192-5p, miR-17-5p, miR-25-3p, miR-143-3p, miR-363-3p, miR-338-3p; miR-451a, miR-192-5p, miR-125b-5p, miR-660-5p, miR-25-3p, miR-143-3p, miR-363-3p; miR-451a, miR-192-5p, miR-125b-5p, miR-660-5p, miR-25-3p, miR-143-3p, miR-338-3p; miR-451a, miR-192-5p, miR-125b-5p, miR-660-5p, miR-25-3p, miR-363-3p, miR-338-3p; miR-451a, miR-192-5p, miR-125b-5p, miR-25-3p, miR-143-3p, miR-363-3p, miR-338-3p; miR-451a, miR-192-5p, miR-660-5p, miR-25-3p, miR-143-3p, miR-363-3p, miR-338-3p; miR-451a, miR-17-5p, miR-125b-5p, miR-660-5p, miR-25-3p, miR-143-3p, miR-363-3p; miR-451a, miR-17-5p, miR-125b-5p, miR-660-5p, miR-25-3p, miR-143-3p, miR-338-3p; miR-451a, miR-17-5p, miR-125b-5p, miR-660-5p, miR-25-3p, miR-363-3p, miR-338-3p; miR-451a, miR-17-5p, miR-125b-5p, miR-660-5p, miR-143-3p, miR-363-3p, miR-338-3p; miR-451a, miR-17-5p, miR-125b-5p, miR-25-3p, miR-143-3p, miR-363-3p, miR-338-3p; miR-451a, miR-17-5p, miR-660-5p, miR-25-3p, miR-143-3p, miR-363-3p, miR-338-3p; miR-451a, miR-125b-5p, miR-660-5p, miR-25-3p, miR-143-3p, miR-363-3p, miR-338-3p; miR-195-5p, miR-126-5p, miR-423-3p, miR-192-5p, miR-17-5p, miR-125b-5p, miR-660-5p; miR-195-5p, miR-126-5p, miR-423-3p, miR-192-5p, miR-17-5p, miR-125b-5p, miR-25-3p; miR-195-5p, miR-126-5p, miR-423-3p, miR-192-5p, miR-17-5p, miR-125b-5p, miR-143-3p; miR-195-5p, miR-126-5p, miR-423-

3p, miR-192-5p, miR-17-5p, miR-125b-5p, miR-363-3p; miR-195-5p, miR-126-5p, miR-423-3p, miR-192-5p, miR-17-5p, miR-125b-5p, miR-338-3p; miR-195-5p, miR-126-5p, miR-423-3p, miR-192-5p, miR-17-5p, miR-660-5p, miR-25-3p; miR-195-5p, miR-126-5p, miR-423-3p, miR-192-5p, miR-17-5p, miR-660-5p, miR-143-3p; miR-195-5p, miR-126-5p, miR-423-3p, miR-192-5p, miR-17-5p, miR-660-5p, miR-363-3p; miR-195-5p, miR-126-5p, miR-423-3p, miR-192-5p, miR-17-5p, miR-660-5p, miR-338-3p; miR-195-5p, miR-126-5p, miR-423-3p, miR-192-5p, miR-17-5p, miR-25-3p, miR-143-3p; miR-195-5p, miR-126-5p, miR-423-3p, miR-192-5p, miR-17-5p, miR-25-3p, miR-363-3p; miR-195-5p, miR-126-5p, miR-423-3p, miR-192-5p, miR-17-5p, miR-25-3p, miR-338-3p; miR-195-5p, miR-126-5p, miR-423-3p, miR-192-5p, miR-17-5p, miR-143-3p, miR-363-3p; miR-195-5p, miR-126-5p, miR-423-3p, miR-192-5p, miR-17-5p, miR-143-3p, miR-338-3p; miR-195-5p, miR-126-5p, miR-423-3p, miR-192-5p, miR-17-5p, miR-363-3p, miR-338-3p; miR-195-5p, miR-126-5p, miR-423-3p, miR-192-5p, miR-125b-5p, miR-660-5p, miR-25-3p; miR-195-5p, miR-126-5p, miR-423-3p, miR-192-5p, miR-125b-5p, miR-660-5p, miR-143-3p; miR-195-5p, miR-126-5p, miR-423-3p, miR-192-5p, miR-125b-5p, miR-660-5p, miR-363-3p; miR-195-5p, miR-126-5p, miR-423-3p, miR-192-5p, miR-125b-5p, miR-660-5p, miR-338-3p; miR-195-5p, miR-126-5p, miR-423-3p, miR-192-5p, miR-125b-5p, miR-25-3p, miR-143-3p; miR-195-5p, miR-126-5p, miR-423-3p, miR-192-5p, miR-125b-5p, miR-25-3p, miR-363-3p; miR-195-5p, miR-126-5p, miR-423-3p, miR-192-5p, miR-125b-5p, miR-25-3p, miR-338-3p; miR-195-5p, miR-126-5p, miR-423-3p, miR-192-5p, miR-125b-5p, miR-143-3p, miR-363-3p; miR-195-5p, miR-126-5p, miR-423-3p, miR-192-5p, miR-125b-5p, miR-143-3p, miR-338-3p; miR-195-5p, miR-126-5p, miR-423-3p, miR-192-5p, miR-125b-5p, miR-363-3p, miR-338-3p; miR-195-5p, miR-126-5p, miR-423-3p, miR-192-5p, miR-660-5p, miR-25-3p, miR-143-3p; miR-195-5p, miR-126-5p, miR-423-3p, miR-192-5p, miR-660-5p, miR-25-3p, miR-363-3p; miR-195-5p, miR-126-5p, miR-423-3p, miR-192-5p, miR-660-5p, miR-25-3p, miR-338-3p; miR-195-5p, miR-126-5p, miR-423-3p, miR-192-5p, miR-660-5p, miR-143-3p, miR-363-3p; miR-195-5p, miR-126-5p, miR-423-3p, miR-192-5p, miR-660-5p, miR-143-3p, miR-338-3p; miR-195-5p, miR-126-5p, miR-423-3p, miR-192-5p, miR-660-5p, miR-363-3p, miR-338-3p; miR-195-5p, miR-126-5p, miR-423-3p, miR-192-5p, miR-25-3p, miR-143-3p, miR-363-3p; miR-195-5p, miR-126-5p, miR-423-3p, miR-192-5p, miR-25-3p, miR-143-3p, miR-338-3p; miR-195-5p, miR-126-5p, miR-423-3p, miR-192-5p, miR-25-3p, miR-363-3p, miR-338-3p; miR-195-5p, miR-126-5p, miR-423-3p, miR-192-5p, miR-143-3p, miR-363-3p, miR-338-3p; miR-195-5p, miR-126-5p, miR-423-3p, miR-17-5p, miR-125b-5p, miR-660-5p, miR-25-3p; miR-195-5p, miR-126-5p, miR-423-3p, miR-17-5p, miR-125b-5p, miR-660-5p, miR-143-3p; miR-195-5p, miR-126-5p, miR-423-3p, miR-17-5p, miR-125b-5p, miR-660-5p, miR-363-3p; miR-195-5p, miR-126-5p, miR-423-3p, miR-17-5p, miR-125b-5p, miR-660-5p, miR-338-3p; miR-195-5p, miR-126-5p, miR-423-3p, miR-17-5p, miR-125b-5p, miR-25-3p, miR-143-3p; miR-195-5p, miR-126-5p, miR-423-3p, miR-17-5p, miR-125b-5p, miR-25-3p, miR-363-3p; miR-195-5p, miR-126-5p, miR-423-3p, miR-17-5p, miR-125b-5p, miR-25-3p, miR-338-3p; miR-195-5p, miR-126-5p, miR-423-3p, miR-17-5p, miR-125b-5p, miR-143-3p, miR-338-3p; miR-195-5p, miR-126-5p, miR-423-3p, miR-17-5p, miR-660-5p, miR-25-3p, miR-143-3p; miR-195-5p, miR-126-5p, miR-423-3p, miR-17-5p, miR-660-5p, miR-25-3p, miR-363-3p; miR-195-5p, miR-126-5p, miR-423-3p, miR-17-5p, miR-660-5p, miR-25-3p, miR-338-3p; miR-195-5p, miR-126-5p, miR-423-3p, miR-17-5p, miR-660-5p, miR-143-3p, miR-363-3p; miR-195-5p, miR-126-5p, miR-423-3p, miR-17-5p, miR-660-5p, miR-143-3p, miR-338-3p; miR-195-5p, miR-126-5p, miR-423-3p, miR-17-5p, miR-660-5p, miR-363-3p, miR-338-3p; miR-195-5p, miR-126-5p, miR-423-3p, miR-17-5p, miR-25-3p, miR-143-3p, miR-363-3p; miR-195-5p, miR-126-5p, miR-423-3p, miR-17-5p, miR-25-3p, miR-143-3p, miR-338-3p; miR-195-5p, miR-126-5p, miR-423-3p, miR-17-5p, miR-25-3p, miR-363-3p, miR-338-3p; miR-195-5p, miR-126-5p, miR-423-3p, miR-17-5p, miR-143-3p, miR-363-3p, miR-338-3p; miR-195-5p, miR-126-5p, miR-423-3p, miR-125b-5p, miR-660-5p, miR-25-3p, miR-143-3p; miR-195-5p, miR-126-5p, miR-423-3p, miR-125b-5p, miR-660-5p, miR-25-3p, miR-363-3p; miR-195-5p, miR-126-5p, miR-423-3p, miR-125b-5p, miR-660-5p, miR-25-3p, miR-338-3p; miR-195-5p, miR-126-5p, miR-423-3p, miR-125b-5p, miR-660-5p, miR-143-3p, miR-363-3p; miR-195-5p, miR-126-5p, miR-423-3p, miR-125b-5p, miR-660-5p, miR-143-3p, miR-338-3p; miR-195-5p, miR-126-5p, miR-423-3p, miR-125b-5p, miR-660-5p, miR-363-3p, miR-338-3p; miR-195-5p, miR-126-5p, miR-423-3p, miR-125b-5p, miR-25-3p, miR-143-3p, miR-363-3p; miR-195-5p, miR-126-5p, miR-423-3p, miR-125b-5p, miR-25-3p, miR-143-3p, miR-338-3p; miR-195-5p, miR-126-5p, miR-423-3p, miR-125b-5p, miR-25-3p, miR-363-3p, miR-338-3p; miR-195-5p, miR-126-5p, miR-423-3p, miR-125b-5p, miR-143-3p, miR-363-3p, miR-338-3p; miR-195-5p, miR-126-5p, miR-423-3p, miR-660-5p, miR-25-3p, miR-143-3p, miR-363-3p; miR-195-5p, miR-126-5p, miR-423-3p, miR-660-5p, miR-25-3p, miR-143-3p, miR-338-3p; miR-195-5p, miR-126-5p, miR-423-3p, miR-660-5p, miR-25-3p, miR-363-3p, miR-338-3p; miR-195-5p, miR-126-5p, miR-423-3p, miR-660-5p, miR-143-3p, miR-363-3p, miR-338-3p; miR-195-5p, miR-126-5p, miR-423-3p, miR-25-3p, miR-143-3p, miR-363-3p, miR-338-3p; miR-195-5p, miR-126-5p, miR-192-5p, miR-17-5p, miR-125b-5p, miR-660-5p, miR-25-3p; miR-195-5p, miR-126-5p, miR-192-5p, miR-17-5p, miR-125b-5p, miR-660-5p, miR-143-3p; miR-195-5p, miR-126-5p, miR-192-5p, miR-17-5p, miR-125b-5p, miR-660-5p, miR-363-3p; miR-195-5p, miR-126-5p, miR-192-5p, miR-17-5p, miR-125b-5p, miR-660-5p, miR-338-3p; miR-195-5p, miR-126-5p, miR-192-5p, miR-17-5p, miR-125b-5p, miR-25-3p, miR-143-3p; miR-195-5p, miR-126-5p, miR-192-5p, miR-17-5p, miR-125b-5p, miR-25-3p, miR-363-3p; miR-195-5p, miR-126-5p, miR-192-5p, miR-17-5p, miR-125b-5p, miR-25-3p, miR-338-3p; miR-195-5p, miR-126-5p, miR-192-5p, miR-17-5p, miR-125b-5p, miR-143-3p, miR-363-3p; miR-195-5p, miR-126-5p, miR-192-5p, miR-17-5p, miR-125b-5p, miR-143-3p, miR-338-3p; miR-195-5p, miR-126-5p, miR-192-5p, miR-17-5p, miR-125b-5p, miR-363-3p, miR-338-3p; miR-195-5p, miR-126-5p, miR-192-5p, miR-17-5p, miR-660-5p, miR-25-3p, miR-143-3p; miR-195-5p, miR-126-5p, miR-192-5p, miR-17-5p, miR-660-5p, miR-25-3p, miR-363-3p; miR-195-5p, miR-126-5p, miR-192-5p, miR-17-5p, miR-660-5p, miR-25-3p, miR-338-3p; miR-195-5p, miR-126-5p, miR-192-5p, miR-17-5p, miR-660-5p, miR-143-3p, miR-363-3p; miR-195-5p, miR-126-5p, miR-192-5p, miR-17-5p, miR-660-5p, miR-143-3p, miR-338-3p; miR-195-5p, miR-126-5p, miR-192-5p, miR-17-5p, miR-660-5p, miR-363-3p, miR-338-3p; miR-195-5p, miR-126-5p, miR-192-5p, miR-17-5p, miR-25-3p, miR-143-3p, miR-363-3p; miR-195-5p, miR-126-5p, miR-192-

5p, miR-17-5p, miR-25-3p, miR-143-3p, miR-338-3p; miR-195-5p, miR-126-5p, miR-192-5p, miR-17-5p, miR-25-3p, miR-363-3p, miR-338-3p; miR-195-5p, miR-126-5p, miR-192-5p, miR-17-5p, miR-143-3p, miR-363-3p, miR-338-3p; miR-195-5p, miR-126-5p, miR-192-5p, miR-125b-5p, miR-660-5p, miR-25-3p, miR-143-3p; miR-195-5p, miR-126-5p, miR-192-5p, miR-125b-5p, miR-660-5p, miR-25-3p, miR-363-3p; miR-195-5p, miR-126-5p, miR-192-5p, miR-125b-5p, miR-660-5p, miR-25-3p, miR-338-3p; miR-195-5p, miR-126-5p, miR-192-5p, miR-125b-5p, miR-660-5p, miR-143-3p, miR-363-3p; miR-195-5p, miR-126-5p, miR-192-5p, miR-125b-5p, miR-660-5p, miR-143-3p, miR-338-3p; miR-195-5p, miR-126-5p, miR-192-5p, miR-125b-5p, miR-660-5p, miR-363-3p, miR-338-3p; miR-195-5p, miR-126-5p, miR-192-5p, miR-125b-5p, miR-25-3p, miR-143-3p, miR-363-3p; miR-195-5p, miR-126-5p, miR-192-5p, miR-125b-5p, miR-25-3p, miR-143-3p, miR-338-3p; miR-195-5p, miR-126-5p, miR-192-5p, miR-125b-5p, miR-25-3p, miR-363-3p, miR-338-3p; miR-195-5p, miR-126-5p, miR-192-5p, miR-125b-5p, miR-143-3p, miR-363-3p, miR-338-3p; miR-195-5p, miR-126-5p, miR-192-5p, miR-660-5p, miR-25-3p, miR-143-3p, miR-363-3p; miR-195-5p, miR-126-5p, miR-192-5p, miR-660-5p, miR-25-3p, miR-143-3p, miR-338-3p; miR-195-5p, miR-126-5p, miR-192-5p, miR-660-5p, miR-25-3p, miR-363-3p, miR-338-3p; miR-195-5p, miR-126-5p, miR-192-5p, miR-660-5p, miR-143-3p, miR-363-3p, miR-338-3p; miR-195-5p, miR-126-5p, miR-192-5p, miR-25-3p, miR-143-3p, miR-363-3p, miR-338-3p; miR-195-5p, miR-126-5p, miR-17-5p, miR-125b-5p, miR-660-5p, miR-25-3p, miR-143-3p; miR-195-5p, miR-126-5p, miR-17-5p, miR-125b-5p, miR-660-5p, miR-25-3p, miR-363-3p; miR-195-5p, miR-126-5p, miR-17-5p, miR-125b-5p, miR-660-5p, miR-25-3p, miR-338-3p; miR-195-5p, miR-126-5p, miR-17-5p, miR-125b-5p, miR-660-5p, miR-143-3p, miR-363-3p; miR-195-5p, miR-126-5p, miR-17-5p, miR-125b-5p, miR-660-5p, miR-143-3p, miR-338-3p; miR-195-5p, miR-126-5p, miR-17-5p, miR-125b-5p, miR-660-5p, miR-363-3p, miR-338-3p; miR-195-5p, miR-126-5p, miR-17-5p, miR-125b-5p, miR-25-3p, miR-143-3p, miR-363-3p; miR-195-5p, miR-126-5p, miR-17-5p, miR-125b-5p, miR-25-3p, miR-143-3p, miR-338-3p; miR-195-5p, miR-126-5p, miR-17-5p, miR-125b-5p, miR-25-3p, miR-363-3p, miR-338-3p; miR-195-5p, miR-126-5p, miR-17-5p, miR-125b-5p, miR-143-3p, miR-363-3p, miR-338-3p; miR-195-5p, miR-126-5p, miR-17-5p, miR-660-5p, miR-25-3p, miR-143-3p, miR-363-3p; miR-195-5p, miR-126-5p, miR-17-5p, miR-660-5p, miR-25-3p, miR-143-3p, miR-338-3p; miR-195-5p, miR-126-5p, miR-17-5p, miR-660-5p, miR-25-3p, miR-363-3p, miR-338-3p; miR-195-5p, miR-126-5p, miR-17-5p, miR-660-5p, miR-143-3p, miR-363-3p, miR-338-3p; miR-195-5p, miR-126-5p, miR-17-5p, miR-25-3p, miR-143-3p, miR-363-3p, miR-338-3p; miR-195-5p, miR-126-5p, miR-125b-5p, miR-660-5p, miR-25-3p, miR-143-3p, miR-363-3p; miR-195-5p, miR-126-5p, miR-125b-5p, miR-660-5p, miR-25-3p, miR-143-3p, miR-338-3p; miR-195-5p, miR-126-5p, miR-125b-5p, miR-660-5p, miR-25-3p, miR-363-3p, miR-338-3p; miR-195-5p, miR-126-5p, miR-125b-5p, miR-660-5p, miR-143-3p, miR-363-3p, miR-338-3p; miR-195-5p, miR-126-5p, miR-125b-5p, miR-25-3p, miR-143-3p, miR-363-3p, miR-338-3p; miR-195-5p, miR-126-5p, miR-660-5p, miR-25-3p, miR-143-3p, miR-363-3p, miR-338-3p; miR-195-5p, miR-423-3p, miR-192-5p, miR-17-5p, miR-125b-5p, miR-660-5p, miR-25-3p; miR-195-5p, miR-423-3p, miR-192-5p, miR-17-5p, miR-125b-5p, miR-660-5p, miR-143-3p; miR-195-5p, miR-423-3p, miR-192-5p, miR-17-5p, miR-125b-5p, miR-660-5p, miR-17-5p, miR-125b-5p, miR-660-5p, miR-338-3p; miR-195-5p, miR-423-3p, miR-192-5p, miR-17-5p, miR-125b-5p, miR-25-3p, miR-143-3p; miR-195-5p, miR-423-3p, miR-192-5p, miR-17-5p, miR-125b-5p, miR-25-3p, miR-363-3p; miR-195-5p, miR-423-3p, miR-192-5p, miR-17-5p, miR-125b-5p, miR-25-3p, miR-338-3p; miR-195-5p, miR-423-3p, miR-192-5p, miR-17-5p, miR-125b-5p, miR-143-3p, miR-363-3p; miR-195-5p, miR-423-3p, miR-192-5p, miR-17-5p, miR-125b-5p, miR-143-3p, miR-338-3p; miR-195-5p, miR-423-3p, miR-192-5p, miR-17-5p, miR-125b-5p, miR-363-3p, miR-338-3p; miR-195-5p, miR-423-3p, miR-192-5p, miR-17-5p, miR-660-5p, miR-25-3p, miR-143-3p; miR-195-5p, miR-423-3p, miR-192-5p, miR-17-5p, miR-660-5p, miR-25-3p, miR-363-3p; miR-195-5p, miR-423-3p, miR-192-5p, miR-17-5p, miR-660-5p, miR-25-3p, miR-338-3p; miR-195-5p, miR-423-3p, miR-192-5p, miR-17-5p, miR-660-5p, miR-143-3p, miR-363-3p; miR-195-5p, miR-423-3p, miR-192-5p, miR-17-5p, miR-660-5p, miR-143-3p, miR-338-3p; miR-195-5p, miR-423-3p, miR-192-5p, miR-17-5p, miR-660-5p, miR-363-3p, miR-338-3p; miR-195-5p, miR-423-3p, miR-192-5p, miR-17-5p, miR-25-3p, miR-143-3p, miR-363-3p; miR-195-5p, miR-423-3p, miR-192-5p, miR-17-5p, miR-25-3p, miR-143-3p, miR-338-3p; miR-195-5p, miR-423-3p, miR-192-5p, miR-17-5p, miR-25-3p, miR-363-3p, miR-338-3p; miR-195-5p, miR-423-3p, miR-192-5p, miR-17-5p, miR-143-3p, miR-363-3p, miR-338-3p; miR-195-5p, miR-423-3p, miR-192-5p, miR-125b-5p, miR-660-5p, miR-25-3p, miR-143-3p; miR-195-5p, miR-423-3p, miR-192-5p, miR-125b-5p, miR-660-5p, miR-25-3p, miR-363-3p; miR-195-5p, miR-423-3p, miR-192-5p, miR-125b-5p, miR-660-5p, miR-25-3p, miR-338-3p; miR-195-5p, miR-423-3p, miR-192-5p, miR-125b-5p, miR-660-5p, miR-143-3p, miR-363-3p; miR-195-5p, miR-423-3p, miR-192-5p, miR-125b-5p, miR-660-5p, miR-143-3p, miR-338-3p; miR-195-5p, miR-423-3p, miR-192-5p, miR-125b-5p, miR-660-5p, miR-363-3p, miR-338-3p; miR-195-5p, miR-423-3p, miR-192-5p, miR-125b-5p, miR-25-3p, miR-143-3p, miR-363-3p; miR-195-5p, miR-423-3p, miR-192-5p, miR-125b-5p, miR-25-3p, miR-143-3p, miR-338-3p; miR-195-5p, miR-423-3p, miR-192-5p, miR-125b-5p, miR-25-3p, miR-363-3p, miR-338-3p; miR-195-5p, miR-423-3p, miR-192-5p, miR-125b-5p, miR-143-3p, miR-363-3p, miR-338-3p; miR-195-5p, miR-423-3p, miR-192-5p, miR-660-5p, miR-25-3p, miR-143-3p, miR-363-3p; miR-195-5p, miR-423-3p, miR-192-5p, miR-660-5p, miR-25-3p, miR-143-3p, miR-338-3p; miR-195-5p, miR-423-3p, miR-192-5p, miR-660-5p, miR-25-3p, miR-363-3p, miR-338-3p; miR-195-5p, miR-423-3p, miR-192-5p, miR-660-5p, miR-143-3p, miR-363-3p, miR-338-3p; miR-195-5p, miR-423-3p, miR-192-5p, miR-25-3p, miR-143-3p, miR-363-3p, miR-338-3p; miR-195-5p, miR-423-3p, miR-17-5p, miR-125b-5p, miR-660-5p, miR-25-3p, miR-143-3p; miR-195-5p, miR-423-3p, miR-17-5p, miR-125b-5p, miR-660-5p, miR-25-3p, miR-363-3p; miR-195-5p, miR-423-3p, miR-17-5p, miR-125b-5p, miR-660-5p, miR-25-3p, miR-338-3p; miR-195-5p, miR-423-3p, miR-17-5p, miR-125b-5p, miR-660-5p, miR-143-3p, miR-363-3p; miR-195-5p, miR-423-3p, miR-17-5p, miR-125b-5p, miR-660-5p, miR-143-3p, miR-338-3p; miR-195-5p, miR-423-3p, miR-17-5p, miR-125b-5p, miR-660-5p, miR-363-3p, miR-338-3p; miR-195-5p, miR-423-3p, miR-17-5p, miR-125b-5p, miR-25-3p, miR-143-3p, miR-363-3p; miR-195-5p, miR-423-3p, miR-17-5p, miR-125b-5p, miR-25-3p, miR-143-3p, miR-338-3p; miR-195-5p, miR-423-3p, miR-17-5p, miR-125b-5p, miR-25-3p, miR-363-3p, miR-338-3p; miR-195-5p, miR-423-3p, miR-17-5p, miR-125b-5p, miR-143-3p, miR-363-3p, miR-338-3p; miR-195-5p, miR-423-3p, miR-17-5p, miR-660-5p, miR-25-3p, miR-143-3p, miR-363-3p; miR-195-5p, miR-423-3p, miR-17-5p, miR-660-5p, miR-25-3p, miR-143-3p, miR-338-3p; miR-195-5p, miR-423-3p, miR-17-5p, miR-660-5p, miR-25-3p, miR-363-3p, miR-338-3p; miR-195-5p, miR-423-3p, miR-17-5p, miR-660-5p, miR-143-3p, miR-363-3p, miR-338-3p; miR-195-5p, miR-423-3p, miR-17-5p, miR-25-3p, miR-143-3p, miR-363-3p, miR-338-3p; miR-195-5p, miR-423-3p, miR-125b-5p, miR-660-5p, miR-25-3p, miR-143-3p, miR-363-3p; miR-195-5p, miR-423-3p, miR-125b-5p, miR-660-5p, miR-25-3p, miR-143-3p, miR-338-3p; miR-195-5p, miR-423-3p, miR-125b-5p, miR-660-5p, miR-25-3p, miR-363-3p, miR-338-3p; miR-195-5p, miR-423-3p, miR-125b-5p, miR-660-5p, miR-143-3p, miR-363-3p, miR-338-3p; miR-195-5p, miR-423-3p, miR-125b-5p, miR-25-3p, miR-143-3p, miR-363-3p, miR-338-3p; miR-195-5p, miR-423-3p, miR-660-5p, miR-25-3p, miR-143-3p, miR-363-3p, miR-338-3p; miR-195-5p, miR-192-5p, miR-17-5p, miR-125b-5p, miR-660-5p, miR-25-3p, miR-143-3p; miR-195-5p, miR-192-5p, miR-17-5p, miR-125b-5p, miR-660-5p, miR-25-3p, miR-363-3p; miR-195-5p, miR-192-5p, miR-17-5p, miR-125b-5p, miR-660-5p, miR-25-3p, miR-338-3p; miR-195-5p, miR-192-5p, miR-17-5p, miR-125b-5p, miR-660-5p, miR-143-3p, miR-363-3p; miR-195-5p, miR-192-5p, miR-17-5p, miR-125b-5p, miR-660-5p, miR-143-3p, miR-338-3p; miR-195-5p, miR-192-5p, miR-17-5p, miR-125b-5p, miR-660-5p, miR-363-3p, miR-338-3p; miR-195-5p, miR-192-5p, miR-17-5p, miR-125b-5p, miR-25-3p, miR-143-3p, miR-363-3p; miR-195-5p, miR-192-5p, miR-17-5p, miR-125b-5p, miR-25-3p, miR-143-3p, miR-338-3p; miR-195-5p, miR-192-5p, miR-17-5p, miR-125b-5p, miR-25-3p, miR-363-3p, miR-338-3p; miR-195-5p, miR-192-5p, miR-17-5p, miR-125b-5p, miR-143-3p, miR-363-3p, miR-338-3p; miR-195-5p, miR-192-5p, miR-17-5p, miR-660-5p, miR-25-3p, miR-143-3p, miR-363-3p; miR-195-5p, miR-192-5p, miR-17-5p, miR-660-5p, miR-25-3p, miR-143-3p, miR-338-3p; miR-195-5p, miR-192-5p, miR-17-5p, miR-660-5p, miR-25-3p, miR-363-3p, miR-338-3p; miR-195-5p, miR-192-5p, miR-17-5p, miR-660-5p, miR-143-3p, miR-363-3p, miR-338-3p; miR-195-5p, miR-192-5p, miR-17-5p, miR-25-3p, miR-143-3p, miR-363-3p, miR-338-3p; miR-195-5p, miR-192-5p, miR-125b-5p, miR-660-5p, miR-25-3p, miR-143-3p, miR-363-3p; miR-195-5p, miR-192-5p, miR-125b-5p, miR-660-5p, miR-25-3p, miR-143-3p, miR-338-3p; miR-195-5p, miR-192-5p, miR-125b-5p, miR-660-5p, miR-25-3p, miR-363-3p, miR-338-3p; miR-195-5p, miR-192-5p, miR-125b-5p, miR-660-5p, miR-143-3p, miR-363-3p, miR-338-3p; miR-195-5p, miR-192-5p, miR-125b-5p, miR-25-3p, miR-143-3p, miR-363-3p, miR-338-3p; miR-195-5p, miR-192-5p, miR-660-5p, miR-25-3p, miR-143-3p, miR-363-3p, miR-338-3p; miR-195-5p, miR-17-5p, miR-125b-5p, miR-660-5p, miR-25-3p, miR-143-3p, miR-363-3p; miR-195-5p, miR-17-5p, miR-125b-5p, miR-660-5p, miR-25-3p, miR-143-3p, miR-338-3p; miR-195-5p, miR-17-5p, miR-125b-5p, miR-660-5p, miR-25-3p, miR-363-3p, miR-338-3p; miR-195-5p, miR-17-5p, miR-125b-5p, miR-660-5p, miR-143-3p, miR-363-3p, miR-338-3p; miR-195-5p, miR-17-5p, miR-125b-5p, miR-25-3p, miR-143-3p, miR-363-3p, miR-338-3p; miR-195-5p, miR-17-5p, miR-660-5p, miR-25-3p, miR-143-3p, miR-363-3p, miR-338-3p; miR-195-5p, miR-125b-5p, miR-660-5p, miR-25-3p, miR-143-3p, miR-363-3p, miR-338-3p; miR-126-5p, miR-423-3p, miR-192-5p, miR-17-5p, miR-125b-5p, miR-660-5p, miR-25-3p; miR-126-5p, miR-423-3p, miR-192-5p, miR-17-5p, miR-125b-5p, miR-660-5p, miR-143-3p; miR-126-5p, miR-423-3p, miR-192-5p, miR-17-5p, miR-125b-5p, miR-660-5p, miR-363-3p; miR-126-5p, miR-423-3p, miR-192-5p, miR-17-5p, miR-125b-5p, miR-660-5p, miR-338-3p; miR-126-5p, miR-423-3p, miR-192-5p, miR-17-5p, miR-125b-5p, miR-25-3p, miR-143-3p; miR-126-5p, miR-423-3p, miR-192-5p, miR-17-5p, miR-125b-5p, miR-25-3p, miR-363-3p; miR-126-5p, miR-423-3p, miR-192-5p, miR-17-5p, miR-125b-5p, miR-25-3p, miR-338-3p; miR-126-5p, miR-423-3p, miR-192-5p, miR-17-5p, miR-125b-5p, miR-143-3p, miR-363-3p; miR-126-5p, miR-423-3p, miR-192-5p, miR-17-5p, miR-125b-5p, miR-143-3p, miR-338-3p; miR-126-5p, miR-423-3p, miR-192-5p, miR-17-5p, miR-125b-5p, miR-363-3p, miR-338-3p; miR-126-5p, miR-423-3p, miR-192-5p, miR-17-5p, miR-660-5p, miR-25-3p, miR-143-3p; miR-126-5p, miR-423-3p, miR-192-5p, miR-17-5p, miR-660-5p, miR-25-3p, miR-363-3p; miR-126-5p, miR-423-3p, miR-192-5p, miR-17-5p, miR-660-5p, miR-25-3p, miR-338-3p; miR-126-5p, miR-423-3p, miR-192-5p, miR-17-5p, miR-660-5p, miR-143-3p, miR-363-3p; miR-126-5p, miR-423-3p, miR-192-5p, miR-17-5p, miR-660-5p, miR-363-3p, miR-338-3p; miR-126-5p, miR-423-3p, miR-192-5p, miR-17-5p, miR-25-3p, miR-143-3p, miR-363-3p; miR-126-5p, miR-423-3p, miR-192-5p, miR-17-5p, miR-25-3p, miR-143-3p, miR-338-3p; miR-126-5p, miR-423-3p, miR-192-5p, miR-17-5p, miR-25-3p, miR-363-3p, miR-338-3p; miR-126-5p, miR-423-3p, miR-192-5p, miR-17-5p, miR-143-3p, miR-363-3p, miR-338-3p; miR-126-5p, miR-423-3p, miR-192-5p, miR-125b-5p, miR-660-5p, miR-25-3p, miR-143-3p; miR-126-5p, miR-423-3p, miR-192-5p, miR-125b-5p, miR-660-5p, miR-25-3p, miR-363-3p; miR-126-5p, miR-423-3p, miR-192-5p, miR-125b-5p, miR-660-5p, miR-25-3p, miR-338-3p; miR-126-5p, miR-423-3p, miR-192-5p, miR-125b-5p, miR-660-5p, miR-143-3p, miR-363-3p; miR-126-5p, miR-423-3p, miR-192-5p, miR-125b-5p, miR-660-5p, miR-143-3p, miR-338-3p; miR-126-5p, miR-423-3p, miR-192-5p, miR-125b-5p, miR-660-5p, miR-363-3p, miR-338-3p; miR-126-5p, miR-423-3p, miR-192-5p, miR-125b-5p, miR-25-3p, miR-143-3p, miR-363-3p; miR-126-5p, miR-423-3p, miR-192-5p, miR-125b-5p, miR-25-3p, miR-143-3p, miR-338-3p; miR-126-5p, miR-423-3p, miR-192-5p, miR-125b-5p, miR-25-3p, miR-363-3p, miR-338-3p; miR-126-5p, miR-423-3p, miR-192-5p, miR-125b-5p, miR-143-3p, miR-363-3p, miR-338-3p; miR-126-5p, miR-423-3p, miR-192-5p, miR-660-5p, miR-25-3p, miR-143-3p, miR-363-3p; miR-126-5p, miR-423-3p, miR-192-5p, miR-660-5p, miR-25-3p, miR-143-3p, miR-338-3p; miR-126-5p, miR-423-3p, miR-192-5p, miR-660-5p, miR-25-3p, miR-363-3p, miR-338-3p; miR-126-5p, miR-423-3p, miR-192-5p, miR-25-3p, miR-143-3p, miR-363-3p, miR-338-3p; miR-126-5p, miR-423-3p, miR-17-5p, miR-125b-5p, miR-660-5p, miR-25-3p, miR-143-3p; miR-126-5p, miR-423-3p, miR-17-5p, miR-125b-5p, miR-660-5p, miR-25-3p, miR-363-3p; miR-126-5p, miR-423-3p, miR-17-5p, miR-125b-5p, miR-660-5p, miR-25-3p, miR-338-3p; miR-126-5p, miR-423-3p, miR-17-5p, miR-125b-5p, miR-660-5p, miR-143-3p, miR-363-3p; miR-126-5p, miR-423-3p, miR-17-5p, miR-125b-5p, miR-660-5p, miR-143-3p, miR-338-3p; miR-126-5p, miR-423-3p, miR-17-5p, miR-125b-5p, miR-660-5p, miR-363-3p, miR-338-3p; miR-126-5p, miR-423-3p, miR-17-5p, miR-125b-5p, miR-25-3p, miR-143-3p, miR-363-3p; miR-126-5p, miR-423-3p, miR-17-5p, miR-125b-5p, miR-25-3p, miR-143-3p, miR-338-3p; miR-126-5p, miR-423-3p, miR-17-5p, miR-125b-5p, miR-25-3p, miR-363-3p, miR-338-3p; miR-126-5p, miR-423-3p, miR-17-5p, miR-660-5p, miR-25-3p, miR-143-3p, miR-363-3p; miR-126-5p, miR-423-3p, miR-17-5p, miR-660-5p, miR-25-3p, miR-143-3p, miR-338-3p; miR-126-5p, miR-423-3p, miR-17-5p, miR-660-5p, miR-25-3p, miR-363-3p, miR-338-3p; miR-126-5p, miR-423-3p, miR-17-5p, miR-125b-5p, miR-143-3p, miR-363-3p, miR-338-3p; miR-126-5p, miR- 423-3p, miR-17-5p, miR-660-5p, miR-25-3p, miR-143-3p, miR-338-3p; miR-126-5p, miR-423-3p, miR-17-5p, miR-660-5p, miR-25-3p, miR-363-3p, miR-338-3p; miR-126-5p, miR-423-3p, miR-17-5p, miR-660-5p, miR-143-3p, miR-363-3p, miR-338-3p; miR-126-5p, miR-423-3p, miR-17-5p, miR-25-3p, miR-143-3p, miR-363-3p, miR-338-3p; miR-126-5p, miR-423-3p, miR-125b-5p, miR-660-5p, miR-25-3p, miR-143-3p, miR-363-3p; miR-126-5p, miR-423-3p, miR-125b-5p, miR-660-5p, miR-25-3p, miR-143-3p, miR-338-3p; miR-126-5p, miR-423-3p, miR-125b-5p, miR-660-5p, miR-25-3p, miR-363-3p, miR-338-3p; miR-126-5p, miR-423-3p, miR-125b-5p, miR-660-5p, miR-143-3p, miR-363-3p, miR-338-3p; miR-126-5p, miR-423-3p, miR-125b-5p, miR-25-3p, miR-143-3p, miR-363-3p, miR-338-3p; miR-126-5p, miR-423-3p, miR-660-5p, miR-25-3p, miR-143-3p, miR-363-3p, miR-338-3p; miR-126-5p, miR-192-5p, miR-17-5p, miR-125b-5p, miR-660-5p, miR-25-3p, miR-143-3p; miR-126-5p, miR-192-5p, miR-17-5p, miR-125b-5p, miR-660-5p, miR-25-3p, miR-363-3p; miR-126-5p, miR-192-5p, miR-17-5p, miR-125b-5p, miR-660-5p, miR-25-3p, miR-338-3p; miR-126-5p, miR-192-5p, miR-17-5p, miR-125b-5p, miR-660-5p, miR-143-3p, miR-363-3p; miR-126-5p, miR-192-5p, miR-17-5p, miR-125b-5p, miR-660-5p, miR-143-3p, miR-338-3p; miR-126-5p, miR-192-5p, miR-17-5p, miR-125b-5p, miR-660-5p, miR-363-3p, miR-338-3p; miR-126-5p, miR-192-5p, miR-17-5p, miR-125b-5p, miR-25-3p, miR-143-3p, miR-363-3p; miR-126-5p, miR-192-5p, miR-17-5p, miR-125b-5p, miR-25-3p, miR-143-3p, miR-338-3p; miR-126-5p, miR-192-5p, miR-17-5p, miR-125b-5p, miR-25-3p, miR-363-3p, miR-338-3p; miR-126-5p, miR-192-5p, miR-17-5p, miR-125b-5p, miR-143-3p, miR-363-3p, miR-338-3p; miR-126-5p, miR-192-5p, miR-17-5p, miR-660-5p, miR-25-3p, miR-143-3p, miR-363-3p; miR-126-5p, miR-192-5p, miR-17-5p, miR-660-5p, miR-25-3p, miR-143-3p, miR-338-3p; miR-126-5p, miR-192-5p, miR-17-5p, miR-660-5p, miR-25-3p, miR-363-3p, miR-338-3p; miR-126-5p, miR-192-5p, miR-17-5p, miR-660-5p, miR-143-3p, miR-363-3p, miR-338-3p; miR-126-5p, miR-192-5p, miR-17-5p, miR-25-3p, miR-143-3p, miR-363-3p, miR-338-3p; miR-126-5p, miR-192-5p, miR-125b-5p, miR-660-5p, miR-25-3p, miR-143-3p, miR-363-3p; miR-126-5p, miR-192-5p, miR-125b-5p, miR-660-5p, miR-25-3p, miR-143-3p, miR-338-3p; miR-126-5p, miR-192-5p, miR-125b-5p, miR-660-5p, miR-25-3p, miR-363-3p, miR-338-3p; miR-126-5p, miR-192-5p, miR-125b-5p, miR-660-5p, miR-143-3p, miR-363-3p, miR-338-3p; miR-126-5p, miR-192-5p, miR-660-5p, miR-25-3p, miR-143-3p, miR-363-3p, miR-338-3p; miR-126-5p, miR-17-5p, miR-125b-5p, miR-660-5p, miR-25-3p, miR-143-3p, miR-363-3p; miR-126-5p, miR-17-5p, miR-125b-5p, miR-660-5p, miR-25-3p, miR-143-3p, miR-338-3p; miR-126-5p, miR-17-5p, miR-125b-5p, miR-660-5p, miR-25-3p, miR-363-3p, miR-338-3p; miR-126-5p, miR-17-5p, miR-125b-5p, miR-660-5p, miR-143-3p, miR-363-3p, miR-338-3p; miR-126-5p, miR-17-5p, miR-125b-5p, miR-25-3p, miR-143-3p, miR-363-3p, miR-338-3p; miR-126-5p, miR-17-5p, miR-660-5p, miR-25-3p, miR-143-3p, miR-363-3p, miR-338-3p; miR-126-5p, miR-125b-5p, miR-660-5p, miR-25-3p, miR-143-3p, miR-363-3p, miR-338-3p; miR-423-3p, miR-192-5p, miR-17-5p, miR-125b-5p, miR-660-5p, miR-25-3p, miR-143-3p; miR-423-3p, miR-192-5p, miR-17-5p, miR-125b-5p, miR-660-5p, miR-25-3p, miR-363-3p; miR-423-3p, miR-192-5p, miR-17-5p, miR-125b-5p, miR-660-5p, miR-25-3p, miR-338-3p; miR-423-3p, miR-192-5p, miR-17-5p, miR-125b-5p, miR-660-5p, miR-143-3p, miR-363-3p; miR-423-3p, miR-192-5p, miR-17-5p, miR-125b-5p, miR-660-5p, miR-143-3p, miR-338-3p; miR-423-3p, miR-192-5p, miR-17-5p, miR-125b-5p, miR-660-5p, miR-363-3p, miR-338-3p; miR-423-3p, miR-192-5p, miR-17-5p, miR-125b-5p, miR-25-3p, miR-143-3p, miR-363-3p; miR-423-3p, miR-192-5p, miR-17-5p, miR-125b-5p, miR-25-3p, miR-143-3p, miR-338-3p; miR-423-3p, miR-192-5p, miR-17-5p, miR-125b-5p, miR-25-3p, miR-363-3p, miR-338-3p; miR-423-3p, miR-192-5p, miR-17-5p, miR-125b-5p, miR-143-3p, miR-363-3p, miR-338-3p; miR-423-3p, miR-192-5p, miR-17-5p, miR-660-5p, miR-25-3p, miR-143-3p, miR-363-3p; miR-423-3p, miR-192-5p, miR-17-5p, miR-660-5p, miR-25-3p, miR-143-3p, miR-338-3p; miR-423-3p, miR-192-5p, miR-17-5p, miR-660-5p, miR-25-3p, miR-363-3p, miR-338-3p; miR-423-3p, miR-192-5p, miR-17-5p, miR-660-5p, miR-143-3p, miR-363-3p, miR-338-3p; miR-423-3p, miR-192-5p, miR-17-5p, miR-25-3p, miR-143-3p, miR-363-3p, miR-338-3p; miR-423-3p, miR-192-5p, miR-125b-5p, miR-660-5p, miR-25-3p, miR-143-3p, miR-363-3p; miR-423-3p, miR-192-5p, miR-125b-5p, miR-660-5p, miR-25-3p, miR-143-3p, miR-338-3p; miR-423-3p, miR-192-5p, miR-125b-5p, miR-660-5p, miR-25-3p, miR-363-3p, miR-338-3p; miR-423-3p, miR-192-5p, miR-125b-5p, miR-660-5p, miR-143-3p, miR-363-3p, miR-338-3p; miR-423-3p, miR-192-5p, miR-125b-5p, miR-25-3p, miR-143-3p, miR-363-3p, miR-338-3p; miR-423-3p, miR-192-5p, miR-660-5p, miR-25-3p, miR-143-3p, miR-363-3p, miR-338-3p; miR-423-3p, miR-17-5p, miR-125b-5p, miR-660-5p, miR-25-3p, miR-143-3p, miR-363-3p; miR-423-3p, miR-17-5p, miR-125b-5p, miR-660-5p, miR-25-3p, miR-143-3p, miR-338-3p; miR-423-3p, miR-17-5p, miR-125b-5p, miR-660-5p, miR-25-3p, miR-363-3p, miR-338-3p; miR-423-3p, miR-17-5p, miR-125b-5p, miR-660-5p, miR-143-3p, miR-363-3p, miR-338-3p; miR-423-3p, miR-17-5p, miR-125b-5p, miR-25-3p, miR-143-3p, miR-363-3p, miR-338-3p; miR-423-3p, miR-17-5p, miR-660-5p, miR-25-3p, miR-143-3p, miR-363-3p, miR-338-3p; miR-423-3p, miR-125b-5p, miR-660-5p, miR-25-3p, miR-143-3p, miR-363-3p, miR-338-3p; miR-192-5p, miR-17-5p, miR-125b-5p, miR-660-5p, miR-25-3p, miR-143-3p, miR-363-3p; miR-192-5p, miR-17-5p, miR-125b-5p, miR-660-5p, miR-25-3p, miR-143-3p, miR-338-3p; miR-192-5p, miR-17-5p, miR-125b-5p, miR-660-5p, miR-25-3p, miR-363-3p, miR-338-3p; miR-192-5p, miR-17-5p, miR-125b-5p, miR-660-5p, miR-143-3p, miR-363-3p, miR-338-3p; miR-192-5p, miR-17-5p, miR-125b-5p, miR-25-3p, miR-143-3p, miR-363-3p, miR-338-3p; miR-192-5p, miR-17-5p, miR-660-5p, miR-25-3p, miR-143-3p, miR-363-3p, miR-338-3p; miR-192-5p, miR-125b-5p, miR-660-5p, miR-25-3p, miR-143-3p, miR-363-3p, miR-338-3p; miR-17-5p, miR-125b-5p, miR-660-5p, miR-25-3p, miR-143-3p, miR-363-3p, miR-338-3p.

In one example, the at least eight miRNAs are, but are not limited to, the following combinations: miR-451a, miR-195-5p, miR-126-5p, miR-423-3p, miR-192-5p, miR-17-5p, miR-125b-5p, miR-660-5p; miR-451a, miR-195-5p, miR-126-5p, miR-423-3p, miR-192-5p, miR-17-5p, miR-125b-5p, miR-25-3p; miR-451a, miR-195-5p, miR-126-5p, miR-423-3p, miR-192-5p, miR-17-5p, miR-125b-5p, miR-143-3p; miR-451a, miR-195-5p, miR-126-5p, miR-423-3p, miR-192-5p, miR-17-5p, miR-125b-5p, miR-363-3p; miR-451a, miR-195-5p, miR-126-5p, miR-423-3p, miR-192-5p, miR-17-5p, miR-125b-5p, miR-338-3p; miR-451a, miR-195-5p, miR-126-5p, miR-423-3p, miR-192-5p, miR-17-5p, miR-660-5p, miR-25-3p; miR-451a, miR-195-5p, miR-126-5p, miR-423-3p, miR-192-5p, miR-17-5p, miR-660-5p, miR-143-3p; miR-451a, miR-195-5p, miR-126-5p, miR-423-3p, miR-192-5p, miR-17-5p, miR-660-5p, miR-363-3p; miR- 451a, miR-195-5p, miR-126-5p, miR-423-3p, miR-192-5p, miR-17-5p, miR-660-5p, miR-338-3p; miR-451a, miR-195-5p, miR-126-5p, miR-423-3p, miR-192-5p, miR-17-5p, miR-25-3p, miR-143-3p; miR-451a, miR-195-5p, miR-126-5p, miR-423-3p, miR-192-5p, miR-17-5p, miR-25-3p, miR-363-3p; miR-451a, miR-195-5p, miR-126-5p, miR-423-3p, miR-192-5p, miR-17-5p, miR-25-3p, miR-338-3p; miR-451a, miR-195-5p, miR-126-5p, miR-423-3p, miR-192-5p, miR-17-5p, miR-143-3p, miR-363-3p; miR-451a, miR-195-5p, miR-126-5p, miR-423-3p, miR-192-5p, miR-17-5p, miR-143-3p, miR-338-3p; miR-451a, miR-195-5p, miR-126-5p, miR-423-3p, miR-192-5p, miR-17-5p, miR-363-3p, miR-338-3p; miR-451a, miR-195-5p, miR-126-5p, miR-423-3p, miR-192-5p, miR-125b-5p, miR-660-5p, miR-25-3p; miR-451a, miR-195-5p, miR-126-5p, miR-423-3p, miR-192-5p, miR-125b-5p, miR-660-5p, miR-143-3p; miR-451a, miR-195-5p, miR-126-5p, miR-423-3p, miR-192-5p, miR-125b-5p, miR-660-5p, miR-363-3p; miR-451a, miR-195-5p, miR-126-5p, miR-423-3p, miR-192-5p, miR-125b-5p, miR-660-5p, miR-338-3p; miR-451a, miR-195-5p, miR-126-5p, miR-423-3p, miR-192-5p, miR-125b-5p, miR-25-3p, miR-143-3p; miR-451a, miR-195-5p, miR-126-5p, miR-423-3p, miR-192-5p, miR-125b-5p, miR-25-3p, miR-363-3p; miR-451a, miR-195-5p, miR-126-5p, miR-423-3p, miR-192-5p, miR-125b-5p, miR-25-3p, miR-338-3p; miR-451a, miR-195-5p, miR-126-5p, miR-423-3p, miR-192-5p, miR-125b-5p, miR-143-3p, miR-363-3p; miR-451a, miR-195-5p, miR-126-5p, miR-423-3p, miR-192-5p, miR-125b-5p, miR-143-3p, miR-338-3p; miR-451a, miR-195-5p, miR-126-5p, miR-423-3p, miR-192-5p, miR-125b-5p, miR-363-3p, miR-338-3p; miR-451a, miR-195-5p, miR-126-5p, miR-423-3p, miR-192-5p, miR-660-5p, miR-25-3p, miR-143-3p; miR-451a, miR-195-5p, miR-126-5p, miR-423-3p, miR-192-5p, miR-660-5p, miR-25-3p, miR-363-3p; miR-451a, miR-195-5p, miR-126-5p, miR-423-3p, miR-192-5p, miR-660-5p, miR-25-3p, miR-338-3p; miR-451a, miR-195-5p, miR-126-5p, miR-423-3p, miR-192-5p, miR-660-5p, miR-143-3p, miR-363-3p; miR-451a, miR-195-5p, miR-126-5p, miR-423-3p, miR-192-5p, miR-660-5p, miR-143-3p, miR-338-3p; miR-451a, miR-195-5p, miR-126-5p, miR-423-3p, miR-192-5p, miR-660-5p, miR-363-3p, miR-338-3p; miR-451a, miR-195-5p, miR-126-5p, miR-423-3p, miR-192-5p, miR-25-3p, miR-143-3p, miR-363-3p; miR-451a, miR-195-5p, miR-126-5p, miR-423-3p, miR-192-5p, miR-25-3p, miR-143-3p, miR-338-3p; miR-451a, miR-195-5p, miR-126-5p, miR-423-3p, miR-192-5p, miR-25-3p, miR-363-3p, miR-338-3p; miR-451a, miR-195-5p, miR-126-5p, miR-423-3p, miR-192-5p, miR-143-3p, miR-363-3p, miR-338-3p; miR-451a, miR-195-5p, miR-126-5p, miR-423-3p, miR-17-5p, miR-125b-5p, miR-660-5p, miR-25-3p; miR-451a, miR-195-5p, miR-126-5p, miR-423-3p, miR-17-5p, miR-125b-5p, miR-660-5p, miR-143-3p; miR-451a, miR-195-5p, miR-126-5p, miR-423-3p, miR-17-5p, miR-125b-5p, miR-660-5p, miR-363-3p; miR-451a, miR-195-5p, miR-126-5p, miR-423-3p, miR-17-5p, miR-125b-5p, miR-660-5p, miR-338-3p; miR-451a, miR-195-5p, miR-126-5p, miR-423-3p, miR-17-5p, miR-125b-5p, miR-25-3p, miR-143-3p; miR-451a, miR-195-5p, miR-126-5p, miR-423-3p, miR-17-5p, miR-125b-5p, miR-25-3p, miR-363-3p; miR-451a, miR-195-5p, miR-126-5p, miR-423-3p, miR-17-5p, miR-125b-5p, miR-25-3p, miR-338-3p; miR-451a, miR-195-5p, miR-126-5p, miR-423-3p, miR-17-5p, miR-125b-5p, miR-143-3p, miR-363-3p; miR-451a, miR-195-5p, miR-126-5p, miR-423-3p, miR-17-5p, miR-125b-5p, miR-143-3p, miR-338-3p; miR-451a, miR-195-5p, miR-126-5p, miR-423-3p, miR-17-5p, miR-125b-5p, miR-363-3p, miR-338-3p; miR-451a, miR-195-5p, miR-126-5p, miR-423-3p, miR-17-5p, miR-660-5p, miR-25-3p, miR-143-3p; miR-451a, miR-195-5p, miR-126-5p, miR-423-3p, miR-17-5p, miR-660-5p, miR-25-3p, miR-363-3p; miR-451a, miR-195-5p, miR-126-5p, miR-423-3p, miR-17-5p, miR-660-5p, miR-25-3p, miR-338-3p; miR-451a, miR-195-5p, miR-126-5p, miR-423-3p, miR-17-5p, miR-660-5p, miR-143-3p, miR-363-3p; miR-451a, miR-195-5p, miR-126-5p, miR-423-3p, miR-17-5p, miR-660-5p, miR-143-3p, miR-338-3p; miR-451a, miR-195-5p, miR-126-5p, miR-423-3p, miR-17-5p, miR-660-5p, miR-363-3p, miR-338-3p; miR-451a, miR-195-5p, miR-126-5p, miR-423-3p, miR-17-5p, miR-25-3p, miR-143-3p, miR-363-3p; miR-451a, miR-195-5p, miR-126-5p, miR-423-3p, miR-17-5p, miR-25-3p, miR-143-3p, miR-338-3p; miR-451a, miR-195-5p, miR-126-5p, miR-423-3p, miR-17-5p, miR-25-3p, miR-363-3p, miR-338-3p; miR-451a, miR-195-5p, miR-126-5p, miR-423-3p, miR-17-5p, miR-143-3p, miR-363-3p, miR-338-3p; miR-451a, miR-195-5p, miR-126-5p, miR-423-3p, miR-660-5p, miR-25-3p, miR-143-3p, miR-363-3p; miR-451a, miR-195-5p, miR-126-5p, miR-423-3p, miR-660-5p, miR-25-3p, miR-143-3p, miR-338-3p; miR-451a, miR-195-5p, miR-126-5p, miR-423-3p, miR-660-5p, miR-25-3p, miR-363-3p, miR-338-3p; miR-451a, miR-195-5p, miR-126-5p, miR-423-3p, miR-660-5p, miR-143-3p, miR-363-3p, miR-338-3p; miR-451a, miR-195-5p, miR-126-5p, miR-192-5p, miR-17-5p, miR-125b-5p, miR-660-5p, miR-25-3p; miR-451a, miR-195-5p, miR-126-5p, miR-192-5p, miR-17-5p, miR-125b-5p, miR-660-5p, miR-143-3p; miR-451a, miR-195-5p, miR-126-5p, miR-192-5p, miR-17-5p, miR-125b-5p, miR-660-5p, miR-363-3p; miR-451a, miR-195-5p, miR-126-5p, miR-192-5p, miR-17-5p, miR-125b-5p, miR-660-5p, miR-338-3p; miR-451a, miR-195-5p, miR-126-5p, miR-192-5p, miR-17-5p, miR-125b-5p, miR-25-3p, miR-143-3p; miR-451a, miR-195-5p, miR-126-5p, miR-192-5p, miR-17-5p, miR-125b-5p, miR-25-3p, miR-363-3p; miR-451a, miR-195-5p, miR-126-5p, miR-192-5p, miR-17-5p, miR-125b-5p, miR-25-3p, miR-338-3p; miR-451a, miR-195-5p, miR-126-5p, miR-192-5p, miR-17-5p, miR-125b-5p, miR-143-3p, miR-363-3p; miR-451a, miR-195-5p, miR-126-5p, miR-192-5p, miR-17-5p, miR-125b-5p, miR-143-3p, miR-338-3p; miR-451a, miR-195-5p, miR-126-5p, miR-192-5p, miR-17-5p, miR-125b-5p, miR-363-3p, miR-338-3p; miR-451a, miR-195-5p, miR-126-5p, miR-192-5p, miR-17-5p, miR-660-5p, miR-25-3p, miR-143-3p; miR-451a, miR-195-5p, miR-126-5p, miR-192-5p, miR-17-5p, miR-660-5p, miR-25-3p, miR-363-3p; miR-451a, miR-195-5p, miR-126-5p, miR-192-5p, miR-17-5p, miR-660-5p, miR-25-3p, miR-338-3p; miR-451a, miR-195-5p, miR-126-5p, miR-192-5p, miR-17-5p, miR-660-5p, miR-143-3p, miR-363-3p; miR-451a, miR-195-5p, miR-126-5p, miR-192-5p, miR-17-5p, miR-660-5p, miR-143-3p, miR-338-3p; miR-451a, miR-195-5p, miR-126-5p, miR-192-5p, miR-17-5p, miR-660-5p, miR-363-3p, miR-338-3p; miR-451a, miR-195-5p, miR-126-5p, miR-192-5p, miR-17-5p, miR-25-3p, miR-143-3p, miR-363-3p; miR-451a, miR-195-5p, miR-126-5p, miR-192-5p, miR-17-5p, miR-25-3p, miR-143-3p, miR-338-3p; miR-451a, miR-195-5p, miR-126-5p, miR-192-5p, miR-17-5p, miR-25-3p, miR-363-3p, miR-338-3p; miR-451a, miR-195-5p, miR-126-5p, miR-192-5p, miR-17-5p, miR-143-3p, miR-363-3p, miR-338-3p; miR-451a, miR-195-5p, miR-126-5p, miR-192-5p, miR-125b-5p, miR-660-5p, miR-25-3p, miR-143-3p; miR-451a, miR-195-5p, miR-126-5p, miR-192-5p, miR-125b-5p, miR-660-5p, miR-25-3p, miR-363-3p; miR-451a, miR-195-5p, miR-126-5p, miR-192-5p, miR-125b-5p, miR-660-5p, miR-25-3p, miR-338-3p; miR-451a, miR-195-5p, miR-126-5p, miR-192-5p, miR-125b-5p, miR-660-5p, miR-143-3p, miR-363-3p; miR-451a, miR-195-5p, miR-126-5p, miR-192-5p, miR-125b-5p, miR-660-5p, miR-143-3p, miR-338-3p; miR-451a, miR-195-5p, miR-126-5p, miR-192-5p, miR-125b-5p, miR-660-5p, miR-363-3p, miR-338-3p; miR-451a, miR-195-5p, miR-126-5p, miR-192-5p, miR-125b-5p, miR-25-3p, miR-143-3p, miR-363-3p; miR-451a, miR-195-5p, miR-126-5p, miR-192-5p, miR-125b-5p, miR-25-3p, miR-143-3p, miR-338-3p; miR-451a, miR-195-5p, miR-126-5p, miR-192-5p, miR-125b-5p, miR-25-3p, miR-363-3p, miR-338-3p; miR-451a, miR-195-5p, miR-126-5p, miR-192-5p, miR-125b-5p, miR-143-3p, miR-363-3p, miR-338-3p; miR-451a, miR-195-5p, miR-126-5p, miR-192-5p, miR-660-5p, miR-25-3p, miR-143-3p, miR-363-3p; miR-451a, miR-195-5p, miR-126-5p, miR-192-5p, miR-660-5p, miR-25-3p, miR-143-3p, miR-338-3p; miR-451a, miR-195-5p, miR-126-5p, miR-192-5p, miR-660-5p, miR-25-3p, miR-363-3p, miR-338-3p; miR-451a, miR-195-5p, miR-126-5p, miR-192-5p, miR-660-5p, miR-143-3p, miR-363-3p, miR-338-3p; miR-451a, miR-195-5p, miR-126-5p, miR-192-5p, miR-25-3p, miR-143-3p, miR-363-3p, miR-338-3p; miR-451a, miR-195-5p, miR-126-5p, miR-17-5p, miR-125b-5p, miR-660-5p, miR-25-3p, miR-143-3p; miR-451a, miR-195-5p, miR-126-5p, miR-17-5p, miR-125b-5p, miR-660-5p, miR-25-3p, miR-363-3p; miR-451a, miR-195-5p, miR-126-5p, miR-17-5p, miR-125b-5p, miR-660-5p, miR-25-3p, miR-338-3p; miR-451a, miR-195-5p, miR-126-5p, miR-17-5p, miR-125b-5p, miR-660-5p, miR-143-3p, miR-363-3p; miR-451a, miR-195-5p, miR-126-5p, miR-17-5p, miR-125b-5p, miR-660-5p, miR-143-3p, miR-338-3p; miR-451a, miR-195-5p, miR-126-5p, miR-17-5p, miR-125b-5p, miR-660-5p, miR-363-3p, miR-338-3p; miR-451a, miR-195-5p, miR-126-5p, miR-17-5p, miR-125b-5p, miR-25-3p, miR-143-3p, miR-363-3p; miR-451a, miR-195-5p, miR-126-5p, miR-17-5p, miR-125b-5p, miR-25-3p, miR-143-3p, miR-338-3p; miR-451a, miR-195-5p, miR-126-5p, miR-17-5p, miR-125b-5p, miR-25-3p, miR-363-3p, miR-338-3p; miR-451a, miR-195-5p, miR-126-5p, miR-17-5p, miR-125b-5p, miR-143-3p, miR-363-3p, miR-338-3p; miR-451a, miR-195-5p, miR-126-5p, miR-17-5p, miR-660-5p, miR-25-3p, miR-143-3p, miR-363-3p; miR-451a, miR-195-5p, miR-126-5p, miR-17-5p, miR-660-5p, miR-25-3p, miR-143-3p, miR-338-3p; miR-451a, miR-195-5p, miR-126-5p, miR-17-5p, miR-660-5p, miR-25-3p, miR-363-3p, miR-338-3p; miR-451a, miR-195-5p, miR-126-5p, miR-17-5p, miR-660-5p, miR-143-3p, miR-363-3p, miR-338-3p; miR-451a, miR-195-5p, miR-126-5p, miR-17-5p, miR-25-3p, miR-143-3p, miR-363-3p, miR-338-3p; miR-451a, miR-195-5p, miR-126-5p, miR-125b-5p, miR-660-5p, miR-25-3p, miR-143-3p, miR-363-3p; miR-451a, miR-195-5p, miR-126-5p, miR-125b-5p, miR-660-5p, miR-25-3p, miR-143-3p, miR-338-3p; miR-451a, miR-195-5p, miR-126-5p, miR-125b-5p, miR-660-5p, miR-25-3p, miR-363-3p, miR-338-3p; miR-451a, miR-195-5p, miR-126-5p, miR-125b-5p, miR-660-5p, miR-143-3p, miR-363-3p, miR-338-3p; miR-451a, miR-195-5p, miR-126-5p, miR-125b-5p, miR-25-3p, miR-143-3p, miR-363-3p, miR-338-3p; miR-451a, miR-195-5p, miR-126-5p, miR-660-5p, miR-25-3p, miR-143-3p, miR-363-3p, miR-338-3p; miR-451a, miR-195-5p, miR-423-3p, miR-192-5p, miR-17-5p, miR-125b-5p, miR-660-5p, miR-25-3p; miR-451a, miR-195-5p, miR-423-3p, miR-192-5p, miR-17-5p, miR-125b-5p, miR-660-5p, miR-143-3p; miR-451a, miR-195-5p, miR-423-3p, miR-192-5p, miR-17-5p, miR-125b-5p, miR-660-5p, miR-363-3p; miR-451a, miR-195-5p, miR-423-3p, miR-192-5p, miR-17-5p, miR-125b-5p, miR-660-5p, miR-338-3p; miR-451a, miR-195-5p, miR-423-3p, miR-192-5p, miR-17-5p, miR-125b-5p, miR-25-3p, miR-143-3p; miR-451a, miR-195-5p, miR-423-3p, miR-192-5p, miR-17-5p, miR-125b-5p, miR-25-3p, miR-363-3p; miR-451a, miR-195-5p, miR-423-3p, miR-192-5p, miR-17-5p, miR-125b-5p, miR-25-3p, miR-338-3p; miR-451a, miR-195-5p, miR-423-3p, miR-192-5p, miR-17-5p, miR-125b-5p, miR-143-3p, miR-363-3p; miR-451a, miR-195-5p, miR-423-3p, miR-192-5p, miR-17-5p, miR-125b-5p, miR-143-3p, miR-338-3p; miR-451a, miR-195-5p, miR-423-3p, miR-192-5p, miR-17-5p, miR-125b-5p, miR-363-3p, miR-338-3p; miR-451a, miR-195-5p, miR-423-3p, miR-192-5p, miR-17-5p, miR-660-5p, miR-25-3p, miR-143-3p; miR-451a, miR-195-5p, miR-423-3p, miR-192-5p, miR-17-5p, miR-660-5p, miR-25-3p, miR-363-3p; miR-451a, miR-195-5p, miR-423-3p, miR-192-5p, miR-17-5p, miR-660-5p, miR-25-3p, miR-338-3p; miR-451a, miR-195-5p, miR-423-3p, miR-192-5p, miR-17-5p, miR-660-5p, miR-143-3p, miR-363-3p; miR-451a, miR-195-5p, miR-423-3p, miR-192-5p, miR-17-5p, miR-660-5p, miR-143-3p, miR-338-3p; miR-451a, miR-195-5p, miR-423-3p, miR-192-5p, miR-17-5p, miR-660-5p, miR-363-3p, miR-338-3p; miR-451a, miR-195-5p, miR-423-3p, miR-192-5p, miR-17-5p, miR-25-3p, miR-143-3p, miR-363-3p; miR-451a, miR-195-5p, miR-423-3p, miR-192-5p, miR-17-5p, miR-25-3p, miR-143-3p, miR-338-3p; miR-451a, miR-195-5p, miR-423-3p, miR-192-5p, miR-17-5p, miR-25-3p, miR-363-3p, miR-338-3p; miR-451a, miR-195-5p, miR-423-3p, miR-192-5p, miR-17-5p, miR-143-3p, miR-363-3p, miR-338-3p; miR-451a, miR-195-5p, miR-423-3p, miR-192-5p, miR-125b-5p, miR-660-5p, miR-25-3p, miR-143-3p; miR-451a, miR-195-5p, miR-423-3p, miR-192-5p, miR-125b-5p, miR-660-5p, miR-25-3p, miR-363-3p; miR-451a, miR-195-5p, miR-423-3p, miR-192-5p, miR-125b-5p, miR-660-5p, miR-25-3p, miR-338-3p; miR-451a, miR-195-5p, miR-423-3p, miR-192-5p, miR-125b-5p, miR-660-5p, miR-143-3p, miR-363-3p; miR-451a, miR-195-5p, miR-423-3p, miR-192-5p, miR-125b-5p, miR-660-5p, miR-143-3p, miR-338-3p; miR-451a, miR-195-5p, miR-423-3p, miR-192-5p, miR-125b-5p, miR-660-5p, miR-363-3p, miR-338-3p; miR-451a, miR-195-5p, miR-423-3p, miR-192-5p, miR-125b-5p, miR-25-3p, miR-143-3p, miR-363-3p; miR-451a, miR-195-5p, miR-423-3p, miR-192-5p, miR-125b-5p, miR-25-3p, miR-143-3p, miR-338-3p; miR-451a, miR-195-5p, miR-423-3p, miR-192-5p, miR-125b-5p, miR-25-3p, miR-363-3p, miR-338-3p; miR-451a, miR-195-5p, miR-423-3p, miR-192-5p, miR-125b-5p, miR-143-3p, miR-363-3p, miR-338-3p; miR-451a, miR-195-5p, miR-423-3p, miR-192-5p, miR-660-5p, miR-25-3p, miR-143-3p, miR-363-3p; miR-451a, miR-195-5p, miR-423-3p, miR-192-5p, miR-660-5p, miR-25-3p, miR-143-3p, miR-338-3p; miR-451a, miR-195-5p, miR-423-3p, miR-192-5p, miR-660-5p, miR-25-3p, miR-363-3p, miR-338-3p; miR-451a, miR-195-5p, miR-423-3p, miR-192-5p, miR-660-5p, miR-143-3p, miR-363-3p, miR-338-3p; miR-451a, miR-195-5p, miR-423-3p, miR-192-5p, miR-25-3p, miR-143-3p, miR-363-3p, miR-338-3p; miR-451a, miR-195-5p, miR-423-3p, miR-17-5p, miR-125b-5p, miR-660-5p, miR-25-3p, miR-143-3p; miR-451a, miR-195-5p, miR-423-3p, miR-17-5p, miR-125b-5p, miR-660-5p, miR-25-3p, miR-363-3p; miR-451a, miR-195-5p, miR-423-3p, miR-17-5p, miR-125b-5p, miR-660-5p, miR-25-3p, miR-338-3p; miR-451a, miR-195-5p, miR-423-3p, miR-17-5p, miR-125b-5p, miR-660-5p, miR-143-3p, miR-363-3p; miR-451a, miR-195-5p, miR-423-3p, miR-17-5p, miR-125b-5p, miR-660-5p, miR-143-3p, miR-338-3p; miR-451a, miR-195-5p, miR-423-3p, miR-17-5p, miR-125b-5p, miR-660-5p, miR-363-3p, miR-338-3p; miR-451a, miR-195-5p, miR-423-3p, miR-17-5p, miR-125b-5p, miR-25-3p, miR-143-3p, miR-363-3p; miR-451a, miR-195-5p, miR-423-3p, miR-17-5p, miR-125b-5p, miR-25-3p, miR-143-3p, miR-338-3p; miR-451a, miR-195-5p, miR-423-3p, miR-17-5p, miR-125b-5p, miR-25-3p, miR-363-3p, miR-338-3p; miR-451a, miR-195-5p, miR-423-3p, miR-17-5p, miR-125b-5p, miR-143-3p, miR-363-3p, miR-338-3p; miR-451a, miR-195-5p, miR-423-3p, miR-17-5p, miR-660-5p, miR-25-3p, miR-143-3p, miR-363-3p; miR-451a, miR-195-5p, miR-423-3p, miR-17-5p, miR-660-5p, miR-25-3p, miR-143-3p, miR-338-3p; miR-451a, miR-195-5p, miR-423-3p, miR-17-5p, miR-660-5p, miR-25-3p, miR-363-3p, miR-338-3p; miR-451a, miR-195-5p, miR-423-3p, miR-17-5p, miR-660-5p, miR-143-3p, miR-363-3p, miR-338-3p; miR-451a, miR-195-5p, miR-423-3p, miR-17-5p, miR-25-3p, miR-143-3p, miR-363-3p, miR-338-3p; miR-451a, miR-195-5p, miR-423-3p, miR-125b-5p, miR-660-5p, miR-25-3p, miR-143-3p, miR-363-3p; miR-451a, miR-195-5p, miR-423-3p, miR-125b-5p, miR-660-5p, miR-25-3p, miR-143-3p, miR-338-3p; miR-451a, miR-195-5p, miR-423-3p, miR-125b-5p, miR-660-5p, miR-25-3p, miR-363-3p, miR-338-3p; miR-451a, miR-195-5p, miR-423-3p, miR-125b-5p, miR-660-5p, miR-143-3p, miR-363-3p, miR-338-3p; miR-451a, miR-195-5p, miR-423-3p, miR-125b-5p, miR-25-3p, miR-143-3p, miR-363-3p, miR-338-3p; miR-451a, miR-195-5p, miR-423-3p, miR-660-5p, miR-25-3p, miR-143-3p, miR-363-3p, miR-338-3p; miR-451a, miR-195-5p, miR-192-5p, miR-17-5p, miR-125b-5p, miR-660-5p, miR-25-3p, miR-143-3p; miR-451a, miR-195-5p, miR-192-5p, miR-17-5p, miR-125b-5p, miR-660-5p, miR-25-3p, miR-363-3p; miR-451a, miR-195-5p, miR-192-5p, miR-17-5p, miR-125b-5p, miR-660-5p, miR-25-3p, miR-338-3p; miR-451a, miR-195-5p, miR-192-5p, miR-17-5p, miR-125b-5p, miR-660-5p, miR-143-3p, miR-363-3p; miR-451a, miR-195-5p, miR-192-5p, miR-17-5p, miR-125b-5p, miR-660-5p, miR-143-3p, miR-338-3p; miR-451a, miR-195-5p, miR-192-5p, miR-17-5p, miR-125b-5p, miR-660-5p, miR-363-3p, miR-338-3p; miR-451a, miR-195-5p, miR-192-5p, miR-17-5p, miR-125b-5p, miR-25-3p, miR-143-3p, miR-363-3p; miR-451a, miR-195-5p, miR-192-5p, miR-17-5p, miR-125b-5p, miR-25-3p, miR-363-3p, miR-338-3p; miR-451a, miR-195-5p, miR-192-5p, miR-17-5p, miR-125b-5p, miR-143-3p, miR-363-3p, miR-338-3p; miR-451a, miR-195-5p, miR-192-5p, miR-17-5p, miR-660-5p, miR-25-3p, miR-143-3p, miR-363-3p; miR-451a, miR-195-5p, miR-192-5p, miR-17-5p, miR-660-5p, miR-25-3p, miR-143-3p, miR-338-3p; miR-451a, miR-195-5p, miR-192-5p, miR-17-5p, miR-660-5p, miR-25-3p, miR-363-3p, miR-338-3p; miR-451a, miR-195-5p, miR-192-5p, miR-17-5p, miR-660-5p, miR-143-3p, miR-363-3p, miR-338-3p; miR-451a, miR-195-5p, miR-192-5p, miR-17-5p, miR-25-3p, miR-143-3p, miR-363-3p, miR-338-3p; miR-451a, miR-195-5p, miR-192-5p, miR-125b-5p, miR-660-5p, miR-25-3p, miR-143-3p, miR-363-3p; miR-451a, miR-195-5p, miR-192-5p, miR-125b-5p, miR-660-5p, miR-25-3p, miR-143-3p, miR-338-3p; miR-451a, miR-195-5p, miR-192-5p, miR-125b-5p, miR-660-5p, miR-143-3p, miR-363-3p, miR-338-3p; miR-451a, miR-195-5p, miR-192-5p, miR-125b-5p, miR-25-3p, miR-143-3p, miR-363-3p, miR-338-3p; miR-451a, miR-195-5p, miR-192-5p, miR-660-5p, miR-25-3p, miR-143-3p, miR-363-3p, miR-338-3p; miR-451a, miR-195-5p, miR-17-5p, miR-125b-5p, miR-660-5p, miR-25-3p, miR-143-3p, miR-363-3p; miR-451a, miR-195-5p, miR-17-5p, miR-125b-5p, miR-660-5p, miR-25-3p, miR-143-3p, miR-338-3p; miR-451a, miR-195-5p, miR-17-5p, miR-125b-5p, miR-660-5p, miR-25-3p, miR-363-3p, miR-338-3p; miR-451a, miR-195-5p, miR-17-5p, miR-125b-5p, miR-660-5p, miR-143-3p, miR-363-3p, miR-338-3p; miR-451a, miR-195-5p, miR-17-5p, miR-125b-5p, miR-25-3p, miR-143-3p, miR-363-3p, miR-338-3p; miR-451a, miR-195-5p, miR-17-5p, miR-660-5p, miR-25-3p, miR-143-3p, miR-363-3p, miR-338-3p; miR-451a, miR-195-5p, miR-125b-5p, miR-660-5p, miR-25-3p, miR-143-3p, miR-363-3p, miR-338-3p; miR-451a, miR-126-5p, miR-423-3p, miR-192-5p, miR-17-5p, miR-125b-5p, miR-660-5p, miR-25-3p; miR-451a, miR-126-5p, miR-423-3p, miR-192-5p, miR-17-5p, miR-125b-5p, miR-660-5p, miR-143-3p; miR-451a, miR-126-5p, miR-423-3p, miR-192-5p, miR-17-5p, miR-125b-5p, miR-660-5p, miR-363-3p; miR-451a, miR-126-5p, miR-423-3p, miR-192-5p, miR-17-5p, miR-125b-5p, miR-660-5p, miR-338-3p; miR-451a, miR-126-5p, miR-423-3p, miR-192-5p, miR-17-5p, miR-125b-5p, miR-25-3p, miR-143-3p; miR-451a, miR-126-5p, miR-423-3p, miR-192-5p, miR-17-5p, miR-125b-5p, miR-25-3p, miR-363-3p; miR-451a, miR-126-5p, miR-423-3p, miR-192-5p, miR-17-5p, miR-125b-5p, miR-25-3p, miR-338-3p; miR-451a, miR-126-5p, miR-423-3p, miR-192-5p, miR-17-5p, miR-125b-5p, miR-143-3p, miR-363-3p; miR-451a, miR-126-5p, miR-423-3p, miR-192-5p, miR-17-5p, miR-125b-5p, miR-143-3p, miR-338-3p; miR-451a, miR-126-5p, miR-423-3p, miR-192-5p, miR-17-5p, miR-125b-5p, miR-363-3p, miR-338-3p; miR-451a, miR-126-5p, miR-423-3p, miR-192-5p, miR-17-5p, miR-660-5p, miR-25-3p, miR-143-3p; miR-451a, miR-126-5p, miR-423-3p, miR-192-5p, miR-17-5p, miR-660-5p, miR-25-3p, miR-363-3p; miR-451a, miR-126-5p, miR-423-3p, miR-192-5p, miR-17-5p, miR-660-5p, miR-25-3p, miR-338-3p; miR-451a, miR-126-5p, miR-423-3p, miR-192-5p, miR-17-5p, miR-660-5p, miR-143-3p, miR-363-3p; miR-451a, miR-126-5p, miR-423-3p, miR-192-5p, miR-17-5p, miR-660-5p, miR-143-3p, miR-338-3p; miR-451a, miR-126-5p, miR-423-3p, miR-192-5p, miR-17-5p, miR-660-5p, miR-363-3p, miR-338-3p; miR-451a, miR-126-5p, miR-423-3p, miR-192-5p, miR-17-5p, miR-25-3p, miR-143-3p, miR-363-3p; miR-451a, miR-126-5p, miR-423-3p, miR-192-5p, miR-17-5p, miR-25-3p, miR-143-3p, miR-338-3p; miR-451a, miR-126-5p, miR-423-3p, miR-192-5p, miR-17-5p, miR-25-3p, miR-363-3p, miR-338-3p; miR-451a, miR-126-5p, miR-423-3p, miR-192-5p, miR-17-5p, miR-143-3p, miR-363-3p, miR-338-3p; miR-451a, miR-126-5p, miR-423-3p, miR-192-5p, miR-125b-5p, miR-660-5p, miR-25-3p, miR-143-3p; miR-451a, miR-126-5p, miR-423-3p, miR-192-5p, miR-125b-5p, miR-660-5p, miR-25-3p, miR-363-3p; miR-451a, miR-126-5p, miR-423-3p, miR-192-5p, miR-125b-5p, miR-660-5p, miR-25-3p, miR-338-3p; miR-451a, miR-126-5p, miR-423-3p, miR-192-5p, miR-125b-5p, miR-660-5p, miR-143-3p, miR-363-3p; miR-451a, miR-126-5p, miR-423-3p, miR-192-5p, miR-125b-5p, miR-660-5p, miR-143-3p, miR-338-3p; miR-451a, miR-126-5p, miR-423-3p, miR-192-5p, miR-125b-5p, miR-660-5p, miR-363-3p, miR-338-3p; miR-451a, miR-126-5p, miR-423-3p, miR-192-5p, miR-125b-5p, miR-25-3p, miR-143-3p, miR-363-3p; miR-451a, miR-126-5p, miR-423-3p, miR-192-5p, miR-125b-5p, miR-25-3p, miR-143-3p, miR-338-3p; miR-451a, miR-126-5p, miR-423-3p, miR-192-5p, miR-125b-5p, miR-25-3p, miR-363-3p, miR-338-3p; miR-451a, miR-126-5p, miR-423-3p, miR-192-5p, miR-125b-5p, miR-143-3p, miR-363-3p, miR-338-3p; miR-451a, miR-126-5p, miR-423-3p, miR-192-5p, miR-660-5p, miR-25-3p, miR-143-3p, miR-363-3p; miR-451a, miR-126-5p, miR-423-3p, miR-192-5p, miR-660-5p, miR-25-3p, miR-143-3p, miR-338-3p; miR-451a, miR-126-5p, miR-423-3p, miR-192-5p, miR-660-5p, miR-25-3p, miR-363-3p, miR-338-3p; miR-451a, miR-126-5p, miR-423-3p, miR-192-5p, miR-660-5p, miR-143-3p, miR-363-3p, miR-338-3p; miR-451a, miR-126-5p, miR-423-3p, miR-192-5p, miR-25-3p, miR-143-3p, miR-363-3p, miR-338-3p; miR-451a, miR-126-5p, miR-423-3p, miR-17-5p, miR-125b-5p, miR-660-5p, miR-25-3p, miR-143-3p; miR-451a, miR-126-5p, miR-423-3p, miR-17-5p, miR-125b-5p, miR-660-5p, miR-25-3p, miR-363-3p; miR-451a, miR-126-5p, miR-423-3p, miR-17-5p, miR-125b-5p, miR-660-5p, miR-25-3p, miR-338-3p; miR-451a, miR-126-5p, miR-423-3p, miR-17-5p, miR-125b-5p, miR-660-5p, miR-143-3p, miR-363-3p; miR-451a, miR-126-5p, miR-423-3p, miR-17-5p, miR-125b-5p, miR-660-5p, miR-143-3p, miR-338-3p; miR-451a, miR-126-5p, miR-423-3p, miR-17-5p, miR-125b-5p, miR-660-5p, miR-363-3p, miR-338-3p; miR-451a, miR-126-5p, miR-423-3p, miR-17-5p, miR-125b-5p, miR-25-3p, miR-143-3p, miR-363-3p; miR-451a, miR-126-5p, miR-423-3p, miR-17-5p, miR-125b-5p, miR-25-3p, miR-143-3p, miR-338-3p; miR-451a, miR-126-5p, miR-423-3p, miR-17-5p, miR-125b-5p, miR-25-3p, miR-363-3p, miR-338-3p; miR-451a, miR-126-5p, miR-423-3p, miR-17-5p, miR-125b-5p, miR-143-3p, miR-363-3p, miR-338-3p; miR-451a, miR-126-5p, miR-423-3p, miR-17-5p, miR-660-5p, miR-25-3p, miR-143-3p, miR-363-3p; miR-451a, miR-126-5p, miR-423-3p, miR-17-5p, miR-660-5p, miR-25-3p, miR-143-3p, miR-338-3p; miR-451a, miR-126-5p, miR-423-3p, miR-17-5p, miR-660-5p, miR-25-3p, miR-363-3p, miR-338-3p; miR-451a, miR-126-5p, miR-423-3p, miR-17-5p, miR-660-5p, miR-143-3p, miR-363-3p, miR-338-3p; miR-451a, miR-126-5p, miR-423-3p, miR-17-5p, miR-25-3p, miR-143-3p, miR-363-3p, miR-338-3p; miR-451a, miR-126-5p, miR-423-3p, miR-125b-5p, miR-660-5p, miR-25-3p, miR-143-3p, miR-363-3p; miR-451a, miR-126-5p, miR-423-3p, miR-125b-5p, miR-660-5p, miR-25-3p, miR-143-3p, miR-338-3p; miR-451a, miR-126-5p, miR-423-3p, miR-125b-5p, miR-660-5p, miR-25-3p, miR-363-3p, miR-338-3p; miR-451a, miR-126-5p, miR-423-3p, miR-125b-5p, miR-660-5p, miR-143-3p, miR-363-3p, miR-338-3p; miR-451a, miR-126-5p, miR-423-3p, miR-125b-5p, miR-25-3p, miR-143-3p, miR-363-3p, miR-338-3p; miR-451a, miR-126-5p, miR-423-3p, miR-660-5p, miR-25-3p, miR-143-3p, miR-363-3p, miR-338-3p; miR-451a, miR-126-5p, miR-192-5p, miR-17-5p, miR-125b-5p, miR-660-5p, miR-25-3p, miR-363-3p; miR-451a, miR-126-5p, miR-192-5p, miR-17-5p, miR-125b-5p, miR-660-5p, miR-25-3p, miR-338-3p; miR-451a, miR-126-5p, miR-192-5p, miR-17-5p, miR-125b-5p, miR-660-5p, miR-363-3p, miR- 338-3p; miR-451a, miR-126-5p, miR-192-5p, miR-17-5p, miR-125b-5p, miR-25-3p, miR-143-3p, miR-363-3p; miR-451a, miR-126-5p, miR-192-5p, miR-17-5p, miR-125b-5p, miR-25-3p, miR-143-3p, miR-338-3p; miR-451a, miR-126-5p, miR-192-5p, miR-17-5p, miR-125b-5p, miR-25-3p, miR-363-3p, miR-338-3p; miR-451a, miR-126-5p, miR-192-5p, miR-17-5p, miR-125b-5p, miR-143-3p, miR-363-3p, miR-338-3p; miR-451a, miR-126-5p, miR-192-5p, miR-17-5p, miR-660-5p, miR-25-3p, miR-143-3p, miR-363-3p; miR-451a, miR-126-5p, miR-192-5p, miR-17-5p, miR-660-5p, miR-25-3p, miR-143-3p, miR-338-3p; miR-451a, miR-126-5p, miR-192-5p, miR-17-5p, miR-660-5p, miR-25-3p, miR-363-3p, miR-338-3p; miR-451a, miR-126-5p, miR-192-5p, miR-17-5p, miR-660-5p, miR-143-3p, miR-363-3p, miR-338-3p; miR-451a, miR-126-5p, miR-192-5p, miR-17-5p, miR-25-3p, miR-143-3p, miR-363-3p, miR-338-3p; miR-451a, miR-126-5p, miR-192-5p, miR-125b-5p, miR-660-5p, miR-25-3p, miR-143-3p, miR-363-3p; miR-451a, miR-126-5p, miR-192-5p, miR-125b-5p, miR-660-5p, miR-25-3p, miR-143-3p, miR-338-3p; miR-451a, miR-126-5p, miR-192-5p, miR-125b-5p, miR-660-5p, miR-25-3p, miR-363-3p, miR-338-3p; miR-451a, miR-126-5p, miR-192-5p, miR-125b-5p, miR-660-5p, miR-143-3p, miR-363-3p, miR-338-3p; miR-451a, miR-126-5p, miR-192-5p, miR-125b-5p, miR-25-3p, miR-143-3p, miR-363-3p, miR-338-3p; miR-451a, miR-126-5p, miR-192-5p, miR-660-5p, miR-25-3p, miR-143-3p, miR-363-3p, miR-338-3p; miR-451a, miR-126-5p, miR-17-5p, miR-125b-5p, miR-660-5p, miR-25-3p, miR-143-3p, miR-363-3p; miR-451a, miR-126-5p, miR-17-5p, miR-125b-5p, miR-660-5p, miR-25-3p, miR-143-3p, miR-338-3p; miR-451a, miR-126-5p, miR-17-5p, miR-125b-5p, miR-660-5p, miR-25-3p, miR-363-3p, miR-338-3p; miR-451a, miR-126-5p, miR-17-5p, miR-125b-5p, miR-660-5p, miR-143-3p, miR-363-3p, miR-338-3p; miR-451a, miR-126-5p, miR-17-5p, miR-125b-5p, miR-25-3p, miR-143-3p, miR-363-3p, miR-338-3p; miR-451a, miR-126-5p, miR-17-5p, miR-660-5p, miR-25-3p, miR-143-3p, miR-363-3p, miR-338-3p; miR-451a, miR-126-5p, miR-125b-5p, miR-660-5p, miR-25-3p, miR-143-3p, miR-363-3p, miR-338-3p; miR-451a, miR-423-3p, miR-192-5p, miR-17-5p, miR-125b-5p, miR-660-5p, miR-25-3p, miR-143-3p; miR-451a, miR-423-3p, miR-192-5p, miR-17-5p, miR-125b-5p, miR-660-5p, miR-25-3p, miR-363-3p; miR-451a, miR-423-3p, miR-192-5p, miR-17-5p, miR-125b-5p, miR-660-5p, miR-25-3p, miR-338-3p; miR-451a, miR-423-3p, miR-192-5p, miR-17-5p, miR-125b-5p, miR-660-5p, miR-143-3p, miR-363-3p; miR-451a, miR-423-3p, miR-192-5p, miR-17-5p, miR-125b-5p, miR-660-5p, miR-143-3p, miR-338-3p; miR-451a, miR-423-3p, miR-192-5p, miR-17-5p, miR-125b-5p, miR-660-5p, miR-363-3p, miR-338-3p; miR-451a, miR-423-3p, miR-192-5p, miR-17-5p, miR-125b-5p, miR-25-3p, miR-143-3p, miR-363-3p; miR-451a, miR-423-3p, miR-192-5p, miR-17-5p, miR-125b-5p, miR-25-3p, miR-143-3p, miR-338-3p; miR-451a, miR-423-3p, miR-192-5p, miR-17-5p, miR-125b-5p, miR-25-3p, miR-363-3p, miR-338-3p; miR-451a, miR-423-3p, miR-192-5p, miR-17-5p, miR-125b-5p, miR-143-3p, miR-363-3p, miR-338-3p; miR-451a, miR-423-3p, miR-192-5p, miR-17-5p, miR-660-5p, miR-25-3p, miR-143-3p, miR-363-3p; miR-451a, miR-423-3p, miR-192-5p, miR-17-5p, miR-660-5p, miR-25-3p, miR-143-3p, miR-338-3p; miR-451a, miR-423-3p, miR-192-5p, miR-17-5p, miR-660-5p, miR-25-3p, miR-363-3p, miR-338-3p; miR-451a, miR-423-3p, miR-192-5p, miR-17-5p, miR-660-5p, miR-143-3p, miR-363-3p, miR-338-3p; miR-451a, miR-423-3p, miR-192-5p, miR-17-5p, miR-25-3p, miR-143-3p, miR-363-3p, miR-338-3p; miR-451a, miR-423-3p, miR-192-5p, miR-125b-5p, miR-660-5p, miR-25-

3p, miR-143-3p, miR-363-3p; miR-451a, miR-423-3p, miR-192-5p, miR-125b-5p, miR-660-5p, miR-25-3p, miR-143-3p, miR-338-3p; miR-451a, miR-423-3p, miR-192-5p, miR-125b-5p, miR-660-5p, miR-25-3p, miR-363-3p, miR-338-3p; miR-451a, miR-423-3p, miR-192-5p, miR-125b-5p, miR-660-5p, miR-143-3p, miR-363-3p, miR-338-3p; miR-451a, miR-423-3p, miR-192-5p, miR-125b-5p, miR-25-3p, miR-143-3p, miR-363-3p, miR-338-3p; miR-451a, miR-423-3p, miR-192-5p, miR-660-5p, miR-25-3p, miR-143-3p, miR-363-3p, miR-338-3p; miR-451a, miR-423-3p, miR-17-5p, miR-125b-5p, miR-660-5p, miR-25-3p, miR-143-3p, miR-363-3p; miR-451a, miR-423-3p, miR-17-5p, miR-125b-5p, miR-660-5p, miR-25-3p, miR-143-3p, miR-338-3p; miR-451a, miR-423-3p, miR-17-5p, miR-125b-5p, miR-660-5p, miR-25-3p, miR-363-3p, miR-338-3p; miR-451a, miR-423-3p, miR-17-5p, miR-125b-5p, miR-660-5p, miR-143-3p, miR-363-3p, miR-338-3p; miR-451a, miR-423-3p, miR-17-5p, miR-125b-5p, miR-25-3p, miR-143-3p, miR-363-3p, miR-338-3p; miR-451a, miR-423-3p, miR-17-5p, miR-660-5p, miR-25-3p, miR-143-3p, miR-363-3p, miR-338-3p; miR-451a, miR-423-3p, miR-125b-5p, miR-660-5p, miR-25-3p, miR-143-3p, miR-363-3p, miR-338-3p; miR-451a, miR-192-5p, miR-17-5p, miR-125b-5p, miR-660-5p, miR-25-3p, miR-143-3p, miR-363-3p; miR-451a, miR-192-5p, miR-17-5p, miR-125b-5p, miR-660-5p, miR-25-3p, miR-143-3p, miR-338-3p; miR-451a, miR-192-5p, miR-17-5p, miR-125b-5p, miR-660-5p, miR-25-3p, miR-363-3p, miR-338-3p; miR-451a, miR-192-5p, miR-17-5p, miR-125b-5p, miR-660-5p, miR-143-3p, miR-363-3p, miR-338-3p; miR-451a, miR-192-5p, miR-17-5p, miR-125b-5p, miR-25-3p, miR-143-3p, miR-363-3p, miR-338-3p; miR-451a, miR-192-5p, miR-17-5p, miR-660-5p, miR-25-3p, miR-143-3p, miR-363-3p, miR-338-3p; miR-451a, miR-192-5p, miR-125b-5p, miR-660-5p, miR-25-3p, miR-143-3p, miR-363-3p, miR-338-3p; miR-451a, miR-17-5p, miR-125b-5p, miR-660-5p, miR-25-3p, miR-143-3p, miR-363-3p, miR-338-3p; miR-195-5p, miR-126-5p, miR-423-3p, miR-192-5p, miR-17-5p, miR-125b-5p, miR-660-5p, miR-25-3p; miR-195-5p, miR-126-5p, miR-423-3p, miR-192-5p, miR-17-5p, miR-125b-5p, miR-660-5p, miR-143-3p; miR-195-5p, miR-126-5p, miR-423-3p, miR-192-5p, miR-17-5p, miR-125b-5p, miR-660-5p, miR-363-3p; miR-195-5p, miR-126-5p, miR-423-3p, miR-192-5p, miR-17-5p, miR-125b-5p, miR-660-5p, miR-338-3p; miR-195-5p, miR-126-5p, miR-423-3p, miR-192-5p, miR-17-5p, miR-125b-5p, miR-25-3p, miR-143-3p; miR-195-5p, miR-126-5p, miR-423-3p, miR-192-5p, miR-17-5p, miR-125b-5p, miR-25-3p, miR-363-3p; miR-195-5p, miR-126-5p, miR-423-3p, miR-192-5p, miR-17-5p, miR-125b-5p, miR-25-3p, miR-338-3p; miR-195-5p, miR-126-5p, miR-423-3p, miR-192-5p, miR-17-5p, miR-125b-5p, miR-143-3p, miR-363-3p; miR-195-5p, miR-126-5p, miR-423-3p, miR-192-5p, miR-17-5p, miR-125b-5p, miR-143-3p, miR-338-3p; miR-195-5p, miR-126-5p, miR-423-3p, miR-192-5p, miR-17-5p, miR-125b-5p, miR-363-3p, miR-338-3p; miR-195-5p, miR-126-5p, miR-423-3p, miR-192-5p, miR-17-5p, miR-660-5p, miR-25-3p, miR-143-3p; miR-195-5p, miR-126-5p, miR-423-3p, miR-192-5p, miR-17-5p, miR-660-5p, miR-25-3p, miR-363-3p; miR-195-5p, miR-126-5p, miR-423-3p, miR-192-5p, miR-17-5p, miR-660-5p, miR-25-3p, miR-338-3p; miR-195-5p, miR-126-5p, miR-423-3p, miR-192-5p, miR-17-5p, miR-660-5p, miR-143-3p, miR-363-3p; miR-195-5p, miR-126-5p, miR-423-3p, miR-192-5p, miR-17-5p, miR-25-3p, miR-143-3p, miR-363-3p; miR-195-5p, miR-126-5p, miR-423-3p, miR-192-5p, miR-17-5p, miR-25-3p, miR-143-3p, miR-338-3p; miR-195-5p, miR-126-5p, miR-423-3p, miR-192-5p, miR-17-5p, miR-25-3p, miR-363-3p, miR-338-3p; miR-195-5p, miR-126-5p, miR-423-3p, miR-192-5p, miR-17-5p, miR-143-3p, miR-363-3p, miR-338-3p; miR-195-5p, miR-126-5p, miR-423-3p, miR-192-5p, miR-125b-5p, miR-660-5p, miR-25-3p, miR-143-3p; miR-195-5p, miR-126-5p, miR-423-3p, miR-192-5p, miR-125b-5p, miR-660-5p, miR-25-3p, miR-363-3p; miR-195-5p, miR-126-5p, miR-423-3p, miR-192-5p, miR-125b-5p, miR-660-5p, miR-25-3p, miR-338-3p; miR-195-5p, miR-126-5p, miR-423-3p, miR-192-5p, miR-125b-5p, miR-660-5p, miR-143-3p, miR-363-3p; miR-195-5p, miR-126-5p, miR-423-3p, miR-192-5p, miR-125b-5p, miR-660-5p, miR-143-3p, miR-338-3p; miR-195-5p, miR-126-5p, miR-423-3p, miR-192-5p, miR-125b-5p, miR-660-5p, miR-363-3p, miR-338-3p; miR-195-5p, miR-126-5p, miR-423-3p, miR-192-5p, miR-125b-5p, miR-25-3p, miR-143-3p, miR-363-3p; miR-195-5p, miR-126-5p, miR-423-3p, miR-192-5p, miR-125b-5p, miR-25-3p, miR-363-3p, miR-338-3p; miR-195-5p, miR-126-5p, miR-423-3p, miR-192-5p, miR-125b-5p, miR-143-3p, miR-363-3p, miR-338-3p; miR-195-5p, miR-126-5p, miR-423-3p, miR-192-5p, miR-660-5p, miR-25-3p, miR-143-3p, miR-363-3p; miR-195-5p, miR-126-5p, miR-423-3p, miR-192-5p, miR-660-5p, miR-25-3p, miR-143-3p, miR-338-3p; miR-195-5p, miR-126-5p, miR-423-3p, miR-192-5p, miR-660-5p, miR-25-3p, miR-363-3p, miR-338-3p; miR-195-5p, miR-126-5p, miR-423-3p, miR-192-5p, miR-660-5p, miR-143-3p, miR-363-3p, miR-338-3p; miR-195-5p, miR-126-5p, miR-423-3p, miR-192-5p, miR-25-3p, miR-143-3p, miR-363-3p, miR-338-3p; miR-195-5p, miR-126-5p, miR-423-3p, miR-17-5p, miR-125b-5p, miR-660-5p, miR-25-3p, miR-143-3p; miR-195-5p, miR-126-5p, miR-423-3p, miR-17-5p, miR-125b-5p, miR-660-5p, miR-25-3p, miR-363-3p; miR-195-5p, miR-126-5p, miR-423-3p, miR-17-5p, miR-125b-5p, miR-660-5p, miR-25-3p, miR-338-3p; miR-195-5p, miR-126-5p, miR-423-3p, miR-17-5p, miR-125b-5p, miR-660-5p, miR-143-3p, miR-363-3p; miR-195-5p, miR-126-5p, miR-423-3p, miR-17-5p, miR-125b-5p, miR-660-5p, miR-143-3p, miR-338-3p; miR-195-5p, miR-126-5p, miR-423-3p, miR-17-5p, miR-125b-5p, miR-660-5p, miR-363-3p, miR-338-3p; miR-195-5p, miR-126-5p, miR-423-3p, miR-17-5p, miR-125b-5p, miR-25-3p, miR-143-3p, miR-363-3p; miR-195-5p, miR-126-5p, miR-423-3p, miR-17-5p, miR-125b-5p, miR-25-3p, miR-143-3p, miR-338-3p; miR-195-5p, miR-126-5p, miR-423-3p, miR-17-5p, miR-125b-5p, miR-25-3p, miR-363-3p, miR-338-3p; miR-195-5p, miR-126-5p, miR-423-3p, miR-17-5p, miR-125b-5p, miR-143-3p, miR-363-3p, miR-338-3p; miR-195-5p, miR-126-5p, miR-423-3p, miR-17-5p, miR-660-5p, miR-25-3p, miR-143-3p, miR-363-3p; miR-195-5p, miR-126-5p, miR-423-3p, miR-17-5p, miR-660-5p, miR-25-3p, miR-143-3p, miR-338-3p; miR-195-5p, miR-126-5p, miR-423-3p, miR-17-5p, miR-660-5p, miR-25-3p, miR-363-3p, miR-338-3p; miR-195-5p, miR-126-5p, miR-423-3p, miR-17-5p, miR-660-5p, miR-143-3p, miR-363-3p, miR-338-3p; miR-195-5p, miR-126-5p, miR-423-3p, miR-125b-5p, miR-660-5p, miR-25-3p, miR-143-3p, miR-363-3p; miR-195-5p, miR-126-5p, miR-423-3p, miR-125b-5p, miR-660-5p, miR-25-3p, miR-143-3p, miR-338-3p; miR-195-5p, miR-126-5p, miR-423-3p, miR-125b-5p, miR-660-5p, miR-25-3p, miR-363-3p, miR-338-3p; miR-423-3p, miR-125b-5p, miR-660-5p, miR-25-3p, miR-363-3p, miR-338-3p; miR-195-5p, miR-126-5p, miR-423-3p, miR-125b-5p, miR-660-5p, miR-143-3p, miR-363-3p, miR-338-3p; miR-195-5p, miR-126-5p, miR-423-3p, miR-125b-5p, miR-25-3p, miR-143-3p, miR-363-3p, miR-338-3p; miR-195-5p, miR-126-5p, miR-423-3p, miR-660-5p, miR-25-3p, miR-143-3p, miR-363-3p, miR-338-3p; miR-195-5p, miR-126-5p, miR-192-5p, miR-17-5p, miR-125b-5p, miR-660-5p, miR-25-3p, miR-143-3p; miR-195-5p, miR-126-5p, miR-192-5p, miR-17-5p, miR-125b-5p, miR-660-5p, miR-25-3p, miR-363-3p; miR-195-5p, miR-126-5p, miR-192-5p, miR-17-5p, miR-125b-5p, miR-660-5p, miR-25-3p, miR-338-3p; miR-195-5p, miR-126-5p, miR-192-5p, miR-17-5p, miR-125b-5p, miR-660-5p, miR-143-3p, miR-363-3p; miR-195-5p, miR-126-5p, miR-192-5p, miR-17-5p, miR-125b-5p, miR-660-5p, miR-143-3p, miR-338-3p; miR-195-5p, miR-126-5p, miR-192-5p, miR-17-5p, miR-125b-5p, miR-660-5p, miR-363-3p, miR-338-3p; miR-195-5p, miR-126-5p, miR-192-5p, miR-17-5p, miR-125b-5p, miR-25-3p, miR-143-3p, miR-363-3p; miR-195-5p, miR-126-5p, miR-192-5p, miR-17-5p, miR-125b-5p, miR-25-3p, miR-143-3p, miR-338-3p; miR-195-5p, miR-126-5p, miR-192-5p, miR-17-5p, miR-125b-5p, miR-25-3p, miR-363-3p, miR-338-3p; miR-195-5p, miR-126-5p, miR-192-5p, miR-17-5p, miR-125b-5p, miR-143-3p, miR-363-3p, miR-338-3p; miR-195-5p, miR-126-5p, miR-192-5p, miR-17-5p, miR-660-5p, miR-25-3p, miR-143-3p, miR-363-3p; miR-195-5p, miR-126-5p, miR-192-5p, miR-17-5p, miR-660-5p, miR-25-3p, miR-143-3p, miR-338-3p; miR-195-5p, miR-126-5p, miR-192-5p, miR-17-5p, miR-660-5p, miR-25-3p, miR-363-3p, miR-338-3p; miR-195-5p, miR-126-5p, miR-192-5p, miR-17-5p, miR-660-5p, miR-143-3p, miR-363-3p, miR-338-3p; miR-195-5p, miR-126-5p, miR-192-5p, miR-17-5p, miR-25-3p, miR-143-3p, miR-363-3p, miR-338-3p; miR-195-5p, miR-126-5p, miR-192-5p, miR-125b-5p, miR-660-5p, miR-25-3p, miR-143-3p, miR-363-3p; miR-195-5p, miR-126-5p, miR-192-5p, miR-125b-5p, miR-660-5p, miR-25-3p, miR-143-3p, miR-338-3p; miR-195-5p, miR-126-5p, miR-192-5p, miR-125b-5p, miR-660-5p, miR-25-3p, miR-363-3p, miR-338-3p; miR-195-5p, miR-126-5p, miR-192-5p, miR-125b-5p, miR-660-5p, miR-143-3p, miR-363-3p, miR-338-3p; miR-195-5p, miR-126-5p, miR-192-5p, miR-125b-5p, miR-25-3p, miR-143-3p, miR-363-3p, miR-338-3p; miR-195-5p, miR-126-5p, miR-192-5p, miR-660-5p, miR-25-3p, miR-143-3p, miR-363-3p, miR-338-3p; miR-195-5p, miR-126-5p, miR-17-5p, miR-125b-5p, miR-660-5p, miR-25-3p, miR-143-3p, miR-363-3p; miR-195-5p, miR-126-5p, miR-17-5p, miR-125b-5p, miR-660-5p, miR-25-3p, miR-143-3p, miR-338-3p; miR-195-5p, miR-126-5p, miR-17-5p, miR-125b-5p, miR-660-5p, miR-25-3p, miR-363-3p, miR-338-3p; miR-195-5p, miR-126-5p, miR-17-5p, miR-125b-5p, miR-660-5p, miR-143-3p, miR-363-3p, miR-338-3p; miR-195-5p, miR-126-5p, miR-17-5p, miR-660-5p, miR-25-3p, miR-143-3p, miR-363-3p, miR-338-3p; miR-195-5p, miR-126-5p, miR-125b-5p, miR-660-5p, miR-25-3p, miR-143-3p, miR-363-3p, miR-338-3p; miR-195-5p, miR-423-3p, miR-192-5p, miR-17-5p, miR-125b-5p, miR-660-5p, miR-25-3p, miR-143-3p; miR-195-5p, miR-423-3p, miR-192-5p, miR-17-5p, miR-125b-5p, miR-660-5p, miR-25-3p, miR-363-3p; miR-195-5p, miR-423-3p, miR-192-5p, miR-17-5p, miR-125b-5p, miR-660-5p, miR-25-3p, miR-338-3p; miR-195-5p, miR-423-3p, miR-192-5p, miR-17-5p, miR-125b-5p, miR-660-5p, miR-143-3p, miR-363-3p; miR-195-5p, miR-423-3p, miR-192-5p, miR-17-5p, miR-125b-5p, miR-660-5p, miR-143-3p, miR-338-3p; miR-195-5p, miR-423-3p, miR-192-5p, miR-17-5p, miR-125b-5p, miR-660-5p, miR-363-3p, miR-338-3p; miR-195-5p, miR-423-3p, miR-192-5p, miR-17-5p, miR-125b-5p, miR-25-3p, miR-143-3p, miR-363-3p; miR-195-5p, miR-423-3p, miR-192-5p, miR-17-5p, miR-125b-5p, miR-25-3p, miR-143-3p, miR-338-3p; miR-195-5p, miR-423-3p, miR-192-5p, miR-17-5p, miR-125b-5p, miR-25-3p, miR-363-3p, miR-338-3p; miR-195-5p, miR-423-3p, miR-192-5p, miR-17-5p, miR-125b-5p, miR-143-3p, miR-363-3p, miR-338-3p; miR-195-5p, miR-423-3p, miR-192-5p, miR-17-5p, miR-660-5p, miR-25-3p, miR-143-3p, miR-363-3p; miR-195-5p, miR-423-3p, miR-192-5p, miR-17-5p, miR-660-5p, miR-25-3p, miR-143-3p, miR-338-3p; miR-195-5p, miR-423-3p, miR-192-5p, miR-17-5p, miR-660-5p, miR-25-3p, miR-363-3p, miR-338-3p; miR-195-5p, miR-423-3p, miR-192-5p, miR-17-5p, miR-660-5p, miR-143-3p, miR-363-3p, miR-338-3p; miR-195-5p, miR-423-3p, miR-192-5p, miR-17-5p, miR-25-3p, miR-143-3p, miR-363-3p, miR-338-3p; miR-195-5p, miR-423-3p, miR-192-5p, miR-125b-5p, miR-660-5p, miR-25-3p, miR-143-3p, miR-363-3p; miR-195-5p, miR-423-3p, miR-192-5p, miR-125b-5p, miR-660-5p, miR-25-3p, miR-143-3p, miR-338-3p; miR-195-5p, miR-423-3p, miR-192-5p, miR-125b-5p, miR-660-5p, miR-25-3p, miR-363-3p, miR-338-3p; miR-195-5p, miR-423-3p, miR-192-5p, miR-125b-5p, miR-660-5p, miR-143-3p, miR-363-3p, miR-338-3p; miR-195-5p, miR-423-3p, miR-192-5p, miR-125b-5p, miR-25-3p, miR-143-3p, miR-363-3p, miR-338-3p; miR-195-5p, miR-423-3p, miR-192-5p, miR-660-5p, miR-25-3p, miR-143-3p, miR-363-3p, miR-338-3p; miR-195-5p, miR-423-3p, miR-17-5p, miR-125b-5p, miR-660-5p, miR-25-3p, miR-143-3p, miR-363-3p; miR-195-5p, miR-423-3p, miR-17-5p, miR-125b-5p, miR-660-5p, miR-25-3p, miR-143-3p, miR-338-3p; miR-195-5p, miR-423-3p, miR-17-5p, miR-125b-5p, miR-660-5p, miR-25-3p, miR-363-3p, miR-338-3p; miR-195-5p, miR-423-3p, miR-17-5p, miR-125b-5p, miR-660-5p, miR-143-3p, miR-363-3p, miR-338-3p; miR-195-5p, miR-423-3p, miR-17-5p, miR-125b-5p, miR-25-3p, miR-143-3p, miR-363-3p, miR-338-3p; miR-195-5p, miR-423-3p, miR-17-5p, miR-660-5p, miR-25-3p, miR-143-3p, miR-363-3p, miR-338-3p; miR-195-5p, miR-423-3p, miR-125b-5p, miR-660-5p, miR-25-3p, miR-143-3p, miR-363-3p, miR-338-3p; miR-195-5p, miR-192-5p, miR-17-5p, miR-125b-5p, miR-660-5p, miR-25-3p, miR-143-3p, miR-363-3p; miR-195-5p, miR-192-5p, miR-17-5p, miR-125b-5p, miR-660-5p, miR-25-3p, miR-143-3p, miR-338-3p; miR-195-5p, miR-192-5p, miR-17-5p, miR-125b-5p, miR-660-5p, miR-25-3p, miR-363-3p, miR-338-3p; miR-192-5p, miR-17-5p, miR-125b-5p, miR-660-5p, miR-143-3p, miR-363-3p, miR-338-3p; miR-195-5p, miR-192-5p, miR-17-5p, miR-125b-5p, miR-25-3p, miR-143-3p, miR-363-3p, miR-338-3p; miR-195-5p, miR-192-5p, miR-17-5p, miR-660-5p, miR-25-3p, miR-143-3p, miR-363-3p, miR-338-3p; miR-195-5p, miR-192-5p, miR-125b-5p, miR-660-5p, miR-25-3p, miR-143-3p, miR-363-3p, miR-338-3p; miR-195-5p, miR-17-5p, miR-125b-5p, miR-660-5p, miR-25-3p, miR-143-3p, miR-363-3p, miR-338-3p; miR-126-5p, miR-423-3p, miR-192-5p, miR-17-5p, miR-125b-5p, miR-660-5p, miR-25-3p, miR-143-3p; miR-126-5p, miR-423-3p, miR-192-5p, miR-17-5p, miR-125b-5p, miR-660-5p, miR-25-3p, miR-363-3p; miR-126-5p, miR-423-3p, miR-192-5p, miR-17-5p, miR-125b-5p, miR-660-5p, miR-25-3p, miR-338-3p; miR-126-5p, miR-423-3p, miR-192-5p, miR-17-5p, miR-125b-5p, miR-660-5p, miR-143-3p, miR-363-3p; miR-126-5p, miR-423-3p, miR-192-5p, miR-17-5p, miR-125b-5p, miR-660-5p, miR-143-3p, miR-338-3p; miR-126-5p, miR-423-3p, miR-192-5p, miR-17-5p, miR-125b-5p, miR-660-5p, miR-363-3p, miR-338-3p; miR-126-5p, miR-423-3p, miR-192-5p, miR-17-5p, miR-125b-5p, miR-25-3p, miR-143-3p, miR-363-3p; miR-126-5p, miR-423-3p, miR-192-5p, miR-17-5p, miR-125b-5p, miR-25-3p, miR-143-3p, miR-338-3p; miR-126-5p, miR-423-3p, miR-192-5p, miR-17-5p, miR-125b-5p, miR-25-3p, miR-363-3p, miR-338-3p; miR-126-5p, miR-423-3p, miR-192-5p, miR-17-5p, miR-125b-5p, miR-143-3p, miR-363-3p, miR-338-3p; miR-126-5p, miR-423-3p, miR-192-5p, miR-17-5p, miR-660-5p, miR-25-3p, miR-143-3p, miR-363-3p; miR-126-5p, miR-423-3p, miR-192-5p, miR-17-5p, miR-660-5p, miR-25-3p, miR-143-3p, miR-338-3p; miR-126-5p, miR-423-3p, miR-192-5p, miR-17-5p, miR-660-5p, miR-25-3p, miR-363-3p, miR-338-3p; miR-126-5p, miR-423-3p, miR-192-5p, miR-17-5p, miR-660-5p, miR-143-3p, miR-363-3p, miR-338-3p; miR-126-5p, miR-423-3p, miR-192-5p, miR-17-5p, miR-25-3p, miR-143-3p, miR-363-3p, miR-338-3p; miR-126-5p, miR-423-3p, miR-192-5p, miR-125b-5p, miR-660-5p, miR-25-3p, miR-143-3p, miR-363-3p; miR-126-5p, miR-423-3p, miR-192-5p, miR-125b-5p, miR-660-5p, miR-25-3p, miR-143-3p, miR-338-3p; miR-126-5p, miR-423-3p, miR-192-5p, miR-125b-5p, miR-660-5p, miR-25-3p, miR-363-3p, miR-338-3p; miR-126-5p, miR-423-3p, miR-192-5p, miR-125b-5p, miR-660-5p, miR-143-3p, miR-363-3p, miR-338-3p; miR-126-5p, miR-423-3p, miR-192-5p, miR-125b-5p, miR-25-3p, miR-143-3p, miR-363-3p, miR-338-3p; miR-126-5p, miR-423-3p, miR-192-5p, miR-660-5p, miR-25-3p, miR-143-3p, miR-363-3p, miR-338-3p; miR-126-5p, miR-423-3p, miR-17-5p, miR-125b-5p, miR-660-5p, miR-25-3p, miR-143-3p, miR-363-3p; miR-126-5p, miR-423-3p, miR-17-5p, miR-125b-5p, miR-660-5p, miR-25-3p, miR-143-3p, miR-338-3p; miR-126-5p, miR-423-3p, miR-17-5p, miR-125b-5p, miR-660-5p, miR-25-3p, miR-363-3p, miR-338-3p; miR-126-5p, miR-423-3p, miR-17-5p, miR-125b-5p, miR-660-5p, miR-143-3p, miR-363-3p, miR-338-3p; miR-126-5p, miR-423-3p, miR-17-5p, miR-125b-5p, miR-25-3p, miR-143-3p, miR-363-3p, miR-338-3p; miR-126-5p, miR-423-3p, miR-17-5p, miR-660-5p, miR-25-3p, miR-143-3p, miR-363-3p, miR-338-3p; miR-126-5p, miR-423-3p, miR-125b-5p, miR-660-5p, miR-25-3p, miR-143-3p, miR-363-3p, miR-338-3p; miR-126-5p, miR-192-5p, miR-17-5p, miR-125b-5p, miR-660-5p, miR-25-3p, miR-143-3p, miR-363-3p; miR-126-5p, miR-192-5p, miR-17-5p, miR-125b-5p, miR-660-5p, miR-25-3p, miR-143-3p, miR-338-3p; miR-126-5p, miR-192-5p, miR-17-5p, miR-125b-5p, miR-660-5p, miR-25-3p, miR-363-3p, miR-338-3p; miR-126-5p, miR-192-5p, miR-17-5p, miR-125b-5p, miR-660-5p, miR-143-3p, miR-363-3p, miR-338-3p; miR-126-5p, miR-192-5p, miR-17-5p, miR-125b-5p, miR-25-3p, miR-143-3p, miR-363-3p, miR-338-3p; miR-126-5p, miR-192-5p, miR-125b-5p, miR-660-5p, miR-25-3p, miR-143-3p, miR-363-3p, miR-338-3p; miR-126-5p, miR-17-5p, miR-125b-5p, miR-660-5p, miR-25-3p, miR-143-3p, miR-363-3p, miR-338-3p; miR-423-3p, miR-192-5p, miR-17-5p, miR-125b-5p, miR-660-5p, miR-25-3p, miR-143-3p, miR-363-3p; miR-423-3p, miR-192-5p, miR-17-5p, miR-125b-5p, miR-660-5p, miR-25-3p, miR-143-3p, miR-338-3p; miR-423-3p, miR-192-5p, miR-17-5p, miR-125b-5p, miR-660-5p, miR-25-3p, miR-363-3p, miR-338-3p; miR-423-3p, miR-192-5p, miR-17-5p, miR-125b-5p, miR-660-5p, miR-143-3p, miR-363-3p, miR-338-3p; miR-423-3p, miR-192-5p, miR-17-5p, miR-125b-5p, miR-25-3p, miR-143-3p, miR-363-3p, miR-338-3p; miR-423-3p, miR-192-5p, miR-17-5p, miR-660-5p, miR-25-3p, miR-143-3p, miR-363-3p, miR-338-3p; miR-423-3p, miR-192-5p, miR-125b-5p, miR-660-5p, miR-25-3p, miR-143-3p, miR-363-3p, miR-338-3p; or miR-192-5p, miR-17-5p, miR-125b-5p, miR-660-5p, miR-25-3p, miR-143-3p, miR-363-3p, miR-338-3p.

In one example, the at least nine miRNAs are, but are not limited to, the following combinations: miR-451a, miR-195-5p, miR-126-5p, miR-423-3p, miR-192-5p, miR-17-5p, miR-125b-5p, miR-660-5p, miR-25-3p; miR-451a, miR-195-5p, miR-126-5p, miR-423-3p, miR-192-5p, miR-17-5p, miR-125b-5p, miR-660-5p, miR-143-3p; miR-451a, miR-195-5p, miR-126-5p, miR-423-3p, miR-192-5p, miR-17-5p, miR-125b-5p, miR-660-5p, miR-363-3p; miR-451a, miR-195-5p, miR-126-5p, miR-423-3p, miR-192-5p, miR-17-5p, miR-125b-5p, miR-660-5p, miR-338-3p; miR-451a, miR-195-5p, miR-126-5p, miR-423-3p, miR-192-5p, miR-17-5p, miR-125b-5p, miR-25-3p, miR-143-3p; miR-451a, miR-195-5p, miR-126-5p, miR-423-3p, miR-192-5p, miR-17-5p, miR-125b-5p, miR-25-3p, miR-363-3p; miR-451a, miR-195-5p, miR-126-5p, miR-423-3p, miR-192-5p, miR-17-5p, miR-125b-5p, miR-25-3p, miR-338-3p; miR-451a, miR-195-5p, miR-126-5p, miR-423-3p, miR-192-5p, miR-17-5p, miR-125b-5p, miR-143-3p, miR-363-3p; miR-451a, miR-195-5p, miR-126-5p, miR-423-3p, miR-192-5p, miR-17-5p, miR-125b-5p, miR-143-3p, miR-338-3p; miR-451a, miR-195-5p, miR-126-5p, miR-423-3p, miR-192-5p, miR-17-5p, miR-125b-5p, miR-363-3p, miR-338-3p; miR-451a, miR-195-5p, miR-126-5p, miR-423-3p, miR-192-5p, miR-17-5p, miR-660-5p, miR-25-3p, miR-143-3p; miR-451a, miR-195-5p, miR-126-5p, miR-423-3p, miR-192-5p, miR-17-5p, miR-660-5p, miR-25-3p, miR-363-3p; miR-451a, miR-195-5p, miR-126-5p, miR-423-3p, miR-192-5p, miR-17-5p, miR-660-5p, miR-25-3p, miR-338-3p; miR-451a, miR-195-5p, miR-126-5p, miR-423-3p, miR-192-5p, miR-17-5p, miR-660-5p, miR-143-3p, miR-363-3p; miR-451a, miR-195-5p, miR-126-5p, miR-423-3p, miR-192-5p, miR-17-5p, miR-660-5p, miR-143-3p, miR-338-3p; miR-451a, miR-195-5p, miR-126-5p, miR-423-3p, miR-192-5p, miR-17-5p, miR-660-5p, miR-363-3p, miR-338-3p; miR-451a, miR-195-5p, miR-126-5p, miR-423-3p, miR-192-5p, miR-17-5p, miR-25-3p, miR-143-3p, miR-363-3p; miR-451a, miR-195-5p, miR-126-5p, miR-423-3p, miR-192-5p, miR-17-5p, miR-25-3p, miR-143-3p, miR-338-3p; miR-451a, miR-195-5p, miR-126-5p, miR-423-3p, miR-192-5p, miR-17-5p, miR-25-3p, miR-363-3p, miR-338-3p; miR-451a, miR-195-5p, miR-126-5p, miR-423-3p, miR-192-5p, miR-17-5p, miR-143-3p, miR-363-3p, miR-338-3p; miR-451a, miR-195-5p, miR-126-5p, miR-423-3p, miR-192-5p, miR-125b-5p, miR-660-5p, miR-25-3p, miR-143-3p; miR-451a, miR-195-5p, miR-126-5p, miR-423-3p, miR-192-5p, miR-125b-5p, miR-660-5p, miR-25-3p, miR-363-3p; miR-451a, miR-195-5p, miR-126-5p, miR-423-3p, miR-192-5p, miR-125b-5p, miR-660-5p, miR-25-3p, miR-338-3p; miR-451a, miR-195-5p, miR-126-5p, miR-423-3p, miR-192-5p, miR-125b-5p, miR-660-5p, miR-143-3p, miR-363-3p; miR-451a, miR-195-5p, miR-126-5p, miR-423-3p, miR-192-5p, miR-125b-5p, miR-660-5p, miR-143-3p, miR-338-3p; miR-451a, miR-195-5p, miR-126-5p, miR-423-3p, miR-192-5p, miR-125b-5p, miR-660-5p, miR-363-3p, miR-338-3p; miR-451a, miR-195-5p, miR-126-5p, miR-423-3p, miR-192-5p, miR-125b-5p, miR-25-3p, miR-143-3p, miR-363-3p; miR-451a, miR-195-5p, miR-126-5p, miR-423-3p, miR-192-5p, miR-125b-5p, miR-25-3p, miR-143-3p, miR-338-3p; miR-451a, miR-195-5p, miR-126-5p, miR-423-3p, miR-192-5p, miR-125b-5p, miR-25-3p, miR-363-3p, miR-338-3p; miR-451a, miR-195-5p, miR-126-5p, miR-423-3p, miR-192-5p, miR-125b-5p, miR-143-3p, miR-363-3p, miR-338-3p; miR-451a, miR-195-5p, miR-126-5p, miR-423-3p, miR-192-5p, miR-660-5p, miR-25-3p, miR-143-3p, miR-363-3p; miR-451a, miR- 195-5p, miR-126-5p, miR-423-3p, miR-192-5p, miR-660-5p, miR-25-3p, miR-143-3p, miR-338-3p; miR-451a, miR-195-5p, miR-126-5p, miR-423-3p, miR-192-5p, miR-660-5p, miR-25-3p, miR-363-3p, miR-338-3p; miR-451a, miR-195-5p, miR-126-5p, miR-423-3p, miR-192-5p, miR-660-5p, miR-143-3p, miR-363-3p, miR-338-3p; miR-451a, miR-195-5p, miR-126-5p, miR-423-3p, miR-192-5p, miR-25-3p, miR-143-3p, miR-363-3p, miR-338-3p; miR-451a, miR-195-5p, miR-126-5p, miR-423-3p, miR-17-5p, miR-125b-5p, miR-660-5p, miR-25-3p, miR-143-3p; miR-451a, miR-195-5p, miR-126-5p, miR-423-3p, miR-17-5p, miR-125b-5p, miR-660-5p, miR-25-3p, miR-363-3p; miR-451a, miR-195-5p, miR-126-5p, miR-423-3p, miR-17-5p, miR-125b-5p, miR-660-5p, miR-25-3p, miR-338-3p; miR-451a, miR-195-5p, miR-126-5p, miR-423-3p, miR-17-5p, miR-125b-5p, miR-660-5p, miR-143-3p, miR-363-3p; miR-451a, miR-195-5p, miR-126-5p, miR-423-3p, miR-17-5p, miR-125b-5p, miR-660-5p, miR-143-3p, miR-338-3p; miR-451a, miR-195-5p, miR-126-5p, miR-423-3p, miR-17-5p, miR-125b-5p, miR-660-5p, miR-363-3p, miR-338-3p; miR-451a, miR-195-5p, miR-126-5p, miR-423-3p, miR-17-5p, miR-125b-5p, miR-25-3p, miR-143-3p, miR-363-3p; miR-451a, miR-195-5p, miR-126-5p, miR-423-3p, miR-17-5p, miR-125b-5p, miR-25-3p, miR-143-3p, miR-338-3p; miR-451a, miR-195-5p, miR-126-5p, miR-423-3p, miR-17-5p, miR-125b-5p, miR-25-3p, miR-363-3p, miR-338-3p; miR-451a, miR-195-5p, miR-126-5p, miR-423-3p, miR-17-5p, miR-125b-5p, miR-143-3p, miR-363-3p, miR-338-3p; miR-451a, miR-195-5p, miR-126-5p, miR-423-3p, miR-17-5p, miR-660-5p, miR-25-3p, miR-143-3p, miR-363-3p; miR-451a, miR-195-5p, miR-126-5p, miR-423-3p, miR-17-5p, miR-660-5p, miR-25-3p, miR-143-3p, miR-338-3p; miR-451a, miR-195-5p, miR-126-5p, miR-423-3p, miR-17-5p, miR-660-5p, miR-25-3p, miR-363-3p, miR-338-3p; miR-451a, miR-195-5p, miR-126-5p, miR-423-3p, miR-17-5p, miR-660-5p, miR-143-3p, miR-363-3p, miR-338-3p; miR-451a, miR-195-5p, miR-126-5p, miR-423-3p, miR-17-5p, miR-25-3p, miR-143-3p, miR-363-3p, miR-338-3p; miR-451a, miR-195-5p, miR-126-5p, miR-423-3p, miR-125b-5p, miR-660-5p, miR-25-3p, miR-143-3p, miR-363-3p; miR-451a, miR-195-5p, miR-126-5p, miR-423-3p, miR-125b-5p, miR-660-5p, miR-25-3p, miR-143-3p, miR-338-3p; miR-451a, miR-195-5p, miR-126-5p, miR-423-3p, miR-125b-5p, miR-660-5p, miR-25-3p, miR-363-3p, miR-338-3p; miR-451a, miR-195-5p, miR-126-5p, miR-423-3p, miR-125b-5p, miR-660-5p, miR-143-3p, miR-363-3p, miR-338-3p; miR-451a, miR-195-5p, miR-126-5p, miR-423-3p, miR-125b-5p, miR-25-3p, miR-143-3p, miR-363-3p, miR-338-3p; miR-451a, miR-195-5p, miR-126-5p, miR-423-3p, miR-660-5p, miR-25-3p, miR-143-3p, miR-363-3p, miR-338-3p; miR-451a, miR-195-5p, miR-126-5p, miR-192-5p, miR-17-5p, miR-125b-5p, miR-660-5p, miR-25-3p, miR-143-3p; miR-451a, miR-195-5p, miR-126-5p, miR-192-5p, miR-17-5p, miR-125b-5p, miR-660-5p, miR-25-3p, miR-363-3p; miR-451a, miR-195-5p, miR-126-5p, miR-192-5p, miR-17-5p, miR-125b-5p, miR-660-5p, miR-25-3p, miR-338-3p; miR-451a, miR-195-5p, miR-126-5p, miR-192-5p, miR-17-5p, miR-125b-5p, miR-660-5p, miR-143-3p, miR-363-3p; miR-451a, miR-195-5p, miR-126-5p, miR-192-5p, miR-17-5p, miR-125b-5p, miR-660-5p, miR-143-3p, miR-338-3p; miR-451a, miR-195-5p, miR-126-5p, miR-192-5p, miR-17-5p, miR-125b-5p, miR-660-5p, miR-363-3p, miR-338-3p; miR-451a, miR-195-5p, miR-126-5p, miR-192-5p, miR-17-5p, miR-125b-5p, miR-25-3p, miR-143-3p, miR-363-3p; miR-451a, miR-195-5p, miR-126-5p, miR-192-5p, miR-17-5p, miR-125b-5p, miR-25-3p, miR-143-3p, miR-338-3p; miR-451a, miR-195-5p, miR-126-5p, miR-192-5p, miR-17-5p, miR-125b-5p, miR-25-3p, miR-363-3p, miR-338-3p; miR-451a, miR-195-5p, miR-126-5p, miR-192-5p, miR-17-5p, miR-125b-5p, miR-143-3p, miR-363-3p, miR-338-3p; miR-451a, miR-195-5p, miR-126-5p, miR-192-5p, miR-17-5p, miR-660-5p, miR-25-3p, miR-143-3p, miR-363-3p; miR-451a, miR-195-5p, miR-126-5p, miR-192-5p, miR-17-5p, miR-660-5p, miR-25-3p, miR-143-3p, miR-338-3p; miR-451a, miR-195-5p, miR-126-5p, miR-192-5p, miR-17-5p, miR-660-5p, miR-25-3p, miR-363-3p, miR-338-3p; miR-451a, miR-195-5p, miR-126-5p, miR-192-5p, miR-17-5p, miR-660-5p, miR-143-3p, miR-363-3p, miR-338-3p; miR-451a, miR-195-5p, miR-126-5p, miR-192-5p, miR-17-5p, miR-25-3p, miR-143-3p, miR-363-3p, miR-338-3p; miR-451a, miR-195-5p, miR-126-5p, miR-192-5p, miR-125b-5p, miR-660-5p, miR-25-3p, miR-143-3p, miR-363-3p; miR-451a, miR-195-5p, miR-126-5p, miR-192-5p, miR-125b-5p, miR-660-5p, miR-25-3p, miR-143-3p, miR-338-3p; miR-451a, miR-195-5p, miR-126-5p, miR-192-5p, miR-125b-5p, miR-660-5p, miR-25-3p, miR-363-3p, miR-338-3p; miR-451a, miR-195-5p, miR-126-5p, miR-192-5p, miR-125b-5p, miR-660-5p, miR-143-3p, miR-363-3p, miR-338-3p; miR-451a, miR-195-5p, miR-126-5p, miR-192-5p, miR-125b-5p, miR-25-3p, miR-143-3p, miR-363-3p, miR-338-3p; miR-451a, miR-195-5p, miR-126-5p, miR-192-5p, miR-660-5p, miR-25-3p, miR-143-3p, miR-363-3p, miR-338-3p; miR-451a, miR-195-5p, miR-126-5p, miR-17-5p, miR-125b-5p, miR-660-5p, miR-25-3p, miR-143-3p, miR-363-3p; miR-451a, miR-195-5p, miR-126-5p, miR-17-5p, miR-125b-5p, miR-660-5p, miR-25-3p, miR-143-3p, miR-338-3p; miR-451a, miR-195-5p, miR-126-5p, miR-17-5p, miR-125b-5p, miR-660-5p, miR-25-3p, miR-363-3p, miR-338-3p; miR-451a, miR-195-5p, miR-126-5p, miR-17-5p, miR-125b-5p, miR-660-5p, miR-143-3p, miR-363-3p, miR-338-3p; miR-451a, miR-195-5p, miR-126-5p, miR-17-5p, miR-125b-5p, miR-25-3p, miR-143-3p, miR-363-3p, miR-338-3p; miR-451a, miR-195-5p, miR-126-5p, miR-17-5p, miR-660-5p, miR-25-3p, miR-143-3p, miR-363-3p, miR-338-3p; miR-451a, miR-195-5p, miR-126-5p, miR-125b-5p, miR-660-5p, miR-25-3p, miR-143-3p, miR-363-3p, miR-338-3p; miR-451a, miR-195-5p, miR-423-3p, miR-192-5p, miR-17-5p, miR-125b-5p, miR-660-5p, miR-25-3p, miR-143-3p; miR-451a, miR-195-5p, miR-423-3p, miR-192-5p, miR-17-5p, miR-125b-5p, miR-660-5p, miR-25-3p, miR-363-3p; miR-451a, miR-195-5p, miR-423-3p, miR-192-5p, miR-17-5p, miR-125b-5p, miR-660-5p, miR-25-3p, miR-338-3p; miR-451a, miR-195-5p, miR-423-3p, miR-192-5p, miR-17-5p, miR-125b-5p, miR-660-5p, miR-143-3p, miR-363-3p; miR-451a, miR-195-5p, miR-423-3p, miR-192-5p, miR-17-5p, miR-125b-5p, miR-660-5p, miR-143-3p, miR-338-3p; miR-451a, miR-195-5p, miR-423-3p, miR-192-5p, miR-17-5p, miR-125b-5p, miR-660-5p, miR-363-3p, miR-338-3p; miR-451a, miR-195-5p, miR-423-3p, miR-192-5p, miR-17-5p, miR-125b-5p, miR-25-3p, miR-143-3p, miR-363-3p; miR-451a, miR-195-5p, miR-423-3p, miR-192-5p, miR-17-5p, miR-125b-5p, miR-25-3p, miR-143-3p, miR-338-3p; miR-451a, miR-195-5p, miR-423-3p, miR-192-5p, miR-17-5p, miR-125b-5p, miR-25-3p, miR-363-3p, miR-338-3p; miR-451a, miR-195-5p, miR-423-3p, miR-192-5p, miR-17-5p, miR-125b-5p, miR-143-3p, miR-363-3p, miR-338-3p; miR-451a, miR-195-5p, miR-423-3p, miR-192-5p, miR-17-5p, miR-660-5p, miR-25-3p, miR-143-3p, miR-363-3p; miR-451a, miR-195-5p, miR-423-3p, miR-192-5p, miR-17-5p, miR-660-5p, miR-25-3p, miR-143-3p, miR-338-3p; miR-451a, miR-195-5p, miR-423-3p, miR-192-5p, miR-17-5p, miR-660-5p, miR-25-3p, miR-363-3p, miR-338-3p; miR-451a, miR-195-5p, miR-423-3p, miR-192-5p, miR-17-5p, miR-660-5p, miR-143-3p, miR-363-3p, miR-338-3p; miR-451a, miR- 195-5p, miR-423-3p, miR-192-5p, miR-17-5p, miR-25-3p, miR-143-3p, miR-363-3p, miR-338-3p; miR-451a, miR-195-5p, miR-423-3p, miR-192-5p, miR-125b-5p, miR-660-5p, miR-25-3p, miR-143-3p, miR-363-3p; miR-451a, miR-195-5p, miR-423-3p, miR-192-5p, miR-125b-5p, miR-660-5p, miR-25-3p, miR-143-3p, miR-338-3p; miR-451a, miR-195-5p, miR-423-3p, miR-192-5p, miR-125b-5p, miR-660-5p, miR-25-3p, miR-363-3p, miR-338-3p; miR-451a, miR-195-5p, miR-423-3p, miR-192-5p, miR-125b-5p, miR-660-5p, miR-143-3p, miR-363-3p, miR-338-3p; miR-451a, miR-195-5p, miR-423-3p, miR-192-5p, miR-125b-5p, miR-25-3p, miR-143-3p, miR-363-3p, miR-338-3p; miR-451a, miR-195-5p, miR-423-3p, miR-192-5p, miR-660-5p, miR-25-3p, miR-143-3p, miR-363-3p, miR-338-3p; miR-451a, miR-195-5p, miR-423-3p, miR-17-5p, miR-125b-5p, miR-660-5p, miR-25-3p, miR-143-3p, miR-363-3p; miR-451a, miR-195-5p, miR-423-3p, miR-17-5p, miR-125b-5p, miR-660-5p, miR-25-3p, miR-143-3p, miR-338-3p; miR-451a, miR-195-5p, miR-423-3p, miR-17-5p, miR-125b-5p, miR-660-5p, miR-25-3p, miR-363-3p, miR-338-3p; miR-451a, miR-195-5p, miR-423-3p, miR-17-5p, miR-125b-5p, miR-660-5p, miR-143-3p, miR-363-3p, miR-338-3p; miR-451a, miR-195-5p, miR-423-3p, miR-17-5p, miR-125b-5p, miR-25-3p, miR-143-3p, miR-363-3p, miR-338-3p; miR-451a, miR-195-5p, miR-423-3p, miR-17-5p, miR-660-5p, miR-25-3p, miR-143-3p, miR-363-3p, miR-338-3p; miR-451a, miR-195-5p, miR-423-3p, miR-125b-5p, miR-660-5p, miR-25-3p, miR-143-3p, miR-363-3p, miR-338-3p; miR-451a, miR-195-5p, miR-192-5p, miR-17-5p, miR-125b-5p, miR-660-5p, miR-25-3p, miR-143-3p, miR-363-3p; miR-451a, miR-195-5p, miR-192-5p, miR-17-5p, miR-125b-5p, miR-660-5p, miR-25-3p, miR-143-3p, miR-338-3p; miR-451a, miR-195-5p, miR-192-5p, miR-17-5p, miR-125b-5p, miR-660-5p, miR-25-3p, miR-363-3p, miR-338-3p; miR-451a, miR-195-5p, miR-192-5p, miR-17-5p, miR-125b-5p, miR-660-5p, miR-143-3p, miR-363-3p, miR-338-3p; miR-451a, miR-195-5p, miR-192-5p, miR-17-5p, miR-125b-5p, miR-25-3p, miR-143-3p, miR-363-3p, miR-338-3p; miR-451a, miR-195-5p, miR-192-5p, miR-17-5p, miR-660-5p, miR-25-3p, miR-143-3p, miR-363-3p, miR-338-3p; miR-451a, miR-195-5p, miR-192-5p, miR-125b-5p, miR-660-5p, miR-25-3p, miR-143-3p, miR-363-3p, miR-338-3p; miR-451a, miR-195-5p, miR-17-5p, miR-125b-5p, miR-660-5p, miR-25-3p, miR-143-3p, miR-363-3p, miR-338-3p; miR-451a, miR-126-5p, miR-423-3p, miR-192-5p, miR-17-5p, miR-125b-5p, miR-660-5p, miR-25-3p, miR-143-3p; miR-451a, miR-126-5p, miR-423-3p, miR-192-5p, miR-17-5p, miR-125b-5p, miR-660-5p, miR-25-3p, miR-363-3p; miR-451a, miR-126-5p, miR-423-3p, miR-192-5p, miR-17-5p, miR-125b-5p, miR-660-5p, miR-25-3p, miR-338-3p; miR-451a, miR-126-5p, miR-423-3p, miR-192-5p, miR-17-5p, miR-125b-5p, miR-660-5p, miR-143-3p, miR-363-3p; miR-451a, miR-126-5p, miR-423-3p, miR-192-5p, miR-17-5p, miR-125b-5p, miR-660-5p, miR-143-3p, miR-338-3p; miR-451a, miR-126-5p, miR-423-3p, miR-192-5p, miR-17-5p, miR-125b-5p, miR-660-5p, miR-363-3p, miR-338-3p; miR-451a, miR-126-5p, miR-423-3p, miR-192-5p, miR-17-5p, miR-125b-5p, miR-25-3p, miR-143-3p, miR-363-3p; miR-451a, miR-126-5p, miR-423-3p, miR-192-5p, miR-17-5p, miR-125b-5p, miR-25-3p, miR-143-3p, miR-338-3p; miR-451a, miR-126-5p, miR-423-3p, miR-192-5p, miR-17-5p, miR-125b-5p, miR-25-3p, miR-363-3p, miR-338-3p; miR-451a, miR-126-5p, miR-423-3p, miR-192-5p, miR-17-5p, miR-125b-5p, miR-143-3p, miR-363-3p, miR-338-3p; miR-451a, miR-126-5p, miR-423-3p, miR-192-5p, miR-17-5p, miR-660-5p, miR-25-3p, miR-143-3p, miR-363-3p; miR-451a, miR-126-5p, miR-423-3p, miR-192-5p, miR-17-5p, miR-660-5p, miR-25-3p, miR-143-3p, miR-338-3p; miR-451a, miR-126-5p, miR-423-3p, miR-192-5p, miR-17-5p, miR-660-5p, miR-25-3p, miR-363-3p, miR-338-3p; miR-451a, miR-126-5p, miR-423-3p, miR-192-5p, miR-17-5p, miR-660-5p, miR-143-3p, miR-363-3p, miR-338-3p; miR-451a, miR-126-5p, miR-423-3p, miR-192-5p, miR-17-5p, miR-25-3p, miR-143-3p, miR-363-3p, miR-338-3p; miR-451a, miR-126-5p, miR-423-3p, miR-192-5p, miR-125b-5p, miR-660-5p, miR-25-3p, miR-143-3p, miR-363-3p; miR-451a, miR-126-5p, miR-423-3p, miR-192-5p, miR-125b-5p, miR-660-5p, miR-25-3p, miR-143-3p, miR-338-3p; miR-451a, miR-126-5p, miR-423-3p, miR-192-5p, miR-125b-5p, miR-660-5p, miR-25-3p, miR-363-3p, miR-338-3p; miR-451a, miR-126-5p, miR-423-3p, miR-192-5p, miR-125b-5p, miR-660-5p, miR-143-3p, miR-363-3p, miR-338-3p; miR-451a, miR-126-5p, miR-423-3p, miR-192-5p, miR-125b-5p, miR-25-3p, miR-143-3p, miR-363-3p, miR-338-3p; miR-451a, miR-126-5p, miR-423-3p, miR-192-5p, miR-660-5p, miR-25-3p, miR-143-3p, miR-363-3p, miR-338-3p; miR-451a, miR-126-5p, miR-423-3p, miR-17-5p, miR-125b-5p, miR-660-5p, miR-25-3p, miR-143-3p, miR-363-3p; miR-451a, miR-126-5p, miR-423-3p, miR-17-5p, miR-125b-5p, miR-660-5p, miR-25-3p, miR-143-3p, miR-338-3p; miR-451a, miR-126-5p, miR-423-3p, miR-17-5p, miR-125b-5p, miR-660-5p, miR-25-3p, miR-363-3p, miR-338-3p; miR-451a, miR-126-5p, miR-423-3p, miR-17-5p, miR-125b-5p, miR-660-5p, miR-143-3p, miR-363-3p, miR-338-3p; miR-451a, miR-126-5p, miR-423-3p, miR-17-5p, miR-125b-5p, miR-25-3p, miR-143-3p, miR-363-3p, miR-338-3p; miR-451a, miR-126-5p, miR-423-3p, miR-17-5p, miR-660-5p, miR-25-3p, miR-143-3p, miR-363-3p, miR-338-3p; miR-451a, miR-126-5p, miR-423-3p, miR-125b-5p, miR-660-5p, miR-25-3p, miR-143-3p, miR-363-3p, miR-338-3p; miR-451a, miR-126-5p, miR-192-5p, miR-17-5p, miR-125b-5p, miR-660-5p, miR-25-3p, miR-143-3p, miR-363-3p; miR-451a, miR-126-5p, miR-192-5p, miR-17-5p, miR-125b-5p, miR-660-5p, miR-25-3p, miR-143-3p, miR-338-3p; miR-451a, miR-126-5p, miR-192-5p, miR-17-5p, miR-125b-5p, miR-660-5p, miR-25-3p, miR-363-3p, miR-338-3p; miR-451a, miR-126-5p, miR-192-5p, miR-17-5p, miR-125b-5p, miR-660-5p, miR-143-3p, miR-363-3p, miR-338-3p; miR-451a, miR-126-5p, miR-192-5p, miR-17-5p, miR-125b-5p, miR-25-3p, miR-143-3p, miR-363-3p, miR-338-3p; miR-451a, miR-126-5p, miR-192-5p, miR-17-5p, miR-660-5p, miR-25-3p, miR-143-3p, miR-363-3p, miR-338-3p; miR-451a, miR-126-5p, miR-192-5p, miR-125b-5p, miR-660-5p, miR-25-3p, miR-143-3p, miR-363-3p, miR-338-3p; miR-451a, miR-126-5p, miR-17-5p, miR-125b-5p, miR-660-5p, miR-25-3p, miR-143-3p, miR-363-3p, miR-338-3p; miR-451a, miR-423-3p, miR-192-5p, miR-17-5p, miR-125b-5p, miR-660-5p, miR-25-3p, miR-143-3p, miR-363-3p; miR-451a, miR-423-3p, miR-192-5p, miR-17-5p, miR-125b-5p, miR-660-5p, miR-25-3p, miR-143-3p, miR-338-3p; miR-451a, miR-423-3p, miR-192-5p, miR-17-5p, miR-125b-5p, miR-660-5p, miR-25-3p, miR-363-3p, miR-338-3p; miR-451a, miR-423-3p, miR-192-5p, miR-17-5p, miR-125b-5p, miR-660-5p, miR-143-3p, miR-363-3p, miR-338-3p; miR-451a, miR-423-3p, miR-192-5p, miR-17-5p, miR-125b-5p, miR-25-3p, miR-143-3p, miR-363-3p, miR-338-3p; miR-451a, miR-423-3p, miR-192-5p, miR-17-5p, miR-660-5p, miR-25-3p, miR-143-3p, miR-363-3p, miR-338-3p; miR-451a, miR-423-3p, miR-192-5p, miR-125b-5p, miR-660-5p, miR-25-3p, miR-143-3p, miR-363-3p, miR-338-3p; miR-451a, miR-423-3p, miR-17-5p, miR-125b-5p, miR-660-5p, miR-25-3p, miR-143-3p, miR-363-3p, miR-338-3p; miR-451a, miR-192-5p, miR-17-5p, miR-125b-5p, miR-660-5p, miR-25-3p, miR-143-3p, miR-363-3p, miR-338-3p; miR-195-5p, miR- 126-5p, miR-423-3p, miR-192-5p, miR-17-5p, miR-125b-5p, miR-660-5p, miR-25-3p, miR-143-3p; miR-195-5p, miR-126-5p, miR-423-3p, miR-192-5p, miR-17-5p, miR-125b-5p, miR-660-5p, miR-25-3p, miR-363-3p; miR-195-5p, miR-126-5p, miR-423-3p, miR-192-5p, miR-17-5p, miR-125b-5p, miR-660-5p, miR-25-3p, miR-338-3p; miR-195-5p, miR-126-5p, miR-423-3p, miR-192-5p, miR-17-5p, miR-125b-5p, miR-660-5p, miR-143-3p, miR-363-3p; miR-195-5p, miR-126-5p, miR-423-3p, miR-192-5p, miR-17-5p, miR-125b-5p, miR-660-5p, miR-143-3p, miR-338-3p; miR-195-5p, miR-126-5p, miR-423-3p, miR-192-5p, miR-17-5p, miR-125b-5p, miR-660-5p, miR-363-3p, miR-338-3p; miR-195-5p, miR-126-5p, miR-423-3p, miR-192-5p, miR-17-5p, miR-125b-5p, miR-25-3p, miR-143-3p, miR-363-3p; miR-195-5p, miR-126-5p, miR-423-3p, miR-192-5p, miR-17-5p, miR-125b-5p, miR-25-3p, miR-143-3p, miR-338-3p; miR-195-5p, miR-126-5p, miR-423-3p, miR-192-5p, miR-17-5p, miR-125b-5p, miR-25-3p, miR-363-3p, miR-338-3p; miR-195-5p, miR-126-5p, miR-423-3p, miR-192-5p, miR-17-5p, miR-125b-5p, miR-143-3p, miR-363-3p, miR-338-3p; miR-195-5p, miR-126-5p, miR-423-3p, miR-192-5p, miR-17-5p, miR-660-5p, miR-25-3p, miR-143-3p, miR-363-3p; miR-195-5p, miR-126-5p, miR-423-3p, miR-192-5p, miR-17-5p, miR-660-5p, miR-25-3p, miR-143-3p, miR-338-3p; miR-195-5p, miR-126-5p, miR-423-3p, miR-192-5p, miR-17-5p, miR-660-5p, miR-25-3p, miR-363-3p, miR-338-3p; miR-195-5p, miR-126-5p, miR-423-3p, miR-192-5p, miR-17-5p, miR-660-5p, miR-143-3p, miR-363-3p, miR-338-3p; miR-195-5p, miR-126-5p, miR-423-3p, miR-192-5p, miR-17-5p, miR-25-3p, miR-143-3p, miR-363-3p, miR-338-3p; miR-195-5p, miR-126-5p, miR-423-3p, miR-192-5p, miR-125b-5p, miR-660-5p, miR-25-3p, miR-143-3p, miR-363-3p; miR-195-5p, miR-126-5p, miR-423-3p, miR-192-5p, miR-125b-5p, miR-660-5p, miR-25-3p, miR-143-3p, miR-338-3p; miR-195-5p, miR-126-5p, miR-423-3p, miR-192-5p, miR-125b-5p, miR-660-5p, miR-25-3p, miR-363-3p, miR-338-3p; miR-195-5p, miR-126-5p, miR-423-3p, miR-192-5p, miR-125b-5p, miR-660-5p, miR-143-3p, miR-363-3p, miR-338-3p; miR-195-5p, miR-126-5p, miR-423-3p, miR-192-5p, miR-125b-5p, miR-25-3p, miR-143-3p, miR-363-3p, miR-338-3p; miR-195-5p, miR-126-5p, miR-423-3p, miR-192-5p, miR-660-5p, miR-25-3p, miR-143-3p, miR-363-3p, miR-338-3p; miR-195-5p, miR-126-5p, miR-423-3p, miR-17-5p, miR-125b-5p, miR-660-5p, miR-25-3p, miR-143-3p, miR-363-3p; miR-195-5p, miR-126-5p, miR-423-3p, miR-17-5p, miR-125b-5p, miR-660-5p, miR-25-3p, miR-143-3p, miR-338-3p; miR-195-5p, miR-126-5p, miR-423-3p, miR-17-5p, miR-125b-5p, miR-660-5p, miR-25-3p, miR-363-3p, miR-338-3p; miR-195-5p, miR-126-5p, miR-423-3p, miR-17-5p, miR-125b-5p, miR-660-5p, miR-143-3p, miR-363-3p, miR-338-3p; miR-195-5p, miR-126-5p, miR-423-3p, miR-17-5p, miR-125b-5p, miR-25-3p, miR-143-3p, miR-363-3p, miR-338-3p; miR-195-5p, miR-126-5p, miR-423-3p, miR-17-5p, miR-660-5p, miR-25-3p, miR-143-3p, miR-363-3p, miR-338-3p; miR-195-5p, miR-126-5p, miR-423-3p, miR-125b-5p, miR-660-5p, miR-25-3p, miR-143-3p, miR-363-3p, miR-338-3p; miR-195-5p, miR-126-5p, miR-192-5p, miR-17-5p, miR-125b-5p, miR-660-5p, miR-25-3p, miR-143-3p, miR-363-3p; miR-195-5p, miR-126-5p, miR-192-5p, miR-17-5p, miR-125b-5p, miR-660-5p, miR-25-3p, miR-143-3p, miR-338-3p; miR-195-5p, miR-126-5p, miR-192-5p, miR-17-5p, miR-125b-5p, miR-660-5p, miR-25-3p, miR-363-3p, miR-338-3p; miR-195-5p, miR-126-5p, miR-192-5p, miR-17-5p, miR-125b-5p, miR-660-5p, miR-143-3p, miR-363-3p, miR-338-3p; miR-195-5p, miR-126-5p, miR-192-5p, miR-17-5p, miR-125b-5p, miR-25-3p, miR-143-3p, miR-363-3p, miR-338-3p; miR-195-5p, miR-126-5p, miR-192-5p, miR-17-5p, miR-660-5p, miR-25-3p, miR-143-3p, miR-363-3p, miR-338-3p; miR-195-5p, miR-126-5p, miR-192-5p, miR-125b-5p, miR-660-5p, miR-25-3p, miR-143-3p, miR-363-3p, miR-338-3p; miR-195-5p, miR-126-5p, miR-17-5p, miR-125b-5p, miR-660-5p, miR-25-3p, miR-143-3p, miR-363-3p, miR-338-3p; miR-195-5p, miR-423-3p, miR-192-5p, miR-17-5p, miR-125b-5p, miR-660-5p, miR-25-3p, miR-143-3p, miR-363-3p; miR-195-5p, miR-423-3p, miR-192-5p, miR-17-5p, miR-125b-5p, miR-660-5p, miR-25-3p, miR-143-3p, miR-338-3p; miR-195-5p, miR-423-3p, miR-192-5p, miR-17-5p, miR-125b-5p, miR-660-5p, miR-25-3p, miR-363-3p, miR-338-3p; miR-195-5p, miR-423-3p, miR-192-5p, miR-17-5p, miR-125b-5p, miR-660-5p, miR-143-3p, miR-363-3p, miR-338-3p; miR-195-5p, miR-423-3p, miR-192-5p, miR-17-5p, miR-125b-5p, miR-25-3p, miR-143-3p, miR-363-3p, miR-338-3p; miR-195-5p, miR-423-3p, miR-192-5p, miR-17-5p, miR-660-5p, miR-25-3p, miR-143-3p, miR-363-3p, miR-338-3p; miR-195-5p, miR-423-3p, miR-192-5p, miR-125b-5p, miR-660-5p, miR-25-3p, miR-143-3p, miR-363-3p, miR-338-3p; miR-195-5p, miR-423-3p, miR-17-5p, miR-125b-5p, miR-660-5p, miR-25-3p, miR-143-3p, miR-363-3p, miR-338-3p; miR-195-5p, miR-192-5p, miR-17-5p, miR-125b-5p, miR-660-5p, miR-25-3p, miR-143-3p, miR-363-3p, miR-338-3p; miR-126-5p, miR-423-3p, miR-192-5p, miR-17-5p, miR-125b-5p, miR-660-5p, miR-25-3p, miR-143-3p, miR-363-3p; miR-126-5p, miR-423-3p, miR-192-5p, miR-17-5p, miR-125b-5p, miR-660-5p, miR-25-3p, miR-143-3p, miR-338-3p; miR-126-5p, miR-423-3p, miR-192-5p, miR-17-5p, miR-125b-5p, miR-660-5p, miR-25-3p, miR-363-3p, miR-338-3p; miR-126-5p, miR-423-3p, miR-192-5p, miR-17-5p, miR-125b-5p, miR-660-5p, miR-143-3p, miR-363-3p, miR-338-3p; miR-126-5p, miR-423-3p, miR-192-5p, miR-17-5p, miR-125b-5p, miR-25-3p, miR-143-3p, miR-363-3p, miR-338-3p; miR-126-5p, miR-423-3p, miR-192-5p, miR-17-5p, miR-660-5p, miR-25-3p, miR-143-3p, miR-363-3p, miR-338-3p; miR-126-5p, miR-423-3p, miR-192-5p, miR-125b-5p, miR-660-5p, miR-25-3p, miR-143-3p, miR-363-3p, miR-338-3p; miR-126-5p, miR-423-3p, miR-17-5p, miR-125b-5p, miR-660-5p, miR-25-3p, miR-143-3p, miR-363-3p, miR-338-3p; miR-126-5p, miR-192-5p, miR-17-5p, miR-125b-5p, miR-660-5p, miR-25-3p, miR-143-3p, miR-363-3p, miR-338-3p; or miR-423-3p, miR-192-5p, miR-17-5p, miR-125b-5p, miR-660-5p, miR-25-3p, miR-143-3p, miR-363-3p, miR-338-3p.

In one example, the at least ten miRNAs are, but are not limited to, the following combinations: miR-451a, miR-195-5p, miR-126-5p, miR-423-3p, miR-192-5p, miR-17-5p, miR-125b-5p, miR-660-5p, miR-25-3p, miR-143-3p; miR-451a, miR-195-5p, miR-126-5p, miR-423-3p, miR-192-5p, miR-17-5p, miR-125b-5p, miR-660-5p, miR-25-3p, miR-363-3p; miR-451a, miR-195-5p, miR-126-5p, miR-423-3p, miR-192-5p, miR-17-5p, miR-125b-5p, miR-660-5p, miR-25-3p, miR-338-3p; miR-451a, miR-195-5p, miR-126-5p, miR-423-3p, miR-192-5p, miR-17-5p, miR-125b-5p, miR-660-5p, miR-143-3p, miR-363-3p; miR-451a, miR-195-5p, miR-126-5p, miR-423-3p, miR-192-5p, miR-17-5p, miR-125b-5p, miR-660-5p, miR-143-3p, miR-338-3p; miR-451a, miR-195-5p, miR-126-5p, miR-423-3p, miR-192-5p, miR-17-5p, miR-125b-5p, miR-660-5p, miR-363-3p, miR-338-3p; miR-451a, miR-195-5p, miR-126-5p, miR-423-3p, miR-192-5p, miR-17-5p, miR-125b-5p, miR-25-3p, miR-143-3p, miR-363-3p; miR-451a, miR-195-5p, miR-126-5p, miR-423-3p, miR-192-5p, miR-17-5p, miR-125b-5p, miR-25-3p, miR-363-3p, miR-338-3p; miR-451a, miR-195-5p, miR-126-5p, miR-423-3p, miR-192-5p, miR-17-5p, miR-125b-5p, miR-143-3p, miR-363-3p, miR-338-3p; miR-451a, miR-195-5p, miR-126-5p, miR-423-3p, miR-192-5p, miR-17-5p, miR-660-5p, miR-25-3p, miR-143-3p, miR-363-3p; miR-451a, miR-195-5p, miR-126-5p, miR-423-3p, miR-192-5p, miR-17-5p, miR-660-5p, miR-25-3p, miR-143-3p, miR-338-3p; miR-451a, miR-195-5p, miR-126-5p, miR-423-3p, miR-192-5p, miR-17-5p, miR-660-5p, miR-25-3p, miR-363-3p, miR-338-3p; miR-451a, miR-195-5p, miR-126-5p, miR-423-3p, miR-192-5p, miR-17-5p, miR-660-5p, miR-143-3p, miR-363-3p, miR-338-3p; miR-451a, miR-195-5p, miR-126-5p, miR-423-3p, miR-192-5p, miR-17-5p, miR-25-3p, miR-143-3p, miR-363-3p, miR-338-3p; miR-451a, miR-195-5p, miR-126-5p, miR-423-3p, miR-192-5p, miR-125b-5p, miR-660-5p, miR-25-3p, miR-143-3p, miR-363-3p; miR-451a, miR-195-5p, miR-126-5p, miR-423-3p, miR-192-5p, miR-125b-5p, miR-660-5p, miR-25-3p, miR-143-3p, miR-338-3p; miR-451a, miR-195-5p, miR-126-5p, miR-423-3p, miR-192-5p, miR-125b-5p, miR-660-5p, miR-25-3p, miR-363-3p, miR-338-3p; miR-451a, miR-195-5p, miR-126-5p, miR-423-3p, miR-192-5p, miR-125b-5p, miR-660-5p, miR-143-3p, miR-363-3p, miR-338-3p; miR-451a, miR-195-5p, miR-126-5p, miR-423-3p, miR-192-5p, miR-125b-5p, miR-25-3p, miR-143-3p, miR-363-3p, miR-338-3p; miR-451a, miR-195-5p, miR-126-5p, miR-423-3p, miR-192-5p, miR-660-5p, miR-25-3p, miR-143-3p, miR-363-3p, miR-338-3p; miR-451a, miR-195-5p, miR-126-5p, miR-423-3p, miR-17-5p, miR-125b-5p, miR-660-5p, miR-25-3p, miR-143-3p, miR-363-3p; miR-451a, miR-195-5p, miR-126-5p, miR-423-3p, miR-17-5p, miR-125b-5p, miR-660-5p, miR-25-3p, miR-143-3p, miR-338-3p; miR-451a, miR-195-5p, miR-126-5p, miR-423-3p, miR-17-5p, miR-125b-5p, miR-660-5p, miR-25-3p, miR-363-3p, miR-338-3p; miR-451a, miR-195-5p, miR-126-5p, miR-423-3p, miR-17-5p, miR-125b-5p, miR-660-5p, miR-143-3p, miR-363-3p, miR-338-3p; miR-451a, miR-195-5p, miR-126-5p, miR-423-3p, miR-17-5p, miR-125b-5p, miR-25-3p, miR-143-3p, miR-363-3p, miR-338-3p; miR-451a, miR-195-5p, miR-126-5p, miR-423-3p, miR-17-5p, miR-660-5p, miR-25-3p, miR-143-3p, miR-363-3p, miR-338-3p; miR-451a, miR-195-5p, miR-126-5p, miR-423-3p, miR-125b-5p, miR-660-5p, miR-25-3p, miR-143-3p, miR-363-3p, miR-338-3p; miR-451a, miR-195-5p, miR-126-5p, miR-192-5p, miR-17-5p, miR-125b-5p, miR-660-5p, miR-25-3p, miR-143-3p, miR-363-3p; miR-451a, miR-195-5p, miR-126-5p, miR-192-5p, miR-17-5p, miR-125b-5p, miR-660-5p, miR-25-3p, miR-143-3p, miR-338-3p; miR-451a, miR-195-5p, miR-126-5p, miR-192-5p, miR-17-5p, miR-125b-5p, miR-660-5p, miR-25-3p, miR-363-3p, miR-338-3p; miR-451a, miR-195-5p, miR-126-5p, miR-192-5p, miR-17-5p, miR-125b-5p, miR-660-5p, miR-25-3p, miR-363-3p, miR-338-3p; miR-451a, miR-195-5p, miR-126-5p, miR-192-5p, miR-17-5p, miR-125b-5p, miR-660-5p, miR-25-3p, miR-363-3p, miR-338-3p; miR-451a, miR-195-5p, miR-423-3p, miR-192-5p, miR-17-5p, miR-125b-5p, miR-660-5p, miR-25-3p, miR-143-3p, miR-363-3p, miR-338-3p; miR-451a, miR-195-5p, miR-423-3p, miR-192-5p, miR-17-5p, miR-125b-5p, miR-660-5p, miR-25-3p, miR-143-3p, miR-363-3p, miR-338-3p; miR-451a, miR-195-5p, miR-423-3p, miR-192-5p, miR-17-5p, miR-660-5p, miR-25-3p, miR-143-3p, miR-363-3p, miR-338-3p; miR-451a, miR-195-5p, miR-423-3p, miR-192-5p, miR-125b-5p, miR-660-5p, miR-25-3p, miR-143-3p, miR-363-3p, miR-338-3p; miR-451a, miR-195-5p, miR-423-3p, miR-17-5p, miR-125b-5p, miR-660-5p, miR-25-3p, miR-143-3p, miR-363-3p, miR-338-3p; miR-451a, miR-195-5p, miR-192-5p, miR-17-5p, miR-125b-5p, miR-660-5p, miR-25-3p, miR-143-3p, miR-363-3p, miR-338-3p; miR-451a, miR-126-5p, miR-423-3p, miR-192-5p, miR-17-5p, miR-125b-5p, miR-660-5p, miR-25-3p, miR-143-3p, miR-363-3p; miR-451a, miR-126-5p, miR-423-3p, miR-192-5p, miR-17-5p, miR-125b-5p, miR-660-5p, miR-25-3p, miR-143-3p, miR-338-3p; miR-451a, miR-126-5p, miR-423-3p, miR-192-5p, miR-17-5p, miR-125b-5p, miR-660-5p, miR-25-3p, miR-363-3p, miR-338-3p; miR-451a, miR-126-5p, miR-423-3p, miR-192-5p, miR-17-5p, miR-125b-5p, miR-660-5p, miR-143-3p, miR-363-3p, miR-338-3p; miR-451a, miR-126-5p, miR-423-3p, miR-192-5p, miR-17-5p, miR-125b-5p, miR-25-3p, miR-143-3p, miR-363-3p, miR-338-3p; miR-451a, miR-126-5p, miR-423-3p, miR-192-5p, miR-17-5p, miR-660-5p, miR-25-3p, miR-143-3p, miR-363-3p, miR-338-3p; miR-451a, miR-126-5p, miR-423-3p, miR-192-5p, miR-125b-5p, miR-660-5p, miR-25-3p, miR-143-3p, miR-363-3p, miR-338-3p; miR-451a, miR-126-5p, miR-423-3p, miR-17-5p, miR-125b-5p, miR-660-5p, miR-25-3p, miR-143-3p, miR-363-3p, miR-338-3p; miR-451a, miR-126-5p, miR-192-5p, miR-17-5p, miR-125b-5p, miR-660-5p, miR-25-3p, miR-143-3p, miR-363-3p, miR-338-3p; miR-451a, miR-423-3p, miR-192-5p, miR-17-5p, miR-125b-5p, miR-660-5p, miR-25-3p, miR-143-3p, miR-363-3p, miR-338-3p; miR-195-5p, miR-126-5p, miR-423-3p, miR-192-5p, miR-17-5p, miR-125b-5p, miR-660-5p, miR-25-3p, miR-143-3p, miR-363-3p; miR-195-5p, miR-126-5p, miR-423-3p, miR-192-5p, miR-17-5p, miR-125b-5p, miR-660-5p, miR-25-3p, miR-143-3p, miR-338-3p; miR-195-5p, miR-126-5p, miR-423-3p, miR-192-5p, miR-17-5p, miR-125b-5p, miR-660-5p, miR-25-3p, miR-363-3p, miR-338-3p; miR-195-5p, miR-126-5p, miR-423-3p, miR-192-5p, miR-17-5p, miR-125b-5p, miR-660-5p, miR-143-3p, miR-363-3p, miR-338-3p; miR-195-5p, miR-126-5p, miR-423-3p, miR-192-5p, miR-17-5p, miR-125b-5p, miR-25-3p, miR-143-3p, miR-363-3p, miR-338-3p; miR-195-5p, miR-126-5p, miR-423-3p, miR-192-5p, miR-17-5p, miR-660-5p, miR-25-3p, miR-143-3p, miR-363-3p, miR-338-3p; miR-195-5p, miR-126-5p, miR-423-3p, miR-192-5p, miR-125b-5p, miR-660-5p, miR-25-3p, miR-143-3p, miR-363-3p, miR-338-3p; miR-195-5p, miR-126-5p, miR-423-3p, miR-17-5p, miR-125b-5p, miR-660-5p, miR-25-3p, miR-143-3p, miR-363-3p, miR-338-3p; miR-195-5p, miR-126-5p, miR-192-5p, miR-17-5p, miR-125b-5p, miR-660-5p, miR-25-3p, miR-143-3p, miR-363-3p, miR-338-3p; miR-195-5p, miR-423-3p, miR-192-5p, miR-17-5p, miR-125b-5p, miR-660-5p, miR-25-3p, miR-143-3p, miR-363-3p, miR-338-3p; or miR-126-5p, miR-423-3p, miR-192-5p, miR-17-5p, miR-125b-5p, miR-660-5p, miR-25-3p, miR-143-3p, miR-363-3p, miR-338-3p.

In one example, the at least eleven miRNAs are, but are not limited to, the following combinations: miR-451a, miR-195-5p, miR-126-5p, miR-423-3p, miR-192-5p, miR-17-5p, miR-125b-5p, miR-660-5p, miR-25-3p, miR-143-3p, miR-363-3p; miR-451a, miR-195-5p, miR-126-5p, miR-423-3p, miR-192-5p, miR-17-5p, miR-125b-5p, miR-660-5p, miR- 25-3p, miR-143-3p, miR-338-3p; miR-451a, miR-195-5p, miR-126-5p, miR-423-3p, miR-192-5p, miR-17-5p, miR-125b-5p, miR-660-5p, miR-25-3p, miR-363-3p, miR-338-3p; miR-451a, miR-195-5p, miR-126-5p, miR-423-3p, miR-192-5p, miR-17-5p, miR-125b-5p, miR-660-5p, miR-143-3p, miR-363-3p, miR-338-3p; miR-451a, miR-195-5p, miR-126-5p, miR-423-3p, miR-192-5p, miR-17-5p, miR-125b-5p, miR-25-3p, miR-143-3p, miR-363-3p, miR-338-3p; miR-451a, miR-195-5p, miR-126-5p, miR-423-3p, miR-192-5p, miR-17-5p, miR-660-5p, miR-25-3p, miR-143-3p, miR-363-3p, miR-338-3p; miR-451a, miR-195-5p, miR-126-5p, miR-423-3p, miR-192-5p, miR-125b-5p, miR-660-5p, miR-25-3p, miR-143-3p, miR-363-3p, miR-338-3p; miR-451a, miR-195-5p, miR-126-5p, miR-423-3p, miR-17-5p, miR-125b-5p, miR-660-5p, miR-25-3p, miR-143-3p, miR-363-3p, miR-338-3p; miR-451a, miR-195-5p, miR-126-5p, miR-192-5p, miR-17-5p, miR-125b-5p, miR-660-5p, miR-25-3p, miR-143-3p, miR-363-3p, miR-338-3p; miR-451a, miR-195-5p, miR-423-3p, miR-192-5p, miR-17-5p, miR-125b-5p, miR-660-5p, miR-25-3p, miR-143-3p, miR-363-3p, miR-338-3p; miR-451a, miR-126-5p, miR-423-3p, miR-192-5p, miR-17-5p, miR-125b-5p, miR-660-5p, miR-25-3p, miR-143-3p, miR-363-3p, miR-338-3p; or miR-195-5p, miR-126-5p, miR-423-3p, miR-192-5p, miR-17-5p, miR-125b-5p, miR-660-5p, miR-25-3p, miR-143-3p, miR-363-3p, miR-338-3p.

In one example, the at least twelve miRNAs are, but are not limited to, the following combinations: miR-451a, miR-195-5p, miR-126-5p, miR-423-3p, miR-192-5p, miR-17-5p, miR-125b-5p, miR-660-5p, miR-25-3p, miR-143-3p, miR-363-3p, and miR-338-3p.

Thus, in a further example, the at least two or more miRNAs described in the method herein are selected from the group consisting of miR-451a, miR-195-5p, miR-125b-5p, miR-126-5p, miR-423-3p, miR-192-5p, miR-660-5p, miR-25-3p, miR-143-3p, miR-363-3p, miR-338-3p, and miR-17-5p.

In one example, the miRNAs disclosed in the methods described herein can be all of the following: miR-451a, miR-195-5p, miR-126-5p, miR-423-3p, miR-192-5p and miR-17-5p.

In another example, the miRNAs can be all of the following: all of the following: miR-195-5p, miR-451a, miR-125-5p, miR-660-5p, miR-25-3p, miR-143-3p, miR-363-3p, and miR-338-3p.

As disclosed herein, the expression levels of the miRNAs can be determined using methods known in the art. Such exemplary methods can be, but are not limited to, polymerase chain reaction (PCR), quantitative polymerase chain reaction (qPCR), reverse transcription polymerase chain reaction (RT-PCR), or real-time quantitative reverse transcription polymerase chain reaction (qRT-PCR). In another example, the expression levels of the miRNAs disclosed herein are providing using units such as, but not limited to, concentration, log(concentration), Ct value, Ct/Cq value, or two to the power of Ct/Cq value.

Various statistical methods and calculations can be applied in order to arrive at the statistical analyses performed in the present disclosure. Statistical characteristics, for example, reliability, robustness, and variability of the data disclosed herein can be illustrated using various methodologies disclosed in the art. A person skilled in the art will be able to calculate the required statistically relevant information based on the data provided herein using methods and means known in the art. Such statistically relevant information can be, but is not limited to, p-values, predictive value, FDR-corrected p-values, AUC values, log fold change values, normalised values, means, medians, and/or correlation coefficients. As disclosed herein, the miRNAs can be chosen based on any one of the following criteria: Receiver Operating Characteristic Area Under the Curve (AUC-ROC) value, Area Under the Curve (AUC) value, p-value, False Discovery Rate (FDR)-adjusted p-value, predictive value, or combinations thereof.

For example, in the context of the present disclosure, mean and median area under the curve (AUC) values are shown in Tables 1 and 2 as disclosed herein for selected exemplary miRNAs, when exemplarily combined with further one, or two, or three, or four, or five miRNAs in addition to an exemplary fixed miRNA.

In another example, the present disclosure describes a method for determining whether a subject is suffering from breast cancer, the method comprising measuring the expression level of at least two or more miRNA selected from the group disclosed herein, wherein differential expression of miRNA expression in the sample, as compared to a control, determines the subject to have breast cancer.

In a further example, the present disclosure refers to a method of treating breast cancer, the method comprising: obtaining a sample from a subject thought to be suffering from or at the risk of developing breast cancer; measuring the expression level of at least two or more miRNAs selected from the group consisting of miR-451a, miR-195-5p, miR-126-5p, miR-423-3p, miR-192-5p, miR-17-5p, miR-125b-5p, miR-660-5p, miR-25-3p, miR-143-3p, miR-363-3p and miR-338-3p in the sample obtained from the subject; wherein differential or unchanged expression level of said miRNA in the sample, as compared to a control, determines the subject is suffering from, or is at risk of developing breast cancer, treating the subject diagnosed with having breast cancer with an anti-breast cancer compound.

In some examples, the present disclosure refers to a method for determining whether a breast lesion in a subject is malignant or benign, the method comprising: measuring the expression level of at least one or more miRNAs selected from the group consisting of miR-451a, miR-195-5p, miR-126-5p, miR-423-3p, miR-192-5p, miR-17-5p, miR-125b-5p, miR-660-5p, miR-25-3p, miR-143-3p, miR-363-3p and miR-338-3p in a sample obtained from the subject, wherein differential expression or unchanged miRNA expression level of said miRNAs in the sample, as compared to a control, determines the lesion is benign or malignant. As disclosed herein, the result of the differential comparison for any one or more of the miRNAs disclosed herein can conclude the expression status of the miRNA being termed to be upregulated, or downregulated, or unchanged. The combined results of the expression status of at least one, at least two, at least three, at least four, at least five, at least six, at least seven, at least eight, at least ten, at least eleven or at least twelve miRNAs thus results in a diagnosis or determination being made of a subject to have breast cancer, to be at risk of having or developing breast cancer, or to be cancer-free. Such a diagnosis or determination can be made on the basis that the expression of a particular miRNA is considered to be upregulated or downregulated compared to a control. In one example, the expression levels of selected miRNAs as shown to be "downregulated" in the present disclosure, as compared to the control, diagnoses the subject to have breast cancer. In another example, the expression levels of selected miRNAs as shown to be "upregulated" in the present disclosure, as compared to the control, diagnoses the subject to have breast cancer. In addition to the miRNA disclosed herein to be differentially expressed, the miRNA disclosed herein also include miRNA that are not differentially expressed compared to a control. These miRNA that are not differentially expressed are included herein as it has been shown that inclusion of said not differentially expressed miRNA increases the robustness of the statistical analysis performed herein over what would be expected the expected outcome of a statistical analysis when the sample sized is increased accordingly. Thus, in one example, the methods disclosed herein further comprise measuring the expression level of at least one miRNA, which when compared to a control, the expression level is not altered in the subject.

Figures 1B, 1C:
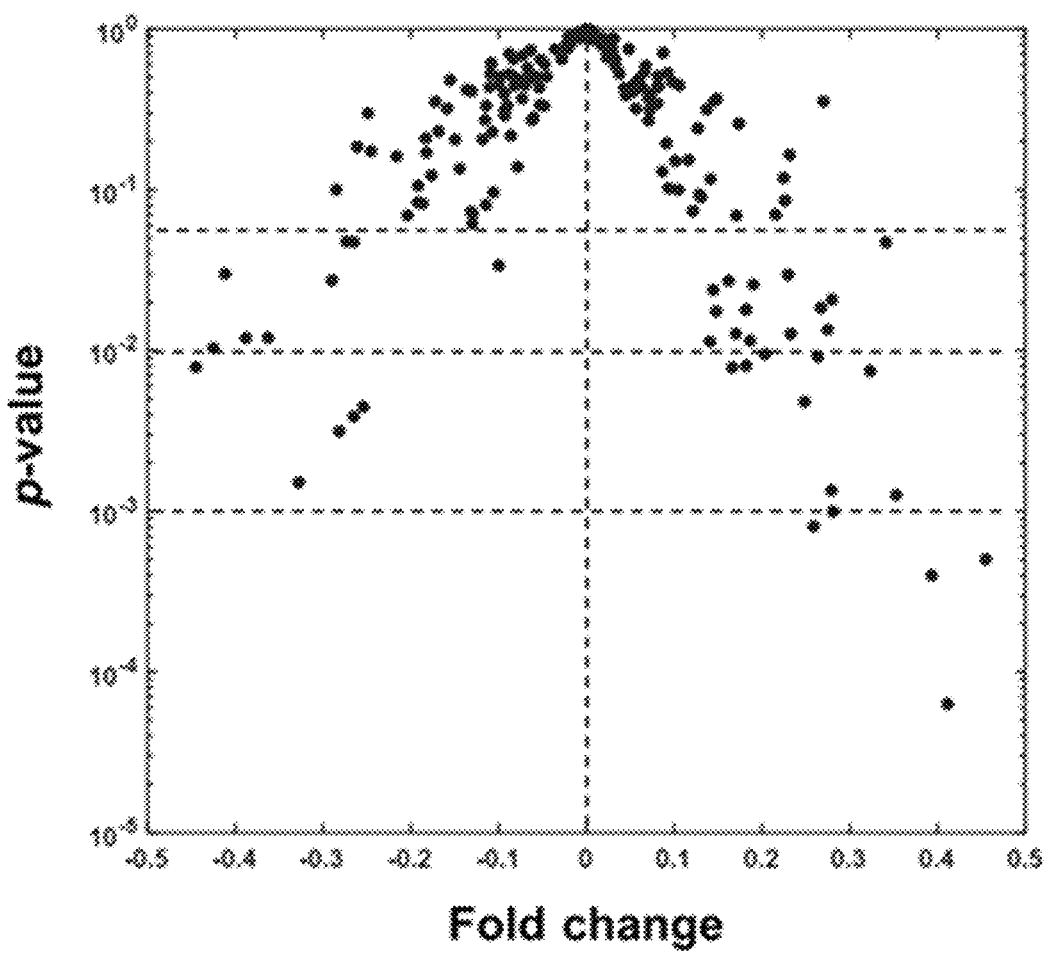
FIG. 1B shows differential miRNA expression in subjects with breast cancer compared to those with benign breast lesions as determined by fold change of miRNA expression and statistical significance (P-value).
FIG. 1C summarizes the differentially regulated miRNAs in subjects with breast cancer compared to those with benign breast lesions (statistical significance determined by False Discovery Rate (FDR)-adjusted P-value<0.05). Ability of miRNA biomarker in distinguishing between breast cancer and benign breast lesions was measured by the Receiver Operating Characteristic Area Under the Curve (AUC-ROC).

As exemplified herein, the term "downregulated" can refer to the expression level of selected miRNA having a negative Log 2 value (fold change). In some examples, the term "upregulated" can refer to the expression level of selected miRNA having a positive Log 2 value (fold change). In some examples, the term "unchanged" refers to the expression level of selected miRNA having a Log 2 value (fold change) equals to zero. In some further examples, the term "unchanged" refers to the expression level of selected miRNA having a Log 2 value (fold change) that is not significantly differentially expressed compared to the control. A person skilled in the art would be able to identify appropriate statistical methods to determine the significance of statistical difference and use appropriate cut-off threshold for statistical significance. In some further examples, the significance of statistical difference can be measured by FDR adjusted p-values. In yet some further examples, the term "unchanged" refers to the expression level of selected miRNA with FDR adjusted p-values of more than or equals to 0.05 as compared to the control. In some examples, the "upregulation" or "downregulation" or "unchanged" expression level of the selected miRNA is listed in Table 3 as disclosed herein. In some further examples, the "upregulation" or "downregulation" or "unchanged" expression level of the selected miRNA is shown in FIG. 1C.

In some further examples, the term "upregulated" or "downregulated" refers to the expression level of selected miRNA having a Log 2 value (fold change) that is significantly higher or lower compared to the control. A person skilled in the art would be able to identify appropriate statistical methods to determine the significance of statistical difference and use appropriate cut-off threshold for statistical significance. In some further examples, the significance of statistical difference can be measured by FDR adjusted p-values. In yet some further examples, the term "upregulated" or "downregulated" refers to the expression level of selected miRNA with FDR adjusted p-values of less than 0.05 as compared to the control.

In some examples, if present, the following miRNAs are upregulated: miR-451a, miR-195-5p, miR-125b-5p, miR-126-5p, miR-660-5p, miR-25-3p, miR-143-3p, and miR-363-3p.

In some examples, if present, miR-338-3p is downregulated.

In some examples, if present, the following miRNA are unchanged: miR-423-3p, miR-192-5p, and miR-17-5p.

Any sample obtained from a subject can be used according to the methods of the present disclosure, so long as the sample in question contains nucleic acid sequences. More specifically, the sample is to contain miRNA. In one example, the sample is obtained from a subject that may or may not have cancer. In another example, the sample is obtained from a subject who has cancer. In another example, the sample is obtained from a subject who is cancer-free. In yet another example, the sample is obtained from a subject who is breast cancer-free. In a further example, the sample is obtained from a subject who is disease-free. In another example, the sample is obtained from a subject who has a benign breast lesion. In some examples, the sample is obtained from a subject who has had an abnormal mammogram result.

Biopsy samples, for example, fine needle aspirates (FNA) and the like, can contain miRNA required for working the methods as described herein. However, such samples would require further manipulation in order to be workable according to the methods described herein. Also, based on the disclosure herein, it is preferred to use samples that are not solid in nature, as the identification methods described herein may not be applicable. Also, in comparison, analyses performed using methods known in the art, for example histological analysis of biopsy samples, are prone to produce false positives. This is because these histological analyses are performed by a, for example, a histopathologist, thus resulting in possible handler-based bias when analysing samples. This means that it is possible that two different people using the same method of analysis could come to different conclusion when histologically analysing tumour biopsy samples. Thus, the methods described herein disclose the use of bodily or extracellular fluids.

Having said that, the sample, as described herein, can be, but is not limited to, a sample of bodily fluid or a sample of extracellular fluid. Examples of bodily or extracellular fluids are, but are not limited to, cellular and non-cellular components of amniotic fluid, breast milk, bronchial lavage, cerebrospinal fluid, colostrum, interstitial fluid, peritoneal fluids, pleural fluid, saliva, seminal fluid, urine, tears, whole blood, blood plasma, red blood cells, white blood cells and serum.

In one example, the bodily fluid is blood serum. In some examples, the sample is a tissue sample or bodily fluid sample. In some further examples, the sample is selected from the group comprising or consisting of cellular and non-cellular components of a liquid biopsy, amniotic fluid, bronchial lavage, cerebrospinal fluid, interstitial fluid, peritoneal fluids, pleural fluid, saliva, seminal fluid, urine, tears, peripheral blood, whole blood, plasma, and serum. In one example, the sample is a serum sample.

In one example, the present disclosure refers to a method of treating breast cancer, the method comprising: obtaining a sample from a subject thought to be suffering from or at the risk of developing breast cancer; measuring the expression level of at least two or more miRNAs selected from the group disclosed herein in the sample obtained from the subject; wherein differential or unchanged expression level of said miRNA in the sample, as compared to a control, determines the subject is suffering from, or is at risk of developing breast cancer, treating the subject diagnosed with having breast cancer with an anti-breast cancer compound.

In some examples, the treatments for subjects determined to suffer from or have breast cancer are, but not limited to, biomarker testing, chemotherapy, hormone therapy, immunotherapy, radiation therapy, stem cell transplant, surgery and targeted therapy.

Examples for the anti-breast cancer compounds for treating subjects determined to suffer from breast cancer are, but not limited to, raloxifene hydrochloride, tamoxifen citrate, abemaciclib, paclitaxel, ado-trastuzumab emtansine, alpelisib, anastrozole, pamidronate disodium, exemestane, atezolizumab, capecitabine, cyclophosphamide, docetaxel, doxorubicin hydrochloride, epirubicin hydrochloride, fam-trastuzumab deruxtecan-nxki, everolimus, fluorouracil, toremifene, letrozole, fulvestrant, gemcitabine hydrochloride, goserelin acetate, eribulin mesylate, trastuzumab, hyaluronidase-oysk, herceptin trastuzumab, palbociclib, ixabepilone, pembrolizumab, ribociclib, lapatinib ditosylate, olaparib, margetuximab-cmkb, megestrol acetate, methotrexate sodium, neratinib maleate, pertuzumab, hyaluronidase-zzxf, sacituzumab govitecan-hziy, talazoparib tosylate, thiotepa, tucatinib and vinblastine sulfate.

In some examples, the present method disclosed herein includes a step of obtaining a mathematical score based on the miRNA selected. The term "predictive score", as defined herein, refers to a mathematical score, which can be calculated using any one of a multitude of mathematical equations and/or algorithms known in the art for the purpose of statistical classification. Without being bound by theory, it is thought that a higher biomarker score indicates a higher probability of the subject having breast cancer.

Examples of such mathematical equations and/or algorithms can be, but are not limited to, a (statistical) classification algorithm selected from the group consisting of support vector machine algorithm, logistic regression algorithm, multinomial logistic regression algorithm, Fisher's linear discriminant algorithm, quadratic classifier algorithm, perceptron algorithm, k-nearest neighbours algorithm, artificial neural network algorithm, random forests algorithm, decision tree algorithm, naive Bayes algorithm, adaptive Bayes network algorithm, and ensemble learning method combining multiple learning algorithms. In another example, the classification algorithm is pre-trained using the expression level of the control. In another example, the classification algorithm compares the expression level of the subject with that of the control and returns a mathematical score that identifies the likelihood of the subject to belong to either one of the control groups. In some further examples, the method disclosed herein includes a step of obtaining a predictive score based on the miRNA selected a mathematical model selected from linear model, logistic regression, support vector machine algorithm, logistic regression algorithm, multinomial logistic regression algorithm, Fisher's linear discriminant algorithm, quadratic classifier algorithm, perceptron algorithm, k-nearest neighbours algorithm, artificial neural network algorithm, random forests algorithm, decision tree algorithm, naive Bayes algorithm, adaptive Bayes network algorithm, and ensemble learning method combining multiple learning algorithms.

In a further example, the present disclosure refers to a kit comprising a combination of primers suitable for detecting the miRNAs as defined in the methods disclosed herein.

As a working example, the performance of an exemplary 6-miRNA biomarker panel is shown in Table 4. As shown in the example, the exemplary 6-miRNA biomarker panel demonstrates the ability to designate a subject who does not have breast cancer as negative, thus reducing the false positive rate. Further, the exemplary 6-miRNA biomarker panel is able to designate a subject with breast cancer as positive, thus producing few false negative results.

TABLE 4

Performance of an exemplary 6-miRNA biomarker panel

| | Specificity<br>Biomarker Score Cut-off | Sensitivity<br>Biomarker Score Cut-off |
|---|---|---|
| Sensitivity | 41.1% (35.2%-47.2%) | 79.5% (74.0%-84.0%) |
| Specificity | 89.8% (85.4%-93.1%) | 62.2% (56.1%-68.0%) |
| PPV | 60.0% (53.9%-65.9%) | 43.9% (38.0%-50.1%) |
| NPV | 80.4% (75.0%-84.9%) | 89.1% (84.5%-92.5%) |

Identification of miRNAs Expressed in Malignant and Benign Breast Lesions

Candidate serum miRNA biomarkers for differentiating between subjects with benign breast lesions and those with breast cancer were identified from analysis of the discovery cohort (Table 5). Absolute expression levels of 324 miRNAs were profiled in 72 breast cancer subjects and compared to those in 197 subjects with benign breast lesions. Among the 324 miRNAs analysed, 179 miRNAs were found to be expressed at 500 or more copies per ml of serum in all subjects.

Identification and Evaluation of miRNA Biomarker Signatures Using Three Strategies (1) Differentially Expressed Individual miRNA Biomarkers Three strategies (FIG. 1A) were used to identify and evaluate miRNA biomarker signatures for use in the methods as disclosed herein. Firstly, miRNAs which were differentially expressed between malignant and benign breast lesions were identified based on fold-change of normalized miRNA expression and statistical testing. Among the 179 miRNAs expressed, 8 miRNAs were found to be either significantly higher (7 miRNAs with FDR-adjusted P<0.05) or lower (1 miRNA with FDR-adjusted P<0.05) in breast cancer cases as compared to those with benign breast lesions (FIG. 1B, 1C). All 8 of these differentially regulated miRNAs were capable of differentiating breast cancer from benign breast lesions with AUC of 0.607 to 0.642 when used individually as biomarkers (FIG. 1C).

(2) Multi-miRNA Biomarker Panels Built Through a Focused Search

Secondly, exemplary multi-miRNA biomarker panels comprising 2 to 8 miRNAs were built by focusing on the 8 individually differentially expressed miRNA biomarkers described herein. The exemplary biomarker panels were evaluated based on their AUC in distinguishing between malignant and benign breast lesions. The maximum AUC was achieved by the focused seven-miRNA and eight-miRNA biomarker panels, each with AUC of 0.877.

(3) Multi-miRNA Biomarker Panels Built Through an Unbiased Search

Thirdly, multi-miRNA panels comprising two to eight miRNAs were built through an unbiased search among all miRNAs expressed in malignant and benign breast lesions. Through the same cross-validation procedure as in the focused search, unbiased two-miRNA to eight-miRNA biomarker panels were built. Using these unbiased multi-miRNA panels, the maximum median AUC achieved was 0.818, with AUC improving with as the number miRNAs in the biomarker panel was increased from two to eight (FIG. 2C). When the unbiased multi-miRNA biomarker panels were validated in the validation cohort, the highest AUC of 0.774 was achieved by an unbiased exemplary six-miRNA biomarker panel (FIG. 2D).

Selection of Exemplary miRNA Biomarker Signature

Figure 3A:
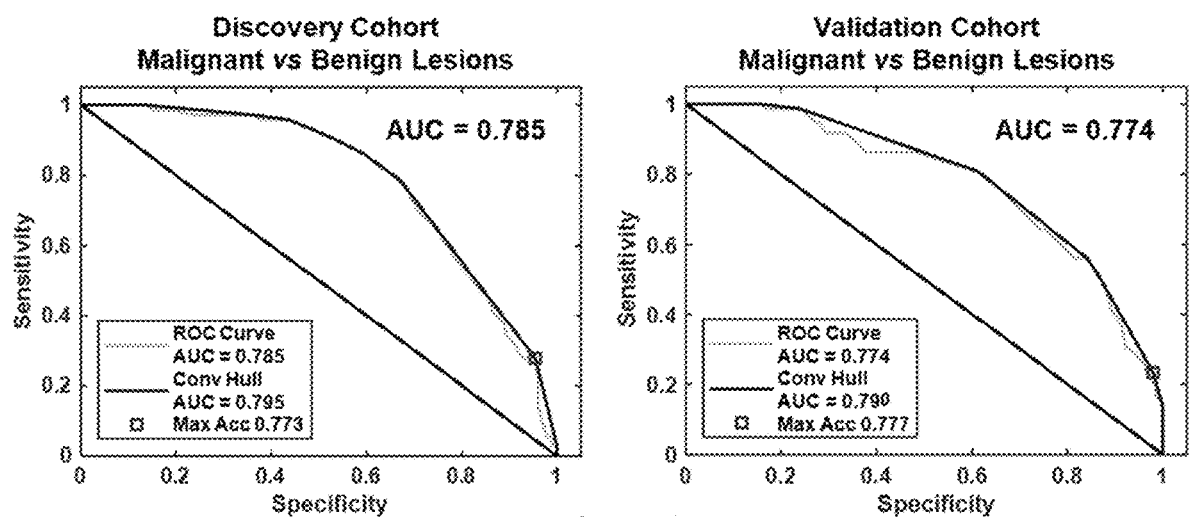
FIG. 3A shows the Receiver Operating Characteristic (ROC) curves for 6-miRNA biomarker panel used in distinguishing subjects with breast cancer from those with benign breast lesion in the Discovery (left panel) and validation cohort (right panel).

Based on the evaluation of miRNA biomarker signatures identified through the three strategies as disclosed herein, an unbiased six-miRNA biomarker panel was selected as an exemplary panel (Table 3). The AUC of this exemplarily selected panel was 0.785 in the discovery cohort and 0.774 in the validation cohort (FIG. 3A). The exemplary six-miRNA panel included 2 differentially regulated miRNAs between breast cancer and benign breast lesions, which were miR-195-5p and miR-451a (with FDR-adjusted P-value<0.05).

Performance of the Exemplary miRNA Biomarker Signature

Figure 3B:
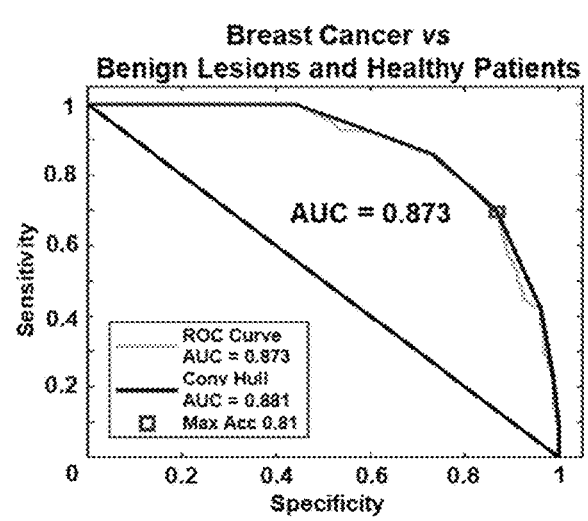
FIG. 3B shows the Receiver Operating Characteristic (ROC) curves for 6-miRNA biomarker panel used in distinguishing subjects with breast cancer from those with benign breast lesions and normal mammograms.
Figure 3C:
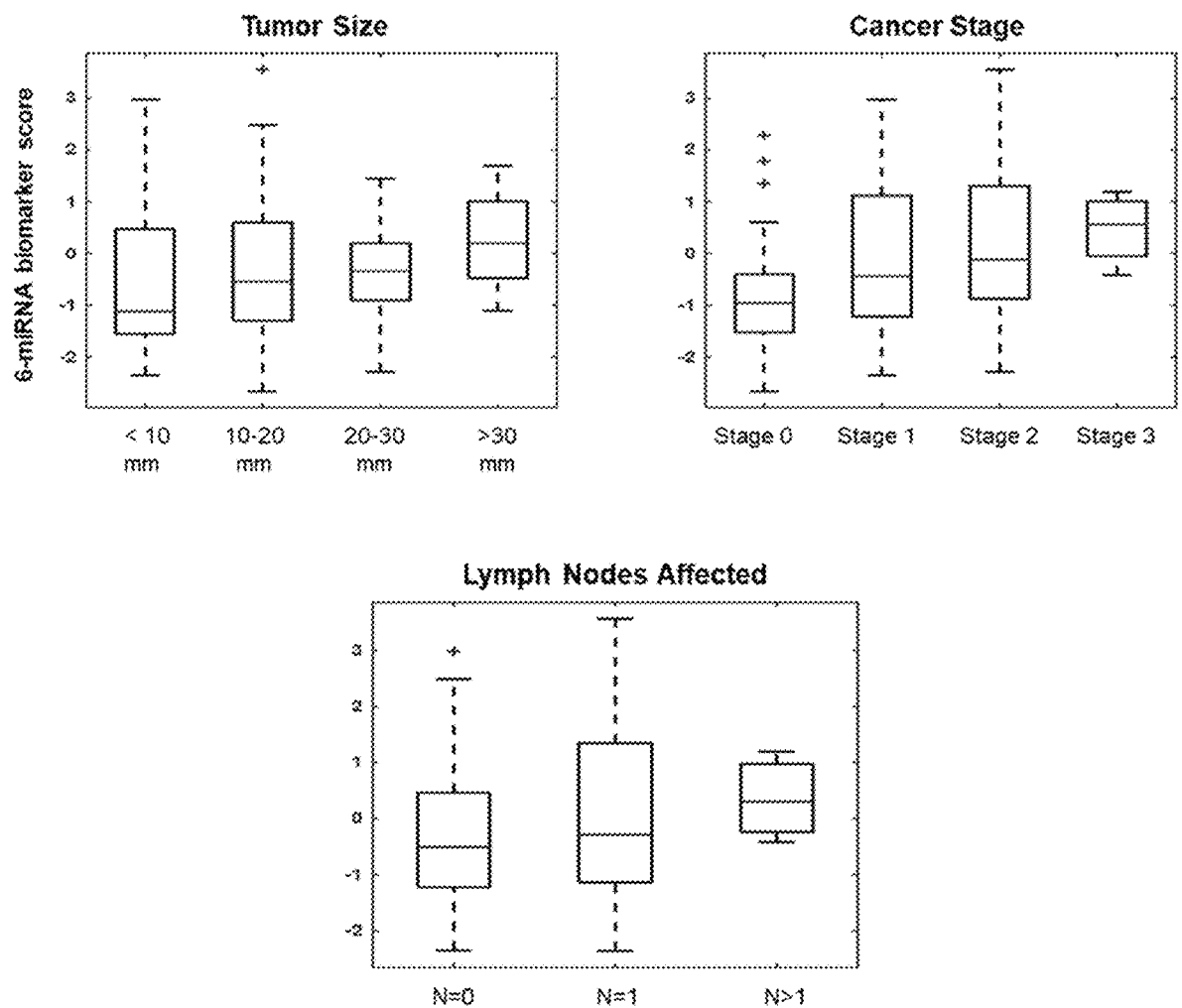
FIG. 3C summarizes the biomarker scores of the 6-miRNA panel in differentiating breast cancers by tumour size, stage, and number of lymph nodes affected.

Having validated that it was possible to discriminate between breast cancer and benign breast lesions using a six-miRNA biomarker panel with a suitable biomarker score cut-off, the subjects were tested with normal mammograms using the six-miRNA panel. The six-miRNA biomarker panel had an AUC of 0.881 for identifying subjects with breast cancer from those with either benign breast lesions or normal screening mammograms (FIG. 3B). From the AUC curve, a high-specificity biomarker score cut-off was identified which gave a specificity of 89.8%, sensitivity of 41.1%, positive predictive value (PPV) of 60%, and negative predictive value (NPV) of 80.4% (Table 4). From the same AUC curve, we also identified an alternative high-sensitivity biomarker score cut-off giving a sensitivity of 79.5%, specificity of 62.2%, PPV of 43.9%, and NPV of 89.1% (Table 4). Among the 145 breast cancer cases in both discovery and validation cohorts, the six-miRNA biomarker scores increased with tumour size, stage, and number of lymph nodes involved (FIG. 3C).

The present disclosure describes the methods using miRNA biomarkers identified for breast cancer in a cohort of a Southeast Asian population that can discriminate between malignant and benign breast lesions among women with abnormal screening mammograms. The miRNAs were identified after an evaluation of three different miRNA biomarker signature identification strategies in the discovery cohort and was validated in the validation cohort. Exemplary serum biomarker comprising six miRNAs (miR-451a, miR-195-5p, miR-126-5p, miR-423-3p, miR-192-5p, and miR-17-5p) had an AUC of 0.774, demonstrated high negative predictive value (>80%) and produced higher predictive scores with increased tumour size, stage and number of lymph nodes involved. In addition, the results showed herein showed that the biomarker panels disclosed herein had a higher diagnostic performance (AUC of 0.881) in differentiating between women with malignant breast lesions versus those with benign breast lesions or healthy women with normal mammograms.

Among the six miRNAs in the panel, three miRNAs, miR-451a, miR-195-5p and miR-126-5p, were statistically significantly upregulated in malignant breast lesions as compared to benign breast lesions.

A person skilled in the art, having possession of the present disclosure, would be capable of working the present invention. An illustrative example as to the use of the present invention is provided as follows: having obtained a sample from a subject, of which is not known if they suffer from breast cancer or if they are breast cancer free, is analysed and a differential expression of a set of miRNAs is determined. This differential expression data is then compared to the differential expression levels as provided herein, and which a person skilled in the art would understand the data. Optionally, a further mathematical score may be determined, which would also take into consideration further statistical parameters relevant to increasing the significance and the accuracy of the provided data set. Based on this information, the person skilled in the art would then be able to determine if the subject in question is cancer-free or has cancer. Similarly, based on the present disclosure, a person skilled in the art would also be able to determine if the subject, known to have a breast lesion, has a benign lesion or a breast cancer.

The disclosure illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The disclosure has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein. Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

Experimental Section

Disclosed herein is an exemplary study that shows the use of independent discovery and validation cohorts (n=269 for each cohort) together with exemplary biomarker panels built using real-time quantitative reverse transcription polymerase chain reaction (qRT-PCR) miRNA profiling. This profiling is then followed by a two-fold cross-validation procedure, incorporating a feature selection algorithm and a logistic regression predictive model.

Subject Cohort

This study included 597 subjects who had abnormal mammograms detected at three sites in Singapore, namely the National University Hospital (NUH), Tan Tock Seng Hospital (TTSH), and National Cancer Centre Singapore (NCCS), between 2016 and 2018. Singapore has a multi-ethnic population comprising of Chinese, Malay, Indian and other ethnic groups, with Chinese making up the majority at 74%. Clinicopathological characteristics of the subjects are shown in Table 5 Peripheral blood samples were collected prior to biopsy or surgery. Of these 597 subjects, 166 were confirmed to have breast cancer (malignant breast lesions) upon histopathological examination. A total of 393 samples from subjects with benign breast lesions and 145 samples from subjects with malignant lesions were analysed. (FIG. 1). 59 of the samples obtained from the 597 subjects were excluded from the analysis due to sample hemolysis in the sample, which caused contamination of serum miRNA with red blood cell miRNA in the sample. In total, 538 samples passed quality control. These samples were equally divided into a discovery cohort of 197 subjects with benign breast lesions and 72 subjects with breast cancer, and a validation cohort of 196 cases with benign breast lesions and 73 breast cancer cases. For "normal" controls, blood samples were collected from 100 subjects who had had normal screening mammograms (that is to say, mammograms without any adverse or abnormal results) from routine screening at SingHealth Polyclinics. The study was approved by Institutional Review Boards at all study sites and written informed consent was obtained from all study participants.

TABLE 5

Clinicopathological characteristics of subject cohort

| | | Discovery | | Validation | |
|---|---|---|---|---|---|
| | | Total number | | | |
| | | 269 | | 269 | |
| | | Benign | Malignant | Benign | Malignant |
| | | Number | | | |
| | | 197 | 72 | 196 | 73 |
| Age | Mean | 50.41 | 55.58 | 50.29 | 54.63 |
| | Median | 50.00 | 55.00 | 50.00 | 56.00 |
| | Range | 30-70 | 32-70 | 25-82 | 40-72 |
| Race | Chinese | 160 | 64 | 152 | 65 |
| | non-Chinese | 37 | 8 | 44 | 8 |
| Stage | Stage 0 | — | 26 | — | 27 |
| | Stage 1 | — | 26 | — | 26 |
| | Stage 2 | — | 18 | — | 16 |
| | Stage 3 | — | 2 | — | 4 |
| Tumour size | ≤10 mm | — | 20 | — | 20 |
| | 11 to 20 mm | — | 30 | — | 25 |
| | >20 mm | — | 24 | — | 28 |
| | Unknown | — | 3 | — | 2 |
| Tumour grade | Grade 1 | — | 16 | — | 18 |
| | Grade 2 | — | 29 | — | 32 |
| | Grade 3 | — | 23 | — | 22 |
| | Unknown | — | 4 | — | 1 |
| Lymph node status | Positive | — | 51 | — | 54 |
| | Negative | — | 17 | — | 14 |
| | Unknown | — | 4 | — | 5 |

Blood Collection and Serum Processing

Peripheral blood samples (20 ml) were collected using venepuncture in plain serum tubes (Becton Dickinson Vacutainer® plus plastic serum tube, Franklin Lakes, NJ, USA). Blood samples were allowed to clot for 30-60 minutes at room temperature and centrifuged at 3000 rpm for 10 minutes at 4° C. After centrifugation, sera were aliquoted into cryotubes for immediate storage at −80° C.

RNA Isolation

Total RNA from 200 µl of each serum sample was extracted using the miRNeasy Serum/Plasma Kit (Qiagen, Venlo, The Netherlands). This was done according to the manufacturer's recommendations, except for the following modifications: (A) A set of 3 proprietary spike-in controls (MiRXES, Singapore), representing high, medium, and low levels of RNA, was added into the sample lysis buffer (QIAzol Lysis Reagent, Qiagen, Venlo, The Netherlands) prior to sample RNA isolation. The spike-in controls are 20-nucleotide RNAs with unique sequences (distinct from any of the 2588 annotated mature human miRNAs in miRBase version 21). These control RNAs are used to monitor RNA isolation efficiency and to normalize for technical variations during RNA isolation; (B) Bacteriophage MS2 RNA was added into sample lysis buffer (1 µg/ml of QIAzol) to improve RNA isolation yield; (C) The samples were centrifuged at 18,000×g for 15 minutes at room temperature after mixing with chloroform; (D) RNA was eluted in 25 µl of RNase-free water.

RT-qPCR Detection of miRNA Expression

A RT-qPCR workflow was used to quantify the expression of miRNAs in each blood sample. Serum RNA was reverse-transcribed using miRNA-specific reverse transcription (RT) primers according to the manufacturer's instructions (MiRXES) on a Veriti™ Thermal Cycler (Applied Biosystems, Waltham, MA, USA). Multiplexed RT reactions were performed using RT primers specific for each miRNA. For discovery, 324 RT primers were divided into 6 multiplex primer pools (50-60-plex per pool) to minimize non-specific cross-overs and primer-primer interactions. For each RNA sample, we performed 6 multiplex RT reactions, each with 2 µl of isolated RNA. Synthetic templates for standard curves of each miRNA (6-log serial dilution of $10^7$ to $10^2$ copies) and a non-template control (nuclease-free water spiked with MS2) were reverse-transcribed concurrently with the serum RNA samples.

All cDNAs were pre-amplified, including those from synthetic miRNA standards, using a 14-cycle PCR reaction with Augmentation Primer Pools (MiRXES) on the Veriti™ Thermal Cycler. Single qPCR was then performed on the amplified cDNA samples using a miRNA-specific qPCR assay and ID3EAL miRNA qPCR Master Mix according to the manufacturer's instructions (MiRXES). The qPCR reactions were then performed with technical duplicates on the ViiA™ qPCR system (384-well configuration, Applied Biosystems).

Raw threshold cycle (Ct) values were calculated using the ViiA™ 7 RUO software with automatic baseline setting and a threshold of 0.5. RT-qPCR efficiency and potential cDNA amplification bias was assessed by analysing the Ct values of the synthetic miRNA standards. The use of synthetic miRNA standard curves allowed us to absolutely quantify the copy numbers of miRNA expressed in each sample. Absolute expression of each miRNA (number of copies present) was calculated by inter-polation of sample Ct values with synthetic miRNA standard curves after correcting for variations in RT-qPCR efficiency.

Biomarker Discovery

The global geometric mean normalization method was used to normalize the miRNA expression and identify miRNAs with statistically significant P-values and log 2-transformed fold changes. The normalized miRNA expression values were used to compare the expression levels of individual miRNAs between malignant and benign breast lesions. Statistical significance of changes in miRNA expression were determined using the Student's t-test. P-values were corrected for multiple hypothesis testing using the false discovery rate (FDR) adjustment. We used FDR-adjusted P-value<0.05 to identify miRNAs that were differentially expressed between malignant and benign lesions.

Biomarker Panel Building and Optimization

A two-fold cross-validation procedure, incorporating a feature selection algorithm and a logistic regression predictive model, was used to build and optimize miRNA biomarker panels in the discovery cohort. Samples were partitioned into equally sized training and test sets for two-fold cross-validation. Prediction model performance was evaluated using the area under the curve (AUC) based on the receiver operating characteristics (ROC) curves. 200 rounds of the two-fold cross-validation procedure was carried out for each biomarker panel comprising two to eight miRNAs. The sequential forward floating selection (SFFS) algorithm was used to select miRNA biomarkers for inclusion in each biomarker panel. A logistic regression model was used to train predictive models for calculating a 6-miRNA biomarker score, which correlates with the probability of a subject being diagnosed with breast cancer given the expression levels of miRNAs included in the biomarker panel.

What is claimed is:

1. A method of diagnosing and treating breast cancer, the method comprising:
   obtaining a bodily fluid sample from a human subject;
   measuring the expression level of at least two or more miRNAs in the sample from the subject,
   wherein the at least two miRNAs are miR-195-5p and miR-451a, wherein, if present, more miRNAs are selected from the group consisting of miR-126-5p, miR-423-3p, miR-192-5p, and miR-17-5p, wherein miR-195-5p and miR-451a are upregulated, wherein, when measured, miR-126-5p is upregulated, and miR-423-3p, miR-192-5p, and miR-17-5p are unchanged, wherein upregulated and/or unchanged expression levels of said miRNAs in the sample, as compared to miRNA expression levels in a cancer-free control, determines the subject to have breast cancer; and treating the subject determined to have breast cancer with an anti-breast cancer compound.

2. The method of claim 1, wherein the method comprises measuring at least 3, at least 4, at least 5, or at least 6 miRNAs in the sample.

3. The method of claim 1, wherein each of miR-451a, miR-195-5p, miR-126-5p, miR-423-3p, miR-192-5p, and miR-17-5p is measured in the sample.

4. The method of claim 1, wherein the expression level of each of miR-451a, miR-195-5p, and miR-126-5p is upregulated.

5. The method of claim 1, wherein the expression level of each of miR-423-3p, miR-192-5p, and miR-17-5p is unchanged.

6. The method according to claim 1, wherein the control is a cancer-free subject, a subject with benign breast lesions, or a subject with normal mammogram results.

7. The method of claim 1, wherein the expression level of the miRNA is any one of concentration, log (concentration), Ct value, Ct/Cq value, or two to the power of Ct/Cq value.

8. The method of claim 1, wherein expression level of the miRNA is determined by Real-Time Quantitative Reverse Transcription Polymerase Chain Reaction (qRT-PCR).

9. The method of claim 1, wherein the bodily fluid is selected from the group consisting of cellular and non-cellular components of a liquid biopsy, amniotic fluid, bronchial lavage, cerebrospinal fluid, interstitial fluid, peritoneal fluids, pleural fluid, saliva, seminal fluid, urine, tears, peripheral blood, whole blood, plasma, and serum.

10. The method of claim 1, wherein the subject has had an abnormal mammogram result.

11. The method of claim 1, wherein the method includes a step of obtaining a predictive score based on the miRNA selected a mathematical model selected from linear model, logistic regression, support vector machine algorithm, logistic regression algorithm, multinomial logistic regression algorithm, Fisher's linear discriminant algorithm, quadratic classifier algorithm, perceptron algorithm, k-nearest neighbours algorithm, artificial neural network algorithm, random forests algorithm, decision tree algorithm, naive Bayes algorithm, adaptive Bayes network algorithm, and ensemble learning method combining multiple learning algorithms.

* * * * *